US010308940B2

(12) United States Patent
Bergsma et al.

(10) Patent No.: US 10,308,940 B2
(45) Date of Patent: Jun. 4, 2019

(54) ANTISENSE OLIGONUCLEOTIDES USEFUL IN TREATMENT OF POMPE DISEASE

(71) Applicant: Erasmus University Medical Center Rotterdam, Rotterdam (NL)

(72) Inventors: Atze Jacobus Bergsma, Rotterdam (NL); Erik van der Wal, Rotterdam (NL); Wilhelmus Wenceslaus Matthias Pijnappel, Rotterdam (NL); Antje Tjitske van der Ploeg, Rotterdam (NL); Arnoldus Reuser, Rotterdam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 0 days.

(21) Appl. No.: 15/315,887

(22) PCT Filed: Jun. 10, 2015

(86) PCT No.: PCT/NL2015/050421
§ 371 (c)(1),
(2) Date: Dec. 2, 2016

(87) PCT Pub. No.: WO2015/190922
PCT Pub. Date: Dec. 17, 2015

(65) Prior Publication Data
US 2017/0247704 A1 Aug. 31, 2017

(30) Foreign Application Priority Data

Jun. 10, 2014 (WO) ................ PCT/NL2014/050374
Jul. 21, 2014 (EP) ..................................... 14177884
Sep. 4, 2014 (EP) ..................................... 14183589

(51) Int. Cl.
*C07H 21/04* (2006.01)
*C12N 15/113* (2010.01)
*C12N 15/11* (2006.01)

(52) U.S. Cl.
CPC ........ *C12N 15/1137* (2013.01); *C12N 15/111* (2013.01); *C12Y 302/0102* (2013.01); *C12N 2310/11* (2013.01); *C12N 2310/321* (2013.01); *C12N 2310/3233* (2013.01); *C12N 2320/33* (2013.01); *C12N 2320/34* (2013.01)

(58) Field of Classification Search
CPC .................................................... A61K 48/00
See application file for complete search history.

(56) References Cited

U.S. PATENT DOCUMENTS

2015/0197534 A1* 7/2015 Wilton ............... C12N 15/1137
514/90

FOREIGN PATENT DOCUMENTS

| WO | 2006021724 A2 | 3/2006 |
| WO | 2006133022 A2 | 12/2006 |
| WO | 2008154098 A2 | 12/2008 |
| WO | 2011024077 A2 | 3/2011 |
| WO | 2011049627 A1 | 4/2011 |
| WO | 2015035231 A1 | 3/2015 |

OTHER PUBLICATIONS

Anonymous, "Dutch using ZFNs for Pompe disease therapy," SGMO Message Board Posts, Jan. 12, 2012, retrieved from the internet: http://www.investorvillage.com/dialogs/print.asp?msgid=11339692, retrieved on Sep. 5, 2014.
Bergsma, et al., "Identification and Characterization of Aberrant GAA Pre-mRNA Splicing in Pompe Disease Using a Generic Approach," Human Mutation, Sep. 22, 2014, pp. 57-68, vol. 36, No. 1.
Dardis, et al., "Functional characterization of the common c.-32-13T>G mutation of GAA gene: identification of potential therapeutic agents," Nucleic Acids Research, Oct. 22, 2013, pp. 1291-1302, vol. 42, No. 2.
Garcia, Luis, "IGBMC—Events, Seminar: RNA-based therapeutics for neuromuscular diseases," Feb. 21, 2014, retrieved from the internet: http://www.igbmc.fr/events/seminar/1090, retrieved on Sep. 5, 2014.
Huie, et al., "Aberrant splicing in adult onset glycogen storage disease type II (GSDII): molecular identification of an IVS1 (-13T->G) mutation in a majority of patients and a novel IVS10 (+1GT->CT) mutation," Human Molecular Genetics, Oxford University Press, Dec. 1994, pp. 2231-2236, vol. 3, No. 12, Great Britain.
International Search Report issued in International Patent Appln. No. PCT/NL2015/050421 dated Nov. 30, 2015.
Kole, et al., "RNA therapeutics: beyond RNA interference and antisense oligonucleotides," Nature Reviews Drug Discovery, Jan. 20, 2012, pp. 125-140, vol. 11, No. 2.
Lu, et al., "Correction/mutation of acid α-D-glucosidase gene by modified single-stranded oligonucleotides: in vitro and in vivo studies," Gene Therapy, Oct. 2, 2003, pp. 1910-1916, vol. 10, No. 22.
Wood, et al., "RNA-targeted splice-correction therapy for neuromuscular disease," Brain, Feb. 11, 2010, pp. 957-972, vol. 133, No. 4.
Zampieri, et al. "Splicing mutations in glycogen-storage disease type II: evaluation of the full spectrum of mutations and their relation to patients' phenotypes," European Journal of Human Genetics, Dec. 22, 2010, pp. 422-431, vol. 19, No. 4.

* cited by examiner

*Primary Examiner* — Kimberly Chong
(74) *Attorney, Agent, or Firm* — McDermott Will & Emery LLP

(57) ABSTRACT

The present invention is directed to antisense oligomeric compounds that may be used in the treatment Pompe disease as well as method for modulating the splicing of the GAA gene and method to treat Pompe disease. Also pharmaceutical compositions comprising the antisense oligomeric compounds are part of the invention.

7 Claims, 57 Drawing Sheets
Specification includes a Sequence Listing.

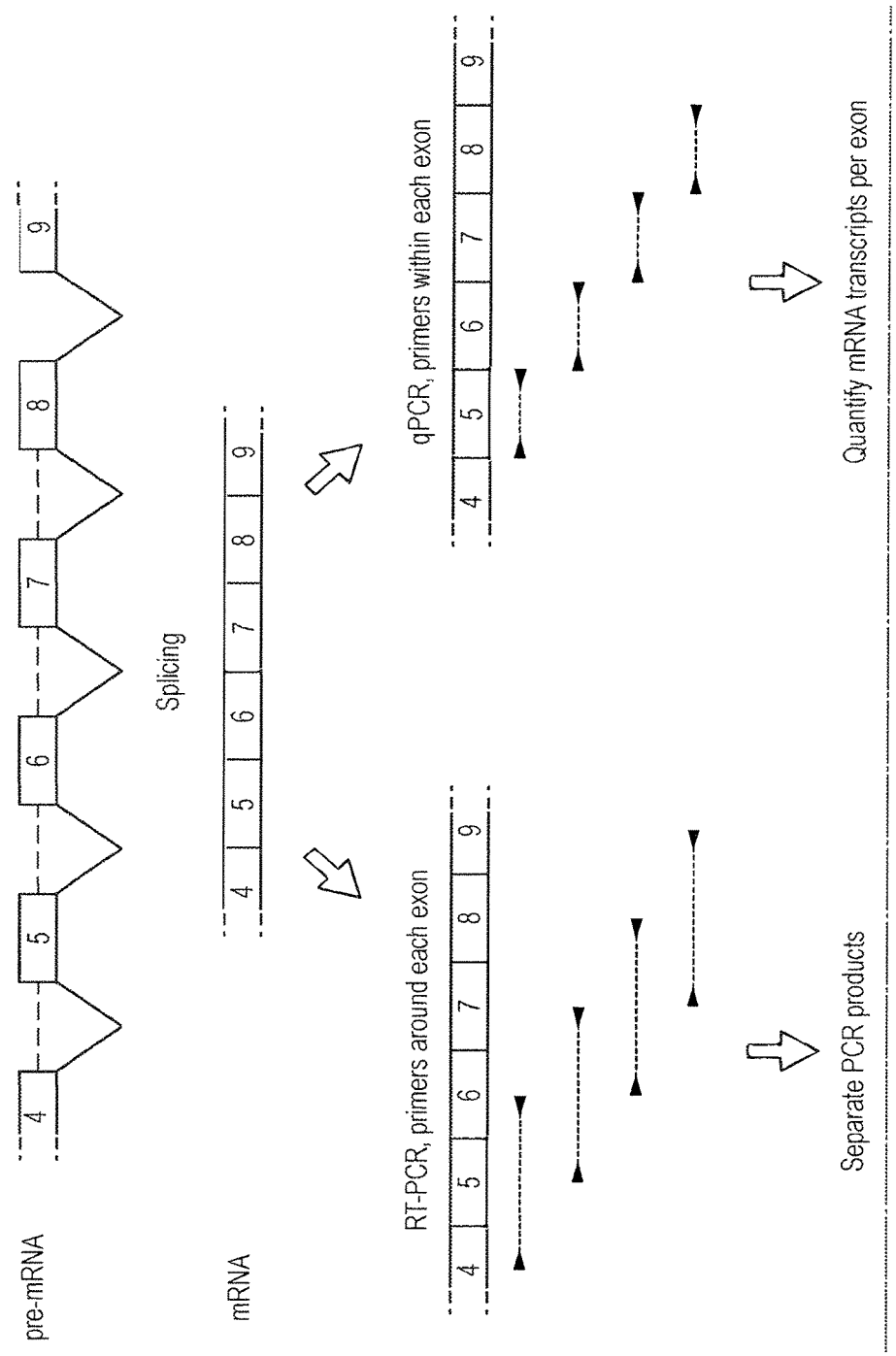

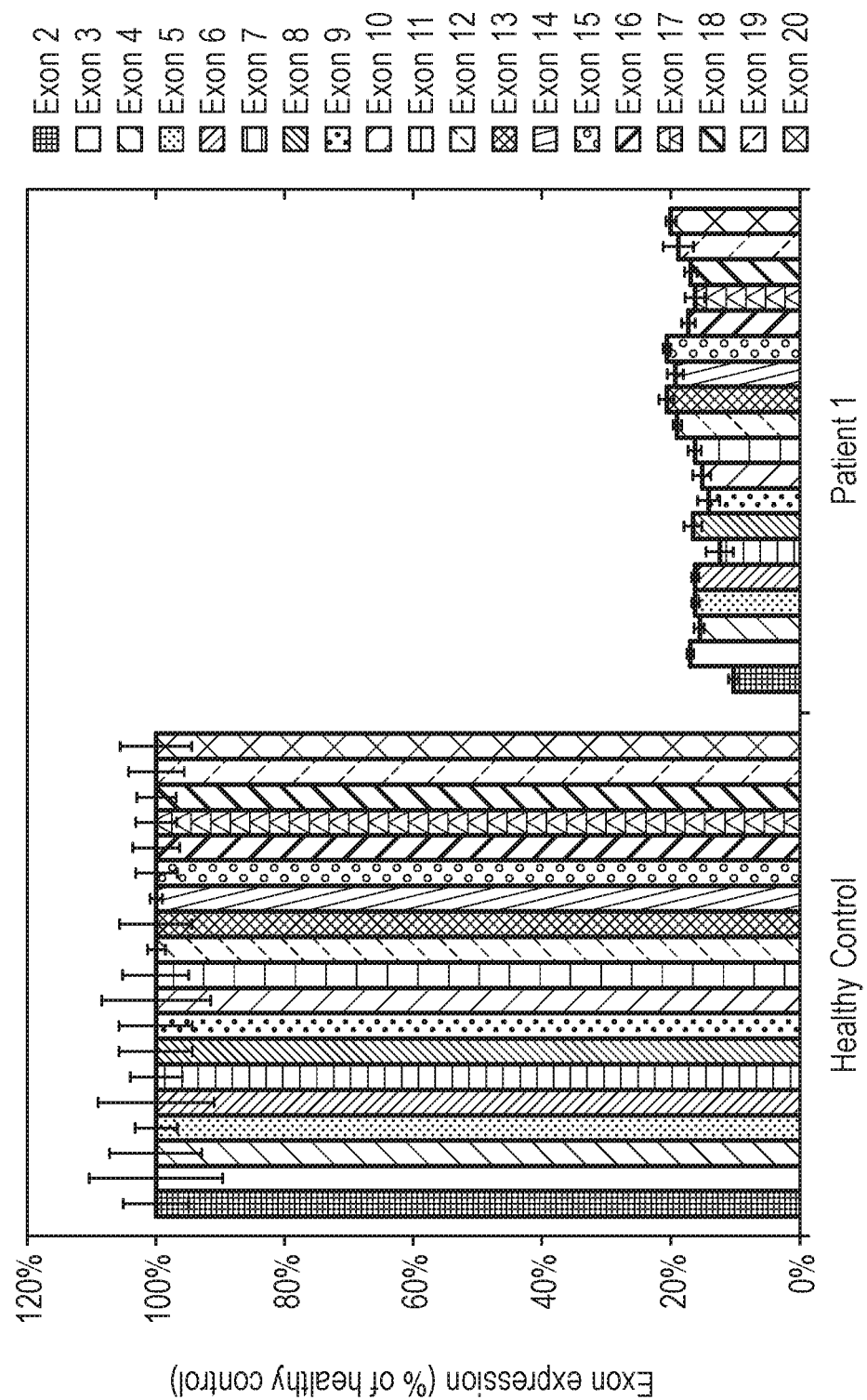

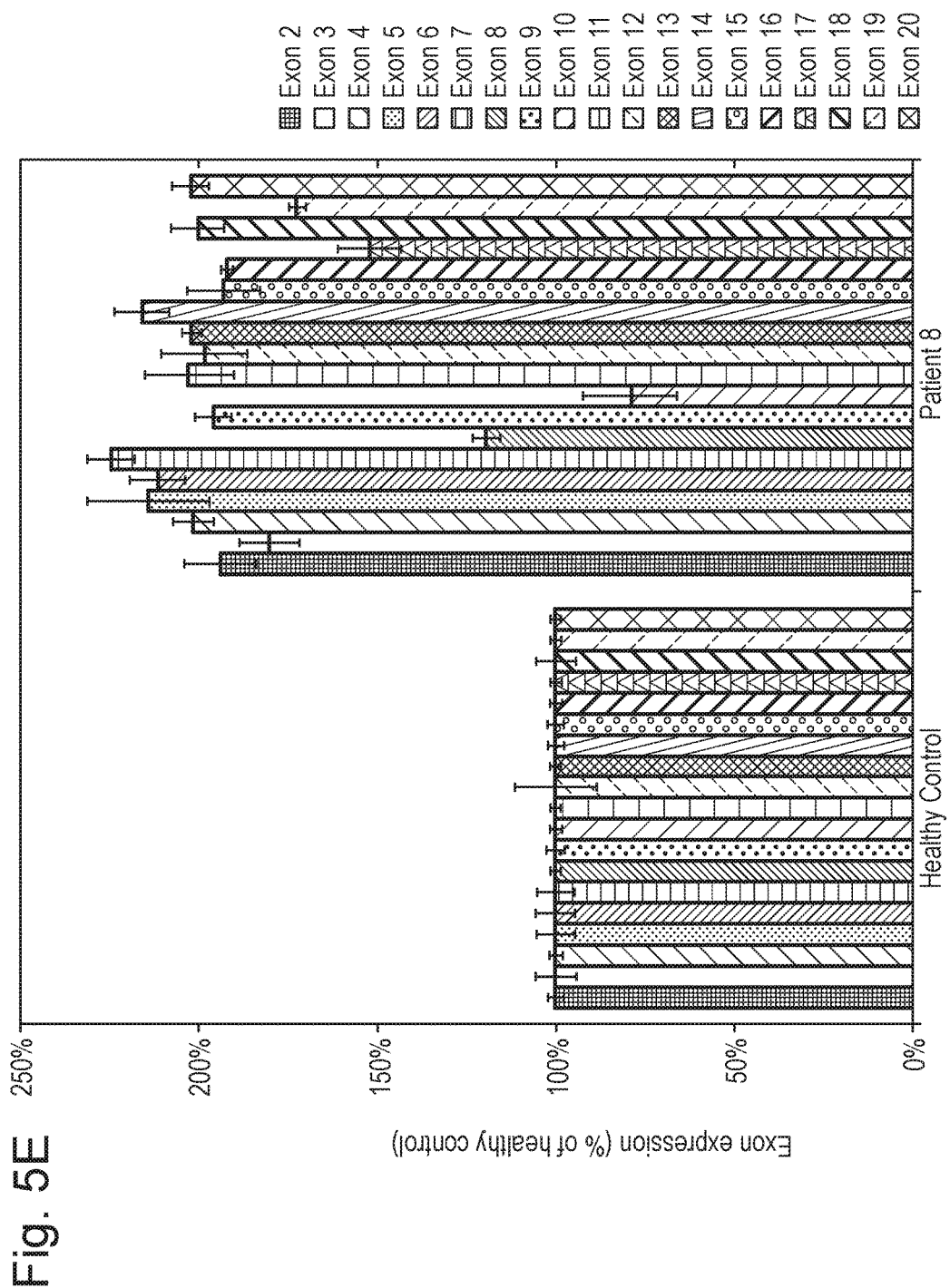

Fig. 6

| | Mutation allele 1 | Mutation allele 2 | GAA activity in primary fibroblasts on 4-MU substrate (nmol 4-MU/hr/mg protein) | GAA activity in primary fibroblasts on Glycogen substrate (nmol glucose/hr/mg protein) | Age at diagnosis | Onset infantile/juvenile/adult |
|---|---|---|---|---|---|---|
| Control | - | - | 122.4 | 1998.2 | - | none |
| Patient 1 | c.-32-13T>G | c.1636+5G>T | 14.1 | 190.6 | 59 years | adult |
| Patient 2 | c.525delT | c.525delT | 1.3 | 0.0 | 0.5 months | infantile |
| Patient 3 | c.1548G>A | c.2481+102_246+31del | 0.1 | 0.0 | 3.5 months | infantile |
| Patient 4 | c.-32-3C>G | c.1551+1G>A | 6.9 | 42.8 | 8.5 years | juvenile |
| Patient 5 | c.1075G>A | c.1075G>A | 0.6 | 0.0 | 8.5 motnhs | infantile |
| Patient 6 | c.1552-3C>G | c.1552-3C>G | 12.6 | 138.8 | 16 years | adult |
| Patient 7 | c.1437G>A | c.1437G>A | 3.0 | 0.0 | 37 years | adult |
| Patient 8 | c.1256A>T | c.1551+1G>T | 5.4 | 10.5 | 1.3 years | juvenile |

Fig. 7

| patient | Mutation (cDNA HGV nomenclature) | Location | codon change | ref on patient/codon change | effect on RNA processing | RNA HGV nomenclature | reading frame | Protein HGV nomenclature | Reference on Splicing |
|---|---|---|---|---|---|---|---|---|---|
| 1 | c.-32-13T>G (IVS1) | intron 1 | | Huie et al., Hum Mol Gen. 1994 | leaky wt splicing | | in frame | | Boerkoel et al., Am. J. Hum. Gen. 1995 |
| | | | | Huie et al., Hum Mol Gen. 1994 | Perfect skipping exon 2 | r.-32_546del | out of frame | p.? | Boerkoel et al., Am. J. Hum. Gen. 1995 |
| | | | | Huie et al., Hum Mol Gen. 1994 | Partial skipping exon 2 | r.-32_486del | out of frame | p.? | Boerkoel et al., Am. J. Hum. Gen. 1995 |
| 1 | c.1636-5G>T | intron 11 | | Kroos et al., JIMD 2006 | intron 11 inclusion | r.1636_1637ins1636+1_1636+957+r.1636+5g>t | out of frame | p.G546_V547ins145X146 | Kroos et al., JIMD 2006 |
| 2 | c.525delT | exon 2 | p.E176fs*45 | Hermans et al., Hum Mol Gen. 1994 | premature stop codon | r.525del | out of frame | p.E176fs*45 | Hermans et al., Hum Mol Gen. 1994 |
| 3 | c.1548G>A | exon 10 | p.W516* | Hermans et al., Hum Mut 2004 | premature stop codon | r.1548g>a | new stop codon | p.W516* | Hermans et al., Hum Mol Gen 1994 |
| 3 | c.2481+102_2646+31del (del ex18) | intron 17-intron 18 | p.G828_N882del | Huie et al., Hum Mol Gen. 1994 | deletion of full exon 18 | r.2481_2646del | in frame | p.G828_N882del | Huie et al., Hum Mut 2004 |
| 4 | c.-32-3C>G | intron 1 | | this study | leaky wt splicing | | in frame | | this study |
| | | | | this study | Partial skipping exon 2 | r.-32_486del | out of frame | p.? | this study |
| | | | | this study | Perfect skipping exon 2 | r.-32_546del | out of frame | p.? | this study |
| 4 | 1551+1G>A | intron 10 | | Orikowski et al., Neuromus. Dis. 2011 | perfect skipping exon 10 | r.1438_1551del | in frame | p.V480_D517del | this study |
| 5 | c.1075G>A | exon 6 | p.G359R | Schoser et al., Neuromus. Dis. 2007 | deletion of 4 nt of exon 6 | r.1072_1075del | out of frame | p.D375fs*33 | this study |
| 6 | c.1552-3C>G | intron 10 | | Kroos et al., JIMD 2006 | leaky wt splicing | | in frame | | Kroos et al., JIMD 2006 |
| | | | | | full intron 10 inclusion | r.1551_1552ins1551+1_1552-1+r1552-3c>g | out of frame | p.D517fs*6 | this study |
| | | | | Kroos et al., JIMD 2006 | partial inclusion intron 10 | r.1551_1552ins1552-30_1551+100+r1552-3c>g | in frame | p.D517_V518ins10 | Kroos et al., JIMD 2006 |
| 7 | c.1437G>A | exon 9 | silent | Kroos et al., Hum Mut 2008 | leaky wt splicing | r.1437g>a | in frame | | Kroos et al., Hum Mut 2008, this study |
| | | | | | perfect skipping exon 9 | r.1327_1437del | in frame | p.D443_K479del | this study |
| 8 | c.1256A>T | exon 8 | p.D419V | Kroos et al., Hum Mut 2012 | leaky wt splicing | r.1256a>t | in frame | p.D419V | this study |
| | | | | this study | partial skip of exon 8 | r.1255_1326del | in frame | p.K418_D443del | this study |
| 8 | c.1551+1G>T | intron 10 | | Kroos et al., Hum Mut 2012 | leaky wt splicing | | in frame | | this study |
| | | | | this study | perfect skipping of exon 10 | r.1438_1551del | in frame | p.V480_D517del | this study |

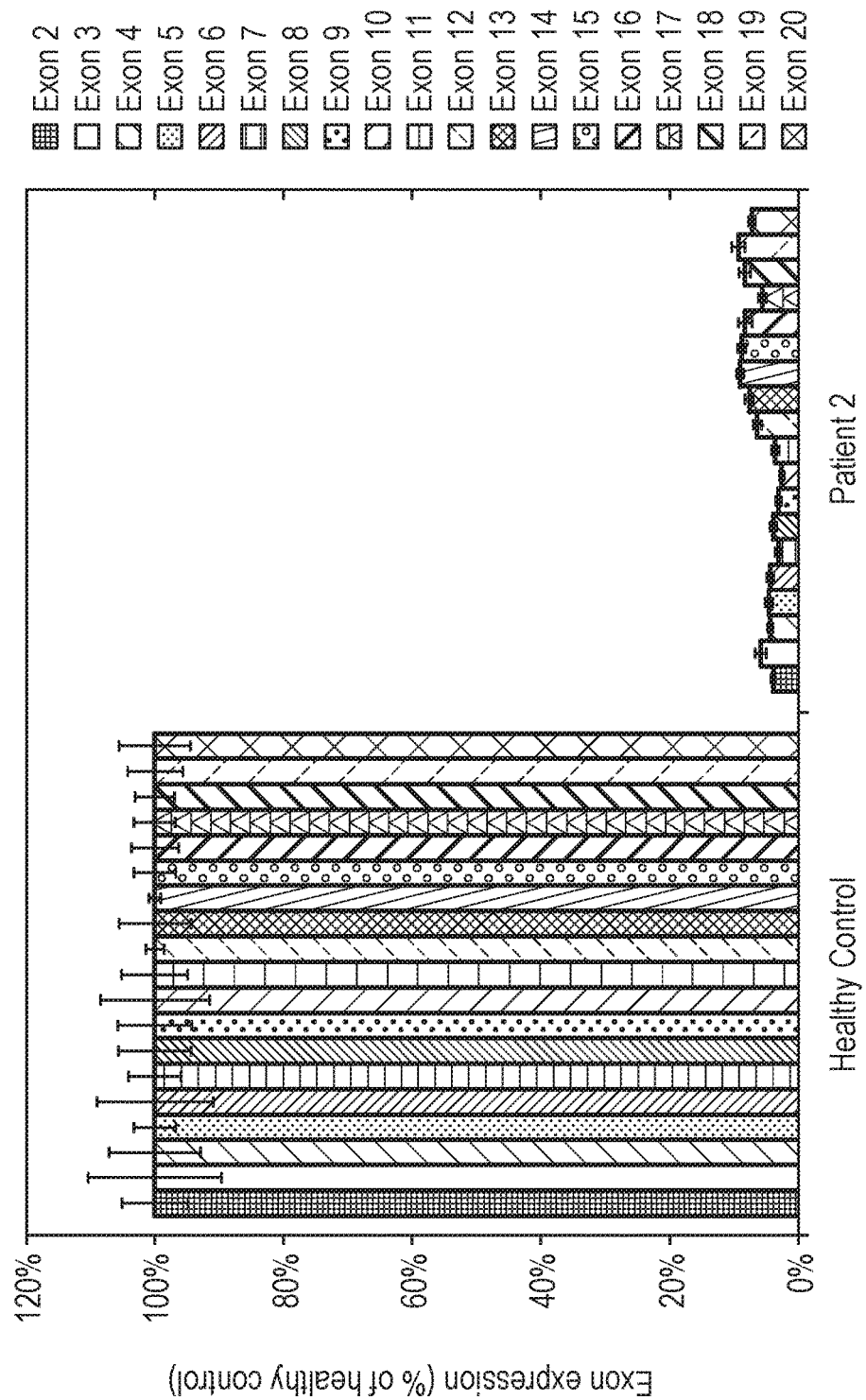

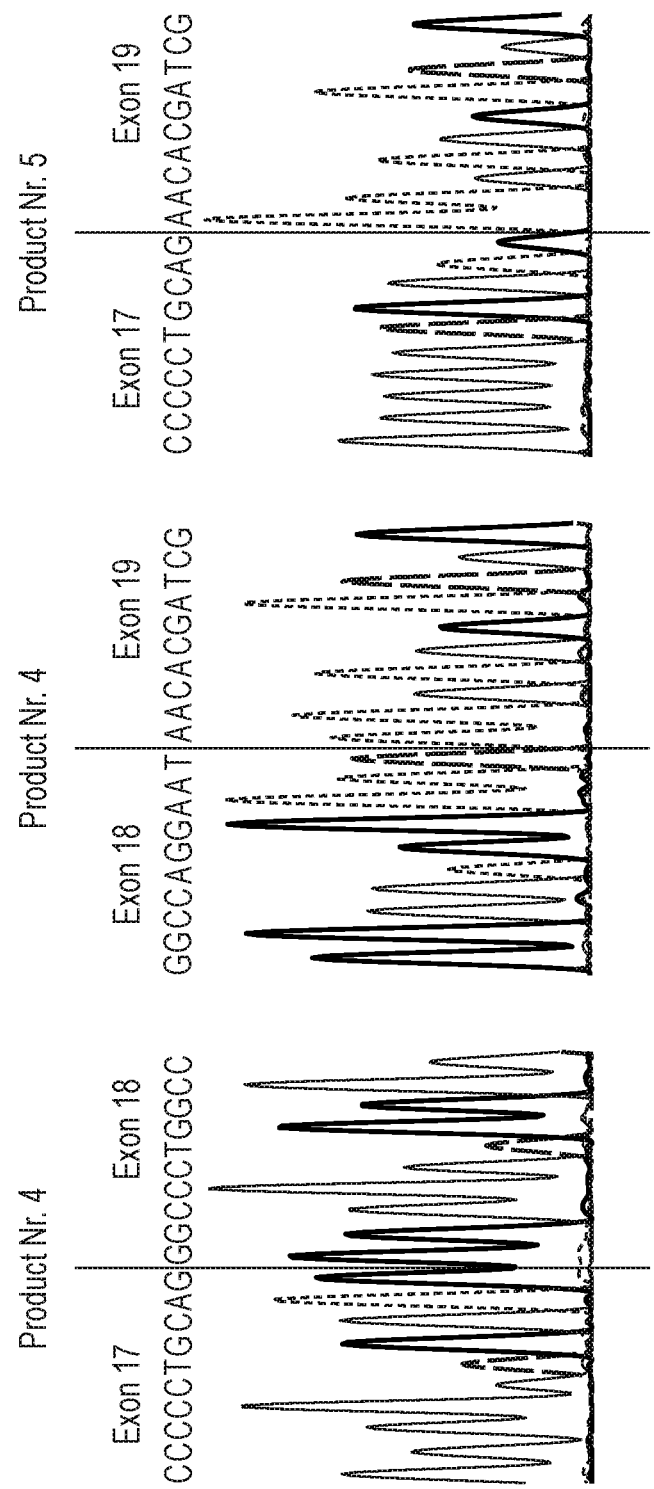

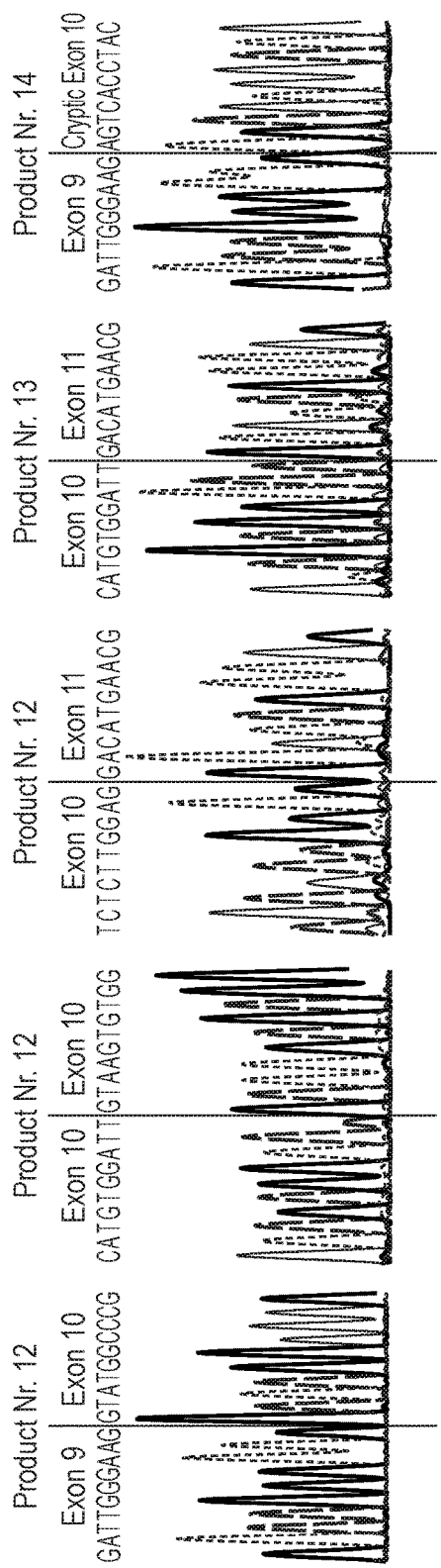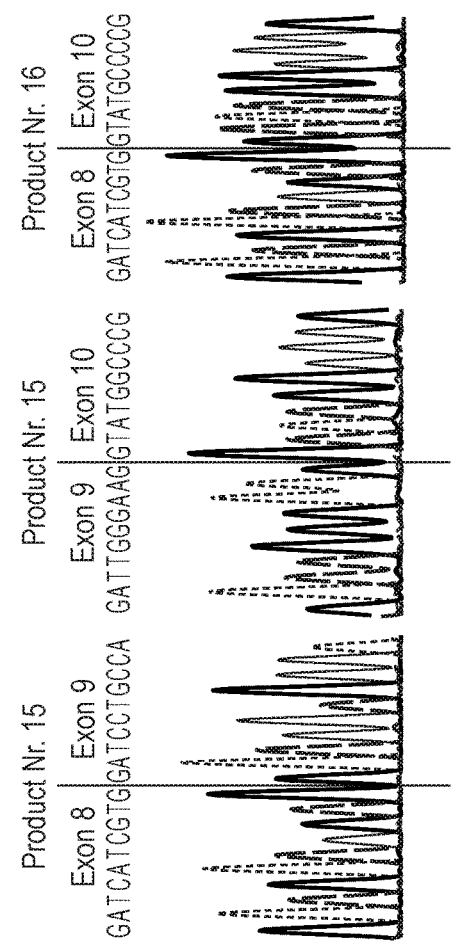
Fig. 11C
Fig. 11D

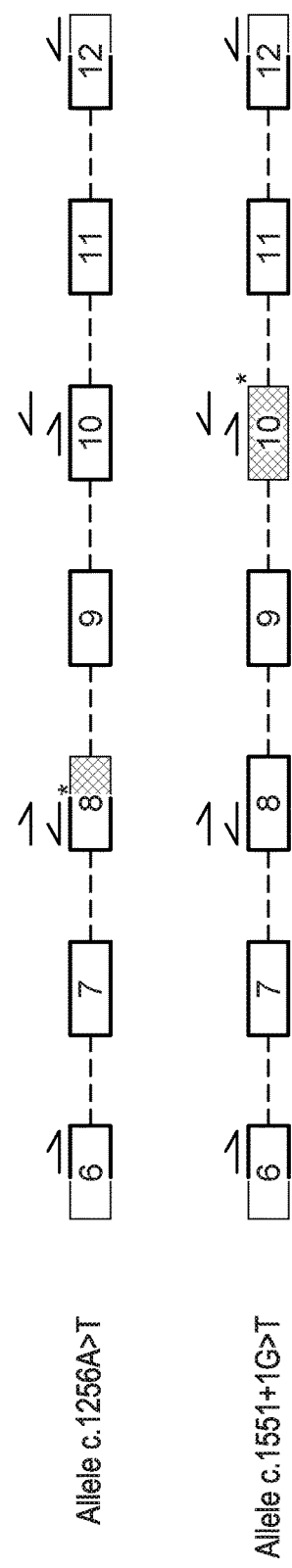

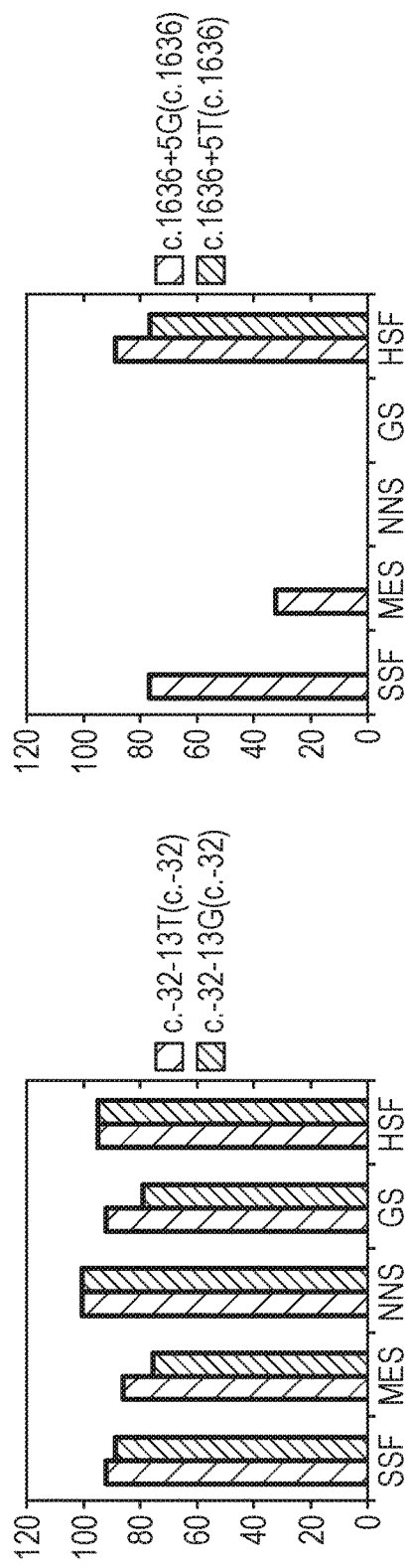
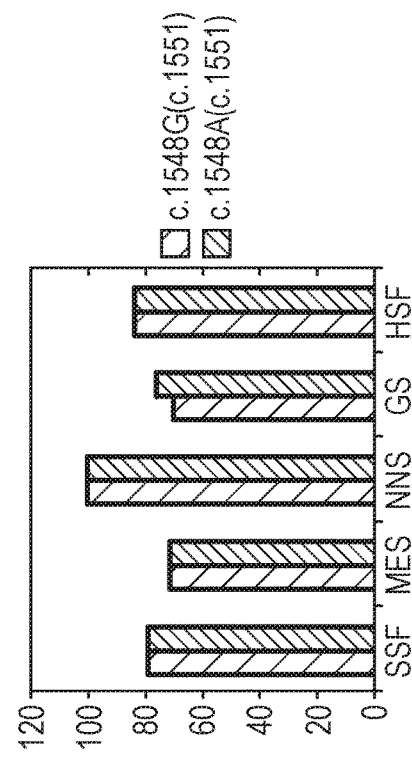
Fig. 14A
Fig. 14B

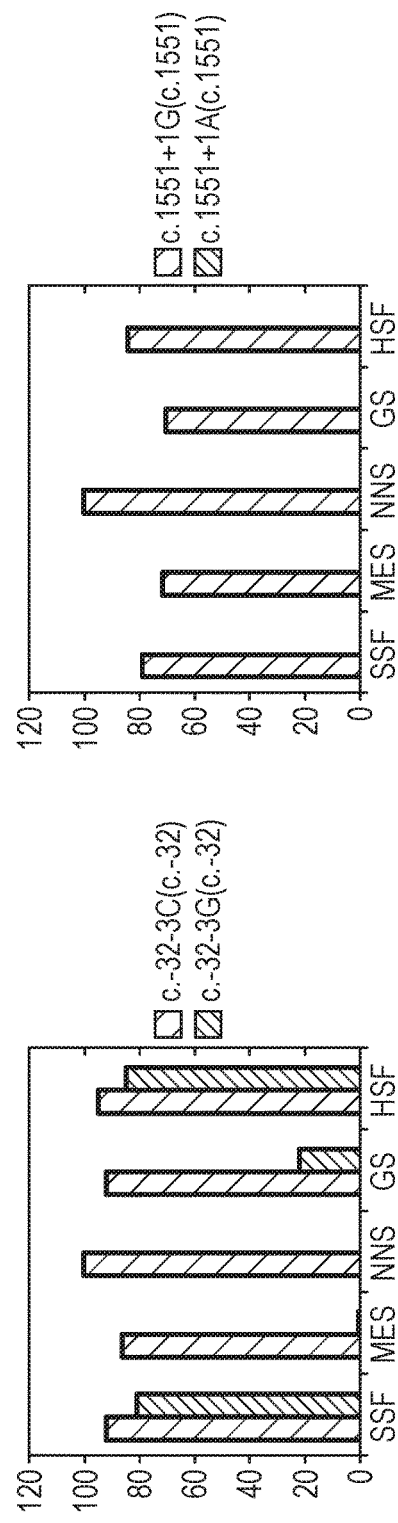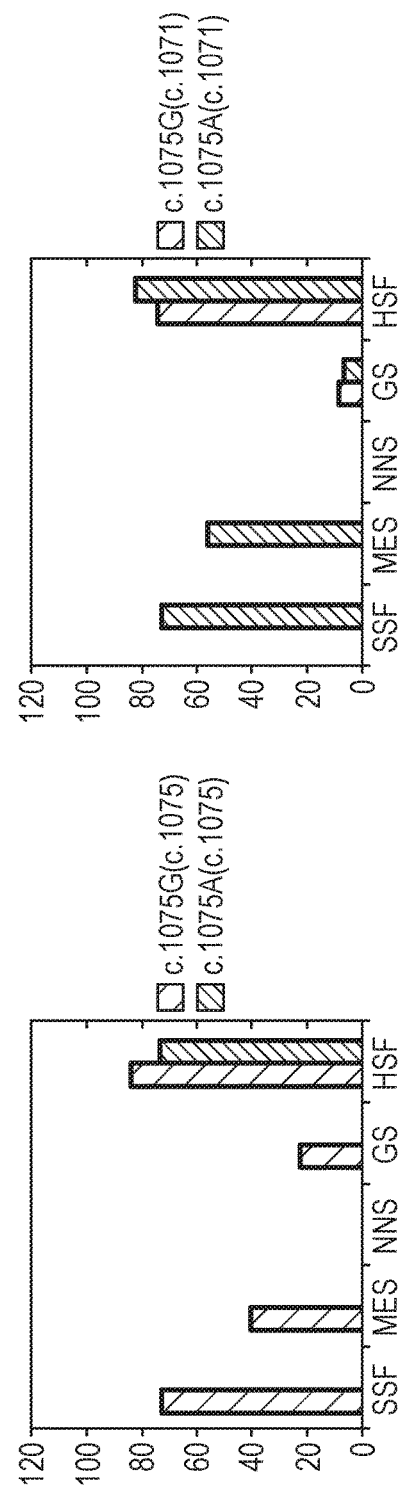
Fig. 14C
Fig. 14D

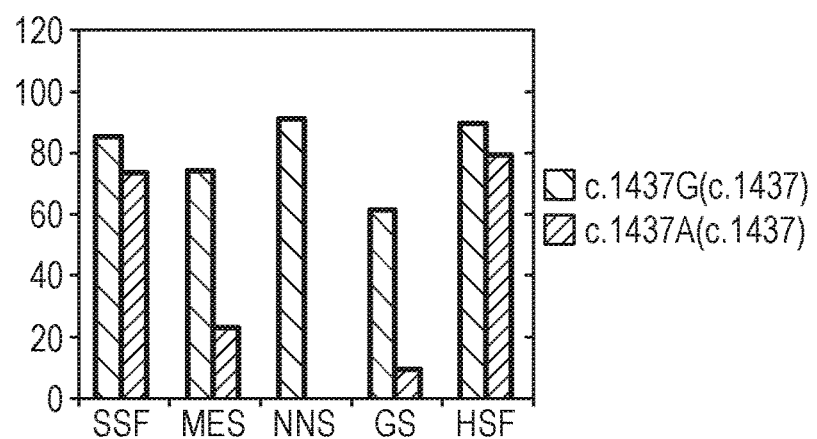

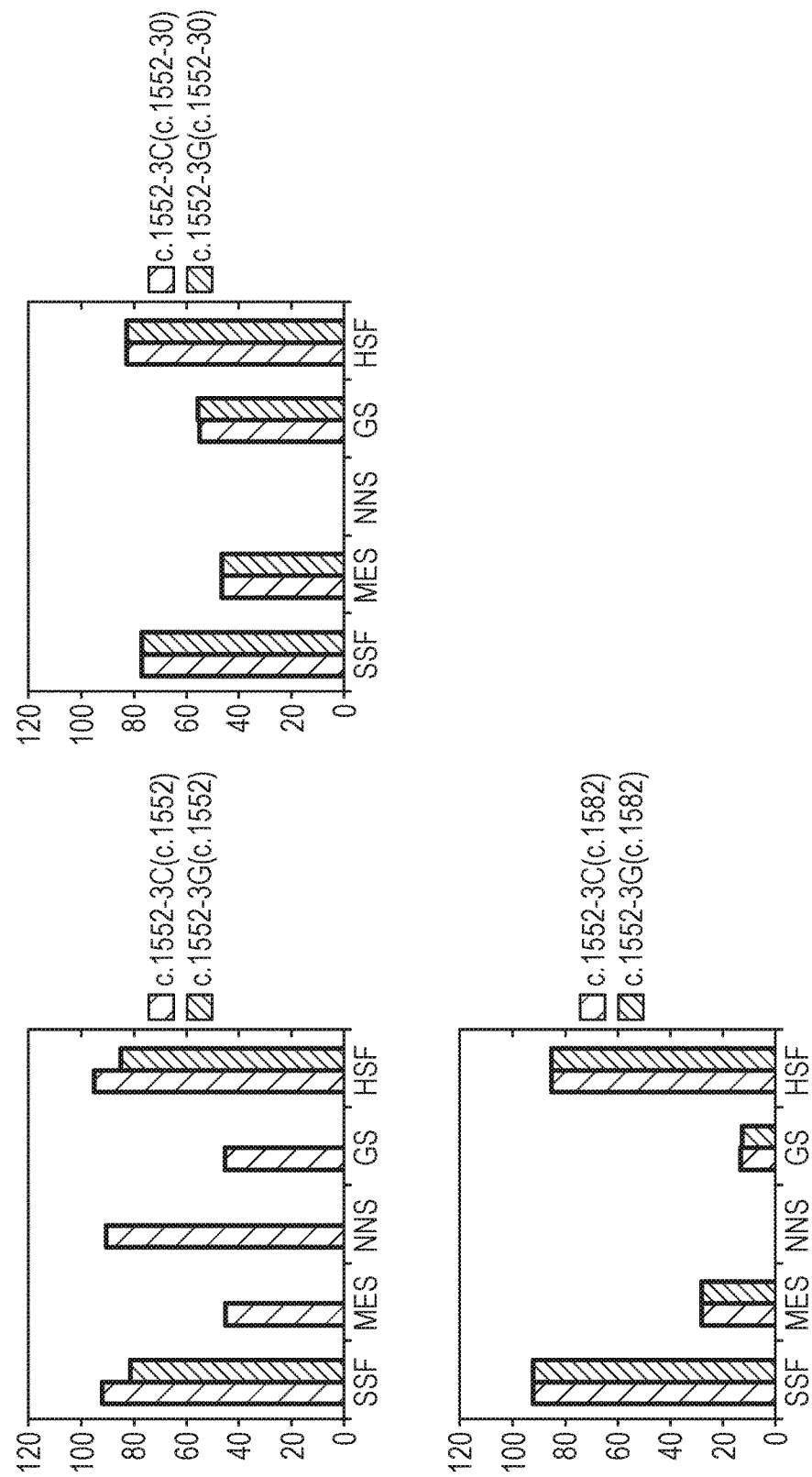

Fig. 15

| Exon tested: | Forward: | Reverse: | Full length Product: | Size Exon: | Skipped Product: |
|---|---|---|---|---|---|
| GAA Exon 2 | AAACTGAGGCACGAGCG | GAAGGGCTCCTCGGAGAA | 705 | 578 | 127 |
| GAA Exon 3 | AGCTCCTCTGAAATGGGCTACA | GCAAGGTCCCGGTTCCACA | 428 | 146 | 282 |
| GAA Exon 4 | GCTAACAGGCGCTACGAGGT | TGCTGTTTAGCAGGAACACCC | 388 | 166 | 222 |
| GAA Exon 5 | CTGTTCTTTGCGGACCAGTTC | CCACAACGTCCAGGTACTGCT | 361 | 97 | 265 |
| GAA Exon 6 | GGTCTCACCCTTTCTACCTGG | GTGATAGCGGTGAGGAGTAG | 274 | 120 | 154 |
| GAA Exon 7 | CAGCAGTACCTGGACGTTGTG | AGTCCATGTAGTCCAGGTCGTT | 175 | 119 | 56 |
| GAA Exon 8 | CGTTCATGCGCGCCATACT | GGTCTCGTTGGTGATGAAAAC | 335 | 132 | 203 |
| GAA Exon 9 | GACGTCCAGTGGAACGACCT | ACCTGGTCATGAACTCAGC | 335 | 111 | 224 |
| GAA Exon 10 | GATCCTGCCATCAGCAGCT | TGGGTTCTCCAGTCATTGT | 297 | 114 | 183 |
| GAA Exon 11 | AGGACATGGTGGCTGAGTTC | CGTAGAGGTTGTGCAGGTTGTA | 228 | 85 | 143 |
| GAA Exon 12 | AACGAGCCTTCCAACTTCATC | GAGCGGGAGATCACAAATGG | 245 | 118 | 127 |
| GAA Exon 13 | CACCAGTTTCTCTCCACACTA | GTTCCGCATGAAGGGGTAGA | 337 | 134 | 202 |
| GAA Exon 14 | ACACGCCCATTTGTGATCTC | GTGTAGAGGTGGGGAGGAGT | 356 | 152 | 204 |
| GAA Exon 15 | AAATCCTGCAGTTAACCTGCTG | GCAGGTCGTACCATGTCC | 438 | 149 | 289 |
| GAA Exon 16 | GAGCCGTACAGCTTCAGCGA | ATGTACCCAGCCCGGAGGT | 422 | 142 | 280 |
| GAA Exon 17 | CCTGGACTGTGGACCACCA | CAGGAAGATGACCTGTGTGTAGG | 428 | 150 | 278 |
| GAA Exon 18 | GTGCCAGTAGAGGCCCTTG | GGCTGTAGGTGAAGTTGGAGAC | 457 | 165 | 292 |
| GAA Exon 19 | TCACAACCACAGAGTCCCG | AGAAACTGCTCTCCCATCAACA | 352 | 153 | 199 |

Fig. 16

| | Forward | Reverse |
|---|---|---|
| B-Actin | AACCGCGAGAAGATGACCC | GCCAGAGGCGTACAGGGATAG |
| GAA Exon 2 | AGCTCCTCTGAAATGGGCTACAC | GGTTCTCAGTCTCCATCATCACG |
| GAA Exon 3 | ATCCAGCTAACAGGCGCTAC | GCTCCTCGGAGAACTCCAC |
| GAA Exon 4 | CTGTTCTTTGCGGACCAGTT | CTGAGCATCAGGGGACTGAG |
| GAA Exon 5 | CGAACCTCTACGGGTCTCAC | TGCTGTTTAGCAGGAACACC |
| GAA Exon 6 | CTTAGCTGGAGGTCGACAGG | CACAACGTCCAGGTACTGCT |
| GAA Exon 7 | CGTTCATGCCGCCATACT | GGTCATGTTCTCCACCACCT |
| GAA Exon 8 | GACGTCCAGTGGAACGACCT | GAAGTCCCGGAAGCCATC |
| GAA Exon 9 | ATCCTGCCATCAGCAGCTC | GGTCTCGTTGGTGATGAAAA |
| GAA Exon 10 | CACTGCCTTCCCCGACTT | ACCTGGTCATGGAACTCAGC |
| GAA Exon 11 | ACATGAACGAGCCTTCCAAC | ACGTAGGGTGGGTTCTCCAG |
| GAA Exon 12 | CCTCCAGCCACCAGTTTCTCT | TGTGGGAGGCGATGGCTT |
| GAA Exon 13 | GACACGCCCATTTGTGATCT | CCAGGAGCTCCACACGTC |
| GAA Exon 14 | CTCAGAGGAGCTGTGTGTGC | CAGACTGAGCAGGCTGTTGT |
| GAA Exon 15 | CAGCAGGCCATGAGGAAG | GGCCTGGTGGAACAGTGTG |
| GAA Exon 16 | CCCAAGGACTCTAGCACCTG | CAAGGGGAAGTAGCCAGTCA |
| GAA Exon 17 | GTGCCAGTAGAGGCCCTTG | GAGGTGGACGTTGATGGTGT |
| GAA Exon 18 | GCCTCACAACCACAGAGTCC | TCTCTCCATCGTCCCAGAAC |
| GAA Exon 19 | TGCAGAAGGTGACTGTCCTG | GGGCTGTAGGTGAAGTTGGA |
| GAA Exon 20 | GGGCGGAGTGTGTTAGTCTC | CTCCAGGTGACACATGCAAC |

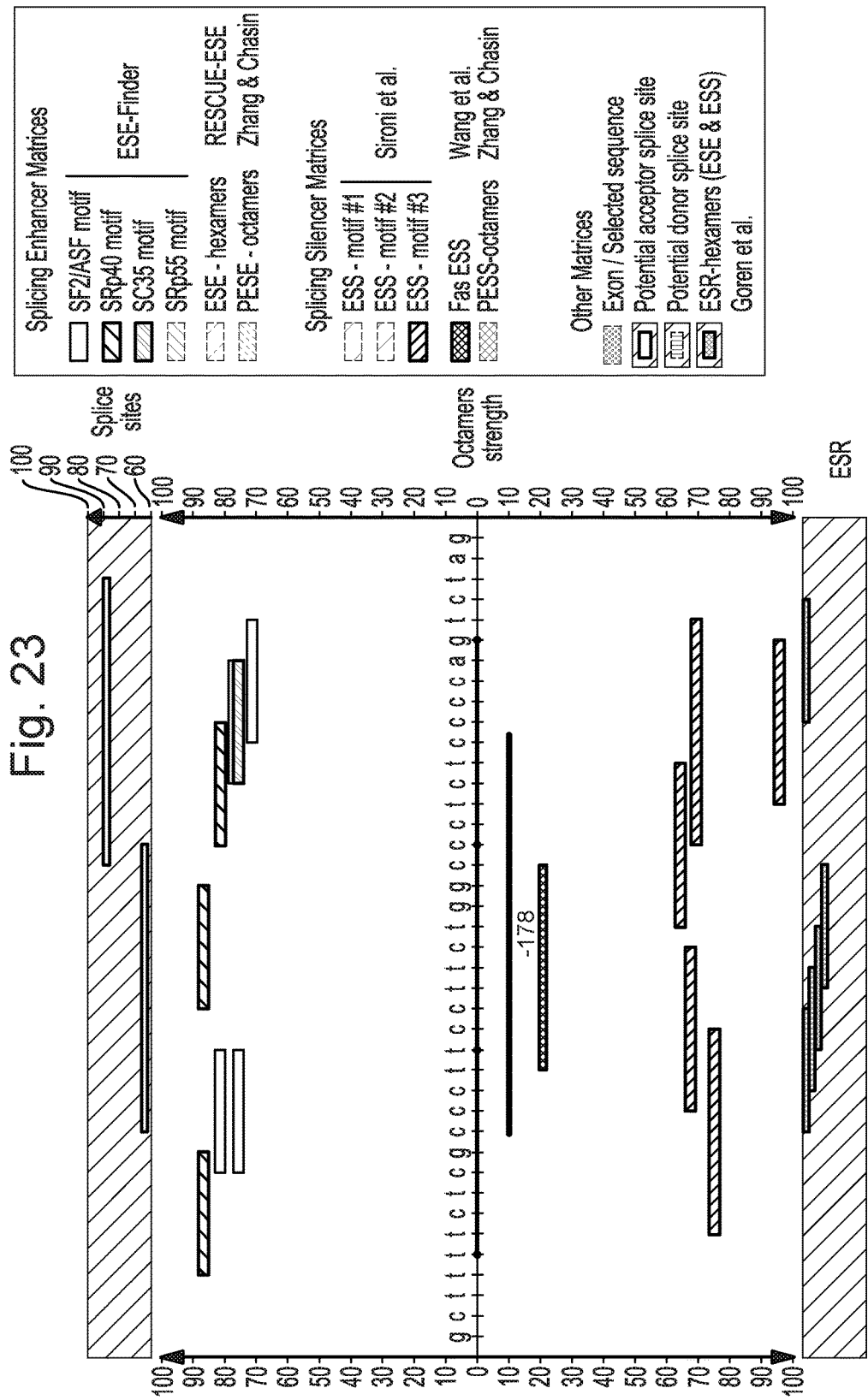

3. Carry out degenerate PCR with the minigene as template

4. Ligate PCR products in vector and generate clones

M = Marker
1 = IVS1 control
2 = Less inclusion
3 = More inclusion

Full length exon 2
Cryptic exon 2
Skipped exon 2

5. Transfect clones in Hek293 cells and analyse RNA for exon 2 inclusion via Exon flanking RT-PCR and exon internal qPCR

CACTTCACGATCAAAGATC (for example) G > A mutation detected

5. Sequence analysis of clone

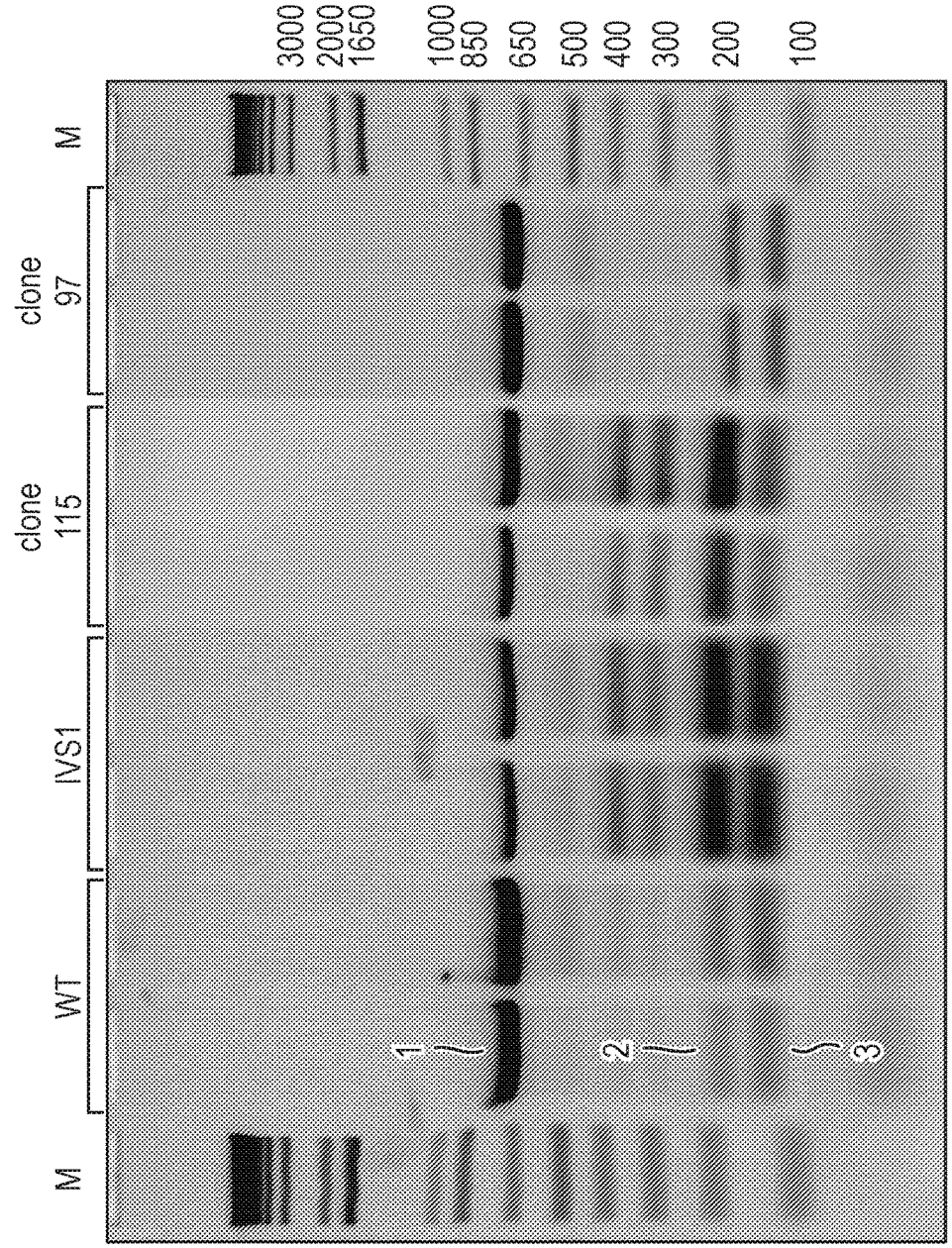

Figure 28:
Patient fibroblast line 1
c.-32-13T>G / c.525delT
A
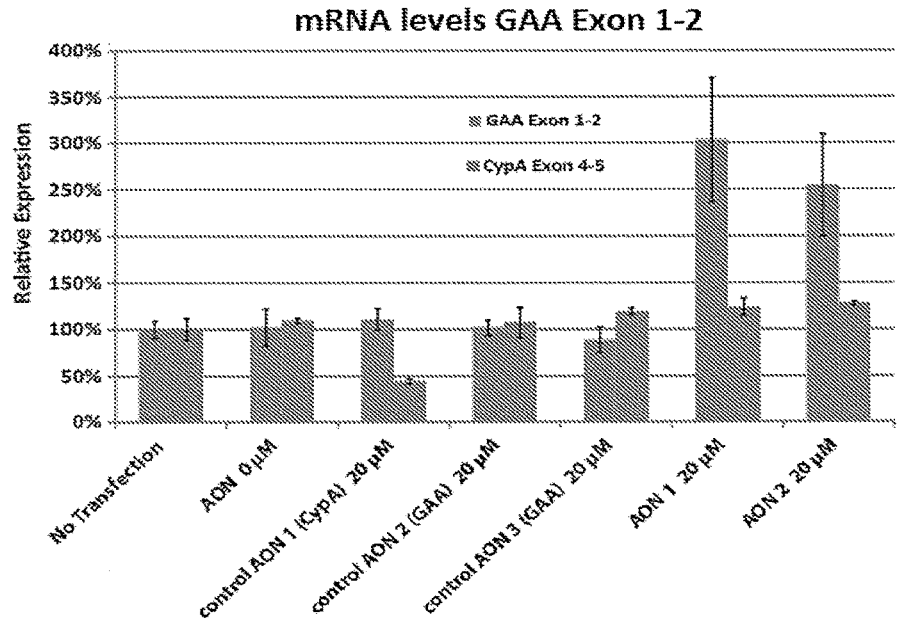
B
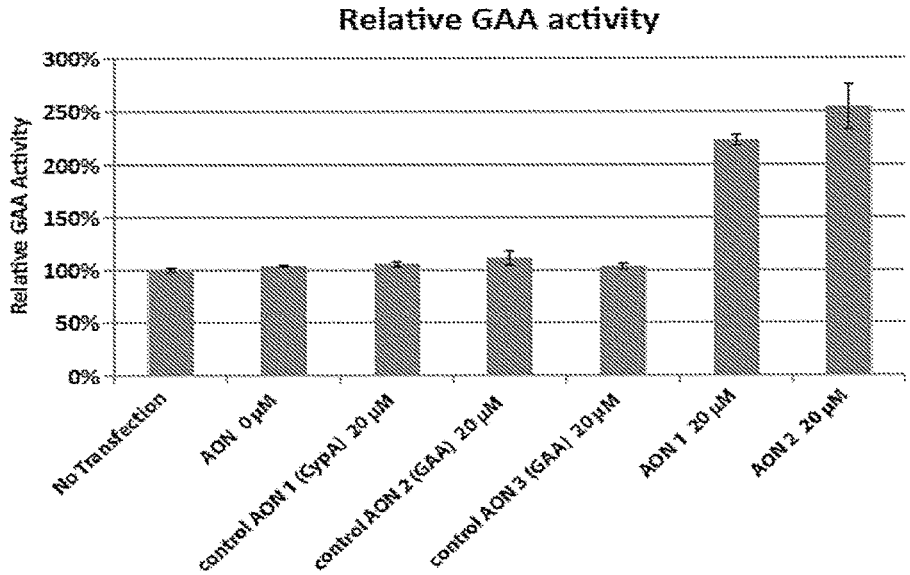

ANTISENSE OLIGONUCLEOTIDES USEFUL IN TREATMENT OF POMPE DISEASE

CROSS REFERENCE TO RELATED APPLICATIONS

This application is a U.S. National Stage of International Patent Application No. PCT/NL2015/050421, filed Jun. 10, 2015, published in English, which claims the benefit of and priority to International Patent Application No. PCT/NL2014/050374, filed Jun. 10, 2014, European Patent Application No. 14177884.5, filed Jul. 21, 2014, and European Patent Application No. 14183589.2, filed Sep. 4, 2014.

SEQUENCE LISTING

The instant application contains a Sequence Listing which has been submitted electronically in ASCII format and is hereby incorporated by reference in its entirety. Said ASCII copy, created on Apr. 17, 2017, named P104580US10 seqlist_ST25.txt and is 351,005 bytes in size.

The invention is related to antisense oligonucleotide that are useful for the treatment of Pompe disease and to pharmaceutical compositions comprising the antisense oligonucleotides. The invention is also related to a method to modulate the splicing of pre-mRNA of the GAA gene and to treatment of Pompe disease.

BACKGROUND

Pompe disease also known as acid maltase deficiency or Glycogen storage disease type II is an autosomal recessive metabolic disorder which damages muscle and nerve cells throughout the body. It is caused by an accumulation of glycogen in the lysosome due to a deficiency of the lysosomal acid alpha-glucosidase enzyme. The build-up of glycogen causes progressive muscle weakness (myopathy) throughout the body and affects various body tissues, particularly in the heart, skeletal muscles, liver and nervous system.

In Pompe disease, a protein, acid alpha-glucosidase (EC 3.2.1.20), also known as acid maltase, which is a lysosomal hydrolase, is defective. The protein is an enzyme that normally degrades the alpha-1,4 and alpha-1,6 linkages in glycogen, maltose and isomaltose and is required for the degradation of 1-3% of cellular glycogen. The deficiency of this enzyme results in the accumulation of structurally normal glycogen in lysosomes and cytoplasm in affected individuals. Excessive glycogen storage within lysosomes may interrupt normal functioning of other organelles and lead to cellular injury. The defective protein is the result of alternative splicing which is caused by mutations in the GAA gene on long arm of chromosome 17 at 17q25.2-q25.3 (base pair 75,689,876 to 75,708,272). The gene spans approximately 20 kb and contains 20 exons with the first exon being noncoding.

Although over 460 GAA mutations have been described (http://cluster15.erasmusmc.nl/klgn/pompe/mutations.html), only a few splicing mutations have been characterized. Severe mutations that completely abrogate GAA enzyme activity cause a classic infantile disease course with hypertrophic cardiomyopathy, general skeletal muscle weakness, and respiratory failure and result in death within 1.5 years of life. Milder mutations leave partial GAA enzyme activity and results in a milder phenotype with onset varying from childhood to adult. In general, a higher residual enzyme activity in primary fibroblasts is associated with later onset of Pompe disease. Enzyme replacement therapy (ERT) has been developed for Pompe disease, in which recombinant human GAA protein is administered intravenously every two weeks. This treatment can rescue the lives of classic infantile patients and delay disease progression of later onset patients, but the effects are heterogeneous. The IVS1 mutation, c.-32-13T>G, a transversion (T to G) mutation that is the most common among children, juveniles and adults with this disorder. This mutation interrupts a site of RNA splicing.

Antisense oligonucleotides (antisense oligomeric compounds) are currently being tested in clinical trials for their ability to modulate splicing. A classical example is Duchenne muscular dystrophy. In this disease, mutation hotspots are present in certain exons. Using antisense oligomeric compounds, the mutated exon is skipped and the mutation is bypassed. This results in a slightly shorter protein that is still partial functional. It is straightforward to induce exon skipping using antisense oligomeric compounds, because it is evident that the antisense oligomeric compound must be targeted to the relevant splice site. Also in Epidermolysis bullosa (WO2013053819) and in Leber congenital amaurosis symptoms (WO2012168435) antisense oligonucleotides are used for exon skipping.

For the IVS1 mutation in Pompe, such a strategy does not work. The IVS mutation causes a skipping of exon 2 resulting in the deletion of the canonical translation start side and leads to non-sense mediated decay and thus no protein is transcribed. For antisense therapy to work for the IVS1 mutation in Pompe disease, it needs to induce exon inclusion. However, it is very difficult to induce exon inclusion, because it relies on targeting a splicing repressor sequence, which cannot be reliably predicted. For the IVS1 mutation, an antisense oligomeric compound that blocks a splicing repressor sequence may promote exon 2 inclusion in the presence of the IVS1 mutation. It is known that such repressor sequences may be present anywhere in the gene, either in an exon (termed exonic splicing silencer or ESS) or in an intron (termed intronic splicing silencer or ISS) and maybe close to the mutation or far away or maybe close to the affected splice site or far away from it.

Although a number of antisense compounds that are capable of modulating splicing of a target gene in vitro have been reported, there remains a need to identify compounds that may modulate the splicing of the GAA gene.

It is therefore an object of the invention to provide an antisense compound that is capable of inducing exon inclusion. Another object of the invention is to provide an antisense compound that is capable of targeting exonic splicing silencer (ESS) or in an intronic splicing silencer (ISS). Yet another object of the invention is to provide a antisense compound that is capable of targeting the IVS-1 mutation. The present invention meets one or more of the objects.

SUMMARY OF THE INVENTION

In one aspect, the invention is directed to an antisense oligomeric compound targeting SEQ ID NO: 1.

In one aspect or embodiment of aspects and/or embodiments thereof, the invention is directed to an antisense oligomeric compound selected from the group comprising SEQ ID NO: 2-33 and sequences having at least 80% identity thereof.

In one aspect or embodiment of aspects and/or embodiments thereof, the invention is directed to an antisense oligomeric compound complementary to a polynucleotide having a sequence selected from the group comprising SEQ ID NO: 1, 37-40, and sequences having at least 80% identity thereof.

In one aspect or embodiment of aspects and/or embodiments thereof, the invention is directed to an antisense oligomeric compound targeting a sequence selected from the group comprising, c.-32-156_-210.

In one aspect or embodiment of aspects and/or embodiments thereof, the invention is directed to an antisense oligomeric compound comprising sequences selected from the group comprising SEQ ID NO: 41-540 and SEQ ID NO: 541-1583 and sequences having at least 80% identity thereof.

In one aspect or embodiment of aspects and/or embodiments thereof, the invention is directed to an antisense oligomeric compound complementary to a genomic nucleic acid sequence of GAA gene targeting the location that comprises the position of the following mutation c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15_17 AAA, c.17C>T, c.19_21 AAA, c.26_28 AAA, c.33_35 AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T, and sequences having at least 80% identity thereof.

In one aspect or embodiment of aspects and/or embodiments thereof, the invention is directed to an antisense oligomeric compound as according to the invention are very useful in the treatment Pompe disease.

In a preferred embodiment of the invention and/or embodiments thereof at least one of the nucleotides is modified, preferably the oligomeric compound is uniformly modified.

In a preferred embodiment of the invention and/or embodiments thereof the sugar of one or more nucleotides is modified, preferably the sugar modification is 2'-O-methyl or 2'-O-methoxyethyl.

In a preferred embodiment of the invention and/or embodiments thereof the base of one or more nucleotides is modified.

In a preferred embodiment of the invention and/or embodiments thereof the backbone of the oligomeric compound is modified, preferably the antisense oligomeric compounds are morpholino phosphorothioates, or morpholino phosphorodiamidate.

In a preferred embodiment of the invention and/or embodiments thereof the antisense oligomeric compound is SEQ ID NO: 12 or SEQ ID NO: 33.

In a preferred embodiment of the invention and/or embodiments thereof the antisense oligomeric compound is complementary to a genomic nucleic acid sequence of GAA targeting the location that comprises the position of a mutation selected from the group comprising c.-32-3C>G, c.17C>T c.469C>T c.546+23C>A, c.-32-102T>C c.-32-56C>T c.11G>A c.112G>A, and c.137C>T.

In a preferred embodiment of the invention and/or embodiments thereof the antisense oligomeric compound is complementary to a sequence selected from the group consisting of SEQ ID NO: 1, 37-40.

In one aspect or embodiment of aspects and/or embodiments thereof, the invention is directed to a method of modulating splicing of GAA pre-mRNA in a cell comprising contacting the cell with an antisense oligomeric compound according to the invention.

In another aspect, the invention is directed to a method for treating Pompe disease in a patient comprising administering said patient with an effective amount of an antisense oligomeric compound according to the invention.

In another aspect, the invention is directed to a method to restore the function of GAA in a cell wherein said method comprises the administration of step an the antisense oligomeric compound according to the invention.

In another aspect, the invention is directed to a method of correcting abnormal gene expression in a cell, preferably a muscular cell, of a subject, the method comprising administering to the subject an antisense oligomeric compound according to the invention.

In a preferred embodiment of the invention and/or embodiments thereof of the present invention and/or embodiments thereof the cell or the patient comprises at least one mutation selected from the group c.-32-13T>G, c.-32-3C>G, c.547-6, c.1071, c.1254, and c.1552-30, preferably the cell or patient comprises mutation c.-32-3C>G or c.-32-13T>G.

In a preferred embodiment of the invention and/or embodiments thereof of the present invention and/or embodiments thereof exon inclusion is accomplished, preferably inclusion of exon 2.

In another aspect, the invention is directed to a compound capable of binding to a genomic nucleic acid sequence of GAA gene targeting the location that comprises the position of the following mutation c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15_17 AAA, c.17C>T, c.19_21 AAA, c.26_28 AAA, c.33_35 AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T.

In another aspect, the invention is directed to a compound capable of binding to a sequence selected from the group consisting of SEQ ID NO: 1, 37-40.

In another aspect, the invention is directed to a pharmaceutical composition comprising at least one antisense oligomeric compound according to the invention or a compound according to the invention.

In a preferred embodiment of the invention and/or embodiments thereof said pharmaceutical composition further comprises a pharmaceutical acceptable excipient and/or a cell delivery agent.

BRIEF DESCRIPTION OF THE DRAWINGS

FIG. 1A, FIG. 1B and FIG. 1C, Workflow for the generic analysis of splice site mutations. Changes in splice site usage are detected by PCR using primers annealing to the flanking exons (flanking exon PCR), followed by sequencing (left part). Aberrant splice products are quantified using primers annealing within each exon (exon-internal qPCR; right part).

FIG. 6: Table 1 Laboratory diagnosis of Pompe patients used in this study.

FIG. 7: Table 2. Summary of splicing events resulting from the mutations studied. Patients 1-3 (in blue) have been characterized previously and served for validation of the assay. Patients 4-8 (in red) have been investigated in this study and all patients revealed novel splicing events.

FIG. 13. Cartoon of exons in patient 8 and the locations of PCR primers used for flanking exon PCR analysis. Only those primer pairs are shown that anneal to exons affected by the splicing mutations.

FIG. 15: Flanking exon PCR primers used in Example 1.

FIG. 16: Exon-internal qPCR primers used in Example 1.

FIG. 23. Example of a splice prediction with the human splice finder demonstrated an ambivalent prediction for the identified −178 sequence as both enhancer and silencer motifs were predicted.

FIG. 28. Specificity of antisense oligomeric compounds.

DETAILED DESCRIPTION

Figure 1B:
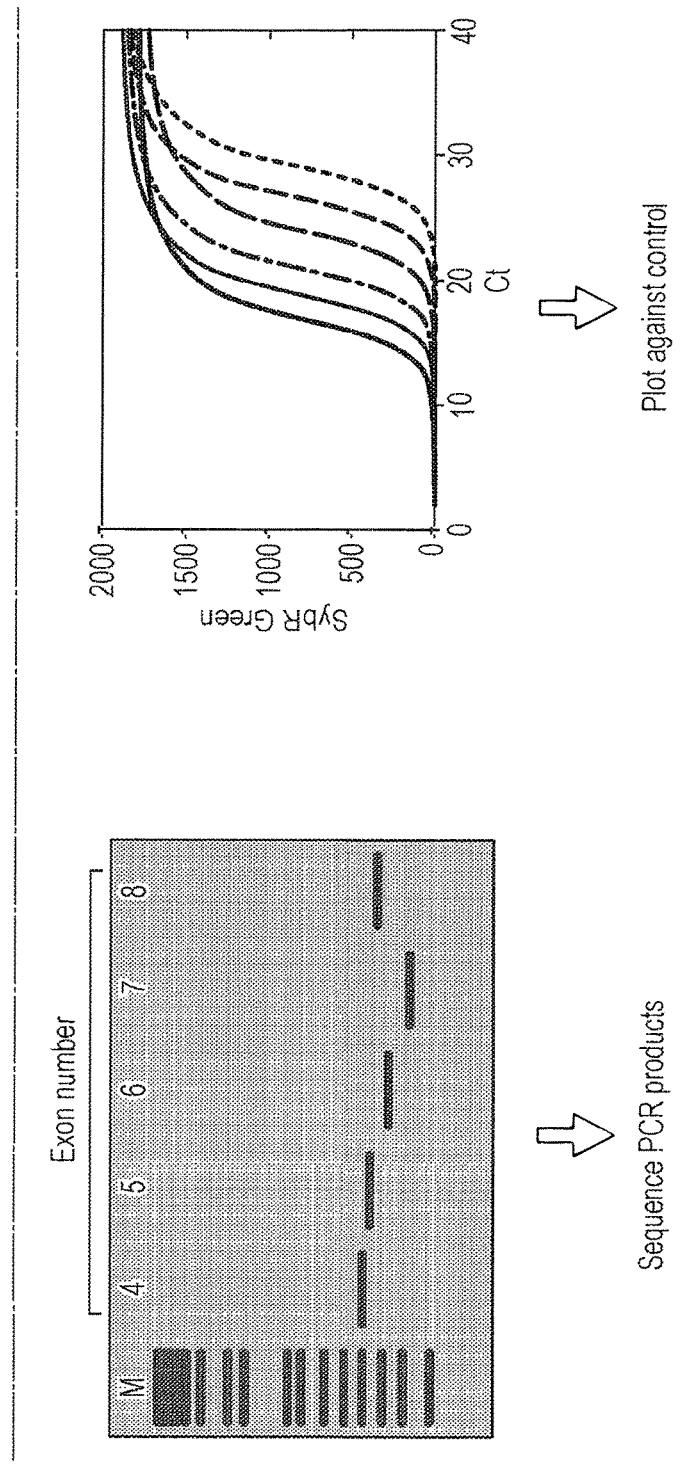

The principle behind antisense technology is that an antisense compound, which hybridizes to a target nucleic acid, modulates gene expression activities such as transcription, splicing or translation. This sequence specificity makes antisense compounds extremely attractive as tools for target validation and gene functionalization, as well as therapeutics to selectively modulate the expression of genes or gene products involved in disease.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article.

The terms "individual", "patient", and "subject" are used interchangeably herein and refer to mammals, in particular primates and preferably humans.

The term "exon" refers to a portion of a gene that is present in the mature form of mRNA. Exons include the ORF (open reading frame), i.e., the sequence which encodes protein, as well as the 5' and 3' UTRs (untranslated regions). The UTRs are important for translation of the protein. Algorithms and computer programs are available for predicting exons in DNA sequences (Grail, Grail 2 and Genscan and US 20040219522 for determining an exon-intron junctions).

As used herein, the term "protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art.

As used herein, the term "internal exon" refers to an exon that is flanked on both its 5' and 3' end by another exon. For an mRNA comprising n exons, exon 2 to exon (n−1) are the internal exons. The first and last exons of an mRNA are referred to herein as "external exons".

The term "intron" refers to a portion of a gene that is not translated into protein and while present in genomic DNA and pre-mRNA, it is removed in the formation of mature mRNA.

The term "messenger RNA" or "mRNA" refers to RNA that is transcribed from genomic DNA and that carries the coding sequence for protein synthesis. Pre-mRNA (precursor mRNA) is transcribed from genomic DNA. In eukaryotes, pre-mRNA is processed into mRNA, which includes removal of the introns, i.e., "splicing", and modifications to the 5' and 3' end (e.g., polyadenylation). mRNA typically comprises from 5' to 3'; a 5'cap (modified guanine nucleotide), 5' UTR (untranslated region), the coding sequence (beginning with a start codon and ending with a stop codon), the 3' UTR, and the poly(A) tail.

The term "nucleic acid sequence" or "nucleic acid molecule" or polynucleotide are used interchangeably and refer to a DNA or RNA molecule in single or double stranded form. An "isolated nucleic acid sequence" refers to a nucleic acid sequence which is no longer in the natural environment from which it was isolated, e.g. the nucleic acid sequence in a cell.

A "mutation" in a nucleic acid molecule is a change of one or more nucleotides compared to the wild type sequence, e.g. by replacement, deletion or insertion of one or more nucleotides. A "point mutation" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximising the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (http://www.ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 70%, 75%, 80%, 85%, 90%, 95%, 98%, 99% or more, preferably 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'variants' herein, e.g. other variants of antisense oligomeric compounds. It should be understood that sequence with substantial sequence identity do not necessarily have the same length and may differ in length. For example sequences that have the same nucleotide sequence but of which one has additional nucleotides on the 3'- and/or 5'-side are 100% identical.

The term "hybridisation" as used herein is generally used to mean hybridisation of nucleic acids at appropriate conditions of stringency as would be readily evident to those skilled in the art depending upon the nature of the probe sequence and target sequences. Conditions of hybridisation and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature (TM) of the duplex. The TM is known to be a function of the G-C content and duplex length as well as the ionic strength of the solution.

The term "allele(s)" means any of one or more alternative forms of a gene at a particular locus, all of which alleles relate to one trait or characteristic at a specific locus. One allele is present on each chromosome of the pair of homologous chromosomes. These may be identical alleles of the gene (homozygous) or two different alleles (heterozygous).

Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different conformation, being targeted to a different sub-cellular compartment, having a modified catalytic domain, having a modified binding activity to nucleic acids or proteins, etc, it may also lead to a different splicing event.

A "fragment" of the gene or nucleotide sequence or antisense oligomeric compound refers to any subset of the molecule, e.g., a shorter polynucleotide or oligonucleotide.

A "variant" refers to a molecule substantially similar to the antisense oligomeric compound or a fragment thereof, such as a nucleotide substitution variant having one or more substituted nucleotides, but which maintains the ability to hybridize with the particular gene. Preferably the variant comprises the mutations as identified by the invention. Variants also include longer sequences.

An "analogue" refers to a non-natural molecule substantially similar to or functioning in relation to either the entire molecule, a variant or a fragment thereof.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is comprised exclusively of exons. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "processing" refers to the modification of a pre-mRNA following transcription, in which introns are removed and exons are joined. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS), exonic silencer sequences (ESS) and terminal stem loop (TSL) sequences.

As used herein, the terms "intronic silencer sequences (ISS)" and "exonic silencer sequences (TSL)" refer to sequence elements within introns and exons, respectively, that control alternative splicing by the binding of trans-acting protein factors within a pre-mRNA thereby resulting in differential use of splice sites. Typically, intronic silencer sequences are less conserved than the splice sites at exon-intron junctions.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and pre-mRNA.

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art.

As used herein "splice donor site" refers to a splice site found at the 5' end of an intron, or alternatively, the 3' end of an exon. Splice donor site is used interchangeably with "5' splice site." As used herein "splice acceptor site" refers to a splice site found at the 3' end of an intron, or alternatively, the 5' end of an exon. Splice acceptor site is used interchangeably with "3' splice site."

As used herein, "targeting" or "targeted to" refer to the process of designing an oligomeric compound such that the compound hybridizes with a selected nucleic acid molecule or region of a nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding GAA" encompass DNA encoding GAA, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes GAA.

The targeting process usually also includes determination of at least one target region, segment, or site within the target nucleic acid for the antisense interaction to occur such that the desired effect, e.g., modulation of expression, will result.

As used herein, "target mRNA" refers to the nucleic acid molecule to which the oligomeric compounds provided herein are designed to hybridize. In the context of the present disclosure, target mRNA is usually unspliced mRNA, or pre-mRNA. In the context of the present invention, the target mRNA is GAA mRNA or GAA pre-mRNA.

"Region" is defined as a portion of the target nucleic acid having at least one identifiable structure, function, or characteristic. Target regions may include, for example, a particular exon or intron, or may include only selected nucleotides within an exon or intron which are identified as appropriate target regions. Target regions may also be splicing repressor sites. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Target degradation can include an RNase H, which is a cellular endonuclease which cleaves the RNA strand of an RNA:DNA duplex. It is known in the art that single-stranded antisense compounds which are "DNA-like" elicit cleavage by RNase H. Occupancy-based antisense mechanisms, whereby antisense compounds hybridize yet do not elicit cleavage of the target, include inhibition of translation, modulation of splicing, modulation of poly(A) site selection and disruption of regulatory RNA structure. For the present invention "RNA-like" antisense compounds for use in occupancy-based antisense mechanisms are preferred.

In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The term "antisense oligonucleotide, AON, or antisense oligomeric compound" refers to an oligonucleotide that is capable of interacting with and/or hybridizing to a pre-mRNA or an mRNA having a complementary nucleotide sequence thereby modifying gene expression and/or splicing. Enzyme-dependent antisense oligonucleotides include forms that are dependent on RNase H activity to degrade target mRNA, and include single-stranded DNA, RNA, and phosphorothioate antisense. Steric blocking antisense oligo-nucleotides (RNase-H independent antisense) interfere with gene expression or other mRNA-dependent cellular processes by binding to a target sequence of mRNA. Steric blocking antisense includes 2'-0 alkyl antisense oligonucleotides, Morpholino antisense oligonucleotides, and tricyclo-DNA antisense oligonucleotides. Steric blocking antisense oligonucleotides are preferred in the present invention.

As used herein, antisense oligonucleotides that are "RNase H-independent" are those compounds which do not elicit cleavage by RNase H when hybridized to a target nucleic acid. RNase H-independent oligomeric compounds modulate gene expression, such as splicing, by a target occupancy-based mechanism. Rnase H-independent antisense oligonucleotides are preferred in the present invention.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences. One of skill in the art will be able to determine when an oligomeric compound is specifically hybridizable.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the antisense oligomeric compound of the present disclosure, the binding free energy for a antisense oligomeric compound with its complementary sequence is sufficient to allow the relevant function of the antisense oligomeric compound to proceed and there is a sufficient degree of complementarity to avoid non-specific binding of the antisense oligomeric compound to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et ah, CSH Symp. Quant. Biol. 1/7:123-133 (1987); Frier et al, Proc. Nat. Acad. Sci. USA 83:9373-77 (1986); and Turner et al, J. Am. Chem. Soc. 109:3783-3785 (1987)). Thus, "complementary" (or "specifically hybridizable") are terms that indicate a sufficient degree of complementarity or precise pairing such that stable and specific binding occurs between a antisense oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, "uniformly modified" or "fully modified" refers to an oligomeric compound, an antisense oligonucleotide, or a region of nucleotides wherein essentially each nucleoside is a sugar modified nucleoside having uniform modification.

As used herein, a "chimeric oligomeric compound", "chimeric antisense compound" or "chimeric antisense oligo-nucleotide compound" is a compound containing two or more chemically distinct regions, each comprising at least one monomer unit (i.e., a nucleotide in the case of an oligonucleotide compound). The term "chimeric antisense compound" specifically refers to an antisense compound, having at least one sugar, nucleobase and/or internucleoside linkage that is differentially modified as compared to the other sugars, nucleotides and internucleoside linkages within the same oligomeric compound. The remainder of the sugars, nucleotides and internucleoside linkages can be independently modified or unmodified. In general a chimeric oligomeric compound will have modified nucleosides that can be in isolated positions or grouped together in regions that will define a particular motif. Chimeric oligomeric compounds typically contain at least one region modified so as to confer increased resistance to nuclease degradation, increased cellular uptake, and/or increased binding affinity for the target nucleic acid. In the context of the present disclosure, a "chimeric RNase H-independent antisense compound" is an antisense compound with at least two chemically distinct regions, but which is not susceptible to cleavage by RNase H when hybridized to a target nucleic acid.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the ribose sugar of the nucleoside has been substituted with a chemically modified sugar moiety. In the context of the present disclosure, the chemically modified sugar moieties include, but are not limited to, 2'-O-methoxyethyl, 2'-fluoro, 2'-dimethylami-nooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

As used herein, compounds "resistant to RNase H degradation" are antisense compounds having a least one chemical modification that increases resistance of the compound to RNase H cleavage. Such modifications include, but are not limited to, nucleotides with sugar modifications. As used herein, a nucleotide with a modified sugar includes, but is not limited to, any nucleotide wherein the 2'-deoxyribose sugar has been substituted with a chemically modified sugar moiety. In the context of the present invention, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, locked nucleic acid (LNA) and ethylene bridged nucleic acid (ENA). Modified compounds resistant to RNase H cleavage are thoroughly described herein and are well know to those of skill in the art.

In the context of the present disclosure, "cellular uptake" refers to delivery and internalization of oligomeric compounds into cells. The oligomeric compounds can be internalized, for example, by cells grown in culture (in vitro), cells harvested from an animal (ex vivo) or by tissues following administration to an animal (in vivo).

By "subject" is meant an organism, which is a donor or recipient of explanted cells or the cells themselves. "Subject" also refers to an organism to which the nucleic acid molecules of this disclosure can be administered. In one embodiment of the invention and/or embodiments thereof, a subject is a mammal or mammalian cell. In another embodiment, a subject is a human or human cell.

As used herein, the term "therapeutically effective amount" means an amount of antisense oligomeric compound that is sufficient, in the subject (e.g., human) to which it is administered, to treat or prevent the stated disease, disorder, or condition. The antisense oligomeric compound of the instant disclosure, individually, or in combination or in conjunction with other drugs, can be used to treat diseases or conditions discussed herein. For example, to treat a particular disease, disorder, or condition, the antisense oligomeric compound can be administered to a patient or can be administered to other appropriate cells evident to those skilled in the art, individually or in combination with one or more drugs, under conditions suitable for treatment. In the present invention the disease is preferably Pompe disease.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "isolated" means that the referenced material is removed from its native environment, e.g., a cell. Thus, an isolated biological material can be free of some or all cellular components, i.e. components of the cells in which the native material occurs naturally (e.g., cytoplasmic or membrane component).

The term "purified" as used herein refers to material that has been isolated under conditions that reduce or eliminate the presence of unrelated materials, i.e. contaminants, including native materials from which the material is obtained. For example, a purified tc-DNA antisense oligomeric compound is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean +−20% of the indicated range, value, or structure, unless otherwise indicated.

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

In one aspect, the invention is directed to an antisense oligomeric compound targeting SEQ ID NO: 1 and single nucleotide polymorphism of SEQ ID NO: 1.

Previous work by others has resulted in the design of antisense oligomeric compounds that promote exon exclusion in several human disorders including Duchenne Muscular Dystrophy (DMD). The strategy is simple and straightforward and relies on blocking a well-defined splice site. This results in exon skipping, thereby removing the exon containing the pathogenic gene variant. The resulting mRNA is a little bit shorter resulting in expression of a truncated protein with considerable residual activity, sufficient to at least partially alleviate the disease. The strategy is simple because canonical splice sites are known for virtually all genes. The only requirement is to design an antisense oligomeric compound that binds to the canonical splice site in the pre-mRNA, which will result in blocking of that site and skipping of the exon involved.

A much more difficult task is the reverse process: to promote inclusion rather than exclusion of an exon. To promote exon inclusion, a splice repressor may be blocked using an antisense oligomeric compound. It is however unknown where splice repressors are located. These can be present in introns or in exons and are named intronic or exonic splice silencers (ISSs or ESSs, respectively). There is software available to predict the presence of such silences but these are very unreliable. This is further illustrated by our own experience using the minigene system containing GAA exon 1-3, which failed to confirm activity of predicted splice silencer motifs. The idea to promote exon 2 inclusion of GAA with an antisense oligomeric compound to treat Pompe disease is entirely novel. We show in this in the accompanying patent application (PCT/NL2014/050375) that splice repressor sequences can be identified by two screens: the U7-snRNA antisense oligomeric compound screen, and the random mutagenesis/minigene screen. One target sequence from this screen was successfully targeted with an antisense oligomeric compound, resulting in enhanced inclusion of GAA exon 2 in the context of the IVS1 variant. This corrected the aberrant splicing of exon 2 caused by the IVS1 variant, as visualized by the enhanced abundance of wild type GAA mRNA.

It was found that sequences targeting SEQ ID NO: 1 are able to enhance inclusion of GAA exon 2. Also sequences targeting SEQ ID NO: 37, SEQ ID NO: 38, SEQ ID NO: 39, SEQ ID NO: 40, were found to be able to enhance inclusion of GAA exon 2. It is to be noted that targeting means that at least part of the sequence SEQ ID NO: 1 is targeted, e.g. by a sequence that hybridizes with at least a part or by the sequence SEQ ID NO: 1, or that binds to at least a part of SEQ ID NO: 1. Sequences that target may be shorter or longer than the target sequence.

| Sequence in cDNA to which AON anneals* | sequence of AON (5'->3'): | SEQ ID NO: |
|---|---|---|
| c-32-156_-210 | GCTCTGCACTCCCCTGCTGGAGCTTTTCTCGCCCTTCCTTCTGGCCCTCTCCCCA | 1 |
| c-32-156_-200 | GCTCTGCACTCCCCTGCTGGAGCTTTTCTCGCCCTTCCTTCTGGC | 37 |
| c-32-160_-190 | TGCACTCCCCTGCTGGAGCTTTTCTCGCCCT | 38 |
| c-32-160_-195 | TGCACTCCCCTGCTGGAGCTTTTCTCGCCCTTCCTT | 39 |
| c-32-165_-195 | TCCCCTGCTGGAGCTTTTCTCGCCCTTCCTT | 40 |

Suitably the sequences targeting SEQ ID NO: 1 hybridize with at least a part of SEQ ID NO: 1. Sequences that hybridize may be shorter or longer than the target sequence. Nucleotide sequences SEQ ID NO: 2-33 are oligomers that are able to enhance GAA exon 2 inclusion.

Two variant antisense oligomeric compounds, one of 21 nucleotides (SEQ ID NO: 33) and one of 25 nucleotides (SEQ ID NO: 12), were tested and both were found to enhance exon 2 inclusion. This was accompanied by enhanced GAA enzyme activity of at least 2 fold. It is known that patients with the IVS1 variant have ~15% leaky wild type splicing. The enhancement of 2 fold results in enzyme activities of ~30%, which are known to be above the disease threshold of 20% and thus are anticipated to restore at least a part, or even fully the lysosomal glycogen degradation.

In one aspect or embodiment of aspects and/or embodiments thereof, the invention is directed to an antisense oligomeric compound selected from the group comprising SEQ ID NO: 2-33 and variants and fragments having at least 80% identity thereof. The antisense oligomeric compound may also target single nucleotide polymorphism of SEQ ID NO: 1, 37, 38, 39, 40. It should be noted that it may not necessary to have the full length of SEQ ID NO: 2-33, fragments having a shorter or longer sequence are also envisioned. The inventors have found the target genomic sequence which enables the inclusion of exon 2 of GAA and a skilled person is capable of finding suitable sequences that target this target genomic sequence, such as SEQ ID NO: 1, 37, 38, 39, 40 and single nucleotide polymorphisms thereof. Exemplary sequences that target this target genomic sequence, such as SEQ ID NO: 1, 37, 38, 39, or 41 may be SEQ ID NO: 2-33, but also variants and fragments having at least 80% identity thereof. In particular shorter fragments such as fragments with 18, 19, 20, 21, 22, 23, or 24 nucleotides of SEQ ID NO: 2-33 are envisioned.

In one aspect or embodiment of aspects and/or embodiments thereof, the invention is directed to an antisense oligomeric compound complementary to a polynucleotide having a sequence selected from the group comprising SEQ ID NO: 1, 37-40 and single nucleotide polymorphisms thereof. Also sequences having at least 80% identity to antisense oligomeric compound complementary to a polynucleotide having a sequence selected from the group comprising SEQ ID NO: 1, 37-40 are envisioned. Antisense oligomeric compound that target one or more than one single nucleotide polymorphisms may be designed.

In one aspect or embodiment of aspects and/or embodiments thereof, the invention is directed to an antisense oligomeric compound targeting a sequence selected from the group comprising the genomic sequence c-32-156_-210.

In one aspect or embodiment of aspects and/or embodiments thereof, the invention is directed to an antisense oligomeric compound comprising sequences selected from the group comprising SEQ ID NO: 2-33, 41-1583 and sequences having at least 80% identity thereof.

In one aspect or embodiment of aspects and/or embodiments thereof, the invention is directed to antisense oligomeric compound comprising a sequences selected from the group comprising SEQ ID NO: 2-33, and 41-540.

In one aspect or embodiment of aspects and/or embodiments thereof the invention is directed to an antisense oligomeric compound complementary to a genomic nucleic acid sequence of GAA gene targeting the location that comprises the position of the following mutation c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15_17 AAA, c.17C>T, c.19_21 AAA, c.26_28 AAA, c.33_35 AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T.

The above identified mutations have been found to modulate splicing. Targeting the location of the mutation may also modulate the splicing. It is therefore understood that the antisense oligomeric compound targets the location the mutation. The nomenclature of the mutation identifies the location and the mutation. It is understood that the antisense oligomeric compound targets the location of the mutation, and the mutation does not need to be present in the genomic sequence or in the pre-mRNA. The location of the mutation is thus the location of the mutated nucleotide, or the location of the wild type nucleotide of the mutation. The antisense oligomeric compound may be targeted to a sequence comprising nucleotides upstream and nucleotides downstream of the location of the mutation. Suitably the antisense oligomeric compound target a sequence comprising 2-50 nucleotides upstream, and/or 2-50 nucleotides downstream of the location of the mutation, more suitably the antisense oligomeric compound target a sequence comprising 3-45 nucleotides upstream, and/or 3-45 nucleotides downstream of the location of the mutation, more suitably the antisense oligomeric compound target a sequence comprising 5-40 nucleotides upstream, and/or 5-40 nucleotides downstream of the location of the mutation, more suitably the antisense oligomeric compound target a sequence comprising 6-35 nucleotides upstream, and/or 6-35 nucleotides downstream of the location of the mutation, more suitably the antisense oligomeric compound target a sequence comprising 7-33 nucleotides upstream, and/or 7-33 nucleotides downstream of the location of the mutation, more suitably the antisense oligomeric compound target a sequence comprising 8-30 nucleotides upstream, and/or 8-30 nucleotides downstream of the location of the mutation, more suitably the antisense oligomeric compound target a sequence comprising 9-28 nucleotides upstream, and/or 9-28 nucleotides downstream of the location of the mutation, more suitably the antisense oligomeric compound target a sequence comprising 10-25 nucleotides upstream, and/or 10-25 nucleotides downstream of the location of the mutation, more suitably the antisense oligomeric compound target a sequence comprising 11-22 nucleotides upstream, and/or 11-22 nucleotides downstream of the location of the mutation, more suitably the antisense oligomeric compound target a sequence comprising 12-20 nucleotides upstream, and/or 12-20 nucleotides downstream of the location of the mutation, more suitably the antisense oligomeric compound target a sequence comprising 13-18 nucleotides upstream, and/or 13-18 nucleotides downstream of the location of the mutation, more suitably the antisense oligomeric compound target a sequence comprising 14-16 nucleotides upstream, and/or 14-16 nucleotides downstream of the location of the mutation.

The nomenclature is well known to a skilled person and can be found in Dunnen and Antonarakis Human mutation 15:7-12(2000) and Antonarakis SE, the Nomenclature Working Group. 1998. Recommendations for a nomenclature system for human gene mutations. Hum Mutat 11:1-3 and on the website (http://www.dmd.nl/mutnomen.html. Genomic positions may also be found on www.pompecenter.nl. All of these are incorporated by reference.

Preferably the genomic nucleic acid sequence is pre-mRNA.

These antisense oligomeric compound are useful in the treatment of glycogen storage disease type II/Pompe disease.

In one aspect or the target sequence is an intronic splicing silencer or ISS. In a preferred embodiment of the invention and/or embodiments thereof of an aspect and/or embodiments of the invention the target sequence is the GCTCTGCACTCCCCTGCTGGAGCTTTTCTCGCCCTTCCTTCTGGCCCTCTCCCCA (SEQ ID NO: 1). It should be noted that also naturally occurring single nucleotide polymorphism are included. Antisense oligomeric compounds targeting SEQ ID NO: 1 are a very suitable to treat Pompe patients. Exemplary antisense oligomeric compounds targeting SEQ ID NO: 1 are SEQ ID NO: 2-33 and in particular SEQ ID NO: 12 and SEQ ID NO 33. However the invention is not limited to these two sequences. A skilled person is capable of designing antisense oligomeric compounds against target sequence SEQ ID NO: 1, 37, 38, 39, or 40. The antisense oligomeric compounds against target sequenced SEQ ID NO: 1 may have length of 10 to 100 nucleotides, preferably 11 to 75 nucleotides, preferably 12 to 73 nucleotides, preferably 13 to 70 nucleotides, preferably 14 to 65 nucleotides, preferably 15 to 60 nucleotides, preferably 16 to 55 nucleotides, preferably 17 to 50 nucleotides, preferably 18 to 45 nucleotides, preferably 19 to 40 nucleotides, preferably 20 to 38 nucleotides, preferably 21 to 35 nucleotides, preferably 22 to 33 nucleotides, preferably 23 to 30 nucleotides, preferably 24 to 29 nucleotides, preferably 25 to 28 nucleotides, preferably 26 to 27 nucleotides.

Hereunder exemplary antisense oligomeric compounds targeting SEQ ID NO: 1 are given

| Sequence in cDNA to which AON anneals* | sequence of AON (5'->3'): | Seq ID |
|---|---|---|
| c.-32-180_-156 | TGGGGAGAGGGCCAGAAGGAAGGGC | 2 |
| c.-32-181_-157 | GGGGAGAGGGCCAGAAGGAAGGGCG | 3 |
| c.-32-182_-158 | GGGAGAGGGCCAGAAGGAAGGGCGA | 4 |
| c.-32-183_-159 | GGAGAGGGCCAGAAGGAAGGGCGAG | 5 |
| c.-32-184_-160 | GAGAGGGCCAGAAGGAAGGGCGAGA | 6 |
| c.-32-185_-161 | AGAGGGCCAGAAGGAAGGGCGAGAA | 7 |
| c.-32-186_-162 | GAGGGCCAGAAGGAAGGGCGAGAAA | 8 |
| c.-32-187_-163 | AGGGCCAGAAGGAAGGGCGAGAAAA | 9 |
| c.-32-188_-164 | GGGCCAGAAGGAAGGGCGAGAAAAG | 10 |
| c.-32-189_-165 | GGCCAGAAGGAAGGGCGAGAAAAGC | 11 |
| c.-32-190_-166 | GCCAGAAGGAAGGGCGAGAAAAGCT | 12 |
| c.-32-191_-167 | CCAGAAGGAAGGGCGAGAAAAGCTC | 13 |
| c.-32-192_-168 | CAGAAGGAAGGGCGAGAAAAGCTCC | 14 |
| c.-32-193_-169 | AGAAGGAAGGGCGAGAAAAGCTCCA | 15 |
| c.-32-194_-170 | GAAGGAAGGGCGAGAAAAGCTCCAG | 16 |
| c.-32-195_-171 | AAGGAAGGGCGAGAAAAGCTCCAGC | 17 |
| c.-32-196_-172 | AGGAAGGGCGAGAAAAGCTCCAGCA | 18 |
| c.-32-197_-173 | GGAAGGGCGAGAAAAGCTCCAGCAG | 19 |
| c.-32-198_-174 | GAAGGGCGAGAAAAGCTCCAGCAGG | 20 |
| c.-32-199_-175 | AAGGGCGAGAAAAGCTCCAGCAGGG | 21 |
| c.-32-200_-176 | AGGGCGAGAAAAGCTCCAGCAGGGG | 22 |
| c.-32-201_-177 | GGGCGAGAAAAGCTCCAGCAGGGGA | 23 |
| c.-32-202_-178 | GGCGAGAAAAGCTCCAGCAGGGGAG | 24 |
| c.-32-203_-179 | GCGAGAAAAGCTCCAGCAGGGGAGT | 25 |
| c.-32-204_-180 | CGAGAAAAGCTCCAGCAGGGGAGTG | 26 |
| c.-32-205_-181 | GAGAAAAGCTCCAGCAGGGGAGTGC | 27 |
| c.-32-206_-182 | AGAAAAGCTCCAGCAGGGGAGTGCA | 28 |
| c.-32-207_-183 | GAAAAGCTCCAGCAGGGGAGTGCAG | 29 |
| c.-32-208_-184 | AAAAGCTCCAGCAGGGGAGTGCAGA | 30 |
| c.-32-209_-185 | AAAGCTCCAGCAGGGGAGTGCAGAG | 31 |
| c.-32-210_-186 | AAGCTCCAGCAGGGGAGTGCAGAGC | 32 |
| c.-32-187_-167 | CCAGAAGGAAGGGCGAGAAAA | 33 |

In the above examples the sequences are 25 nucleotides long however longer variants or shorter fragment are also envisioned. Exemplary is SEQ ID NO: 33 which is only 21 nucleotides long and comprises the same nucleotides as SEQ ID NO: 12 but is shorter. In a preferred embodiment of the invention and/or embodiments thereof of the present invention and/or embodiments thereof the antisense oligomeric compounds are selected from the group of SEQ ID NO: 2-33 and fragments and variants thereof having at least 80% sequence identity. In a preferred embodiment of the invention and/or embodiments thereof of the present invention and/or embodiments thereof the antisense oligomeric compounds are selected from the group of SEQ ID NO: 2-33 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 2-33.

The present invention is also directed to sequences that are at least 80% identical to SEQ ID NO: 2-33. Preferably at least 85% identical to SEQ ID NO: 2-33, more preferably at least 88% identical to SEQ ID NO: 2-33, more preferably at least 90% identical to SEQ ID NO: 2-33. more preferably at least 91% identical to SEQ ID NO: 2-33, more preferably at least 92% identical to SEQ ID NO: 2-33, more preferably at least 93% identical to SEQ ID NO: 2-33, more preferably at least 94% identical to SEQ ID NO: 2-33, more preferably at least 95% identical to SEQ ID NO: 2-33, more preferably at least 96% identical to SEQ ID NO: 2-33, more preferably at least 97% identical to SEQ ID NO: 2-33, more preferably at least 98% identical to SEQ ID NO: 2-33, more preferably at least 99% identical to SEQ ID NO: 2-33.

Preferred antisense sequences are SEQ ID NO: 12, and SEQ ID NO:33 or sequences that are at least 80% identical thereto, preferably at least 85% identical, more preferably at least 88% identical, more preferably at least 90% identical, more preferably at least 91% identical, more preferably at least 92% identical, more preferably at least 93% identical, more preferably at least 94% identical, more preferably at least 95% identical, more preferably at least 96% identical, more preferably at least 97% identical, more preferably at least 98% identical, more preferably at least 99% identical to SEQ ID NO: 12, and/or 33.

In a preferred embodiment of the invention and/or embodiments thereof of the present invention and/or embodiments thereof the antisense oligomeric compounds are selected from the group of fragments SEQ ID NO: 2-33, wherein the fragment is 16, 17, 18, 19, 20, 21, 22, 23, or 24 nucleotides long. In a preferred embodiment of the invention and/or embodiments thereof of the present invention and/or embodiments thereof the antisense oligomeric compounds are selected from the group of fragments SEQ ID NO: 2-33, wherein the fragment is 17, 18, 19, 20, 21, or 22 nucleotides long. In a preferred embodiment of the invention and/or embodiments thereof of the present invention and/or embodiments thereof the antisense oligomeric compounds are selected from the group of fragments SEQ ID NO: 2-33, wherein the fragment is 19, 20, or 21 nucleotides long.

The antisense oligomeric compounds may be selected from the group of SEQ ID NO: 41-540:
Sequences identified with U7 screen: SEQ ID NO 41-97

| Sequence in GAA cDNA to which AON anneals | AON sequence 5' -> 3' | Seq ID |
|---|---|---|
| c.-32-319_-300 | CCAAACAGCTGTCGCCTGGG | 41 |
| c.-32-299_-280 | AGGTAGACACTTGAAACAGG | 42 |
| c.-32-279_-260 | CCCAGGAAGACCAGCAAGGC | 43 |
| c.-32-259_-240 | TCAAACACGCTTAGAATGTC | 44 |
| c.-32-239_-220 | GTCTGCTAAAATGTTACAAA | 45 |
| c.-32-219_-200 | GAGTGCAGAGCACTTGCACA | 46 |
| c.-32-199_-180 | CGAGAAAAGCTCCAGCAGGG | 47 |
| c.-32-179_-160 | GAGAGGGCCAGAAGGAAGGG | 48 |
| c.-32-159_-140 | GCCCTGCTGTCTAGACTGGG | 49 |
| c.-32-139_-120 | AGGTGGCCAGGGTGGGTGTT | 50 |
| c.-32-119_-100 | GCACCCAGGCAGGTGGGTA | 51 |
| c.-32-99_-80 | CAACCGCGGCTGGCACTGCA | 52 |
| c.-32-79_-60 | TCAAAGCAGCTCTGAGACAT | 53 |
| c.-32-59_-40 | GGGCGGCACTCACGGGGCTC | 54 |
| c.-32-39_-20 | GCTCAGCAGGGAGGCGGGAG | 55 |
| c.-32-19_-0 | CCTGCGGGAGAAGAAAGCGG | 56 |
| c.-30_-12 | GCCTGGACAGCTCCTACAGG | 57 |
| c.-10_+9 | CACTCCCATGGTTGGAGATG | 58 |
| c.10_+29 | TGGGAGCAGGGCGGGTGCCT | 59 |
| c.30_+49 | CGCAGACGGCCAGGAGCCGG | 60 |
| c.50_+69 | GGTTGCCAAGGACACGAGGG | 61 |
| c.70_+89 | ATGTGCCCCAGGAGTGCAGC | 62 |
| c.90_+109 | GCAGGAAATCATGGAGTAGG | 63 |
| c.110_+129 | ACTCAGCTCTCGGGGAACCA | 64 |
| c.130_+149 | TCCAGGACTGGGGAGGAGCC | 65 |
| c.150_+169 | GGTGAGCTGGGTGAGTCTCC | 66 |
| c.170_+189 | TGGTCTGCTGGCTCCCTGCT | 67 |
| c.190_+209 | GCCTGGGCATCCCGGGGCCC | 68 |
| c.210_+229 | CTCTGGGACGGCCGGGGTGT | 69 |
| c.230_+249 | GTCGCACTGTGTGGGCACTG | 70 |
| c.250_+269 | AAGCGGCTGTTGGGGGGGAC | 71 |
| c.270_+289 | CCTTGTCAGGGGCGCAATCG | 72 |
| c.290_+309 | GCACTGTTCCTGGGTGATGG | 73 |
| c.310_+329 | TAGCAACAGCCGCGGGCCTC | 74 |
| c.330_+349 | GCCCCTGCTTTGCAGGGATG | 75 |
| c.350_+369 | CCCCATCTGGGCTCCCTGCA | 76 |
| c.370_+389 | GGGAAGAAGCACCAGGGCTG | 77 |
| c.390_+409 | TGTAGCTGGGGTAGCTGGGT | 78 |
| c.410_+429 | GGAGCTCAGGTTCTCCAGCT | 79 |
| c.430_+449 | GCCGTGTAGCCCATTTCAGA | 80 |
| c.450_+469 | GGGTGGTACGGGTCAGGGTG | 81 |
| c.470_+489 | GTCCTTGGGGAAGAAGGTGG | 82 |
| c.490_+509 | TCCAGCCGCAGGGTCAGGAT | 83 |

-continued

| | | |
|---|---|---|
| c.510_+529 | TCTCAGTCTCCATCATCACG | 84 |
| c.530_+546 | GTGAAGTGGAGGCGGT | 85 |
| c.-32-225_-206 | AGAGCACTTGCACAGTCTGC | 86 |
| c.-32-223_-204 | GCAGAGCACTTGCACAGTCT | 87 |
| c.-32-221_-202 | GTGCAGAGCACTTGCACAGT | 88 |
| c.-32-217_-198 | GGGAGTGCAGAGCACTTGCA | 89 |
| c.-32-215_-196 | AGGGGAGTGCAGAGCACTTG | 90 |
| c.-32-213_-194 | GCAGGGGAGTGCAGAGCACT | 91 |
| c.-32-185_-166 | GCCAGAAGGAAGGGCGAGAA | 92 |
| c.-32-183_-164 | GGGCCAGAAGGAAGGGCGAG | 93 |
| c.-32-181_-162 | GAGGGCCAGAAGGAAGGGCG | 94 |
| c.-32-177_-158 | GGGAGAGGGCCAGAAGGAAG | 95 |
| c.-32-175_-156 | TGGGGAGAGGGCCAGAAGGA | 96 |
| c.-32-173_-154 | ACTGGGGAGAGGGCCAGAAG | 97 |

| variants that affect aberrant splicing of exon 2 caused by IVS1 in GAA exon 1-3 minigene system | AON sequence designed to block the region surrounding the identified splice element (5' -> 3') | Seq ID |
|---|---|---|
| c.-32-102C>T | CACCCAGGCAGGTGGGGTAAGGTGG | 98 |
| | AGCACCCAGGCAGGTGGGGTAAGGT | 99 |
| | GCAGCACCCAGGCAGGTGGGGTAAG | 100 |
| | CTGCAGCACCCAGGCAGGTGGGGTA | 101 |
| | CACTGCAGCACCCAGGCAGGTGGGG | 102 |
| | GGCACTGCAGCACCCAGGCAGGTGG | 103 |
| | CTGGCACTGCAGCACCCAGGCAGGT | 104 |
| | GGCTGGCACTGCAGCACCCAGGCAG | 105 |
| | GCGGCTGGCACTGCAGCACCCAGGC | 106 |
| | CCGCGGCTGGCACTGCAGCACCCAG | 107 |
| | TCAACCGCGGCTGGCACTGCAGCAC | 108 |
| | ACCCAGGCAGGTGGGGTAAGGTGGC | 109 |
| | GCACCCAGGCAGGTGGGGTAAGGTG | 110 |
| | CAGCACCCAGGCAGGTGGGGTAAGG | 111 |
| | TGCAGCACCCAGGCAGGTGGGGTAA | 112 |
| | ACTGCAGCACCCAGGCAGGTGGGGT | 113 |
| | GCACTGCAGCACCCAGGCAGGTGGG | 114 |
| | TGGCACTGCAGCACCCAGGCAGGTG | 115 |
| | GCTGGCACTGCAGCACCCAGGCAGG | 116 |
| | CGGCTGGCACTGCAGCACCCAGGCA | 117 |
| | CGCGGCTGGCACTGCAGCACCCAGG | 118 |
| | ACCGCGGCTGGCACTGCAGCACCCA | 119 |
| | CAACCGCGGCTGGCACTGCAGCACC | 120 |
| | ATCAACCGCGGCTGGCACTGCAGCA | 121 |
| c.-32-56C>T, c.-32-46G>A, c.-32-28C>A, c.-32-28C>T, c.-32-21G>A | GGCTCTCAAAGCAGCTCTGAGACAT | 122 |
| | GGGGCTCTCAAAGCAGCTCTGAGAC | 123 |
| | ACGGGGCTCTCAAAGCAGCTCTGAG | 124 |
| | TCACGGGGCTCTCAAAGCAGCTCTG | 125 |
| | ACTCACGGGGCTCTCAAAGCAGCTC | 126 |
| | GCACTCACGGGGCTCTCAAAGCAGC | 127 |
| | CGGCACTCACGGGGCTCTCAAAGCA | 128 |
| | GGCGGCACTCACGGGGCTCTCAAAG | 129 |
| | GGGGCGGCACTCACGGGGCTCTCAA | 130 |
| | GAGGGGCGGCACTCACGGGGCTCTC | 131 |
| | GGGAGGGGCGGCACTCACGGGGCTC | 132 |
| | GCGGGAGGGGCGGCACTCACGGGGC | 133 |
| | AGGCGGGAGGGGCGGCACTCACGGG | 134 |
| | GGAGGCGGGAGGGGCGGCACTCACG | 135 |
| | AGGGAGGCGGGAGGGGCGGCACTCA | 136 |
| | GCAGGGAGGCGGGAGGGGCGGCACT | 137 |
| | CAGCAGGGAGGCGGGAGGGGCGGCA | 138 |
| | CTCAGCAGGGAGGCGGGAGGGGCGG | 139 |
| | GGCTCAGCAGGGAGGCGGGAGGGGC | 140 |
| | CGGGCTCAGCAGGGAGGCGGGAGGG | 141 |
| | AGCGGGCTCAGCAGGGAGGCGGGAG | 142 |
| | AAAGCGGGCTCAGCAGGGAGGCGGG | 143 |
| | AGAAAGCGGGCTCAGCAGGGAGGCG | 144 |
| | GAAGAAAGCGGGCTCAGCAGGGAGG | 145 |
| | GAGAAGAAAGCGGGCTCAGCAGGGA | 146 |
| | GGGAGAAGAAAGCGGGCTCAGCAGG | 147 |
| | GCGGGAGAAGAAAGCGGGCTCAGCA | 148 |
| | CTGCGGGAGAAGAAAGCGGGCTCAG | 149 |
| | GCCTGCGGGAGAAGAAAGCGGGCTC | 150 |
| | AGGCCTGCGGGAGAAGAAAGCGGGC | 151 |
| | ACTCCCATGGTTGGAGATGGCCTGG | 152 |
| | TCACTCCCATGGTTGGAGATGGCCT | 153 |
| | CCTCACTCCCATGGTTGGAGATGGC | 154 |
| | TGCCTCACTCCCATGGTTGGAGATG | 155 |
| | GGTGCCTCACTCCCATGGTTGGAGA | 156 |
| | CGGGTGCCTCACTCCCATGGTTGGA | 157 |
| | GGCGGGTGCCTCACTCCCATGGTTG | 158 |
| | AGGGCGGGTGCCTCACTCCCATGGT | 159 |
| | GCAGGGCGGGTGCCTCACTCCCATG | 160 |
| | GAGCAGGGCGGGTGCCTCACTCCCA | 161 |
| | GGGAGCAGGGCGGGTGCCTCACTCC | 162 |
| | GTGGGAGCAGGGCGGGTGCCTCACT | 163 |
| | CGGTGGGAGCAGGGCGGGTGCCTCA | 164 |
| | GCCGGTGGGAGCAGGGCGGGTGCCT | 165 |
| | GAGCCGGTGGGAGCAGGGCGGGTGC | 166 |
| | AGGAGCCGGTGGGAGCAGGGCGGGT | 167 |
| | CCAGGAGCCGGTGGGAGCAGGGCGG | 168 |
| | GGCCAGGAGCCGGTGGGAGCAGGGC | 169 |
| | ACGGCCAGGAGCCGGTGGGAGCAGG | 170 |
| | AGACGGCCAGGAGCCGGTGGGAGCA | 171 |
| | GCAGACGGCCAGGAGCCGGTGGGAG | 172 |
| | GCGCAGACGGCCAGGAGCCGGTGGG | 173 |
| | GGGCGCAGACGGCCAGGAGCCGGTG | 174 |
| | GAGGGCGCAGACGGCCAGGAGCCGG | 175 |
| | ACGAGGGCGCAGACGGCCAGGAGCC | 176 |
| | ACACGAGGGCGCAGACGGCCAGGAG | 177 |
| | GGACACGAGGGCGCAGACGGCCAGG | 178 |
| | AAGGACACGAGGGCGCAGACGGCCA | 179 |
| | CCAAGGACACGAGGGCGCAGACGGC | 180 |
| | TGCCAAGGACACGAGGGCGCAGACG | 181 |
| | GCTCTCAAAGCAGCTCTGAGACATC | 182 |
| | GGGCTCTCAAAGCAGCTCTGAGACA | 183 |
| | CTCACGGGGCTCTCAAAGCAGCTCT | 184 |
| | CACTCACGGGGCTCTCAAAGCAGCT | 185 |
| | GGCACTCACGGGGCTCTCAAAGCAG | 186 |
| | GCGGCACTCACGGGGCTCTCAAAGC | 187 |
| | GGGCGGCACTCACGGGGCTCTCAAA | 188 |
| | AGGGGCGGCACTCACGGGGCTCTCA | 189 |
| | GGAGGGGCGGCACTCACGGGGCTCT | 190 |
| | CGGGAGGGGCGGCACTCACGGGGCT | 191 |
| | GCGGGAGGGGCGGCACTCACGGGG | 192 |
| | GAGGCGGGAGGGGCGGCACTCACG | 193 |
| | GGGAGGCGGGAGGGGCGGCACTCAC | 194 |
| | CAGGGAGGCGGGAGGGGCGGCACTC | 195 |
| | AGCAGGGAGGCGGGAGGGGCGGCAC | 196 |
| | TCAGCAGGGAGGCGGGAGGGGCGGC | 197 |
| | GCTCAGCAGGGAGGCGGGAGGGGCG | 198 |
| | GGGCTCAGCAGGGAGGCGGGAGGGG | 199 |
| | GCGGGCTCAGCAGGGAGGCGGGAGG | 200 |
| | AAGCGGGCTCAGCAGGGAGGCGGGA | 201 |
| | GAAAGCGGGCTCAGCAGGGAGGCGG | 202 |
| | AAGAAAGCGGGCTCAGCAGGGAGGC | 203 |
| | AGAAGAAAGCGGGCTCAGCAGGGAG | 204 |
| | GGAGAAGAAAGCGGGCTCAGCAGGG | 205 |
| | CGGGAGAAGAAAGCGGGCTCAGCAG | 206 |
| | TGCGGGAGAAGAAAGCGGGCTCAGC | 207 |
| | CCTGCGGGAGAAGAAAGCGGGCTCA | 208 |
| | GGCCTGCGGGAGAAGAAAGCGGGCT | 209 |
| | CAGGCCTGCGGGAGAAGAAAGCGGG | 210 |
| | CGGGGCTCTCAAAGCAGCTCTGAGA | 211 |
| | CACGGGGCTCTCAAAGCAGCTCTGA | 212 |

| Variants | Sequence | SEQ ID |
|---|---|---|
| c.7G>A, c.11G>A, c.15_17AAA, c.17C>T, c.19_21AAA, c.26_28AAA, c.33_35AAA, c.39G>A, c.42C>T | CTCCCATGGTTGGAGATGGCCTGGA | 213 |
| | CACTCCCATGGTTGGAGATGGCCTG | 214 |
| | CTCACTCCCATGGTTGGAGATGGCC | 215 |
| | GCCTCACTCCCATGGTTGGAGATGG | 216 |
| | GTGCCTCACTCCCATGGTTGGAGAT | 217 |
| | GGGTGCCTCACTCCCATGGTTGGAG | 218 |
| | GCGGGTGCCTCACTCCCATGGTTGG | 219 |
| | GGGCGGGTGCCTCACTCCCATGGTT | 220 |
| | CAGGGCGGGTGCCTCACTCCCATGG | 221 |
| | AGCAGGGCGGGTGCCTCACTCCCAT | 222 |
| | GGAGCAGGGCGGGTGCCTCACTCCC | 223 |
| | TGGGAGCAGGGCGGGTGCCTCACTC | 224 |
| | GGTGGGAGCAGGGCGGGTGCCTCAC | 225 |
| | CCGGTGGGAGCAGGGCGGGTGCCTC | 226 |
| | AGCCGGTGGGAGCAGGGCGGGTGCC | 227 |
| | GGAGCCGGTGGGAGCAGGGCGGGTG | 228 |
| | CAGGAGCCGGTGGGAGCAGGGCGGG | 229 |
| | GCCAGGAGCCGGTGGGAGCAGGGCG | 230 |
| | CGGCCAGGAGCCGGTGGGAGCAGGG | 231 |
| | GACGGCCAGGAGCCGGTGGGAGCAG | 232 |
| | CAGACGGCCAGGAGCCGGTGGGAGC | 233 |
| | CGCAGACGGCCAGGAGCCGGTGGGA | 234 |
| | GGCGCAGACGGCCAGGAGCCGGTGG | 235 |
| | AGGGCGCAGACGGCCAGGAGCCGGT | 236 |
| | CGAGGGCGCAGACGGCCAGGAGCCG | 237 |
| | CACGAGGGCGCAGACGGCCAGGAGC | 238 |
| | GACACGAGGGCGCAGACGGCCAGGA | 239 |
| | AGGACACGAGGGCGCAGACGGCCAG | 240 |
| | CAAGGACACGAGGGCGCAGACGGCC | 241 |
| | GCCAAGGACACGAGGGCGCAGACGG | 242 |
| | TTGCCAAGGACACGAGGGCGCAGAC | 243 |
| c.90C>T, c.112G>A, c.137C>T, c.164C>T | GGATGTGCCCCAGGAGTGCAGCGGT | 244 |
| | TAGGATGTGCCCCAGGAGTGCAGCG | 245 |
| | AGTAGGATGTGCCCCAGGAGTGCAG | 246 |
| | GGAGTAGGATGTGCCCCAGGAGTGC | 247 |
| | ATGGAGTAGGATGTGCCCCAGGAGT | 248 |
| | TCATGGAGTAGGATGTGCCCCAGGA | 249 |
| | AATCATGGAGTAGGATGTGCCCCAG | 250 |
| | GAAATCATGGAGTAGGATGTGCCCC | 251 |
| | AGGAAATCATGGAGTAGGATGTGCC | 252 |
| | GCAGGAAATCATGGAGTAGGATGTG | 253 |
| | CAGCAGGAAATCATGGAGTAGGATG | 254 |
| | ACCAGCAGGAAATCATGGAGTAGGA | 255 |
| | GAACCAGCAGGAAATCATGGAGTAG | 256 |
| | GGGAACCAGCAGGAAATCATGGAGT | 257 |
| | CGGGGAACCAGCAGGAAATCATGGA | 258 |
| | CTCGGGGAACCAGCAGGAAATCATG | 259 |
| | CTCTCGGGGAACCAGCAGGAAATCA | 260 |
| | AGCTCTCGGGGAACCAGCAGGAAAT | 261 |
| | TCAGCTCTCGGGGAACCAGCAGGAA | 262 |
| | ACTCAGCTCTCGGGGAACCAGCAGG | 263 |
| | CCACTCAGCTCTCGGGGAACCAGCA | 264 |
| | AGCCACTCAGCTCTCGGGGAACCAG | 265 |
| | GGAGCCACTCAGCTCTCGGGGAACC | 266 |
| | GAGGAGCCACTCAGCTCTCGGGGAA | 267 |
| | GGGAGGAGCCACTCAGCTCTCGGGG | 268 |
| | TGGGGAGGAGCCACTCAGCTCTCGG | 269 |
| | ACTGGGGAGGAGCCACTCAGCTCTC | 270 |
| | GGACTGGGGAGGAGCCACTCAGCTC | 271 |
| | CAGGACTGGGGAGGAGCCACTCAGC | 272 |
| | TCCAGGACTGGGGAGGAGCCACTCA | 273 |
| | CCTCCAGGACTGGGGAGGAGCCACT | 274 |
| | CTCCTCCAGGACTGGGGAGGAGCCA | 275 |
| | GTCCTCCAGGACTGGGGAGGAGC | 276 |
| | GAGTCTCCTCCAGGACTGGGGAGGA | 277 |
| | GTGAGTCTCCTCCAGGACTGGGGAG | 278 |
| | GGGTGAGTCTCCTCCAGGACTGGGG | 279 |
| | CTGGGTGAGTCTCCTCCAGGACTGG | 280 |
| | AGCTGGGTGAGTCTCCTCCAGGACT | 281 |
| | TGAGCTGGGTGAGTCTCCTCCAGGA | 282 |
| | GGTGAGCTGGGTGAGTCTCCTCCAG | 283 |
| | CTGGTGAGCTGGGTGAGTCTCCTCC | 284 |
| | TGCTGGTGAGCTGGGTGAGTCTCCT | 285 |
| | CCTGCTGGTGAGCTGGGTGAGTCTC | 286 |
| | TCCCTGCTGGTGAGCTGGGTGAGTC | 287 |
| | GCTCCCTGCTGGTGAGCTGGGTGAG | 288 |
| | TGGCTCCCTGCTGGTGAGCTGGGTG | 289 |
| | GCTGGCTCCCTGCTGGTGAGCTGGG | 290 |
| | CTGCTGGCTCCCTGCTGGTGAGCTG | 291 |
| | GTCTGCTGGCTCCCTGCTGGTGAGC | 292 |
| | GATGTGCCCCAGGAGTGCAGCGGTT | 293 |
| | AGGATGTGCCCCAGGAGTGCAGCGG | 294 |
| | GTAGGATGTGCCCCAGGAGTGCAGC | 295 |
| | GAGTAGGATGTGCCCCAGGAGTGCA | 296 |
| | TGGAGTAGGATGTGCCCCAGGAGTG | 297 |
| | CATGGAGTAGGATGTGCCCCAGGAG | 298 |
| | ATCATGGAGTAGGATGTGCCCCAGG | 299 |
| | AAATCATGGAGTAGGATGTGCCCCA | 300 |
| | GGAAATCATGGAGTAGGATGTGCCC | 301 |
| | CAGGAAATCATGGAGTAGGATGTGC | 302 |
| | AGCAGGAAATCATGGAGTAGGATGT | 303 |
| | CCAGCAGGAAATCATGGAGTAGGAT | 304 |
| | AACCAGCAGGAAATCATGGAGTAGG | 305 |
| | GGAACCAGCAGGAAATCATGGAGTA | 306 |
| | GGGGAACCAGCAGGAAATCATGGAG | 307 |
| | TCGGGGAACCAGCAGGAAATCATGG | 308 |
| | TCTCGGGGAACCAGCAGGAAATCAT | 309 |
| | GCTCTCGGGGAACCAGCAGGAAATC | 310 |
| | CAGCTCTCGGGGAACCAGCAGGAAA | 311 |
| | CTCAGCTCTCGGGGAACCAGCAGGA | 312 |
| | CACTCAGCTCTCGGGGAACCAGCAG | 313 |
| | GCCACTCAGCTCTCGGGGAACCAGC | 314 |
| | GAGCCACTCAGCTCTCGGGGAACCA | 315 |
| | AGGAGCCACTCAGCTCTCGGGGAAC | 316 |
| | GGAGGAGCCACTCAGCTCTCGGGGA | 317 |
| | GGGGAGGAGCCACTCAGCTCTCGGG | 318 |
| | CTGGGGAGGAGCCACTCAGCTCTCG | 319 |
| | GACTGGGGAGGAGCCACTCAGCTCT | 320 |
| | AGGACTGGGGAGGAGCCACTCAGCT | 321 |
| | CCAGGACTGGGGAGGAGCCACTCAG | 322 |
| | CTCCAGGACTGGGGAGGAGCCACTC | 323 |
| | TCCTCCAGGACTGGGGAGGAGCCAC | 324 |
| | TCCTCCTCCAGGACTGGGGAGGAGC | 325 |
| | AGTCTCCTCCAGGACTGGGGAGGAG | 326 |
| | TGAGTCTCCTCCAGGACTGGGGAGG | 327 |
| | GGTGAGTCTCCTCCAGGACTGGGAG | 328 |
| | TGGGTGAGTCTCCTCCAGGACTGGG | 329 |
| | GCTGGGTGAGTCTCCTCCAGGACTG | 330 |
| | GAGCTGGGTGAGTCTCCTCCAGGAC | 331 |
| | GTGAGCTGGGTGAGTCTCCTCCAGG | 332 |
| | TGGTGAGCTGGGTGAGTCTCCTCCA | 333 |
| | GCTGGTGAGCTGGGTGAGTCTCCTC | 334 |
| | CTGCTGGTGAGCTGGGTGAGTCTCC | 335 |
| | CCCTGCTGGTGAGCTGGGTGAGTCT | 336 |
| | CTCCCTGCTGGTGAGCTGGGTGAGT | 337 |
| | GGCTCCCTGCTGGTGAGCTGGGTGA | 338 |
| | CTGGCTCCCTGCTGGTGAGCTGGGT | 339 |
| | TGCTGGCTCCCTGCTGGTGAGCTGG | 340 |
| | TCTGCTGGCTCCCTGCTGGTGAGCT | 341 |
| | GGTCTGCTGGCTCCCTGCTGGTGAG | 342 |
| c.348G>A, c.373C>T | AGCCCCTGCTTTGCAGGGATGTAGC | 343 |
| | GCAGCCCCTGCTTTGCAGGGATGTA | 344 |
| | CTGCAGCCCCTGCTTTGCAGGGATG | 345 |
| | CCCTGCAGCCCCTGCTTTGCAGGGA | 346 |
| | CTCCCTGCAGCCCCTGCTTTGCAGG | 347 |
| | GGCTCCCTGCAGCCCCTGCTTTGCA | 348 |
| | TGGGCTCCCTGCAGCCCCTGCTTTG | 349 |
| | TCTGGGCTCCCTGCAGCCCCTGCTT | 350 |
| | CATCTGGGCTCCCTGCAGCCCCTGC | 351 |
| | CCCATCTGGGCTCCCTGCAGCCCCT | 352 |
| | GCCCATCTGGGCTCCCTGCAGCCC | 353 |
| | CTGCCCCATCTGGGCTCCCTGCAGC | 354 |
| | GGCTGCCCCATCTGGGCTCCCTGCA | 355 |
| | AGGGCTGCCCCATCTGGGCTCCCTG | 356 |
| | CCAGGGCTGCCCCATCTGGGCTCCC | 357 |
| | CACCAGGGCTGCCCCATCTGGGCTC | 358 |
| | AGCACCAGGGCTGCCCCATCTGGGC | 359 |
| | GAAGCACCAGGGCTGCCCCATCTGG | 360 |
| | AAGAAGCACCAGGGCTGCCCCATCT | 361 |
| | GGAAGAAGCACCAGGGCTGCCCCAT | 362 |
| | TGGGAAGAAGCACCAGGGCTGCCCC | 363 |
| | GGTGGGAAGAAGCACCAGGGCTGCC | 364 |
| | TGGGTGGGAAGAAGCACCAGGGCTG | 365 |
| | GCTGGGTGGGAAGAAGCACCAGGGC | 366 |
| | GCCCCTGCTTTGCAGGGATGTAGCA | 367 |
| | CAGCCCCTGCTTTGCAGGGATGTAG | 368 |

| | | |
|---|---|---|
| | TGCAGCCCCTGCTTTGCAGGGATGT | 369 |
| | CCTGCAGCCCCTGCTTTGCAGGGAT | 370 |
| | TCCCTGCAGCCCCTGCTTTGCAGGG | 371 |
| | GCTCCCTGCAGCCCCTGCTTTGCAG | 372 |
| | GGGCTCCCTGCAGCCCCTGCTTTGC | 373 |
| | CTGGGCTCCCTGCAGCCCCTGCTTT | 374 |
| | ATCTGGGCTCCCTGCAGCCCCTGCT | 375 |
| | CCATCTGGGCTCCCTGCAGCCCCTG | 376 |
| | CCCCATCTGGGCTCCCTGCAGCCCC | 377 |
| | TGCCCCATCTGGGCTCCCTGCAGCC | 378 |
| | GCTGCCCCATCTGGGCTCCCTGCAG | 379 |
| | GGGCTGCCCCATCTGGGCTCCCTGC | 380 |
| | CAGGGCTGCCCCATCTGGGCTCCCT | 381 |
| | ACCAGGGCTGCCCCATCTGGGCTCC | 382 |
| | GCACCAGGGCTGCCCCATCTGGGCT | 383 |
| | AAGCACCAGGGCTGCCCCATCTGGG | 384 |
| | AGAAGCACCAGGGCTGCCCCATCTG | 385 |
| | GAAGAAGCACCAGGGCTGCCCCATC | 386 |
| | GGGAAGAAGCACCAGGGCTGCCCCA | 387 |
| | GTGGGAAGAAGCACCAGGGCTGCCC | 388 |
| | GGGTGGGAAGAAGCACCAGGGCTGC | 389 |
| | CTGGGTGGGAAGAAGCACCAGGGCT | 390 |
| | AGCTGGGTGGGAAGAAGCACCAGGG | 391 |
| c.413T>A | CAGCTTGTAGCTGGGGTAGCTGGGT | 392 |
| | TCCAGCTTGTAGCTGGGGTAGCTGG | 393 |
| | TCTCCAGCTTGTAGCTGGGGTAGCT | 394 |
| | GTTCTCCAGCTTGTAGCTGGGGTAG | 395 |
| | AGGTTCTCCAGCTTGTAGCTGGGGT | 396 |
| | TCAGGTTCTCCAGCTTGTAGCTGGG | 397 |
| | GCTCAGGTTCTCCAGCTTGTAGCTG | 398 |
| | GAGCTCAGGTTCTCCAGCTTGTAGC | 399 |
| | AGGAGCTCAGGTTCTCCAGCTTGTA | 400 |
| | AGAGGAGCTCAGGTTCTCCAGCTTG | 401 |
| | TCAGAGGAGCTCAGGTTCTCCAGCT | 402 |
| | TTTCAGAGGAGCTCAGGTTCTCCAG | 403 |
| | AGCTTGTAGCTGGGGTAGCTGGGTG | 404 |
| | CCAGCTTGTAGCTGGGGTAGCTGGG | 405 |
| | CTCCAGCTTGTAGCTGGGGTAGCTG | 406 |
| | TTCTCCAGCTTGTAGCTGGGGTAGC | 407 |
| | GGTTCTCCAGCTTGTAGCTGGGGTA | 408 |
| | CAGGTTCTCCAGCTTGTAGCTGGGG | 409 |
| | CTCAGGTTCTCCAGCTTGTAGCTGG | 410 |
| | AGCTCAGGTTCTCCAGCTTGTAGCT | 411 |
| | GGAGCTCAGGTTCTCCAGCTTGTAG | 412 |
| | GAGGAGCTCAGGTTCTCCAGCTTGT | 413 |
| | CAGAGGAGCTCAGGTTCTCCAGCTT | 414 |
| | TTCAGAGGAGCTCAGGTTCTCCAGC | 415 |
| | ATTTCAGAGGAGCTCAGGTTCTCCA | 416 |
| c.469C>T, | GGGGTGGTACGGGTCAGGGTGGCCG | 417 |
| c.476T>C, | TGGGGGTGGTACGGGTCAGGGTGGC | 418 |
| c.476T>G, | GGTGGGGGTGGTACGGGTCAGGGTG | 419 |
| c.478T>G, | AAGGTGGGGGTGGTACGGGTCAGGG | 420 |
| c.482C>T | AGAAGGTGGGGGTGGTACGGGTCAG | 421 |
| | GAAGAAGGTGGGGGTGGTACGGGTC | 422 |
| | GGGAAGAAGGTGGGGGTGGTACGGG | 423 |
| | TGGGAAGAAGGTGGGGGTGGTACGG | 424 |
| | CTTGGGAAGAAGGTGGGGGTGGTA | 425 |
| | TCCTTGGGAAGAAGGTGGGGGTGG | 426 |
| | TGTCCTTGGGAAGAAGGTGGGGGT | 427 |
| | GATGTCCTTGGGAAGAAGGTGGGG | 428 |
| | AGGATGTCCTTGGGAAGAAGGTGG | 429 |
| | TCAGGATGTCCTTGGGAAGAAGGT | 430 |
| | GGTCAGGATGTCCTTGGGAAGAAG | 431 |
| | AGGGTCAGGATGTCCTTGGGAAGA | 432 |
| | GCAGGGTCAGGATGTCCTTGGGAA | 433 |
| | CCGCAGGGTCAGGATGTCCTTGGGG | 434 |
| | AGCCGCAGGGTCAGGATGTCCTTG | 435 |
| | GGGTGGTACGGGTCAGGGTGGCCGT | 436 |
| | GGGGGTGGTACGGGTCAGGGTGGCC | 437 |
| | GTGGGGGTGGTACGGGTCAGGGTGG | 438 |
| | AGGTGGGGGTGGTACGGGTCAGGGT | 439 |
| | GAAGGTGGGGGTGGTACGGGTCAGG | 440 |
| | AAGAAGGTGGGGGTGGTACGGGTCA | 441 |
| | GGAAGAAGGTGGGGGTGGTACGGGT | 442 |
| | GGGGAAGAAGGTGGGGGTGGTACGG | 443 |
| | TTGGGAAGAAGGTGGGGGTGGTAC | 444 |
| | CCTTGGGAAGAAGGTGGGGGTGGT | 445 |
| | GTCCTTGGGAAGAAGGTGGGGGTG | 446 |
| | ATGTCCTTGGGAAGAAGGTGGGGG | 447 |
| | GGATGTCCTTGGGAAGAAGGTGGG | 448 |
| | CAGGATGTCCTTGGGAAGAAGGTG | 449 |
| | GTCAGGATGTCCTTGGGAAGAAGG | 450 |
| | GGGTCAGGATGTCCTTGGGAAGAA | 451 |
| | CAGGGTCAGGATGTCCTTGGGAAG | 452 |
| | CGCAGGGTCAGGATGTCCTTGGGA | 453 |
| | GCCGCAGGGTCAGGATGTCCTTGGG | 454 |
| | CAGCCGCAGGGTCAGGATGTCCTTG | 455 |
| c.510C>T, | CGTCCAGCCGCAGGGTCAGGATGTC | 456 |
| c.515T>A, | CACGTCCAGCCGCAGGGTCAGGATG | 457 |
| c.520G>A | ATCACGTCCAGCCGCAGGGTCAGGA | 458 |
| | TCATCACGTCCAGCCGCAGGGTCAG | 459 |
| | CATCATCACGTCCAGCCGCAGGGTC | 460 |
| | TCCATCATCACGTCCAGCCGCAGGG | 461 |
| | TCTCCATCATCACGTCCAGCCGCAG | 462 |
| | AGTCTCCATCATCACGTCCAGCCGC | 463 |
| | TCAGTCTCCATCATCACGTCCAGCC | 464 |
| | TCTCAGTCTCCATCATCACGTCCAG | 465 |
| | GTTCTCAGTCTCCATCATCACGTCC | 466 |
| | CGGTTCTCAGTCTCCATCATCACGT | 467 |
| | GGCGGTTCTCAGTCTCCATCATCAC | 468 |
| | GAGGCGGTTCTCAGTCTCCATCATC | 469 |
| | TGGAGGCGGTTCTCAGTCTCCATCA | 470 |
| | AGTGGAGGCGGTTCTCAGTCTCCAT | 471 |
| | GAAGTGGAGGCGGTTCTCAGTCTCC | 472 |
| | GTCCAGCCGCAGGGTCAGGATGTCC | 473 |
| | ACGTCCAGCCGCAGGGTCAGGATGT | 474 |
| | TCACGTCCAGCCGCAGGGTCAGGAT | 475 |
| | CATCACGTCCAGCCGCAGGGTCAGG | 476 |
| | ATCATCACGTCCAGCCGCAGGGTCA | 477 |
| | CCATCATCACGTCCAGCCGCAGGGT | 478 |
| | CTCCATCATCACGTCCAGCCGCAGG | 479 |
| | GTCTCCATCATCACGTCCAGCCGCA | 480 |
| | CAGTCTCCATCATCACGTCCAGCCG | 481 |
| | CTCAGTCTCCATCATCACGTCCAGC | 482 |
| | TTCTCAGTCTCCATCATCACGTCCA | 483 |
| | GGTTCTCAGTCTCCATCATCACGTC | 484 |
| | GCGGTTCTCAGTCTCCATCATCACG | 485 |
| | AGGCGGTTCTCAGTCTCCATCATCA | 486 |
| | GGAGGCGGTTCTCAGTCTCCATCAT | 487 |
| | GTGGAGGCGGTTCTCAGTCTCCATC | 488 |
| | AAGTGGAGGCGGTTCTCAGTCTCCA | 489 |
| | TGAAGTGGAGGCGGTTCTCAGTCTC | 490 |
| c.546+11C>T, | TGCCCTGCCCACCGTGAAGTGGAGG | 491 |
| c.546+14G>A, | CCTGCCCTGCCCACCGTGAAGTGGA | 492 |
| c.546+19G>A, | CCCCTGCCCTGCCCACCGTGAAGTG | 493 |
| c.546+23C>A | CGCCCCTGCCCTGCCCACCGTGAAG | 494 |
| | CCCGCCCCTGCCCTGCCCACCGTGA | 495 |
| | GCCCTGCCCACCGTGAAGTGGAGGC | 496 |
| | CTGCCCTGCCCACCGTGAAGTGGAG | 497 |
| | CCTGCCCTGCCCACCGTGAAGTGG | 498 |
| | GCCCTGCCCTGCCCACCGTGAAGT | 499 |
| | CCGCCCCTGCCCTGCCCACCGTGAA | 500 |
| | CCCCGCCCCTGCCCTGCCCACCGTG | 501 |
| | GCCCCGCCCCTGCCCTGCCCACCG | 502 |
| | CCGCCCCGCCCCTGCCCTGCCCAC | 503 |
| | CGCCGCCCCGCCCCTGCCCTGCCC | 504 |
| | GCCGCCGCCCCGCCCCTGCCCTGC | 505 |
| | TGGCCGCCGCCCCGCCCCTGCCCT | 506 |
| | CCTGGCCGCCGCCCCGCCCCTGCC | 507 |
| | GCCCTGGCCGCCGCCCCGCCCCTG | 508 |
| | CTGCCCTGGCCGCCGCCCCGCCCC | 509 |
| | CTCTGCCCTGGCCGCCGCCCCGCC | 510 |
| | CCCTCTGCCCTGGCCGCCGCCCCC | 511 |
| | CACCCTCTGCCCTGGCCGCCGCCC | 512 |
| | CGCACCCTCTGCCCTGGCCGCCGC | 513 |
| | CGCGCACCCTCTGCCCTGGCCGCCG | 514 |
| | CCCCCGCCCCTGCCCTGCCCACCGT | 515 |
| | CGCCCCCGCCCCTGCCCTGCCCACC | 516 |
| | GCCGCCCCCGCCCCTGCCCTGCCCA | 517 |
| | CCGCCGCCCCCGCCCCTGCCCTGCC | 518 |
| | GGCGCCGCCCCGCCCCTGCCCTG | 519 |
| | CTGGCCGCCGCCCCGCCCCTGCCC | 520 |
| | CCCTGGCCGCCGCCCCGCCCCTGC | 521 |
| | TGCCCTGGCCGCCGCCCCGCCCCT | 522 |

-continued

|  | | |
|---|---|---|
| | TCTGCCCTGGCCGCCGCCCCGCCC | 523 |
| | CCTCTGCCCTGGCCGCCGCCCCCGC | 524 |
| | ACCCTCTGCCCTGGCCGCCGCCCCC | 525 |
| | GCACCCTCTGCCCTGGCCGCCGCCC | 526 |
| | GCGCACCCTCTGCCCTGGCCGCCGC | 527 |
| c.547-6 | AGAGATGGGGGTTTATTGATGTTCC | 528 |
| | GAAGAGATGGGGGTTTATTGATGTT | 529 |
| | TAGAAGAGATGGGGGTTTATTGATG | 530 |
| | TCTAGAAGAGATGGGGGTTTATTGA | 531 |
| | GATCTAGAAGAGATGGGGGTTTATT | 532 |
| | TTGATCTAGAAGAGATGGGGGTTTA | 533 |
| | CTTTGATCTAGAAGAGATGGGGGTT | 534 |
| | ATCTTTGATCTAGAAGAGATGGGGG | 535 |
| | GGATCTTTGATCTAGAAGAGATGGG | 536 |
| | CTGGATCTTTGATCTAGAAGAGATG | 537 |
| | AGCTGGATCTTTGATCTAGAAGAGA | 538 |
| | TTAGCTGGATCTTTGATCTAGAAGA | 539 |
| | TGTTAGCTGGATCTTTGATCTAGAA | 540 |

In the above examples the sequences are 25 nucleotides long however longer variants or shorter fragment are also envisioned. In a preferred embodiment of the invention and/or embodiments thereof of the present invention and/or embodiments thereof the antisense oligomeric compounds are selected from the group of SEQ ID NO: 41-540 and fragments and variants thereof having at least 80% sequence identity. In a preferred embodiment of the invention and/or embodiments thereof of the present invention and/or embodiments thereof the antisense oligomeric compounds are selected from the group of SEQ ID NO: 41-540 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 41-540.

The present invention is also directed to sequences that are at least 80% identical to SEQ ID NO: 41-540. Preferably at least 85% identical to SEQ ID NO: 41-540, more preferably at least 88% identical to SEQ ID NO: 41-540, more preferably at least 90% identical to SEQ ID NO: 41-540. more preferably at least 91% identical to SEQ ID NO: 41-540, more preferably at least 92% identical to SEQ ID NO: 41-540, more preferably at least 93% identical to SEQ ID NO: 41-540, more preferably at least 94% identical to SEQ ID NO: 41-540, more preferably at least 95% identical to SEQ ID NO: 41-540, more preferably at least 96% identical to SEQ ID NO: 41-540, more preferably at least 97% identical to SEQ ID NO: 41-540, more preferably at least 98% identical to SEQ ID NO: 41-540, more preferably at least 99% identical to SEQ ID NO: 41-540.

In a preferred embodiment of the invention and/or embodiments thereof of the present invention and/or embodiments thereof the antisense oligomeric compounds are selected from the group of fragments SEQ ID NO: 41-540, wherein the fragment is 16, 17, 18, 19, 20, 21, 22, 23, or 24 nucleotides long. In a preferred embodiment of the invention and/or embodiments thereof of the present invention and/or embodiments thereof the antisense oligomeric compounds are selected from the group of fragments SEQ ID NO: 41-540, wherein the fragment is 17, 18, 19, 20, 21, or 22 nucleotides long. In a preferred embodiment of the invention and/or embodiments thereof of the present invention and/or embodiments thereof the antisense oligomeric compounds are selected from the group of fragments SEQ ID NO: 41-540, wherein the fragment is 19, 20, or 21 nucleotides long.

In a preferred embodiment of the invention and/or embodiments thereof the target sequence provides exclusion of intron 6. It was found that SEQ ID NO: 1584 provides the target sequence for exclusion of intron 6.

In a preferred embodiment of the invention and/or embodiments thereof of an aspect and/or embodiments of the invention the target sequence is the AACCCCAGAGCT-GCTTCCCTTCCAGATGTGGTCCTGCAGCCGAGC-CCTGCCCT TAGCTGGAGGTCGACAGGTGGGATC-CTGGATGTCTACATCTTCCTGGGCCCAG AGCCCAAGAGCGTGGTGCAGCAGTACCTGGACGT-TGTGGGTAGGGCCTGCTC CCTGGCCGCGGC-CCCCGCCCCAAGGCTCCCTCCTCCCTCCCTCAT-GAAGTCGG CGTTGGCCTGCAGGATACCCGTTCATGCCGCCAT-ACTGGGGCCTGGGCTTCCA CCTGTGC-CGCTGGGGCTACTCCTCCACCGCTATCACCCGCCA-GGTGGTGGAGA ACATGACCAGGGCCCACTTCCCCCTGGTGAGT-TGGGGTGGTGGCAGGGGAG (SEQ ID NO: 1584). It should be noted that also naturally occurring single nucleotide polymorphism are included.

Also the following genomic sequences are target sequences for exclusion of intron 6 of GAA:

| Sequence in cDNA to which AON anneals* | sequence of region (5'->3'): | Seq ID |
|---|---|---|
| c.956-25_1194+25 | AACCCCAGAGCTGCTTCCCTTCCAGATGTGGTCCTGC AGCCGAGCCCTGCCCTTAGCTGGAGGTCGACAGGTG GGATCCTGGATGTCTACATCTTCCTGGGCCCAGAGC CCAAGAGCGTGGTGCAGCAGTACCTGGACGTTGTGG GTAGGGCCTGCTCCCTGGCCGCGGCCCCCGCCCCAA GGCTCCCTCCTCCCTCCCTCATGAAGTCGGCGTTGG CCTGCAGGATACCCGTTCATGCCGCCATACTGGGGC CTGGGCTTCCACCTGTGCCGCTGGGGCTACTCCTCC ACCGCTATCACCCGCCAGGTGGTGGAGAACATGACC AGGGCCCACTTCCCCCTGGTGAGTTGGGGTGGTGGC AGGGGAG | 1584 |
| c.956-25_1004 | AACCCCAGAGCTGCTTCCCTTCCAGATGTGGTCCTGC AGCCGAGCCCTGCCCTTAGCTGGAGGTCGACAGGTG G | 1585 |
| c.1005_1075+3 | GATCCTGGATGTCTACATCTTCCTGGGCCCAGAGCC CAAGAGCGTGGTGCAGCAGTACCTGGACGTTGTGGG TA | 1586 |
| c.1075+4_1076-2 | GGGCCTGCTCCCTGGCCGCGGCCCCCGCCCCAAGGC TCCCTCCTCCCTCCCTCATGAAGTCGGCGTTGGCCTG C | 1587 |
| c.1076-2_1147 | AGGATACCCGTTCATGCCGCCATACTGGGGCCTGGG CTTCCACCTGTGCCGCTGGGGCTACTCCTCCACCGCT A | 1588 |
| c.1148_1194+25 | TCACCCGCCAGGTGGTGGAGAACATGACCAGGGCCC ACTTCCCCCTGGTGAGTTGGGGTGGTGGCAGGGGAG | 1589 |

It is to be noted that targeting means that at least part of the sequence SEQ ID NO: 1584-1589 is targeted, e.g. by a sequence that hybridizes with at least a part or by the sequence SEQ ID NO: 1584-1589, or that binds to at least a part of SEQ ID NO: 1584-1589. Sequences that target may be shorter or longer than the target sequence.

Suitably the sequences targeting SEQ ID NO: 1584-1589 hybridize with at least a part of SEQ ID NO: 1584-1589. Sequences that hybridize may be shorter or longer than the target sequence. Nucleotide sequences SEQ ID NO: 541-1583 are oligomers that are able to enhance GAA intron 6 exclusion.

In one aspect or embodiment of aspects and/or embodiments thereof, the invention is directed to an antisense oligomeric compound selected from the group comprising SEQ ID NO: 541-1583 and variants and fragments having at least 80% identity thereof. The antisense oligomeric compound may also target single nucleotide polymorphism of SEQ ID NO: 1584-1589. It should be noted that it may not necessary to have the full length of SEQ ID NO: 541-1583, fragments having a shorter or longer sequence are also envisioned. The inventors have found the target genomic sequence which enables the exclusion of intron 6 and a skilled person is capable of finding suitable sequences that target this target genomic sequence, such as SEQ ID NO: 1584-1589 and single nucleotide polymorphisms thereof. Exemplary sequences that target this target genomic sequence, such as SEQ ID NO: 1584-1589 may be SEQ ID NO: 541-1583, but also variants and fragments having at least 80% identity thereof. In particular shorter fragments such as fragments with 18, 19, 20, 21, 22, 23, or 24 nucleotides of SEQ ID NO: 541-1583 are envisioned.

In one aspect or embodiment of aspects and/or embodiments thereof, the invention is directed to an antisense oligomeric compound complementary to a polynucleotide having a sequence selected from the group comprising SEQ ID NO: 1584-1589 and single nucleotide polymorphisms thereof. Also sequences having at least 80% identity to antisense oligomeric compound complementary to a polynucleotide having a sequence selected from the group comprising SEQ ID NO: 1584-1589 are envisioned. Antisense oligomeric compound that target one or more than one single nucleotide polymorphisms may be designed.

In one aspect or embodiment of aspects and/or embodiments thereof, the invention is directed to an antisense oligomeric compound targeting a sequence selected from the group comprising the genomic sequence c.956-25_1194+25.

In one aspect or embodiment of aspects and/or embodiments thereof, the invention is directed to an antisense oligomeric compound comprising sequences selected from the group comprising SEQ ID NO: 41-1583 and sequences having at least 80% identity thereof.

In one aspect or embodiment of aspects and/or embodiments thereof, the invention is directed to antisense oligomeric compound comprising a sequences selected from the group comprising SEQ ID NO: 541-1583.

Antisense oligomeric compounds targeting SEQ ID NO: 1584 are a very suitable to treat Pompe patients. Exemplary antisense oligomeric compounds targeting SEQ ID NO: 1584 are SEQ ID NO: 541-1853. However the invention is not limited to these sequences. A skilled person is capable of designing antisense oligomeric compounds against target sequence SEQ ID NO: 1584, 1885, 1586, 1587, 1588, 1589. The antisense oligomeric compounds against target sequenced SEQ ID NO: 1584, 1885, 1586, 1587, 1588, or 1589 may have length of 10 to 100 nucleotides, preferably 11 to 75 nucleotides, preferably 12 to 73 nucleotides, preferably 13 to 70 nucleotides, preferably 14 to 65 nucleotides, preferably 15 to 60 nucleotides, preferably 16 to 55 nucleotides, preferably 17 to 50 nucleotides, preferably 18 to 45 nucleotides, preferably 19 to 40 nucleotides, preferably 20 to 38 nucleotides, preferably 21 to 35 nucleotides, preferably 22 to 33 nucleotides, preferably 23 to 30 nucleotides, preferably 24 to 29 nucleotides, preferably 25 to 28 nucleotides, preferably 26 to 27 nucleotides.

The antisense oligomeric compounds may be selected from the group of SEQ ID NO 541-1583:

| Sequence in cDNA to which AON anneals for intron 6 exclusion | AON sequence 5' -> 3' | Seq ID |
|---|---|---|
| c.956-25_-1 | CTGGAAGGGAAGCAGCTCTGGGGTT | 541 |
| c.956-24_956 | TCTGGAAGGGAAGCAGCTCTGGGGT | 542 |
| c.956-23_957 | ATCTGGAAGGGAAGCAGCTCTGGGG | 543 |
| c.956-22_958 | CATCTGGAAGGGAAGCAGCTCTGGG | 544 |
| c.956-21_959 | ACATCTGGAAGGGAAGCAGCTCTGG | 545 |
| c.956-20_960 | CACATCTGGAAGGGAAGCAGCTCTG | 546 |
| c.956-19_961 | CCACATCTGGAAGGGAAGCAGCTCT | 547 |
| c.956-18_962 | ACCACATCTGGAAGGGAAGCAGCTC | 548 |
| c.956-17_963 | GACCACATCTGGAAGGGAAGCAGCT | 549 |
| c.956-16_964 | GGACCACATCTGGAAGGGAAGCAGC | 550 |
| c.956-15_965 | AGGACCACATCTGGAAGGGAAGCAG | 551 |
| c.956-14_966 | CAGGACCACATCTGGAAGGGAAGCA | 552 |
| c.956-13_967 | GCAGGACCACATCTGGAAGGGAAGC | 553 |
| c.956-12_968 | TGCAGGACCACATCTGGAAGGGAAG | 554 |
| c.956-11_969 | CTGCAGGACCACATCTGGAAGGGAA | 555 |
| c.956-10_970 | GCTGCAGGACCACATCTGGAAGGGA | 556 |
| c.956-9_971 | GGCTGCAGGACCACATCTGGAAGGG | 557 |
| c.956-8_972 | CGGCTGCAGGACCACATCTGGAAGG | 558 |
| c.956-7_973 | TCGGCTGCAGGACCACATCTGGAAG | 559 |
| c.956-6_974 | CTCGGCTGCAGGACCACATCTGGAA | 560 |
| c.956-5_975 | GCTCGGCTGCAGGACCACATCTGGA | 561 |
| c.956-4_976 | GGCTCGGCTGCAGGACCACATCTGG | 562 |
| c.956-3_977 | GGGCTCGGCTGCAGGACCACATCTG | 563 |
| c.956-2_978 | AGGGCTCGGCTGCAGGACCACATCT | 564 |
| c.956-1_979 | CAGGGCTCGGCTGCAGGACCACATC | 565 |
| c.956_980 | GCAGGGCTCGGCTGCAGGACCACAT | 566 |
| c.957_981 | GGCAGGGCTCGGCTGCAGGACCACA | 567 |
| c.958_982 | GGGCAGGGCTCGGCTGCAGGACCAC | 568 |
| c.959_983 | AGGGCAGGGCTCGGCTGCAGGACCA | 569 |
| c.960_984 | AAGGGCAGGGCTCGGCTGCAGGACC | 570 |
| c.961_985 | TAAGGGCAGGGCTCGGCTGCAGGAC | 571 |
| c.962_986 | CTAAGGGCAGGGCTCGGCTGCAGGA | 572 |
| c.963_987 | GCTAAGGGCAGGGCTCGGCTGCAGG | 573 |
| c.964_988 | AGCTAAGGGCAGGGCTCGGCTGCAG | 574 |
| c.965_989 | CAGCTAAGGGCAGGGCTCGGCTGCA | 575 |
| c.966_990 | CCAGCTAAGGGCAGGGCTCGGCTGC | 576 |
| c.967_991 | TCCAGCTAAGGGCAGGGCTCGGCTG | 577 |
| c.968_992 | CTCCAGCTAAGGGCAGGGCTCGGCT | 578 |

| Sequence in cDNA to which AON anneals for intron 6 exclusion | AON sequence 5' -> 3' | Seq ID |
| --- | --- | --- |
| c.969_993 | CCTCCAGCTAAGGGCAGGGCTCGGC | 579 |
| c.970_994 | ACCTCCAGCTAAGGGCAGGGCTCGG | 580 |
| c.971_995 | GACCTCCAGCTAAGGGCAGGGCTCG | 581 |
| c.972_996 | CGACCTCCAGCTAAGGGCAGGGCTC | 582 |
| c.973_997 | TCGACCTCCAGCTAAGGGCAGGGCT | 583 |
| c.974_998 | GTCGACCTCCAGCTAAGGGCAGGGC | 584 |
| c.975_999 | TGTCGACCTCCAGCTAAGGGCAGGG | 585 |
| c.976_1000 | CTGTCGACCTCCAGCTAAGGGCAGG | 586 |
| c.977_1001 | CCTGTCGACCTCCAGCTAAGGGCAG | 587 |
| c.978_1002 | ACCTGTCGACCTCCAGCTAAGGGCA | 588 |
| c.979_1003 | CACCTGTCGACCTCCAGCTAAGGGC | 589 |
| c.980_1004 | CCACCTGTCGACCTCCAGCTAAGGG | 590 |
| c.981_1005 | CCCACCTGTCGACCTCCAGCTAAGG | 591 |
| c.982_1006 | TCCCACCTGTCGACCTCCAGCTAAG | 592 |
| c.983_1007 | ATCCCACCTGTCGACCTCCAGCTAA | 593 |
| c.984_1008 | GATCCCACCTGTCGACCTCCAGCTA | 594 |
| c.985_1009 | GGATCCCACCTGTCGACCTCCAGCT | 595 |
| c.986_1010 | AGGATCCCACCTGTCGACCTCCAGC | 596 |
| c.987_1011 | CAGGATCCCACCTGTCGACCTCCAG | 597 |
| c.988_1012 | CCAGGATCCCACCTGTCGACCTCCA | 598 |
| c.989_1013 | TCCAGGATCCCACCTGTCGACCTCC | 599 |
| c.990_1014 | ATCCAGGATCCCACCTGTCGACCTC | 600 |
| c.991_1015 | CATCCAGGATCCCACCTGTCGACCT | 601 |
| c.992_1016 | ACATCCAGGATCCCACCTGTCGACC | 602 |
| c.993_1017 | GACATCCAGGATCCCACCTGTCGAC | 603 |
| c.994_1018 | AGACATCCAGGATCCCACCTGTCGA | 604 |
| c.995_1019 | TAGACATCCAGGATCCCACCTGTCG | 605 |
| c.996_1020 | GTAGACATCCAGGATCCCACCTGTC | 606 |
| c.997_1021 | TGTAGACATCCAGGATCCCACCTGT | 607 |
| c.998_1022 | ATGTAGACATCCAGGATCCCACCTG | 608 |
| c.999_1023 | GATGTAGACATCCAGGATCCCACCT | 609 |
| c.1000_1024 | AGATGTAGACATCCAGGATCCCACC | 610 |
| c.1001_1025 | AAGATGTAGACATCCAGGATCCCAC | 611 |
| c.1002_1026 | GAAGATGTAGACATCCAGGATCCCA | 612 |
| c.1003_1027 | GGAAGATGTAGACATCCAGGATCCC | 613 |
| c.1004_1028 | AGGAAGATGTAGACATCCAGGATCC | 614 |
| c.1005_1029 | CAGGAAGATGTAGACATCCAGGATC | 615 |
| c.1006_1030 | CCAGGAAGATGTAGACATCCAGGAT | 616 |
| c.1007_1031 | CCCAGGAAGATGTAGACATCCAGGA | 617 |
| c.1008_1032 | GCCCAGGAAGATGTAGACATCCAGG | 618 |
| c.1009_1033 | GGCCCAGGAAGATGTAGACATCCAG | 619 |
| c.1010_1034 | GGGCCCAGGAAGATGTAGACATCCA | 620 |
| c.1011_1035 | TGGGCCCAGGAAGATGTAGACATCC | 621 |
| c.1012_1036 | CTGGGCCCAGGAAGATGTAGACATC | 622 |
| c.1013_1037 | TCTGGGCCCAGGAAGATGTAGACAT | 623 |
| c.1014_1038 | CTCTGGGCCCAGGAAGATGTAGACA | 624 |
| c.1015_1039 | GCTCTGGGCCCAGGAAGATGTAGAC | 625 |
| c.1016_1040 | GGCTCTGGGCCCAGGAAGATGTAGA | 626 |
| c.1017_1041 | GGGCTCTGGGCCCAGGAAGATGTAG | 627 |
| c.1018_1042 | TGGGCTCTGGGCCCAGGAAGATGTA | 628 |
| c.1019_1043 | TTGGGCTCTGGGCCCAGGAAGATGT | 629 |
| c.1020_1044 | CTTGGGCTCTGGGCCCAGGAAGATG | 630 |
| c.1021_1045 | TCTTGGGCTCTGGGCCCAGGAAGAT | 631 |
| c.1022_1046 | CTCTTGGGCTCTGGGCCCAGGAAGA | 632 |
| c.1023_1047 | GCTCTTGGGCTCTGGGCCCAGGAAG | 633 |
| c.1024_1048 | CGCTCTTGGGCTCTGGGCCCAGGAA | 634 |
| c.1025_1049 | ACGCTCTTGGGCTCTGGGCCCAGGA | 635 |
| c.1026_1050 | CACGCTCTTGGGCTCTGGGCCCAGG | 636 |
| c.1027_1051 | CCACGCTCTTGGGCTCTGGGCCCAG | 637 |
| c.1028_1052 | ACCACGCTCTTGGGCTCTGGGCCCA | 638 |
| c.1029_1053 | CACCACGCTCTTGGGCTCTGGGCCC | 639 |
| c.1030_1054 | GCACCACGCTCTTGGGCTCTGGGCC | 640 |
| c.1031_1055 | TGCACCACGCTCTTGGGCTCTGGGC | 641 |
| c.1032_1056 | CTGCACCACGCTCTTGGGCTCTGGG | 642 |
| c.1033_1057 | GCTGCACCACGCTCTTGGGCTCTGG | 643 |
| c.1034_1058 | TGCTGCACCACGCTCTTGGGCTCTG | 644 |
| c.1035_1059 | CTGCTGCACCACGCTCTTGGGCTCT | 645 |
| c.1036_1060 | ACTGCTGCACCACGCTCTTGGGCTC | 646 |
| c.1037_1061 | TACTGCTGCACCACGCTCTTGGGCT | 647 |
| c.1038_1062 | GTACTGCTGCACCACGCTCTTGGGC | 648 |
| c.1039_1063 | GGTACTGCTGCACCACGCTCTTGGG | 649 |
| c.1040_1064 | AGGTACTGCTGCACCACGCTCTTGG | 650 |
| c.1041_1065 | CAGGTACTGCTGCACCACGCTCTTG | 651 |
| c.1042_1066 | CCAGGTACTGCTGCACCACGCTCTT | 652 |

| Sequence in cDNA to which AON anneals for intron 6 exclusion | AON sequence 5' -> 3' | Seq ID |
| --- | --- | --- |
| c.1043_1067 | TCCAGGTACTGCTGCACCACGCTCT | 653 |
| c.1044_1068 | GTCCAGGTACTGCTGCACCACGCTC | 654 |
| c.1045_1069 | CGTCCAGGTACTGCTGCACCACGCT | 655 |
| c.1046_1070 | ACGTCCAGGTACTGCTGCACCACGC | 656 |
| c.1047_1071 | AACGTCCAGGTACTGCTGCACCACG | 657 |
| c.1048_1072 | CAACGTCCAGGTACTGCTGCACCAC | 658 |
| c.1049_1073 | ACAACGTCCAGGTACTGCTGCACCA | 659 |
| c.1050_1074 | CACAACGTCCAGGTACTGCTGCACC | 660 |
| c.1051_1075 | CCACAACGTCCAGGTACTGCTGCAC | 661 |
| c.1052_1075+1 | CCCACAACGTCCAGGTACTGCTGCA | 662 |
| c.1053_1075+2 | ACCCACAACGTCCAGGTACTGCTGC | 663 |
| c.1054_1075+3 | TACCCACAACGTCCAGGTACTGCTG | 664 |
| c.1055_1075+4 | CTACCCACAACGTCCAGGTACTGCT | 665 |
| c.1056_1075+5 | CCTACCCACAACGTCCAGGTACTGC | 666 |
| c.1057_1075+6 | CCCTACCCACAACGTCCAGGTACTG | 667 |
| c.1058_1075+7 | GCCCTACCCACAACGTCCAGGTACT | 668 |
| c.1059_1075+8 | GGCCCTACCCACAACGTCCAGGTAC | 669 |
| c.1060_1075+9 | AGGCCCTACCCACAACGTCCAGGTA | 670 |
| c.1061_1075+10 | CAGGCCCTACCCACAACGTCCAGGT | 671 |
| c.1062_1075+11 | GCAGGCCCTACCCACAACGTCCAGG | 672 |
| c.1063_1075+12 | AGCAGGCCCTACCCACAACGTCCAG | 673 |
| c.1064_1075+13 | GAGCAGGCCCTACCCACAACGTCCA | 674 |
| c.1065_1075+14 | GGAGCAGGCCCTACCCACAACGTCC | 675 |
| c.1066_1075+15 | GGGAGCAGGCCCTACCCACAACGTC | 676 |
| c.1067_1075+16 | AGGGAGCAGGCCCTACCCACAACGT | 677 |
| c.1068_1075+17 | CAGGGAGCAGGCCCTACCCACAACG | 678 |
| c.1069_1075+18 | CCAGGGAGCAGGCCCTACCCACAAC | 679 |
| c.1070_1075+19 | GCCAGGGAGCAGGCCCTACCCACAA | 680 |
| c.1071_1075+20 | GGCCAGGGAGCAGGCCCTACCCACA | 681 |
| c.1072_1075+21 | CGGCCAGGGAGCAGGCCCTACCCAC | 682 |
| c.1073_1075+22 | GCGGCCAGGGAGCAGGCCCTACCCA | 683 |
| c.1074_1075+23 | CGCGGCCAGGGAGCAGGCCCTACCC | 684 |
| c.1075_1075+24 | CCGCGGCCAGGGAGCAGGCCCTACC | 685 |
| C.1075+1_+25 | GCCGCGGCCAGGGAGCAGGCCCTAC | 686 |
| C.1075+2_+26 | GGCCGCGGCCAGGGAGCAGGCCCTA | 687 |
| C.1075+3_+27 | GGGCCGCGGCCAGGGAGCAGGCCCT | 688 |
| C.1075+4_+28 | GGGGCCGCGGCCAGGGAGCAGGCCC | 689 |
| C.1075+5_+29 | GGGGGCCGCGGCCAGGGAGCAGGCC | 690 |
| C.1075+6_+30 | CGGGGGCCGCGGCCAGGGAGCAGGC | 691 |
| C.1075+7_+31 | GCGGGGGCCGCGGCCAGGGAGCAGG | 692 |
| C.1075+8_+32 | GGCGGGGGCCGCGGCCAGGGAGCAG | 693 |
| C.1075+9_+33 | GGGCGGGGGCCGCGGCCAGGGAGCA | 694 |
| C.1075+10_+34 | GGGGCGGGGGCCGCGGCCAGGGAGC | 695 |
| C.1075+11_+35 | TGGGGCGGGGGCCGCGGCCAGGGAG | 696 |
| C.1075+12_+36 | TTGGGGCGGGGGCCGCGGCCAGGGA | 697 |
| C.1075+13_+37 | CTTGGGGCGGGGGCCGCGGCCAGGG | 698 |
| C.1075+14_+38 | CCTTGGGGCGGGGGCCGCGGCCAGG | 699 |
| C.1075+15_+39 | GCCTTGGGGCGGGGGCCGCGGCCAG | 700 |
| C.1075+16_+40 | AGCCTTGGGGCGGGGGCCGCGGCCA | 701 |
| C.1075+17_1076-39 | GAGCCTTGGGGCGGGGGCCGCGGCC | 702 |
| C.1075+18_1076-38 | GGAGCCTTGGGGCGGGGGCCGCGGC | 703 |
| C.1075+19_1076-37 | GGGAGCCTTGGGGCGGGGGCCGCGG | 704 |
| C.1075+20_1076-36 | AGGGAGCCTTGGGGCGGGGGCCGCG | 705 |
| C.1075+21_1076-35 | GAGGGAGCCTTGGGGCGGGGGCCGC | 706 |
| C.1075+22_1076-34 | GGAGGGAGCCTTGGGGCGGGGGCCG | 707 |
| C.1075+23_1076-33 | AGGAGGGAGCCTTGGGGCGGGGGCC | 708 |
| C.1075+24_1076-32 | GAGGAGGGAGCCTTGGGGCGGGGGC | 709 |
| C.1075+25_1076-31 | GGAGGAGGGAGCCTTGGGGCGGGGG | 710 |
| C.1075+26_1076-30 | GGGAGGAGGGAGCCTTGGGGCGGGG | 711 |
| C.1075+27_1076-29 | AGGGAGGAGGGAGCCTTGGGGCGGG | 712 |
| C.1075+28_1076-28 | GAGGGAGGAGGGAGCCTTGGGGCGG | 713 |
| C.1075+29_1076-27 | GGAGGGAGGAGGGAGCCTTGGGGCG | 714 |
| C.1075+30_1076-26 | GGGAGGGAGGAGGGAGCCTTGGGGC | 715 |
| C.1075+31_1076-25 | AGGGAGGGAGGAGGGAGCCTTGGGG | 716 |
| C.1075+32_1076-24 | GAGGGAGGGAGGAGGGAGCCTTGGG | 717 |
| C.1075+33_1076-23 | TGAGGGAGGGAGGAGGGAGCCTTGG | 718 |
| C.1075+34_1076-22 | ATGAGGGAGGGAGGAGGGAGCCTTG | 719 |
| C.1075+35_1076-21 | CATGAGGGAGGGAGGAGGGAGCCTT | 720 |
| C.1075+36_1076-20 | TCATGAGGGAGGGAGGAGGGAGCCT | 721 |
| C.1075+37_1076-19 | TTCATGAGGGAGGGAGGAGGGAGCC | 722 |
| C.1075+38_1076-18 | CTTCATGAGGGAGGGAGGAGGGAGC | 723 |
| C.1075+39_1076-17 | ACTTCATGAGGGAGGGAGGAGGGAG | 724 |
| C.1075+40_1076-16 | GACTTCATGAGGGAGGGAGGAGGGA | 725 |
| c.1076-39_-15 | CGACTTCATGAGGGAGGGAGGAGGG | 726 |

| Sequence in cDNA to which AON anneals for intron 6 exclusion | AON sequence 5' -> 3' | Seq ID |
| --- | --- | --- |
| c.1076-38_-14 | CCGACTTCATGAGGGAGGGAGGAGG | 727 |
| c.1076-37_-13 | GCCGACTTCATGAGGGAGGGAGGAG | 728 |
| c.1076-36_-12 | CGCCGACTTCATGAGGGAGGGAGGA | 729 |
| c.1076-35_-11 | ACGCCGACTTCATGAGGGAGGGAGG | 730 |
| c.1076-34_-10 | AACGCCGACTTCATGAGGGAGGGAG | 731 |
| c.1076-33_-9 | CAACGCCGACTTCATGAGGGAGGGA | 732 |
| c.1076-32_-8 | CCAACGCCGACTTCATGAGGGAGGG | 733 |
| c.1076-31_-7 | GCCAACGCCGACTTCATGAGGGAGG | 734 |
| c.1076-30_-6 | GGCCAACGCCGACTTCATGAGGGAG | 735 |
| c.1076-29_-5 | AGGCCAACGCCGACTTCATGAGGGA | 736 |
| c.1076-28_-4 | CAGGCCAACGCCGACTTCATGAGGG | 737 |
| c.1076-27_-3 | GCAGGCCAACGCCGACTTCATGAGG | 738 |
| c.1076-26_-2 | TGCAGGCCAACGCCGACTTCATGAG | 739 |
| c.1076-25_-1 | CTGCAGGCCAACGCCGACTTCATGA | 740 |
| c.1076-24_1076 | CCTGCAGGCCAACGCCGACTTCATG | 741 |
| c.1076-23_1077 | TCCTGCAGGCCAACGCCGACTTCAT | 742 |
| c.1076-22_1078 | ATCCTGCAGGCCAACGCCGACTTCA | 743 |
| c.1076-21_1079 | TATCCTGCAGGCCAACGCCGACTTC | 744 |
| c.1076-20_1080 | GTATCCTGCAGGCCAACGCCGACTT | 745 |
| c.1076-19_1081 | GGTATCCTGCAGGCCAACGCCGACT | 746 |
| c.1076-18_1082 | GGGTATCCTGCAGGCCAACGCCGAC | 747 |
| c.1076-17_1083 | CGGGTATCCTGCAGGCCAACGCCGA | 748 |
| c.1076-16_1084 | ACGGGTATCCTGCAGGCCAACGCCG | 749 |
| c.1076-15_1085 | AACGGGTATCCTGCAGGCCAACGCC | 750 |
| c.1076-14_1086 | GAACGGGTATCCTGCAGGCCAACGC | 751 |
| c.1076-13_1087 | TGAACGGGTATCCTGCAGGCCAACG | 752 |
| c.1076-12_1088 | ATGAACGGGTATCCTGCAGGCCAAC | 753 |
| c.1076-11_1089 | CATGAACGGGTATCCTGCAGGCCAA | 754 |
| c.1076-10_1090 | GCATGAACGGGTATCCTGCAGGCCA | 755 |
| c.1076-9_1091 | GGCATGAACGGGTATCCTGCAGGCC | 756 |
| c.1076-8_1092 | CGGCATGAACGGGTATCCTGCAGGC | 757 |
| c.1076-7_1093 | GCGGCATGAACGGGTATCCTGCAGG | 758 |
| c.1076-6_1094 | GGCGGCATGAACGGGTATCCTGCAG | 759 |
| c.1076-5_1095 | TGGCGGCATGAACGGGTATCCTGCA | 760 |
| c.1076-4_1096 | ATGGCGGCATGAACGGGTATCCTGC | 761 |
| c.1076-3_1097 | TATGGCGGCATGAACGGGTATCCTG | 762 |
| c.1076-2_1098 | GTATGGCGGCATGAACGGGTATCCT | 763 |
| c.1076-1_1099 | AGTATGGCGGCATGAACGGGTATCC | 764 |
| c.1076_1100 | CAGTATGGCGGCATGAACGGGTATC | 765 |
| c.1077_1101 | CCAGTATGGCGGCATGAACGGGTAT | 766 |
| c.1078_1102 | CCCAGTATGGCGGCATGAACGGGTA | 767 |
| c.1079_1103 | CCCCAGTATGGCGGCATGAACGGGT | 768 |
| c.1080_1104 | GCCCCAGTATGGCGGCATGAACGGG | 769 |
| c.1081_1105 | GGCCCCAGTATGGCGGCATGAACGG | 770 |
| c.1082_1106 | AGGCCCCAGTATGGCGGCATGAACG | 771 |
| c.1083_1107 | CAGGCCCCAGTATGGCGGCATGAAC | 772 |
| c.1084_1108 | CCAGGCCCCAGTATGGCGGCATGAA | 773 |
| c.1085_1109 | CCCAGGCCCCAGTATGGCGGCATGA | 774 |
| c.1086_1110 | GCCCAGGCCCCAGTATGGCGGCATG | 775 |
| c.1087_1111 | AGCCCAGGCCCCAGTATGGCGGCAT | 776 |
| c.1088_1112 | AAGCCCAGGCCCCAGTATGGCGGCA | 777 |
| c.1089_1113 | GAAGCCCAGGCCCCAGTATGGCGGC | 778 |
| c.1090_1114 | GGAAGCCCAGGCCCCAGTATGGCGG | 779 |
| c.1091_1115 | TGGAAGCCCAGGCCCCAGTATGGCG | 780 |
| c.1092_1116 | GTGGAAGCCCAGGCCCCAGTATGGC | 781 |
| c.1093_1117 | GGTGGAAGCCCAGGCCCCAGTATGG | 782 |
| c.1094_1118 | AGGTGGAAGCCCAGGCCCCAGTATG | 783 |
| c.1095_1119 | CAGGTGGAAGCCCAGGCCCCAGTAT | 784 |
| c.1096_1120 | ACAGGTGGAAGCCCAGGCCCCAGTA | 785 |
| c.1097_1121 | CACAGGTGGAAGCCCAGGCCCCAGT | 786 |
| c.1098_1122 | GCACAGGTGGAAGCCCAGGCCCCAG | 787 |
| c.1099_1123 | GGCACAGGTGGAAGCCCAGGCCCCA | 788 |
| c.1100_1124 | CGGCACAGGTGGAAGCCCAGGCCCC | 789 |
| c.1101_1125 | GCGGCACAGGTGGAAGCCCAGGCCC | 790 |
| c.1102_1126 | AGCGGCACAGGTGGAAGCCCAGGCC | 791 |
| c.1103_1127 | CAGCGGCACAGGTGGAAGCCCAGGC | 792 |
| c.1104_1128 | CCAGCGGCACAGGTGGAAGCCCAGG | 793 |
| c.1105_1129 | CCCAGCGGCACAGGTGGAAGCCCAG | 794 |
| c.1106_1130 | CCCCAGCGGCACAGGTGGAAGCCCA | 795 |
| c.1107_1131 | GCCCCAGCGGCACAGGTGGAAGCCC | 796 |
| c.1108_1132 | AGCCCCAGCGGCACAGGTGGAAGCC | 797 |
| c.1109_1133 | TAGCCCCAGCGGCACAGGTGGAAGC | 798 |
| c.1110_1134 | GTAGCCCCAGCGGCACAGGTGGAAG | 799 |
| c.1111_1135 | AGTAGCCCCAGCGGCACAGGTGGAA | 800 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.1112_1136 | GAGTAGCCCCAGCGGCACAGGTGGA | 801 | c.1149_1173 | CATGTTCTCCACCACCTGGCGGGTG | 838 |
| c.1113_1137 | GGAGTAGCCCCAGCGGCACAGGTGG | 802 | c.1150_1174 | TCATGTTCTCCACCACCTGGCGGGT | 839 |
| c.1114_1138 | AGGAGTAGCCCCAGCGGCACAGGTG | 803 | c.1151_1175 | GTCATGTTCTCCACCACCTGGCGGG | 840 |
| c.1115_1139 | GAGGAGTAGCCCCAGCGGCACAGGT | 804 | c.1152_1176 | GGTCATGTTCTCCACCACCTGGCGG | 841 |
| c.1116_1140 | GGAGGAGTAGCCCCAGCGGCACAGG | 805 | c.1153_1177 | TGGTCATGTTCTCCACCACCTGGCG | 842 |
| c.1117_1141 | TGGAGGAGTAGCCCCAGCGGCACAG | 806 | c.1154_1178 | CTGGTCATGTTCTCCACCACCTGGC | 843 |
| c.1118_1142 | GTGGAGGAGTAGCCCCAGCGGCACA | 807 | c.1155_1179 | CCTGGTCATGTTCTCCACCACCTGG | 844 |
| c.1119_1143 | GGTGGAGGAGTAGCCCCAGCGGCAC | 808 | c.1156_1180 | CCCTGGTCATGTTCTCCACCACCTG | 845 |
| c.1120_1144 | CGGTGGAGGAGTAGCCCCAGCGGCA | 809 | c.1157_1181 | GCCCTGGTCATGTTCTCCACCACCT | 846 |
| c.1121_1145 | GCGGTGGAGGAGTAGCCCCAGCGGC | 810 | c.1158_1182 | GGCCCTGGTCATGTTCTCCACCACC | 847 |
| c.1122_1146 | AGCGGTGGAGGAGTAGCCCCAGCGG | 811 | c.1159_1183 | GGGCCCTGGTCATGTTCTCCACCAC | 848 |
| c.1123_1147 | TAGCGGTGGAGGAGTAGCCCCAGCG | 812 | c.1160_1184 | TGGGCCCTGGTCATGTTCTCCACCA | 849 |
| c.1124_1148 | ATAGCGGTGGAGGAGTAGCCCCAGC | 813 | c.1161_1185 | GTGGGCCCTGGTCATGTTCTCCACC | 850 |
| c.1125_1149 | GATAGCGGTGGAGGAGTAGCCCCAG | 814 | c.1162_1186 | AGTGGGCCCTGGTCATGTTCTCCAC | 851 |
| c.1126_1150 | TGATAGCGGTGGAGGAGTAGCCCCA | 815 | c.1163_1187 | AAGTGGGCCCTGGTCATGTTCTCCA | 852 |
| c.1127_1151 | GTGATAGCGGTGGAGGAGTAGCCCC | 816 | c.1164_1188 | GAAGTGGGCCCTGGTCATGTTCTCC | 853 |
| c.1128_1152 | GGTGATAGCGGTGGAGGAGTAGCCC | 817 | c.1165_1189 | GGAAGTGGGCCCTGGTCATGTTCTC | 854 |
| c.1129_1153 | GGGTGATAGCGGTGGAGGAGTAGCC | 818 | c.1166_1190 | GGGAAGTGGGCCCTGGTCATGTTCT | 855 |
| c.1130_1154 | CGGGTGATAGCGGTGGAGGAGTAGC | 819 | c.1167_1191 | GGGGAAGTGGGCCCTGGTCATGTTC | 856 |
| c.1131_1155 | GCGGGTGATAGCGGTGGAGGAGTAG | 820 | c.1168_1192 | GGGGGAAGTGGGCCCTGGTCATGTT | 857 |
| c.1132_1156 | GGCGGGTGATAGCGGTGGAGGAGTA | 821 | c.1169_1193 | AGGGGGAAGTGGGCCCTGGTCATGT | 858 |
| c.1133_1157 | TGGCGGGTGATAGCGGTGGAGGAGT | 822 | c.1170_1194 | CAGGGGGAAGTGGGCCCTGGTCATG | 859 |
| c.1134_1158 | CTGGCGGGTGATAGCGGTGGAGGAG | 823 | c.1171_1194+1 | CCAGGGGGAAGTGGGCCCTGGTCAT | 860 |
| c.1135_1159 | CCTGGCGGGTGATAGCGGTGGAGGA | 824 | c.1172_1194+2 | ACCAGGGGGAAGTGGGCCCTGGTCA | 861 |
| c.1136_1160 | ACCTGGCGGGTGATAGCGGTGGAGG | 825 | c.1173_1194+3 | CACCAGGGGGAAGTGGGCCCTGGTC | 862 |
| c.1137_1161 | CACCTGGCGGGTGATAGCGGTGGAG | 826 | c.1174_1194+4 | TCACCAGGGGGAAGTGGGCCCTGGT | 863 |
| c.1138_1162 | CCACCTGGCGGGTGATAGCGGTGGA | 827 | c.1175_1194+5 | CTCACCAGGGGGAAGTGGGCCCTGG | 864 |
| c.1139_1163 | ACCACCTGGCGGGTGATAGCGGTGG | 828 | c.1176_1194+6 | ACTCACCAGGGGGAAGTGGGCCCTG | 865 |
| c.1140_1164 | CACCACCTGGCGGGTGATAGCGGTG | 829 | c.1177_1194+7 | AACTCACCAGGGGGAAGTGGGCCCT | 866 |
| c.1141_1165 | CCACCACCTGGCGGGTGATAGCGGT | 830 | c.1178_1194+8 | CAACTCACCAGGGGGAAGTGGGCCC | 867 |
| c.1142_1166 | TCCACCACCTGGCGGGTGATAGCGG | 831 | c.1179_1194+9 | CCAACTCACCAGGGGGAAGTGGGCC | 868 |
| c.1143_1167 | CTCCACCACCTGGCGGGTGATAGCG | 832 | c.1180_1194+10 | CCCAACTCACCAGGGGGAAGTGGGC | 869 |
| c.1144_1168 | TCTCCACCACCTGGCGGGTGATAGC | 833 | c.1181_1194+11 | CCCCAACTCACCAGGGGGAAGTGGG | 870 |
| c.1145_1169 | TTCTCCACCACCTGGCGGGTGATAG | 834 | c.1182_1194+12 | ACCCCAACTCACCAGGGGGAAGTGG | 871 |
| c.1146_1170 | GTTCTCCACCACCTGGCGGGTGATA | 835 | c.1183_1194+13 | CACCCCAACTCACCAGGGGGAAGTG | 872 |
| c.1147_1171 | TGTTCTCCACCACCTGGCGGGTGAT | 836 | c.1184_1194+14 | CCACCCCAACTCACCAGGGGGAAGT | 873 |
| c.1148_1172 | ATGTTCTCCACCACCTGGCGGGTGA | 837 | c.1185_1194+15 | ACCACCCCAACTCACCAGGGGGAAG | 874 |

| Sequence in cDNA to which AON anneals for intron 6 exclusion | AON sequence 5' -> 3' | Seq ID |
| --- | --- | --- |
| c.1186_1194+16 | CACCACCCCAACTCACCAGGGGGAA | 875 |
| c.1187_1194+17 | CCACCACCCCAACTCACCAGGGGGA | 876 |
| c.1188_1194+18 | GCCACCACCCCAACTCACCAGGGGG | 877 |
| c.1189_1194+19 | TGCCACCACCCCAACTCACCAGGGG | 878 |
| c.1190_1194+20 | CTGCCACCACCCCAACTCACCAGGG | 879 |
| c.1191_1194+21 | CCTGCCACCACCCCAACTCACCAGG | 880 |
| c.1192_1194+22 | CCCTGCCACCACCCCAACTCACCAG | 881 |
| c.1193_1194+23 | CCCCTGCCACCACCCCAACTCACCA | 882 |
| c.1194_1194+24 | TCCCCTGCCACCACCCCAACTCACC | 883 |
| c.1194+1_+25 | CTCCCCTGCCACCACCCCAACTCAC | 884 |
| c.956-25_-5 | AAGGGAAGCAGCTCTGGGGTT | 885 |
| c.956-24_-4 | GAAGGGAAGCAGCTCTGGGGT | 886 |
| c.956-23_-3 | GGAAGGGAAGCAGCTCTGGGG | 887 |
| c.956-22_-2 | TGGAAGGGAAGCAGCTCTGGG | 888 |
| c.956-21_-1 | CTGGAAGGGAAGCAGCTCTGG | 889 |
| c.956-20_956 | TCTGGAAGGGAAGCAGCTCT | 890 |
| c.956-19_957 | ATCTGGAAGGGAAGCAGCTCT | 891 |
| c.956-18_958 | CATCTGGAAGGGAAGCAGCTC | 892 |
| c.956-17_959 | ACATCTGGAAGGGAAGCAGCT | 893 |
| c.956-16_960 | CACATCTGGAAGGGAAGCAGC | 894 |
| c.956-15_961 | CCACATCTGGAAGGGAAGCAG | 895 |
| c.956-14_962 | ACCACATCTGGAAGGGAAGCA | 896 |
| c.956-13_963 | GACCACATCTGGAAGGGAAGC | 897 |
| c.956-12_964 | GGACCACATCTGGAAGGGAAG | 898 |
| c.956-11_965 | AGGACCACATCTGGAAGGGAA | 899 |
| c.956-10_966 | CAGGACCACATCTGGAAGGGA | 900 |
| c.956-9_967 | GCAGGACCACATCTGGAAGGG | 901 |
| c.956-8_968 | TGCAGGACCACATCTGGAAGG | 902 |
| c.956-7_969 | CTGCAGGACCACATCTGGAAG | 903 |
| c.956-6_970 | GCTGCAGGACCACATCTGGAA | 904 |
| c.956-5_971 | GGCTGCAGGACCACATCTGGA | 905 |
| c.956-4_972 | CGGCTGCAGGACCACATCTGG | 906 |
| c.956-3_973 | TCGGCTGCAGGACCACATCTG | 907 |
| c.956-2_974 | CTCGGCTGCAGGACCACATCT | 908 |
| c.956-1_975 | GCTCGGCTGCAGGACCACATC | 909 |
| c.956_976 | GGCTCGGCTGCAGGACCACAT | 910 |
| c.957_977 | GGGCTCGGCTGCAGGACCACA | 911 |
| c.958_978 | AGGGCTCGGCTGCAGGACCAC | 912 |
| c.959_979 | CAGGGCTCGGCTGCAGGACCA | 913 |
| c.960_980 | GCAGGGCTCGGCTGCAGGACC | 914 |
| c.961_981 | GGCAGGGCTCGGCTGCAGGAC | 915 |
| c.962_982 | GGGCAGGGCTCGGCTGCAGGA | 916 |
| c.963_983 | AGGGCAGGGCTCGGCTGCAGG | 917 |
| c.964_984 | AAGGGCAGGGCTCGGCTGCAG | 918 |
| c.965_985 | TAAGGGCAGGGCTCGGCTGCA | 919 |
| c.966_986 | CTAAGGGCAGGGCTCGGCTGC | 920 |
| c.967_987 | GCTAAGGGCAGGGCTCGGCTG | 921 |
| c.968_988 | AGCTAAGGGCAGGGCTCGGCT | 922 |
| c.969_989 | CAGCTAAGGGCAGGGCTCGGC | 923 |
| c.970_990 | CCAGCTAAGGGCAGGGCTCGG | 924 |
| c.971_991 | TCCAGCTAAGGGCAGGGCTCG | 925 |
| c.972_992 | CTCCAGCTAAGGGCAGGGCTC | 926 |
| c.973_993 | CCTCCAGCTAAGGGCAGGGCT | 927 |
| c.974_994 | ACCTCCAGCTAAGGGCAGGGC | 928 |
| c.975_995 | GACCTCCAGCTAAGGGCAGGG | 929 |
| c.976_996 | CGACCTCCAGCTAAGGGCAGG | 930 |
| c.977_997 | TCGACCTCCAGCTAAGGGCAG | 931 |
| c.978_998 | GTCGACCTCCAGCTAAGGGCA | 932 |
| c.979_999 | TGTCGACCTCCAGCTAAGGGC | 933 |
| c.980_1000 | CTGTCGACCTCCAGCTAAGGG | 934 |
| c.981_1001 | CCTGTCGACCTCCAGCTAAGG | 935 |
| c.982_1002 | ACCTGTCGACCTCCAGCTAAG | 936 |
| c.983_1003 | CACCTGTCGACCTCCAGCTAA | 937 |
| c.984_1004 | CCACCTGTCGACCTCCAGCTA | 938 |
| c.985_1005 | CCCACCTGTCGACCTCCAGCT | 939 |
| c.986_1006 | TCCCACCTGTCGACCTCCAGC | 940 |
| c.987_1007 | ATCCCACCTGTCGACCTCCAG | 941 |
| c.988_1008 | GATCCCACCTGTCGACCTCCA | 942 |
| c.989_1009 | GGATCCCACCTGTCGACCTCC | 943 |
| c.990_1010 | AGGATCCCACCTGTCGACCTC | 944 |
| c.991_1011 | CAGGATCCCACCTGTCGACCT | 945 |
| c.992_1012 | CCAGGATCCCACCTGTCGACC | 946 |
| c.993_1013 | TCCAGGATCCCACCTGTCGAC | 947 |
| c.994_1014 | ATCCAGGATCCCACCTGTCGA | 948 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.995_1015 | CATCCAGGATCCCACCTGTCG | 949 | c.1032_1052 | ACCACGCTCTTGGGCTCTGGG | 986 |
| c.996_1016 | ACATCCAGGATCCCACCTGTC | 950 | c.1033_1053 | CACCACGCTCTTGGGCTCTGG | 987 |
| c.997_1017 | GACATCCAGGATCCCACCTGT | 951 | c.1034_1054 | GCACCACGCTCTTGGGCTCTG | 988 |
| c.998_1018 | AGACATCCAGGATCCCACCTG | 952 | c.1035_1055 | TGCACCACGCTCTTGGGCTCT | 989 |
| c.999_1019 | TAGACATCCAGGATCCCACCT | 953 | c.1036_1056 | CTGCACCACGCTCTTGGGCTC | 990 |
| c.1000_1020 | GTAGACATCCAGGATCCCACC | 954 | c.1037_1057 | GCTGCACCACGCTCTTGGGCT | 991 |
| c.1001_1021 | TGTAGACATCCAGGATCCCAC | 955 | c.1038_1058 | TGCTGCACCACGCTCTTGGGC | 992 |
| c.1002_1022 | ATGTAGACATCCAGGATCCCA | 956 | c.1039_1059 | CTGCTGCACCACGCTCTTGGG | 993 |
| c.1003_1023 | GATGTAGACATCCAGGATCCC | 957 | c.1040_1060 | ACTGCTGCACCACGCTCTTGG | 994 |
| c.1004_1024 | AGATGTAGACATCCAGGATCC | 958 | c.1041_1061 | TACTGCTGCACCACGCTCTTG | 995 |
| c.1005_1025 | AAGATGTAGACATCCAGGATC | 959 | c.1042_1062 | GTACTGCTGCACCACGCTCTT | 996 |
| c.1006_1026 | GAAGATGTAGACATCCAGGAT | 960 | c.1043_1063 | GGTACTGCTGCACCACGCTCT | 997 |
| c.1007_1027 | GGAAGATGTAGACATCCAGGA | 961 | c.1044_1064 | AGGTACTGCTGCACCACGCTC | 998 |
| c.1008_1028 | AGGAAGATGTAGACATCCAGG | 962 | c.1045_1065 | CAGGTACTGCTGCACCACGCT | 999 |
| c.1009_1029 | CAGGAAGATGTAGACATCCAG | 963 | c.1046_1066 | CCAGGTACTGCTGCACCACGC | 1000 |
| c.1010_1030 | CCAGGAAGATGTAGACATCCA | 964 | c.1047_1067 | TCCAGGTACTGCTGCACCACG | 1001 |
| c.1011_1031 | CCCAGGAAGATGTAGACATCC | 965 | c.1048_1068 | GTCCAGGTACTGCTGCACCAC | 1002 |
| c.1012_1032 | GCCCAGGAAGATGTAGACATC | 966 | c.1049_1069 | CGTCCAGGTACTGCTGCACCA | 1003 |
| c.1013_1033 | GGCCCAGGAAGATGTAGACAT | 967 | c.1050_1070 | ACGTCCAGGTACTGCTGCACC | 1004 |
| c.1014_1034 | GGGCCCAGGAAGATGTAGACA | 968 | c.1051_1071 | AACGTCCAGGTACTGCTGCAC | 1005 |
| c.1015_1035 | TGGGCCCAGGAAGATGTAGAC | 969 | c.1052_1072 | CAACGTCCAGGTACTGCTGCA | 1006 |
| c.1016_1036 | CTGGGCCCAGGAAGATGTAGA | 970 | c.1053_1073 | ACAACGTCCAGGTACTGCTGC | 1007 |
| c.1017_1037 | TCTGGGCCCAGGAAGATGTAG | 971 | c.1054_1074 | CACAACGTCCAGGTACTGCTG | 1008 |
| c.1018_1038 | CTCTGGGCCCAGGAAGATGTA | 972 | c.1055_1075 | CCACAACGTCCAGGTACTGCT | 1009 |
| c.1019_1039 | GCTCTGGGCCCAGGAAGATGT | 973 | c.1056_1075+1 | CCCACAACGTCCAGGTACTGC | 1010 |
| c.1020_1040 | GGCTCTGGGCCCAGGAAGATG | 974 | c.1057_1075+2 | ACCCACAACGTCCAGGTACTG | 1011 |
| c.1021_1041 | GGGCTCTGGGCCCAGGAAGAT | 975 | c.1058_1075+3 | TACCCACAACGTCCAGGTACT | 1012 |
| c.1022_1042 | TGGGCTCTGGGCCCAGGAAGA | 976 | c.1059_1075+4 | CTACCCACAACGTCCAGGTAC | 1013 |
| c.1023_1043 | TTGGGCTCTGGGCCCAGGAAG | 977 | c.1060_1075+5 | CCTACCCACAACGTCCAGGTA | 1014 |
| c.1024_1044 | CTTGGGCTCTGGGCCCAGGAA | 978 | c.1061_1075+6 | CCCTACCCACAACGTCCAGGT | 1015 |
| c.1025_1045 | TCTTGGGCTCTGGGCCCAGGA | 979 | c.1062_1075+7 | GCCCTACCCACAACGTCCAGG | 1016 |
| c.1026_1046 | CTCTTGGGCTCTGGGCCCAGG | 980 | c.1063_1075+8 | GGCCCTACCCACAACGTCCAG | 1017 |
| c.1027_1047 | GCTCTTGGGCTCTGGGCCCAG | 981 | c.1064_1075+9 | AGGCCCTACCCACAACGTCCA | 1018 |
| c.1028_1048 | CGCTCTTGGGCTCTGGGCCCA | 982 | c.1065_1075+10 | CAGGCCCTACCCACAACGTCC | 1019 |
| c.1029_1049 | ACGCTCTTGGGCTCTGGGCCC | 983 | c.1066_1075+11 | GCAGGCCCTACCCACAACGTC | 1020 |
| c.1030_1050 | CACGCTCTTGGGCTCTGGGCC | 984 | c.1067_1075+12 | AGCAGGCCCTACCCACAACGT | 1021 |
| c.1031_1051 | CCACGCTCTTGGGCTCTGGGC | 985 | c.1068_1075+13 | GAGCAGGCCCTACCCACAACG | 1022 |

| Sequence in cDNA to which AON anneals for intron 6 exclusion | AON sequence 5' -> 3' | Seq ID |
| --- | --- | --- |
| c.1069_1075+14 | GGAGCAGGCCCTACCCACAAC | 1023 |
| c.1070_1075+15 | GGGAGCAGGCCCTACCCACAA | 1024 |
| c.1071_1075+16 | AGGGAGCAGGCCCTACCCACA | 1025 |
| c.1072_1075+17 | CAGGGAGCAGGCCCTACCCAC | 1026 |
| c.1073_1075+18 | CCAGGGAGCAGGCCCTACCCA | 1027 |
| c.1074_1075+19 | GCCAGGGAGCAGGCCCTACCC | 1028 |
| c.1075_1075+20 | GGCCAGGGAGCAGGCCCTACC | 1029 |
| c.1075+1_+21 | CGGCCAGGGAGCAGGCCCTAC | 1030 |
| c.1075+2_+22 | GCGGCCAGGGAGCAGGCCCTA | 1031 |
| c.1075+3_+23 | CGCGGCCAGGGAGCAGGCCCT | 1032 |
| c.1075+4_+24 | CCGCGGCCAGGGAGCAGGCCC | 1033 |
| c.1075+5_+25 | GCCGCGGCCAGGGAGCAGGCC | 1034 |
| c.1075+6_+26 | GGCCGCGGCCAGGGAGCAGGC | 1035 |
| c.1075+7_+27 | GGGCCGCGGCCAGGGAGCAGG | 1036 |
| c.1075+8_+28 | GGGGCCGCGGCCAGGGAGCAG | 1037 |
| c.1075+9_+29 | GGGGGCCGCGGCCAGGGAGCA | 1038 |
| c.1075+10_+30 | CGGGGGCCGCGGCCAGGGAGC | 1039 |
| c.1075+11_+31 | GCGGGGGCCGCGGCCAGGGAG | 1040 |
| c.1075+12_+32 | GGCGGGGGCCGCGGCCAGGGA | 1041 |
| c.1075+13_+33 | GGGCGGGGGCCGCGGCCAGGG | 1042 |
| c.1075+14_+34 | GGGGCGGGGGCCGCGGCCAGG | 1043 |
| c.1075+15_+35 | TGGGGCGGGGGCCGCGGCCAG | 1044 |
| c.1075+16_+36 | TTGGGGCGGGGGCCGCGGCCA | 1045 |
| c.1075+17_+37 | CTTGGGGCGGGGGCCGCGGCC | 1046 |
| c.1075+18_+38 | CCTTGGGGCGGGGGCCGCGGC | 1047 |
| c.1075+19_+39 | GCCTTGGGGCGGGGGCCGCGG | 1048 |
| c.1075+20_+40 | AGCCTTGGGGCGGGGGCCGCG | 1049 |
| c.1075+21_1076-39 | GAGCCTTGGGGCGGGGGCCGC | 1050 |
| c.1075+22_1076-38 | GGAGCCTTGGGGCGGGGGCCG | 1051 |
| c.1075+23_1076-37 | GGGAGCCTTGGGGCGGGGGCC | 1052 |
| c.1075+24_1076-36 | AGGGAGCCTTGGGGCGGGGGC | 1053 |
| c.1075+25_1076-35 | GAGGGAGCCTTGGGGCGGGGG | 1054 |
| c.1075+26_1076-34 | GGAGGGAGCCTTGGGGCGGGG | 1055 |
| c.1075+27_1076-33 | AGGAGGGAGCCTTGGGGCGGG | 1056 |
| c.1075+28_1076-32 | GAGGAGGGAGCCTTGGGGCGG | 1057 |
| c.1075+29_1076-31 | GGAGGAGGGAGCCTTGGGGCG | 1058 |
| c.1075+30_1076-30 | GGGAGGAGGGAGCCTTGGGGC | 1059 |
| c.1075+31_1076-29 | AGGGAGGAGGGAGCCTTGGGG | 1060 |
| c.1075+32_1076-28 | GAGGGAGGAGGGAGCCTTGGG | 1061 |
| c.1075+33_1076-27 | GGAGGGAGGAGGGAGCCTTGG | 1062 |
| c.1075+34_1076-26 | GGGAGGGAGGAGGGAGCCTTG | 1063 |
| c.1075+35_1076-25 | AGGGAGGGAGGAGGGAGCCTT | 1064 |
| c.1075+36_1076-24 | GAGGGAGGGAGGAGGGAGCCT | 1065 |
| c.1075+37_1076-23 | TGAGGGAGGGAGGAGGGAGCC | 1066 |
| c.1075+38_1076-22 | ATGAGGGAGGGAGGAGGGAGC | 1067 |
| c.1075+39_1076-21 | CATGAGGGAGGGAGGAGGGAG | 1068 |
| c.1075+40_1076-20 | TCATGAGGGAGGGAGGAGGGA | 1069 |
| c.1076-39_-19 | TTCATGAGGGAGGGAGGAGGG | 1070 |
| c.1076-38_-18 | CTTCATGAGGGAGGGAGGAGG | 1071 |
| c.1076-37_-17 | ACTTCATGAGGGAGGGAGGAG | 1072 |
| c.1076-36_-16 | GACTTCATGAGGGAGGGAGGA | 1073 |
| c.1076-35_-15 | CGACTTCATGAGGGAGGGAGG | 1074 |
| c.1076-34_-14 | CCGACTTCATGAGGGAGGGAG | 1075 |
| c.1076-33_-13 | GCCGACTTCATGAGGGAGGGA | 1076 |
| c.1076-32_-12 | CGCCGACTTCATGAGGGAGGG | 1077 |
| c.1076-31_-11 | ACGCCGACTTCATGAGGGAGG | 1078 |
| c.1076-30_-10 | AACGCCGACTTCATGAGGGAG | 1079 |
| c.1076-29_-9 | CAACGCCGACTTCATGAGGGA | 1080 |
| c.1076-28_-8 | CCAACGCCGACTTCATGAGGG | 1081 |
| c.1076-27_-7 | GCCAACGCCGACTTCATGAGG | 1082 |
| c.1076-26_-6 | GGCCAACGCCGACTTCATGAG | 1083 |
| c.1076-25_-5 | AGGCCAACGCCGACTTCATGA | 1084 |
| c.1076-24_-4 | CAGGCCAACGCCGACTTCATG | 1085 |
| c.1076-23_-3 | GCAGGCCAACGCCGACTTCAT | 1086 |
| c.1076-22_-2 | TGCAGGCCAACGCCGACTTCA | 1087 |
| c.1076-21_-1 | CTGCAGGCCAACGCCGACTTC | 1088 |
| c.1076-20_1076 | CCTGCAGGCCAACGCCGACTT | 1089 |
| c.1076-19_1077 | TCCTGCAGGCCAACGCCGACT | 1090 |
| c.1076-18_1078 | ATCCTGCAGGCCAACGCCGAC | 1091 |
| c.1076-17_1079 | TATCCTGCAGGCCAACGCCGA | 1092 |
| c.1076-16_1080 | GTATCCTGCAGGCCAACGCCG | 1093 |
| c.1076-15_1081 | GGTATCCTGCAGGCCAACGCC | 1094 |
| c.1076-14_1082 | GGGTATCCTGCAGGCCAACGC | 1095 |
| c.1076-13_1083 | CGGGTATCCTGCAGGCCAACG | 1096 |

| Sequence in cDNA to which AON anneals for intron 6 exclusion | AON sequence 5' -> 3' | Seq ID |
| --- | --- | --- |
| c.1076-12_1084 | ACGGGTATCCTGCAGGCCAAC | 1097 |
| c.1076-11_1085 | AACGGGTATCCTGCAGGCCAA | 1098 |
| c.1076-10_1086 | GAACGGGTATCCTGCAGGCCA | 1099 |
| c.1076-9_1087 | TGAACGGGTATCCTGCAGGCC | 1100 |
| c.1076-8_1088 | ATGAACGGGTATCCTGCAGGC | 1101 |
| c.1076-7_1089 | CATGAACGGGTATCCTGCAGG | 1102 |
| c.1076-6_1090 | GCATGAACGGGTATCCTGCAG | 1103 |
| c.1076-5_1091 | GGCATGAACGGGTATCCTGCA | 1104 |
| c.1076-4_1092 | CGGCATGAACGGGTATCCTGC | 1105 |
| c.1076-3_1093 | GCGGCATGAACGGGTATCCTG | 1106 |
| c.1076-2_1094 | GGCGGCATGAACGGGTATCCT | 1107 |
| c.1076-1_1095 | TGGCGGCATGAACGGGTATCC | 1108 |
| c.1076_1096 | ATGGCGGCATGAACGGGTATC | 1109 |
| c.1077_1097 | TATGGCGGCATGAACGGGTAT | 1110 |
| c.1078_1098 | GTATGGCGGCATGAACGGGTA | 1111 |
| c.1079_1099 | AGTATGGCGGCATGAACGGGT | 1112 |
| c.1080_1100 | CAGTATGGCGGCATGAACGGG | 1113 |
| c.1081_1101 | CCAGTATGGCGGCATGAACGG | 1114 |
| c.1082_1102 | CCCAGTATGGCGGCATGAACG | 1115 |
| c.1083_1103 | CCCCAGTATGGCGGCATGAAC | 1116 |
| c.1084_1104 | GCCCCAGTATGGCGGCATGAA | 1117 |
| c.1085_1105 | GGCCCCAGTATGGCGGCATGA | 1118 |
| c.1086_1106 | AGGCCCCAGTATGGCGGCATG | 1119 |
| c.1087_1107 | CAGGCCCCAGTATGGCGGCAT | 1120 |
| c.1088_1108 | CCAGGCCCCAGTATGGCGGCA | 1121 |
| c.1089_1109 | CCCAGGCCCCAGTATGGCGGC | 1122 |
| c.1090_1110 | GCCCAGGCCCCAGTATGGCGG | 1123 |
| c.1091_1111 | AGCCCAGGCCCCAGTATGGCG | 1124 |
| c.1092_1112 | AAGCCCAGGCCCCAGTATGGC | 1125 |
| c.1093_1113 | GAAGCCCAGGCCCCAGTATGG | 1126 |
| c.1094_1114 | GGAAGCCCAGGCCCCAGTATG | 1127 |
| c.1095_1115 | TGGAAGCCCAGGCCCCAGTAT | 1128 |
| c.1096_1116 | GTGGAAGCCCAGGCCCCAGTA | 1129 |
| c.1097_1117 | GGTGGAAGCCCAGGCCCCAGT | 1130 |
| c.1098_1118 | AGGTGGAAGCCCAGGCCCCAG | 1131 |
| c.1099_1119 | CAGGTGGAAGCCCAGGCCCCA | 1132 |
| c.1100_1120 | ACAGGTGGAAGCCCAGGCCCC | 1133 |
| c.1101_1121 | CACAGGTGGAAGCCCAGGCCC | 1134 |
| c.1102_1122 | GCACAGGTGGAAGCCCAGGCC | 1135 |
| c.1103_1123 | GGCACAGGTGGAAGCCCAGGC | 1136 |
| c.1104_1124 | CGGCACAGGTGGAAGCCCAGG | 1137 |
| c.1105_1125 | GCGGCACAGGTGGAAGCCCAG | 1138 |
| c.1106_1126 | AGCGGCACAGGTGGAAGCCCA | 1139 |
| c.1107_1127 | CAGCGGCACAGGTGGAAGCCC | 1140 |
| c.1108_1128 | CCAGCGGCACAGGTGGAAGCC | 1141 |
| c.1109_1129 | CCCAGCGGCACAGGTGGAAGC | 1142 |
| c.1110_1130 | CCCCAGCGGCACAGGTGGAAG | 1143 |
| c.1111_1131 | GCCCCAGCGGCACAGGTGGAA | 1144 |
| c.1112_1132 | AGCCCCAGCGGCACAGGTGGA | 1145 |
| c.1113_1133 | TAGCCCCAGCGGCACAGGTGG | 1146 |
| c.1114_1134 | GTAGCCCCAGCGGCACAGGTG | 1147 |
| c.1115_1135 | AGTAGCCCCAGCGGCACAGGT | 1148 |
| c.1116_1136 | GAGTAGCCCCAGCGGCACAGG | 1149 |
| c.1117_1137 | GGAGTAGCCCCAGCGGCACAG | 1150 |
| c.1118_1138 | AGGAGTAGCCCCAGCGGCACA | 1151 |
| c.1119_1139 | GAGGAGTAGCCCCAGCGGCAC | 1152 |
| c.1120_1140 | GGAGGAGTAGCCCCAGCGGCA | 1153 |
| c.1121_1141 | TGGAGGAGTAGCCCCAGCGGC | 1154 |
| c.1122_1142 | GTGGAGGAGTAGCCCCAGCGG | 1155 |
| c.1123_1143 | GGTGGAGGAGTAGCCCCAGCG | 1156 |
| c.1124_1144 | CGGTGGAGGAGTAGCCCCAGC | 1157 |
| c.1125_1145 | GCGGTGGAGGAGTAGCCCCAG | 1158 |
| c.1126_1146 | AGCGGTGGAGGAGTAGCCCCA | 1159 |
| c.1127_1147 | TAGCGGTGGAGGAGTAGCCCC | 1160 |
| c.1128_1148 | ATAGCGGTGGAGGAGTAGCCC | 1161 |
| c.1129_1149 | GATAGCGGTGGAGGAGTAGCC | 1162 |
| c.1130_1150 | TGATAGCGGTGGAGGAGTAGC | 1163 |
| c.1131_1151 | GTGATAGCGGTGGAGGAGTAG | 1164 |
| c.1132_1152 | GGTGATAGCGGTGGAGGAGTA | 1165 |
| c.1133_1153 | GGGTGATAGCGGTGGAGGAGT | 1166 |
| c.1134_1154 | CGGGTGATAGCGGTGGAGGAG | 1167 |
| c.1135_1155 | GCGGGTGATAGCGGTGGAGGA | 1168 |
| c.1136_1156 | GGCGGGTGATAGCGGTGGAGG | 1169 |
| c.1137_1157 | TGGCGGGTGATAGCGGTGGAG | 1170 |

| Sequence in cDNA to which AON anneals for intron 6 exclusion | AON sequence 5' -> 3' | Seq ID |
| --- | --- | --- |
| c.1138_1158 | CTGGCGGGTGATAGCGGTGGA | 1171 |
| c.1139_1159 | CCTGGCGGGTGATAGCGGTGG | 1172 |
| c.1140_1160 | ACCTGGCGGGTGATAGCGGTG | 1173 |
| c.1141_1161 | CACCTGGCGGGTGATAGCGGT | 1174 |
| c.1142_1162 | CCACCTGGCGGGTGATAGCGG | 1175 |
| c.1143_1163 | ACCACCTGGCGGGTGATAGCG | 1176 |
| c.1144_1164 | CACCACCTGGCGGGTGATAGC | 1177 |
| c.1145_1165 | CCACCACCTGGCGGGTGATAG | 1178 |
| c.1146_1166 | TCCACCACCTGGCGGGTGATA | 1179 |
| c.1147_1167 | CTCCACCACCTGGCGGGTGAT | 1180 |
| c.1148_1168 | TCTCCACCACCTGGCGGGTGA | 1181 |
| c.1149_1169 | TTCTCCACCACCTGGCGGGTG | 1182 |
| c.1150_1170 | GTTCTCCACCACCTGGCGGGT | 1183 |
| c.1151_1171 | TGTTCTCCACCACCTGGCGGG | 1184 |
| c.1152_1172 | ATGTTCTCCACCACCTGGCGG | 1185 |
| c.1153_1173 | CATGTTCTCCACCACCTGGCG | 1186 |
| c.1154_1174 | TCATGTTCTCCACCACCTGGC | 1187 |
| c.1155_1175 | GTCATGTTCTCCACCACCTGG | 1188 |
| c.1156_1176 | GGTCATGTTCTCCACCACCTG | 1189 |
| c.1157_1177 | TGGTCATGTTCTCCACCACCT | 1190 |
| c.1158_1178 | CTGGTCATGTTCTCCACCACC | 1191 |
| c.1159_1179 | CCTGGTCATGTTCTCCACCAC | 1192 |
| c.1160_1180 | CCCTGGTCATGTTCTCCACCA | 1193 |
| c.1161_1181 | GCCCTGGTCATGTTCTCCACC | 1194 |
| c.1162_1182 | GGCCCTGGTCATGTTCTCCAC | 1195 |
| c.1163_1183 | GGGCCCTGGTCATGTTCTCCA | 1196 |
| c.1164_1184 | TGGGCCCTGGTCATGTTCTCC | 1197 |
| c.1165_1185 | GTGGGCCCTGGTCATGTTCTC | 1198 |
| c.1166_1186 | AGTGGGCCCTGGTCATGTTCT | 1199 |
| c.1167_1187 | AAGTGGGCCCTGGTCATGTTC | 1200 |
| c.1168_1188 | GAAGTGGGCCCTGGTCATGTT | 1201 |
| c.1169_1189 | GGAAGTGGGCCCTGGTCATGT | 1202 |
| c.1170_1190 | GGGAAGTGGGCCCTGGTCATG | 1203 |
| c.1171_1191 | GGGGAAGTGGGCCCTGGTCAT | 1204 |
| c.1172_1192 | GGGGGAAGTGGGCCCTGGTCA | 1205 |
| c.1173_1193 | AGGGGGAAGTGGGCCCTGGTC | 1206 |
| c.1174_1194 | CAGGGGGAAGTGGGCCCTGGT | 1207 |
| c.1175_1194+1 | CCAGGGGGAAGTGGGCCCTGG | 1208 |
| c.1176_1194+2 | ACCAGGGGGAAGTGGGCCCTG | 1209 |
| c.1177_1194+3 | CACCAGGGGGAAGTGGGCCCT | 1210 |
| c.1178_1194+4 | TCACCAGGGGGAAGTGGGCCC | 1211 |
| c.1179_1194+5 | CTCACCAGGGGGAAGTGGGCC | 1212 |
| c.1180_1194+6 | ACTCACCAGGGGGAAGTGGGC | 1213 |
| c.1181_1194+7 | AACTCACCAGGGGGAAGTGGG | 1214 |
| c.1182_1194+8 | CAACTCACCAGGGGGAAGTGG | 1215 |
| c.1183_1194+9 | CCAACTCACCAGGGGGAAGTG | 1216 |
| c.1184_1194+10 | CCCAACTCACCAGGGGGAAGT | 1217 |
| c.1185_1194+11 | CCCCAACTCACCAGGGGGAAG | 1218 |
| c.1186_1194+12 | ACCCCAACTCACCAGGGGGAA | 1219 |
| c.1187_1194+13 | CACCCCAACTCACCAGGGGGA | 1220 |
| c.1188_1194+14 | CCACCCCAACTCACCAGGGGG | 1221 |
| c.1189_1194+15 | ACCACCCCAACTCACCAGGGG | 1222 |
| c.1190_1194+16 | CACCACCCCAACTCACCAGGG | 1223 |
| c.1191_1194+17 | CCACCACCCCAACTCACCAGG | 1224 |
| c.1192_1194+18 | GCCACCACCCCAACTCACCAG | 1225 |
| c.1193_1194+19 | TGCCACCACCCCAACTCACCA | 1226 |
| c.1194_1194+20 | CTGCCACCACCCCAACTCACC | 1227 |
| c.1194+1_+21 | CCTGCCACCACCCCAACTCAC | 1228 |
| c.1194+2_+22 | CCCTGCCACCACCCCAACTCA | 1229 |
| c.1194+3_+23 | CCCCTGCCACCACCCCAACTC | 1230 |
| c.1194+4_+24 | TCCCCTGCCACCACCCCAACT | 1231 |
| c.1194+5_+25 | CTCCCCTGCCACCACCCCAAC | 1232 |
| c.956-25_-8 | GGAAGCAGCTCTGGGGTT | 1233 |
| c.956-24_-7 | GGGAAGCAGCTCTGGGGT | 1234 |
| c.956-23_-6 | AGGGAAGCAGCTCTGGGG | 1235 |
| c.956-22_-5 | AAGGGAAGCAGCTCTGGG | 1236 |
| c.956-21_-4 | GAAGGGAAGCAGCTCTGG | 1237 |
| c.956-20_-3 | GGAAGGGAAGCAGCTCTG | 1238 |
| c.956-19_-2 | TGGAAGGGAAGCAGCTCT | 1239 |
| c.956-18_-1 | CTGGAAGGGAAGCAGCTC | 1240 |
| c.956-17_956 | TCTGGAAGGGAAGCAGCT | 1241 |
| c.956-16_957 | ATCTGGAAGGGAAGCAGC | 1242 |
| c.956-15_958 | CATCTGGAAGGGAAGCAG | 1243 |
| c.956-14_959 | ACATCTGGAAGGGAAGCA | 1244 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.956-13_960 | CACATCTGGAAGGGAAGC | 1245 | c.980_997 | TCGACCTCCAGCTAAGGG | 1282 |
| c.956-12_961 | CCACATCTGGAAGGGAAG | 1246 | c.981_998 | GTCGACCTCCAGCTAAGG | 1283 |
| c.956-11_962 | ACCACATCTGGAAGGGAA | 1247 | c.982_999 | TGTCGACCTCCAGCTAAG | 1284 |
| c.956-10_963 | GACCACATCTGGAAGGGA | 1248 | c.983_1000 | CTGTCGACCTCCAGCTAA | 1285 |
| c.956-9_964 | GGACCACATCTGGAAGGG | 1249 | c.984_1001 | CCTGTCGACCTCCAGCTA | 1286 |
| c.956-8_965 | AGGACCACATCTGGAAGG | 1250 | c.985_1002 | ACCTGTCGACCTCCAGCT | 1287 |
| c.956-7_966 | CAGGACCACATCTGGAAG | 1251 | c.986_1003 | CACCTGTCGACCTCCAGC | 1288 |
| c.956-6_967 | GCAGGACCACATCTGGAA | 1252 | c.987_1004 | CCACCTGTCGACCTCCAG | 1289 |
| c.956-5_968 | TGCAGGACCACATCTGGA | 1253 | c.988_1005 | CCCACCTGTCGACCTCCA | 1290 |
| c.956-4_969 | CTGCAGGACCACATCTGG | 1254 | c.989_1006 | TCCCACCTGTCGACCTCC | 1291 |
| c.956-3_970 | GCTGCAGGACCACATCTG | 1255 | c.990_1007 | ATCCCACCTGTCGACCTC | 1292 |
| c.956-2_971 | GGCTGCAGGACCACATCT | 1256 | c.991_1008 | GATCCCACCTGTCGACCT | 1293 |
| c.956-1_972 | CGGCTGCAGGACCACATC | 1257 | c.992_1009 | GGATCCCACCTGTCGACC | 1294 |
| c.956_973 | TCGGCTGCAGGACCACAT | 1258 | c.993_1010 | AGGATCCCACCTGTCGAC | 1295 |
| c.957_974 | CTCGGCTGCAGGACCACA | 1259 | c.994_1011 | CAGGATCCCACCTGTCGA | 1296 |
| c.958_975 | GCTCGGCTGCAGGACCAC | 1260 | c.995_1012 | CCAGGATCCCACCTGTCG | 1297 |
| c.959_976 | GGCTCGGCTGCAGGACCA | 1261 | c.996_1013 | TCCAGGATCCCACCTGTC | 1298 |
| c.960_977 | GGGCTCGGCTGCAGGACC | 1262 | c.997_1014 | ATCCAGGATCCCACCTGT | 1299 |
| c.961_978 | AGGGCTCGGCTGCAGGAC | 1263 | c.998_1015 | CATCCAGGATCCCACCTG | 1300 |
| c.962_979 | CAGGGCTCGGCTGCAGGA | 1264 | c.999_1016 | ACATCCAGGATCCCACCT | 1301 |
| c.963_980 | GCAGGGCTCGGCTGCAGG | 1265 | c.1000_1017 | GACATCCAGGATCCCACC | 1302 |
| c.964_981 | GGCAGGGCTCGGCTGCAG | 1266 | c.1001_1018 | AGACATCCAGGATCCCAC | 1303 |
| c.965_982 | GGGCAGGGCTCGGCTGCA | 1267 | c.1002_1019 | TAGACATCCAGGATCCCA | 1304 |
| c.966_983 | AGGGCAGGGCTCGGCTGC | 1268 | c.1003_1020 | GTAGACATCCAGGATCCC | 1305 |
| c.967_984 | AAGGGCAGGGCTCGGCTG | 1269 | c.1004_1021 | TGTAGACATCCAGGATCC | 1306 |
| c.968_985 | TAAGGGCAGGGCTCGGCT | 1270 | c.1005_1022 | ATGTAGACATCCAGGATC | 1307 |
| c.969_986 | CTAAGGGCAGGGCTCGGC | 1271 | c.1006_1023 | GATGTAGACATCCAGGAT | 1308 |
| c.970_987 | GCTAAGGGCAGGGCTCGG | 1272 | c.1007_1024 | AGATGTAGACATCCAGGA | 1309 |
| c.971_988 | AGCTAAGGGCAGGGCTCG | 1273 | c.1008_1025 | AAGATGTAGACATCCAGG | 1310 |
| c.972_989 | CAGCTAAGGGCAGGGCTC | 1274 | c.1009_1026 | GAAGATGTAGACATCCAG | 1311 |
| c.973_990 | CCAGCTAAGGGCAGGGCT | 1275 | c.1010_1027 | GGAAGATGTAGACATCCA | 1312 |
| c.974_991 | TCCAGCTAAGGGCAGGGC | 1276 | c.1011_1028 | AGGAAGATGTAGACATCC | 1313 |
| c.975_992 | CTCCAGCTAAGGGCAGGG | 1277 | c.1012_1029 | CAGGAAGATGTAGACATC | 1314 |
| c.976_993 | CCTCCAGCTAAGGGCAGG | 1278 | c.1013_1030 | CCAGGAAGATGTAGACAT | 1315 |
| c.977_994 | ACCTCCAGCTAAGGGCAG | 1279 | c.1014_1031 | CCCAGGAAGATGTAGACA | 1316 |
| c.978_995 | GACCTCCAGCTAAGGGCA | 1280 | c.1015_1032 | GCCCAGGAAGATGTAGAC | 1317 |
| c.979_996 | CGACCTCCAGCTAAGGGC | 1281 | c.1016_1033 | GGCCCAGGAAGATGTAGA | 1318 |

| Sequence in cDNA to which AON anneals for intron 6 exclusion | AON sequence 5' -> 3' | Seq ID | Sequence in cDNA to which AON anneals for intron 6 exclusion | AON sequence 5' -> 3' | Seq ID |
|---|---|---|---|---|---|
| c.1017_1034 | GGGCCCAGGAAGATGTAG | 1319 | c.1054_1071 | AACGTCCAGGTACTGCTG | 1356 |
| c.1018_1035 | TGGGCCCAGGAAGATGTA | 1320 | c.1055_1072 | CAACGTCCAGGTACTGCT | 1357 |
| c.1019_1036 | CTGGGCCCAGGAAGATGT | 1321 | c.1056_1073 | ACAACGTCCAGGTACTGC | 1358 |
| c.1020_1037 | TCTGGGCCCAGGAAGATG | 1322 | c.1057_1074 | CACAACGTCCAGGTACTG | 1359 |
| c.1021_1038 | CTCTGGGCCCAGGAAGAT | 1323 | c.1058_1075 | CCACAACGTCCAGGTACT | 1360 |
| c.1022_1039 | GCTCTGGGCCCAGGAAGA | 1324 | c.1059_1075+1 | CCCACAACGTCCAGGTAC | 1361 |
| c.1023_1040 | GGCTCTGGGCCCAGGAAG | 1325 | c.1060_1075+2 | ACCCACAACGTCCAGGTA | 1362 |
| c.1024_1041 | GGGCTCTGGGCCCAGGAA | 1326 | c.1061_1075+3 | TACCCACAACGTCCAGGT | 1363 |
| c.1025_1042 | TGGGCTCTGGGCCAGGA | 1327 | c.1062_1075+4 | CTACCCACAACGTCCAGG | 1364 |
| c.1026_1043 | TTGGGCTCTGGGCCCAGG | 1328 | c.1063_1075+5 | CCTACCCACAACGTCCAG | 1365 |
| c.1027_1044 | CTTGGGCTCTGGGCCCAG | 1329 | c.1064_1075+6 | CCCTACCCACAACGTCCA | 1366 |
| c.1028_1045 | TCTTGGGCTCTGGGCCCA | 1330 | c.1065_1075+7 | GCCCTACCCACAACGTCC | 1367 |
| c.1029_1046 | CTCTTGGGCTCTGGGCCC | 1331 | c.1066_1075+8 | GGCCCTACCCACAACGTC | 1368 |
| c.1030_1047 | GCTCTTGGGCTCTGGGCC | 1332 | c.1067_1075+9 | AGGCCCTACCCACAACGT | 1369 |
| c.1031_1048 | CGCTCTTGGGCTCTGGGC | 1333 | c.1068_1075+10 | CAGGCCCTACCCACAACG | 1370 |
| c.1032_1049 | ACGCTCTTGGGCTCTGGG | 1334 | c.1069_1075+11 | GCAGGCCCTACCCACAAC | 1371 |
| c.1033_1050 | CACGCTCTTGGGCTCTGG | 1335 | c.1070_1075+12 | AGCAGGCCCTACCCACAA | 1372 |
| c.1034_1051 | CCACGCTCTTGGGCTCTG | 1336 | c.1071_1075+13 | GAGCAGGCCCTACCCACA | 1373 |
| c.1035_1052 | ACCACGCTCTTGGGCTCT | 1337 | c.1072_1075+14 | GGAGCAGGCCCTACCCAC | 1374 |
| c.1036_1053 | CACCACGCTCTTGGGCTC | 1338 | c.1073_1075+15 | GGGAGCAGGCCCTACCCA | 1375 |
| c.1037_1054 | GCACCACGCTCTTGGGCT | 1339 | c.1074_1075+16 | AGGGAGCAGGCCCTACCC | 1376 |
| c.1038_1055 | TGCACCACGCTCTTGGGC | 1340 | c.1075_1075+17 | CAGGGAGCAGGCCCTACC | 1377 |
| c.1039_1056 | CTGCACCACGCTCTTGGG | 1341 | c.1075+1_+18 | CCAGGGAGCAGGCCCTAC | 1378 |
| c.1040_1057 | GCTGCACCACGCTCTTGG | 1342 | c.1075+2_+19 | GCCAGGGAGCAGGCCCTA | 1379 |
| c.1041_1058 | TGCTGCACCACGCTCTTG | 1343 | c.1075+3_+20 | GGCCAGGGAGCAGGCCCT | 1380 |
| c.1042_1059 | CTGCTGCACCACGCTCTT | 1344 | c.1075+4_+21 | CGGCCAGGGAGCAGGCCC | 1381 |
| c.1043_1060 | ACTGCTGCACCACGCTCT | 1345 | c.1075+5_+22 | GCGGCCAGGGAGCAGGCC | 1382 |
| c.1044_1061 | TACTGCTGCACCACGCTC | 1346 | c.1075+6_+23 | CGCGGCCAGGGAGCAGGC | 1383 |
| c.1045_1062 | GTACTGCTGCACCACGCT | 1347 | c.1075+7_+24 | CCGCGGCCAGGGAGCAGG | 1384 |
| c.1046_1063 | GGTACTGCTGCACCACGC | 1348 | c.1075+8_+25 | GCCGCGGCCAGGGAGCAG | 1385 |
| c.1047_1064 | AGGTACTGCTGCACCACG | 1349 | c.1075+9_+26 | GGCCGCGGCCAGGGAGCA | 1386 |
| c.1048_1065 | CAGGTACTGCTGCACCAC | 1350 | c.1075+10_+27 | GGGCCGCGGCCAGGGAGC | 1387 |
| c.1049_1066 | CCAGGTACTGCTGCACCA | 1351 | c.1075+11_+28 | GGGGCCGCGGCCAGGGAG | 1388 |
| c.1050_1067 | TCCAGGTACTGCTGCACC | 1352 | c.1075+12_+29 | GGGGGCCGCGGCCAGGGA | 1389 |
| c.1051_1068 | GTCCAGGTACTGCTGCAC | 1353 | c.1075+13_+30 | CGGGGGCCGCGGCCAGGG | 1390 |
| c.1052_1069 | CGTCCAGGTACTGCTGCA | 1354 | c.1075+14_+31 | GCGGGGCCGCGGCCAGG | 1391 |
| c.1053_1070 | ACGTCCAGGTACTGCTGC | 1355 | c.1075+15_+32 | GGCGGGGCCGCGGCCAG | 1392 |

-continued

| Sequence in cDNA to which AON anneals for intron 6 exclusion | AON sequence 5' -> 3' | Seq ID |
|---|---|---|
| c.1075+16_+33 | GGGCGGGGGCCGCGGCCA | 1393 |
| c.1075+17_+34 | GGGGCGGGGGCCGCGGCC | 1394 |
| c.1075+18_+35 | TGGGGCGGGGGCCGCGGC | 1395 |
| c.1075+19_+36 | TTGGGGCGGGGGCCGCGG | 1396 |
| c.1075+20_+37 | CTTGGGGCGGGGGCCGCG | 1397 |
| c.1075+21_+38 | CCTTGGGGCGGGGGCCGC | 1398 |
| c.1075+22_+39 | GCCTTGGGGCGGGGGCCG | 1399 |
| c.1075+23_+40 | AGCCTTGGGGCGGGGGCC | 1400 |
| c.1075+24_1076-39 | GAGCCTTGGGGCGGGGGC | 1401 |
| c.1075+25_1076-38 | GGAGCCTTGGGGCGGGGG | 1402 |
| c.1075+26_1076-37 | GGGAGCCTTGGGGCGGGG | 1403 |
| c.1075+27_1076-36 | AGGGAGCCTTGGGGCGGG | 1404 |
| c.1075+28_1076-35 | GAGGGAGCCTTGGGGCGG | 1405 |
| c.1075+29_1076-34 | GGAGGGAGCCTTGGGGCG | 1406 |
| c.1075+30_1076-33 | AGGAGGGAGCCTTGGGGC | 1407 |
| c.1075+31_1076-32 | GAGGAGGGAGCCTTGGGG | 1408 |
| c.1075+32_1076-31 | GGAGGAGGGAGCCTTGGG | 1409 |
| c.1075+33_1076-30 | GGGAGGAGGGAGCCTTGG | 1410 |
| c.1075+34_1076-29 | AGGGAGGAGGGAGCCTTG | 1411 |
| c.1075+35_1076-28 | GAGGGAGGAGGGAGCCTT | 1412 |
| c.1075+36_1076-27 | GGAGGGAGGAGGGAGCCT | 1413 |
| c.1075+37_1076-26 | GGGAGGGAGGAGGGAGCC | 1414 |
| c.1075+38_1076-25 | AGGGAGGGAGGAGGGAGC | 1415 |
| c.1075+39_1076-24 | GAGGGAGGGAGGAGGGAG | 1416 |
| c.1075+40_1076-23 | TGAGGGAGGGAGGAGGGA | 1417 |
| c.1076-39_-22 | ATGAGGGAGGGAGGAGGG | 1418 |
| c.1076-38_-21 | CATGAGGGAGGGAGGAGG | 1419 |
| c.1076-37_-20 | TCATGAGGGAGGGAGGAG | 1420 |
| c.1076-36_-19 | TTCATGAGGGAGGGAGGA | 1421 |
| c.1076-35_-18 | CTTCATGAGGGAGGGAGG | 1422 |
| c.1076-34_-17 | ACTTCATGAGGGAGGGAG | 1423 |
| c.1076-33_-16 | GACTTCATGAGGGAGGGA | 1424 |
| c.1076-32_-15 | CGACTTCATGAGGGAGGG | 1425 |
| c.1076-31_-14 | CCGACTTCATGAGGGAGG | 1426 |
| c.1076-30_-13 | GCCGACTTCATGAGGGAG | 1427 |
| c.1076-29_-12 | CGCCGACTTCATGAGGGA | 1428 |
| c.1076-28_-11 | ACGCCGACTTCATGAGGG | 1429 |
| c.1076-27_-10 | AACGCCGACTTCATGAGG | 1430 |
| c.1076-26_-9 | CAACGCCGACTTCATGAG | 1431 |
| c.1076-25_-8 | CCAACGCCGACTTCATGA | 1432 |
| c.1076-24_-7 | GCCAACGCCGACTTCATG | 1433 |
| c.1076-23_-6 | GGCCAACGCCGACTTCAT | 1434 |
| c.1076-22_-5 | AGGCCAACGCCGACTTCA | 1435 |
| c.1076-21_-4 | CAGGCCAACGCCGACTTC | 1436 |
| c.1076-20_-3 | GCAGGCCAACGCCGACTT | 1437 |
| c.1076-19_-2 | TGCAGGCCAACGCCGACT | 1438 |
| c.1076-18_-1 | CTGCAGGCCAACGCCGAC | 1439 |
| c.1076-17_1076 | CCTGCAGGCCAACGCCGA | 1440 |
| c.1076-16_1077 | TCCTGCAGGCCAACGCCG | 1441 |
| c.1076-15_1078 | ATCCTGCAGGCCAACGCC | 1442 |
| c.1076-14_1079 | TATCCTGCAGGCCAACGC | 1443 |
| c.1076-13_1080 | GTATCCTGCAGGCCAACG | 1444 |
| c.1076-12_1081 | GGTATCCTGCAGGCCAAC | 1445 |
| c.1076-11_1082 | GGGTATCCTGCAGGCCAA | 1446 |
| c.1076-10_1083 | CGGGTATCCTGCAGGCCA | 1447 |
| c.1076-9_1084 | ACGGGTATCCTGCAGGCC | 1448 |
| c.1076-8_1085 | AACGGGTATCCTGCAGGC | 1449 |
| c.1076-7_1086 | GAACGGGTATCCTGCAGG | 1450 |
| c.1076-6_1087 | TGAACGGGTATCCTGCAG | 1451 |
| c.1076-5_1088 | ATGAACGGGTATCCTGCA | 1452 |
| c.1076-4_1089 | CATGAACGGGTATCCTGC | 1453 |
| c.1076-3_1090 | GCATGAACGGGTATCCTG | 1454 |
| c.1076-2_1091 | GGCATGAACGGGTATCCT | 1455 |
| c.1076-1_1092 | CGGCATGAACGGGTATCC | 1456 |
| c.1076_1093 | GCGGCATGAACGGGTATC | 1457 |
| c.1077_1094 | GGCGGCATGAACGGGTAT | 1458 |
| c.1078_1095 | TGGCGGCATGAACGGGTA | 1459 |
| c.1079_1096 | ATGGCGGCATGAACGGGT | 1460 |
| c.1080_1097 | TATGGCGGCATGAACGGG | 1461 |
| c.1081_1098 | GTATGGCGGCATGAACGG | 1462 |
| c.1082_1099 | AGTATGGCGGCATGAACG | 1463 |
| c.1083_1100 | CAGTATGGCGGCATGAAC | 1464 |
| c.1084_1101 | CCAGTATGGCGGCATGAA | 1465 |
| c.1085_1102 | CCCAGTATGGCGGCATGA | 1466 |

-continued

| Sequence in cDNA to which AON anneals for intron 6 exclusion | AON sequence 5' -> 3' | Seq ID |
|---|---|---|
| c.1086_1103 | CCCCAGTATGGCGGCATG | 1467 |
| c.1087_1104 | GCCCCAGTATGGCGGCAT | 1468 |
| c.1088_1105 | GGCCCCAGTATGGCGGCA | 1469 |
| c.1089_1106 | AGGCCCCAGTATGGCGGC | 1470 |
| c.1090_1107 | CAGGCCCCAGTATGGCGG | 1471 |
| c.1091_1108 | CCAGGCCCCAGTATGGCG | 1472 |
| c.1092_1109 | CCCAGGCCCCAGTATGGC | 1473 |
| c.1093_1110 | GCCCAGGCCCCAGTATGG | 1474 |
| c.1094_1111 | AGCCCAGGCCCCAGTATG | 1475 |
| c.1095_1112 | AAGCCCAGGCCCCAGTAT | 1476 |
| c.1096_1113 | GAAGCCCAGGCCCCAGTA | 1477 |
| c.1097_1114 | GGAAGCCCAGGCCCCAGT | 1478 |
| c.1098_1115 | TGGAAGCCCAGGCCCCAG | 1479 |
| c.1099_1116 | GTGGAAGCCCAGGCCCCA | 1480 |
| c.1100_1117 | GGTGGAAGCCCAGGCCCC | 1481 |
| c.1101_1118 | AGGTGGAAGCCCAGGCCC | 1482 |
| c.1102_1119 | CAGGTGGAAGCCCAGGCC | 1483 |
| c.1103_1120 | ACAGGTGGAAGCCCAGGC | 1484 |
| c.1104_1121 | CACAGGTGGAAGCCCAGG | 1485 |
| c.1105_1122 | GCACAGGTGGAAGCCCAG | 1486 |
| c.1106_1123 | GGCACAGGTGGAAGCCCA | 1487 |
| c.1107_1124 | CGGCACAGGTGGAAGCCC | 1488 |
| c.1108_1125 | GCGGCACAGGTGGAAGCC | 1489 |
| c.1109_1126 | AGCGGCACAGGTGGAAGC | 1490 |
| c.1110_1127 | CAGCGGCACAGGTGGAAG | 1491 |
| c.1111_1128 | CCAGCGGCACAGGTGGAA | 1492 |
| c.1112_1129 | CCCAGCGGCACAGGTGGA | 1493 |
| c.1113_1130 | CCCCAGCGGCACAGGTGG | 1494 |
| c.1114_1131 | GCCCCAGCGGCACAGGTG | 1495 |
| c.1115_1132 | AGCCCCAGCGGCACAGGT | 1496 |
| c.1116_1133 | TAGCCCCAGCGGCACAGG | 1497 |
| c.1117_1134 | GTAGCCCCAGCGGCACAG | 1498 |
| c.1118_1135 | AGTAGCCCCAGCGGCACA | 1499 |
| c.1119_1136 | GAGTAGCCCCAGCGGCAC | 1500 |
| c.1120_1137 | GGAGTAGCCCCAGCGGCA | 1501 |
| c.1121_1138 | AGGAGTAGCCCCAGCGGC | 1502 |
| c.1122_1139 | GAGGAGTAGCCCCAGCGG | 1503 |
| c.1123_1140 | GGAGGAGTAGCCCCAGCG | 1504 |
| c.1124_1141 | TGGAGGAGTAGCCCCAGC | 1505 |
| c.1125_1142 | GTGGAGGAGTAGCCCCAG | 1506 |
| c.1126_1143 | GGTGGAGGAGTAGCCCCA | 1507 |
| c.1127_1144 | CGGTGGAGGAGTAGCCCC | 1508 |
| c.1128_1145 | GCGGTGGAGGAGTAGCCC | 1509 |
| c.1129_1146 | AGCGGTGGAGGAGTAGCC | 1510 |
| c.1130_1147 | TAGCGGTGGAGGAGTAGC | 1511 |
| c.1131_1148 | ATAGCGGTGGAGGAGTAG | 1512 |
| c.1132_1149 | GATAGCGGTGGAGGAGTA | 1513 |
| c.1133_1150 | TGATAGCGGTGGAGGAGT | 1514 |
| c.1134_1151 | GTGATAGCGGTGGAGGAG | 1515 |
| c.1135_1152 | GGTGATAGCGGTGGAGGA | 1516 |
| c.1136_1153 | GGGTGATAGCGGTGGAGG | 1517 |
| c.1137_1154 | CGGGTGATAGCGGTGGAG | 1518 |
| c.1138_1155 | GCGGGTGATAGCGGTGGA | 1519 |
| c.1139_1156 | GGCGGGTGATAGCGGTGG | 1520 |
| c.1140_1157 | TGGCGGGTGATAGCGGTG | 1521 |
| c.1141_1158 | CTGGCGGGTGATAGCGGT | 1522 |
| c.1142_1159 | CCTGGCGGGTGATAGCGG | 1523 |
| c.1143_1160 | ACCTGGCGGGTGATAGCG | 1524 |
| c.1144_1161 | CACCTGGCGGGTGATAGC | 1525 |
| c.1145_1162 | CCACCTGGCGGGTGATAG | 1526 |
| c.1146_1163 | ACCACCTGGCGGGTGATA | 1527 |
| c.1147_1164 | CACCACCTGGCGGGTGAT | 1528 |
| c.1148_1165 | CCACCACCTGGCGGGTGA | 1529 |
| c.1149_1166 | TCCACCACCTGGCGGGTG | 1530 |
| c.1150_1167 | CTCCACCACCTGGCGGGT | 1531 |
| c.1151_1168 | TCTCCACCACCTGGCGGG | 1532 |
| c.1152_1169 | TTCTCCACCACCTGGCGG | 1533 |
| c.1153_1170 | GTTCTCCACCACCTGGCG | 1534 |
| c.1154_1171 | TGTTCTCCACCACCTGGC | 1535 |
| c.1155_1172 | ATGTTCTCCACCACCTGG | 1536 |
| c.1156_1173 | CATGTTCTCCACCACCTG | 1537 |
| c.1157_1174 | TCATGTTCTCCACCACCT | 1538 |
| c.1158_1175 | GTCATGTTCTCCACCACC | 1539 |
| c.1159_1176 | GGTCATGTTCTCCACCAC | 1540 |

| Sequence in cDNA to which AON anneals for intron 6 exclusion | AON sequence 5' -> 3' | Seq ID |
|---|---|---|
| c.1160_1177 | TGGTCATGTTCTCCACCA | 1541 |
| c.1161_1178 | CTGGTCATGTTCTCCACC | 1542 |
| c.1162_1179 | CCTGGTCATGTTCTCCAC | 1543 |
| c.1163_1180 | CCCTGGTCATGTTCTCCA | 1544 |
| c.1164_1181 | GCCCTGGTCATGTTCTCC | 1545 |
| c.1165_1182 | GGCCCTGGTCATGTTCTC | 1546 |
| c.1166_1183 | GGGCCCTGGTCATGTTCT | 1547 |
| c.1167_1184 | TGGGCCCTGGTCATGTTC | 1548 |
| c.1168_1185 | GTGGGCCCTGGTCATGTT | 1549 |
| c.1169_1186 | AGTGGGCCCTGGTCATGT | 1550 |
| c.1170_1187 | AAGTGGGCCCTGGTCATG | 1551 |
| c.1171_1188 | GAAGTGGGCCCTGGTCAT | 1552 |
| c.1172_1189 | GGAAGTGGGCCCTGGTCA | 1553 |
| c.1173_1190 | GGGAAGTGGGCCCTGGTC | 1554 |
| c.1174_1191 | GGGGAAGTGGGCCCTGGT | 1555 |
| c.1175_1192 | GGGGGAAGTGGGCCCTGG | 1556 |
| c.1176_1193 | AGGGGGAAGTGGGCCCTG | 1557 |
| c.1177_1194 | CAGGGGGAAGTGGGCCCT | 1558 |
| c.1178_1194+1 | CCAGGGGGAAGTGGGCCC | 1559 |
| c.1179_1194+2 | ACCAGGGGGAAGTGGGCC | 1560 |
| c.1180_1194+3 | CACCAGGGGGAAGTGGGC | 1561 |
| c.1181_1194+4 | TCACCAGGGGGAAGTGGG | 1562 |
| c.1182_1194+5 | CTCACCAGGGGGAAGTGG | 1563 |
| c.1183_1194+6 | ACTCACCAGGGGGAAGTG | 1564 |
| c.1184_1194+7 | AACTCACCAGGGGGAAGT | 1565 |
| c.1185_1194+8 | CAACTCACCAGGGGGAAG | 1566 |
| c.1186_1194+9 | CCAACTCACCAGGGGGAA | 1567 |
| c.1187_1194+10 | CCCAACTCACCAGGGGGA | 1568 |
| c.1188_1194+11 | CCCCAACTCACCAGGGGG | 1569 |
| c.1189_1194+12 | ACCCCAACTCACCAGGGG | 1570 |
| c.1190_1194+13 | CACCCCAACTCACCAGGG | 1571 |
| c.1191_1194+14 | CCACCCCAACTCACCAGG | 1572 |
| c.1192_1194+15 | ACCACCCCAACTCACCAG | 1573 |
| c.1193_1194+16 | CACCACCCCAACTCACCA | 1574 |
| c.1194_1194+17 | CCACCACCCCAACTCACC | 1575 |
| c.1194+1_+18 | GCCACCACCCCAACTCAC | 1576 |
| c.1194+2_+19 | TGCCACCACCCCAACTCA | 1577 |
| c.1194+3_+20 | CTGCCACCACCCCAACTC | 1578 |
| c.1194+4_+21 | CCTGCCACCACCCCAACT | 1579 |
| c.1194+5_+22 | CCCTGCCACCACCCCAAC | 1580 |
| c.1194+6_+23 | CCCCTGCCACCACCCCAA | 1581 |
| c.1194+7_+24 | TCCCCTGCCACCACCCCA | 1582 |
| c.1194+8_+25 | CTCCCCTGCCACCACCCC | 1583 |

In the above examples the sequences are 18, 21 and 25 nucleotides long however longer variants or shorter fragment are also envisioned. In a preferred embodiment of the invention and/or embodiments thereof of the present invention and/or embodiments thereof the antisense oligomeric compounds are selected from the group of SEQ ID NO: 541-1583 and fragments and variants thereof having at least 80% sequence identity. In a preferred embodiment of the invention and/or embodiments thereof of the present invention and/or embodiments thereof the antisense oligomeric compounds are selected from the group of SEQ ID NO: 541-1583 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 541-1583.

Or sequences that are at least 80% identical to SEQ ID NO: 541-1583. Preferably at least 85% identical to SEQ ID NO: 541-1583, more preferably at least 88% identical to SEQ ID NO: 541-1583, more preferably at least 90% identical to SEQ ID NO: 541-1583. more preferably at least 91% identical to SEQ ID NO: 541-1583, more preferably at least 92% identical to SEQ ID NO: 541-1583, more preferably at least 93% identical to SEQ ID NO: 541-1583, more preferably at least 94% identical to SEQ ID NO: 541-1583, more preferably at least 95% identical to SEQ ID NO: 541-1583, more preferably at least 96% identical to SEQ ID NO: 541-1583, more preferably at least 97% identical to SEQ ID NO: 541-1583, more preferably at least 98% identical to SEQ ID NO: 541-1583, more preferably at least 99% identical to SEQ ID NO: 541-1583.

In a preferred embodiment of the invention and/or embodiments thereof of the present invention and/or embodiments thereof the antisense oligomeric compounds are selected from the group of fragments SEQ ID NO: 541-1583, wherein the fragment is 16, 17, 18, 19, 20, 21, 22, 23, or 24 nucleotides long. In a preferred embodiment of the invention and/or embodiments thereof of the present invention and/or embodiments thereof the antisense oligomeric compounds are selected from the group of fragments SEQ ID NO: 541-1583, wherein the fragment is 17, 18, 19, 20, 21, or 22 nucleotides long. In a preferred embodiment of the invention and/or embodiments thereof of the present invention and/or embodiments thereof the antisense oligomeric compounds are selected from the group of fragments SEQ ID NO: 541-1583, wherein the fragment is 19, 20, or 21 nucleotides long.

The antisense oligomeric compound may be also be complementary to a genomic nucleic acid sequence of GAA gene targeting the location that comprises the position of a mutation selected from the group c.-32-13T>G (IVS1), c.1636+5G>T, c.525delT, c.-32-3C>G, c. 1551+1G>A, c.1075G>A, c.1552-3C>G, c.1437G>A, c.1256A>T, c.1551+1G>T.

Preferably the genomic nucleic acid sequence is pre-mRNA.

In a preferred embodiment of the invention and/or embodiments thereof, the antisense oligomeric compound may be also be complementary to a genomic nucleic acid sequence of GAA gene targeting the location that comprises the position of a mutation selected from the group comprising
c.-32-3C>G, c.-32-13T>G, c.-32-102T>C, c.-32-56C>T, c.-32-46G>A, c.-32-28C>A, c.-32-28C>T, c.-32-21G>A, c.7G>A, c.11G>A, c.15_17 AAA, c.17C>T, c.19_21 AAA, c.26_28 AAA, c.33_35 AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, and c.1552-30.

Preferably the genomic nucleic acid sequence is pre-mRNA

In a preferred embodiment of the invention and/or embodiments thereof, the antisense oligomeric compound may be also be complementary to a genomic nucleic acid sequence of GAA gene targeting the location that comprises the position of a mutation selected from the group comprising c.17C>T c.469C>T c.546+23C>A, c.-32-102T>C c.-32-56C>T c.11G>A c.112G>A c.137C>T.

In a preferred embodiment of the invention and/or embodiments thereof, the antisense oligomeric compound may be also be complementary to a genomic nucleic acid sequence of GAA gene targeting the location that comprises the position of a mutation selected from the group comprising c.17C>T c.469C>T c.546+23C>A.

In a preferred embodiment of the invention and/or embodiments thereof, the antisense oligomeric compound may be also be complementary to a genomic nucleic acid sequence of GAA gene targeting the location that comprises the position of a mutation selected from the group comprising c.-32-102T>C c.-32-56C>T c.11G>A c.112G>A c.137C>T.

Most preferred are antisense oligomeric compounds that are complementary to a genomic nucleic acid sequence of GAA gene targeting the location that comprises the position of a mutation c.-32-13T>G (IVS1).

Most preferred are antisense oligomeric compounds that are complementary to a genomic nucleic acid sequence of GAA gene targeting the location that comprises the position of a mutation c.-32-3C>G, c.1256A>T, c.1551+1G>T, c.546G>T.

Most preferred are antisense oligomeric compounds that are complementary to a genomic nucleic acid sequence of GAA gene targeting the location that comprises the position of a mutation c.-32-3C>G.

Most preferred are antisense oligomeric compounds that are complementary to a genomic nucleic acid sequence of GAA gene targeting SEQ ID NO: 1.

(SEQ ID NO: 1)
GCTCTGCACTCCCCTGCTGGAGCTTTTCTCGCCCTTCCTTCTGGCCCTCT

CCCCA.

In a preferred embodiment of the invention and/or embodiments thereof, the antisense oligomeric compound are 8 to 80 nucleotides in length, 9 to 50 nucleotides in length, 10 to 30 nucleotides in length, 12 to 30 nucleotides in length, 15 to 25 nucleotides in length or about 20 nucleotides in length. One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 80 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 50 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleotides.

In one embodiment of the invention and/or embodiments thereof, the antisense compounds comprise 13 to 30 nucleotides. One having ordinary skill in the art will appreciate that this embodies antisense compounds of 13, 14, 15, 16, 17, 18, 19, 20, 21, 22, 23, 24, 25, 26, 27, 28, 29 or 30 nucleotides.

In one embodiment of the invention and/or embodiments thereof, the antisense compounds comprise 20 to 30 nucleotides. One having ordinary skill in the art will appreciate that this embodies antisense compounds of 20, 21, 22, 23, 24, 25, 26, 27, 28, 29, or 30 nucleotides.

In one embodiment of the invention and/or embodiments thereof, the antisense compounds comprise 15 to 25 nucleotides. One having ordinary skill in the art will appreciate that this embodies antisense compounds of 15, 16, 17, 18, 19, 20, 21, 22, 23, 24 or 25.

In one embodiment of the invention and/or embodiments thereof, the antisense compounds comprise 20 nucleotides.

In one embodiment of the invention and/or embodiments thereof, the antisense compounds comprise 19 nucleotides.

In one embodiment of the invention and/or embodiments thereof, the antisense compounds comprise 18 nucleotides.

In one embodiment of the invention and/or embodiments thereof, the antisense compounds comprise 17 nucleotides.

In one embodiment of the invention and/or embodiments thereof, the antisense compounds comprise 16 nucleotides.

In one embodiment of the invention and/or embodiments thereof, the antisense compounds comprise 15 nucleotides.

In one embodiment of the invention and/or embodiments thereof, the antisense compounds comprise 14 nucleotides.

In one embodiment of the invention and/or embodiments thereof, the antisense compounds comprise 13 nucleotides.

In one embodiment of the invention and/or embodiments thereof, compounds include oligonucleotide sequences that comprise at least the 8 consecutive nucleotides from one of the antisense compounds as claimed.

Preferably at least 9 consecutive nucleotides from one of the antisense compounds as claimed, more preferably at least 10 consecutive nucleotides from one of the antisense compounds as claimed, more preferably at least 11 consecutive nucleotides from one of the antisense compounds as claimed, more preferably at least 12 consecutive nucleotides from one of the antisense compounds as claimed, more preferably at least 13 consecutive nucleotides from one of the antisense compounds as claimed, more preferably at least 14 consecutive nucleotides from one of the antisense compounds as claimed, more preferably at least 15 consecutive nucleotides from one of the antisense compounds as claimed, more preferably at least 16 consecutive nucleotides from one of the antisense compounds as claimed, more preferably at least 17 consecutive nucleotides from one of the antisense compounds as claimed, more preferably at least 18 consecutive nucleotides from one of the antisense compounds as claimed, more preferably at least 19 consecutive nucleotides from one of the antisense compounds as claimed, more preferably at least 20 consecutive nucleotides from one of the antisense compounds as claimed.

Any remaining nucleotides from the oligonuclotides may be oligonucleotides that improve resistance to Rnase H, cell-targeting sequences, cell penetrating sequences, marker sequences or any other sequences.

One having skill in the art armed with the antisense compounds disclosed herein will be able, without undue experimentation, to identify further antisense compounds.

In order for an antisense oligonucleotide to achieve therapeutic success, oligonucleotide chemistry must allow for adequate cellular uptake (Kurreck, J. (2003) Eur. J. Biochem. 270:1628-1644). Splicing oligonucleotides have traditionally been comprised of uniform modifications that render the oligonucleotide RNA-like, and thus resistant to cleavage by RNase H, which is critical to achieve modulation of splicing. Provided herein are antisense compounds for modulation of splicing.

In a preferred embodiment of the invention and/or embodiments thereof, the antisense compounds are chimeric, with regions of RNA-like and DNA-like chemistry. Despite regions of DNA-like chemistry, the chimeric compounds are preferably RNase H-resistant and effectively modulate splicing of target mRNA in vitro and in vivo. In another preferred embodiment the disclosed antisense oligomeric compounds show enhanced cellular uptake and greater pharmacologic activity compared with uniformly modified oligonucleotides.

Contemplated herein are antisense oligomeric compound which are targeted to a splice site of a target mRNA or to splicing repressor sequences, or to splicing enhancer sequences, preferably to splicing repressor sequences. Splice sites include aberrant and cryptic splice sites.

One skilled in the art recognizes that the inclusion of mismatches is possible without eliminating the activity of the antisense compound. Compounds provided herein are therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

It is known by a skilled person that hybridization to a target mRNA depends on the conditions. "Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences would be considered identical as they both pair with adenine. This identity may be over the entire length of the oligomeric compound, or in a portion of the antisense compound (e.g., nucleotides 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleotides 2-17 of a 20-mer is 80% identical to the 20-mer. Alternatively, a 20-mer containing four nucleotides not identical to the 20-mer is also 80% identical to the 20-mer. A 14-mer having the same sequence as nucleotides 1-14 of an 18-mer is 78% identical to the 18-mer. Such calculations are well within the ability of those skilled in the art.

The percent identity is based on the percent of nucleotides in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. In a preferred embodiment of the invention and/or embodiments thereof, the oligonucleotides are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7310, 1992, incorporated herein by reference), a series of antisense oligomeric compounds of 13-25 nucleotides in length were tested for their ability to induce cleavage of a target RNA. Antisense oligomeric compounds of 25 nucleotides in length with 8 or 11 mismatch bases near the ends of the antisense oligomeric compounds were able to direct specific cleavage of the target mRNA, albeit to a lesser extent than the antisense oligomeric compounds that contained no mismatches. Similarly, target specific cleavage was achieved using a 13 nucleobase antisense oligomeric compounds, including those with 1 or 3 mismatches. Maher and Dolnick (Nuc. Acid. Res. 16:3341-3358, 1988, incorporated herein by reference) tested a series of tandem 14 nucleobase antisense oligomeric compounds, and a 28 and 42 nucleobase antisense oligomeric compounds comprised of the sequence of two or three of the tandem antisense oligomeric compounds, respectively, for their ability to arrest translation of human DHFR in a rabbit reticulocyte assay. Each of the three 14 nucleobase antisense oligomeric compounds alone were able to inhibit translation, albeit at a more modest level than the 28 or 42 nucleobase antisense oligomeric compounds. It is understood that antisense compounds can vary in length and percent complementarity to the target provided that they maintain the desired activity. Methods to determine desired activity are disclosed herein and well known to those skilled in the art. In a preferred embodiment of the invention and/or embodiments thereof, the antisense oligomeric compounds have at least 80% complementarity to the target mRNA, more preferably at least 85% complementarity to the target mRNA, more preferably at least 90% complementarity to the target mRNA, more preferably at least 95% complementarity to the target mRNA, more preferably at least 96% complementarity to the target mRNA, more preferably at least 97% complementarity to the target mRNA, more preferably at least 98% complementarity to the target mRNA, more preferably at least 99% complementarity to the target mRNA, more preferably at least 100% complementarity to the target mRNA.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R1)(R2) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH2)2-O-2' bridge); and substituted sugars, especially 2'-substituted sugars having a 2'-F, 2'-OCH2 or a 2'-O(CH2)2-OCH3 substituent group. Sugars can also be replaced with sugar mimetic groups among others. Methods for the preparations of modified sugars are well known to those skilled in the art. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Also suitable are O((CH2)nO)mCH3, O(CH2)nOCH3, O(CH2)nNH2, O(CH2)nCH3, O(CH2)nONH2, and O(CH2)nON((CH2)nCH3)2, where n and m are from 1 to about 10. Other oligonucleotides comprise one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504), i.e., an alkoxyalkoxy group. A further modification includes 2'-dimethylaminooxyethoxy, i.e., a O(CH2)2ON(CH3)2 group, also known as 2'-DMAOE, and 2'-dimethylaminoethoxyethoxy (also known in the art as 2'-O-dimethyl-amino-ethoxy-ethyl or 2'-DMAEOE), i.e., 2'-O—(CH2)2-O—(CH2)2-N(CH3)2. Other modifications include 2'-methoxy (2'-O—CH3), 2'-aminopropoxy (2'-OCH2CH2CH2NH2), 2'-allyl (2'-CH2-CH═CH2), 2'-O-allyl (2'-O—CH2-CH═CH2) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

In one aspect of the present invention oligomeric compounds include nucleosides modified to induce a 3'-endo sugar conformation. A nucleoside can incorporate modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

In the present invention there is a preference for an RNA type duplex (A form helix, predominantly 3'-endo) as they are RnasH resistant. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, one or more nucleosides may be modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

Preferred modification of the sugar are selected from the group consisting of 2'-O-methyl 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methyl or 2'-O-methoxyethyl.

Oligomeric compounds can also include nucleobase (often referred to in the art as heterocyclic base or simply as "base") modifications or substitutions. As used herein, "unmodified" or "natural" nucleotides include the purine bases adenine (A) and guanine (G), and the pyrimidine bases thymine (T), cytosine (C) and uracil (U). A "substitution" is the replacement of an unmodified or natural base with another unmodified or natural base. "Modified" nucleotides mean other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C[identical to]C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleotides include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleotides may also include those in which the purine or pyrimidine base is replaced with other heterocycles, for example 7-deaza-adenine, 7-deazaguanosine, 2-aminopyridine and 2-pyridone. Further nucleotides include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleotides are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleotides as well as other modified nucleotides include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention may also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., Nucleosides and Nucleotides, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta$Tm of up to 18° C. relative to 5-methyl cytosine, which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Modified internucleoside linkages, compared to natural phosphodiester linkages, can be used to alter, typically increase, nuclease resistance of the antisense compound. Internucleoside linkages having a chiral atom may be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

Suitable modified internucleoside linking groups are for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al., Nucleic Acids Research, 2003, 31(14), 4109-4118 and Dellinger et al., J. Am. Chem. Soc., 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., J. Am. Chem. Soc., 1994, 116, 3143-3144). N3'-P5'-phosphoramidates have been studied with some success in vivo to specifically down regulate the expression of the c-myc gene (Skorski et al., Proc. Natl. Acad. Sci., 1997, 94, 3966-3971; and Faira et al., Nat. Biotechnol., 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —CH2-NH—O—CH2-, —CH2-N(CH3)-O—CH2- (known as a methylene (methylimino) or MMI backbone), —CH2-O—N(CH3)-CH2-, —CH2-N(CH3)-N(CH3)-CH2- and —O—N(CH3)-CH2-CH2- (wherein the native phosphodiester internucleotide linkage is represented as —O—P(—O)(OH)—O—CH2-). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In a preferred embodiment of the invention and/or embodiments thereof the internucleoside linkage is phosphorothioate, or phosphorodiamidate It is further intended that multiple modifications can be made to one or more of the oligomeric compounds of the invention at multiple sites of one or more monomeric subunits (nucleosides are suitable) and/or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

In a preferred embodiment of the invention and/or embodiments thereof, the oligomeric compounds of the present invention are morpholino phosphorothioates, or phosphorodiamidate morpholino.

Another group of oligomeric compounds includes oligonucleotide mimetics. As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art. The heterocyclic base moiety or a modified heterocyclic base moiety is preferably maintained for hybridization with an appropriate target nucleic acid.

The compounds described herein may contain one or more asymmetric centers and thus give rise to enantiomers, diastereomers, and other stereoisomeric configurations that may be defined, in terms of absolute stereochemistry, as (R) or (S), [alpha] or [beta], or as (D) or (L) such as for amino acids et al. The present disclosure is meant to include all such possible isomers, as well as their racemic and optically pure forms.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleotides are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719, 262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule. A polyarginine tail may be a suitable for enhancing cell penetration.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound.

Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(—O)(N (CH3)2)-O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—CH2-) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10[deg.] C.), stability towards 3'-exonucleolytic degradation and good solubility properties. LNAs are commercially available from ProLigo (Paris, France and Boulder, Colo., USA).

An isomer of LNA that has also been studied is alpha-L-LNA which has been shown to have superior stability against a 3'-exonuclease. The alpha-L-LNAs were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11[deg.] C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sc U.S.A., 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Natl. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-alpha-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim Acta, 1997, 80, 2426-2439; Steffens et al., J. Am. Chem. Soc., 1999, 121, 3249-3255; Renneberg et al., J. Am. Chem. Soc., 2002, 124, 5993-6002; and Renneberg et al., Nucleic acids res., 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

In certain embodiments, oligomeric compounds, may be conjugated with a wide variety of different positively charged polymers. Examples of positively charged polymers include peptides, such as argine rich peptides (Examples of positively charged peptides that may be used in the practice of the invention include R9F2C; (RXR)4 XB (where X can be any amino acid); R5F2R4c; (RFF)3; Tat proteins, such as TAT sequence CYGRKKRRQRRR; and (RFF)3R), cationic polymers, such as dendrimeric octaguanindine polymer, and other positively charged molecules as known in the art for conjugation to antisense oligonucleotide compounds. In one embodiment of the invention and/or embodiments thereof, the antisense oligonucleotides are conjugated with positively charged polymer comprising a polymer having a molecular weight that is from about 1,000 to 20,000 Daltons, and preferably from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

In a preferred embodiment of the invention and/or embodiments thereof the oligomeric compounds are modified with cell penetrating sequences. Suitable cell penetrating sequences include cell penetrating peptides, such as TAT peptide, MPG, Pep-1, MAP, fusogenic, antimicrobial peptides (AMPs), bacteriocidal peptides, fungicidal peptides, virucidal peptides, Cell-penetrating peptides (CPPs) are short peptides that facilitate cellular uptake of the particles of the invention. The particle of the invention is associated with the CPP peptides either through chemical linkage via covalent bonds or through non-covalent interactions. The function of the CPPs are to deliver the particles into cells, a process that commonly occurs through endocytosis with the cargo delivered to the endosomes of living mammalian cells. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake.

An exemplary cell penetrating peptide is the trans-activating transcriptional activator (Tat) from Human Immunodeficiency Virus 1 (HIV-1) could be efficiently taken up from the surrounding media by numerous cell types in culture. Other cell penetrating peptides are MPG, Pep-1, transportan, penetratin, CADY, TP, TP10, arginine octamer. polyarginine sequences, Arg8, VP22 HSV-1 structural protein, SAP Proline-rich motifs, Vectocell® peptides, hCT (9-32), SynB, Pvec, and PPTG1. Cell penetrating peptides may be cationic, essentially containing clusters of polyarginine in their primary sequence or amphipathic. CPPs are generally peptides of less than 30 amino acids, derived from natural or unnatural protein or chimeric sequences.

In suitable embodiments, the oligomeric compounds are incorporated or otherwise associated with nanoparticles. Nanoparticles may suitably modified for targeting specific cells and optimised for penetrating cells. A skilled person is aware of methods to employ nanoparticles for oligomeric compounds delivery to cells.

In suitable embodiments of the present invention, the oligomeric compounds are modified with an endosomal escape agent moiety. The endocytic pathway is a major uptake mechanism of cells. Compounds taken up by the endocytic pathway become entrapped in endosomes and may be degraded by specific enzymes in the lysosome. This may be desired or not desired depending on the purpose. If taken up by the endosomes is not desired, endosomal escape agent may be used. Suitable endosomal escape agents may be chloroquine, TAT peptide.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytityl-2'-deoxy-N4-benzoyl-5-methylcytidine penultimate intermediate for 5-methyl dC amidite, (5'-O-(4,4'-Dimethoxytriphenylmethyl)-2'-deoxy-N4-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-

Dimethoxytrityl-2'-O-(2-methoxyethyl)-5-methylcytidine intermediate, 5'-O-dimethoxytrityl-2'-O-(2-methoxyethyl)-N<4>-benzoyl-5-methyl-cytidine penultimate intermediate, (5'-O-(4,4'-Dimethoxytriphenylmethyl)-2'-O-(2-methoxyethyl)-N<4>-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N<6>-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N<4>-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O<2>-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., Nucleic Acids Research, 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., J. Med. Chem., 1993, 36, 831-841) and U.S. Pat. No. 5,670,633.

2'-O-Methoxyethyl-substituted nucleoside amidites can be prepared routinely as per the methods of Martin, P., Helvetica Chimica Acta, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P-S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Methylenemethylimino linked oligonucleosides, also identified as MMI linked oligonucleosides, methylene dimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P—O or P—S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, 5,719,262, 6,559,279 and 6,762,281.

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound may vary from one at any site or the strategy can be used to prepare up to a full 2'-OH modified oligomeric compound.

The main RNA synthesis strategies that are presently being used commercially include 5'-[beta]-DMT-2'-O-t-butyldimethylsilyl (TBDMS), 5'-O-DMT-2'-[1(2-fluorophenyl)-4-methoxypiperidin-4-yl] (FPMP), 2'-O-[(triisopropylsilyl)oxy]methyl (2'-O—CH2-O—Si(iPr)3 (TOM), and the 5'-O-silyl ether-2'-ACE (5'-O-bis(trimethylsiloxy)cyclododecyloxysilyl ether (DOD)-2'-O-bis(2-acetoxyethoxy) methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting group from another strategy is also contemplated herein.

Chimeric oligonucleotides, chimeric oligonucleosides and mixed chimeric oligonucleotides/oligonucleosides can be synthesized according to U.S. Pat. No. 5,623,065.

Chimeric oligomeric compounds exhibiting enhanced cellular uptake and greater pharmacologic activity may be made in accordance to U.S. Pat. No. 8,501,703.

Another form of oligomeric compounds comprise tricyclo-DNA (tc-DNA) antisense oligonucleotides. Tricyclo-DNA nucleotides are nucleotides modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Antisense oligomeric compound that contains between 6-22 tricyclo nucleotides in length, in particular between 8-20 tricyclo nucleotides, more particularly between 10 and 18 or between 11 and 18 tricyclo nucleotides are suitable. See e.g. WO2010115993 for examples of tricyclo-DNA (tc-DNA) antisense oligonucleotides.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

In a preferred embodiment of the invention and/or embodiments thereof, the antisense compounds provided herein are resistant to RNase H degradation.

In one embodiment of the invention and/or embodiments thereof, the antisense compounds comprise at least one modified nucleotide. In another embodiment, the antisense compounds comprise a modified nucleotide at each position. In yet another embodiment, the antisense compounds are uniformly modified at each position.

Modulation of splicing can be assayed in a variety of ways known in the art. Target mRNA levels can be quantitated by, e.g., Northern blot analysis, competitive polymerase chain reaction (PCR), or real-time PCR. RNA analysis can be performed on total cellular RNA or poly(A)+mRNA by methods of RNA isolation are known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by a target mRNA can be quantitated in a variety of ways well known in the art, such as immunoprecipitation, Western blot analysis (immunoblotting), ELISA or fluorescence-activated cell sorting (FACS). Antibodies directed to a protein encoded by a target mRNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

The effect of the oligomeric compounds of the present invention may be analysed by RT PCT, qPCR, flanking exon PCR and/or a method comprising flanking exon PCR on each internal exon corresponding to the mRNA to obtain one or more flanking exon amplification products, and detecting the presence and length of the said flanking exon amplification products, quantifying of each protein encoding exon of said mRNA.

The oligomeric compounds provided herein may be utilized for therapeutics or research. Furthermore, antisense compounds, which are able to inhibit gene expression or modulate splicing with specificity, may be used to elucidate the function of particular genes or gene products or to distinguish between functions of various members of a biological pathway. In a preferred embodiment of the invention and/or embodiments thereof the oligomeric compounds are used for the treatment of Pompe disease. In a preferred embodiment of the invention and/or embodiments thereof the oligomeric compounds are used in research of the function of the GAA gene.

Compounds described herein can be used to modulate splicing of a target mRNA in an metazoans, preferably mammals preferably human. In one non-limiting embodiment of the invention and/or embodiments thereof, the methods comprise the step of administering to said animal an effective amount of an antisense compound that modulates splicing of a target mRNA.

For example, modulation of splicing of a target mRNA can be measured by determining levels of mRNA splicing products in a bodily fluid, tissue, organ of cells of the animal Bodily fluids include, but are not limited to, blood (serum or plasma), lymphatic fluid, cerebrospinal fluid, semen, urine, synovial fluid and saliva and can be obtained by methods routine to those skilled in the art. Tissues, organs or cells include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, connective tissue, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues, organs and cells can be routinely obtained by biopsy. In some alternative situations, samples of tissues or organs can be recovered from an animal after death. In a preferred embodiment of the invention and/or embodiments thereof modulation of splicing is measured in fibroblast, preferably primary fibroblasts, preferably primary fibroblasts from patients suffering from Pompe disease.

The effects of treatment with the oligomeric compounds can be assessed by measuring biomarkers associated with modulation of splicing of a target mRNA in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes. In a preferred embodiment of the invention and/or embodiments thereof the biomarker is glycogen.

The compounds disclosed herein can be utilized in pharmaceutical compositions by adding an effective amount of a compound to a suitable pharmaceutically acceptable diluent or carrier. The compounds can also be used in the manufacture of a medicament for the treatment of diseases and disorders related to alterations in splicing. In a preferred embodiment of the invention and/or embodiments thereof, the disease is Pompe disease.

Methods whereby bodily fluids, organs or tissues are contacted with an effective amount of one or more of the antisense compounds or compositions of the disclosure are also contemplated. Bodily fluids, organs or tissues can be contacted with one or more of the compounds of the disclosure resulting in modulation of splicing of target mRNA in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

A sufficient amount of an antisense oligomeric compound to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). The amount may also vary according to the method of administration such as systemically or locally.

Typical dosage amounts of the antisense oligonucleotide molecules in pharmaceutical formulations may range from about 0.05 to 1000 mg/kg body weight, and in particular from about 5 to 500 mg/kg body weight. In one embodiment of the invention and/or embodiments thereof, the dosage amount is from about 50 to 300 mg/kg body weight once in 2 weeks, or once or twice a week, or any frequency required to achieve therapeutic effect. Suitably amounts are from 3-50 mg/kg, more suitably 10-40 mg/kg, more suitably 15-25 mg/kg.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment of the invention and/or embodiments thereof, dosage forms (compositions) of the inventive pharmaceutical composition may contain about 1 microgram to 50,000 micrograms of active ingredient per unit, and in particular, from about 10 to 10,000 micrograms of active ingredient per unit. (if here a unit means a vial or one package for one injection, then it will be much higher, up to 15 g if the weight of a patient is 50 kg) For intravenous delivery, a unit dose of the pharmaceutical formulation will generally contain from 0.5 to 500 micrograms per kg body weight and preferably will contain from 5 to 300 micrograms, in particular 10, 15, 20, 30, 40, 50, 100, 200, or 300 micrograms per kg body weight ([mu] g/kg body weight) of the antisense oligonucleotide molecule. Preferred intravenous dosage ranges from 10 ng to 2000 microg, preferably 3 to 300 [mg, more preferably 10 to 100 [mu]g of compound per kg of body weight. Alternatively the unit dose may contain from 2 to 20 milligrams of the antisense oligonucleotide molecule and be administered in multiples, if desired, to give the preceding daily dose. In these pharmaceutical compositions, the antisense oligonucleotide molecule will ordinarily be present in an amount of about 0.5-95% by weight based on the total weight of the composition.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

Preferably the compounds are administered daily, once every 2 days, once every 3 days, once a week, once every two weeks, or once every month.

In another preferred embodiment the administration is only one time, e.g. when using a viral vector.

If a viral-based delivery of antisense oligomeric compounds is chosen, suitable doses will depend on different factors such as the viral strain that is employed, the route of delivery (intramuscular, intravenous, intra-arterial or other), Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the antisense oligomeric compounds of the invention will likely be administered on multiple occasions, that may be, depending on the results obtained, several days apart, several weeks apart, or several months apart, or even several years apart.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein. In preferred embodiment the functionality of the GAA protein is measured. This is suitably performed with an enzymatic activity assays as is well known to a skilled person.

In a particular embodiment of the invention and/or embodiments thereof; antisense oligonucleotides of the invention may be delivered in vivo alone or in association with a vector. In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: R A viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Preferred viral vectors according to the invention include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al, 1989. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected intramuscular, or intravenous. It may also be administered into the epidermis or a mucosal surface using a gene-gun. The plasmids may be given in an aqueous solution, dried onto gold particles or in association with another DNA delivery system including but not limited to liposomes, dendrimers, cochleate and micro-encapsulation.

In a preferred embodiment of the invention and/or embodiments thereof, the antisense oligonucleotide nucleic acid sequence is under the control of a heterologous regulatory region, e.g., a heterologous promoter. The promoter can also be, e.g., a viral promoter, such as CMV promoter or any synthetic promoters.

In a preferred embodiment of the invention and/or embodiments thereof, the vector may code for more than one antisense oligomeric compound. Each antisense oligomeric compound is directed to different targets.

Pharmaceutical composition comprising the antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleotides that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment of the invention and/or embodiments thereof, sodium salts of dsRNA compounds are also provided.

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. In a preferred embodiment of the invention and/or embodiments thereof, administration is intramuscular or intravenous.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment of the invention and/or embodiments thereof, the pharmaceutical formulations are prepared for intramuscular administration in an appropriate solvent, e.g., water or normal saline, possibly in a sterile formulation, with carriers or other agents.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Compositions provided herein may contain two or more antisense compounds. In another related embodiment, compositions may contain one or more antisense compounds, particularly oligonucleotides, targeted to a first nucleic acid and one or more additional antisense compounds targeted to a second nucleic acid target. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

The antisense oligomeric compound described herein may be in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives. antisense oligomeric compound compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes antisense oligomeric compound compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxy ethylene sorbitan monooleate.

The antisense oligomeric compound of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus the antisense oligomeric compound of the present disclosure may be administered in any form, for example intramuscular or by local, systemic, or intrathecal injection.

This disclosure also features the use of antisense oligomeric compound compositions comprising surface-modified liposomes containing poly(ethylene glycol) lipids (PEG-modif[iota]ed, or long-circulating liposomes or stealth liposomes). These formulations offer a method for increasing the accumulation of antisense oligomeric compound in target tissues. This class of drug carriers resists opsonization and elimination by the mononuclear phagocytic system (MPS or RES), thereby enabling longer blood circulation times and enhanced tissue exposure for the encapsulated antisense oligomeric compound (Lasic et al, Chem. Rev. 95:2601-2627 (1995) and Ishiwata et al, Chem. Pharm. Bull. 43:1005-1011 (1995). Long-circulating liposomes enhance the pharmacokinetics and pharmacodynamics of antisense oligomeric compound, particularly compared to conventional cationic liposomes which are known to accumulate in tissues of the MPS (Liu et al, J. Biol. Chem. 42:24864-24870 (1995); Choi et al, PCT Publication No. WO 96/10391; Ansell et al, PCT Publication No. WO 96/10390; Holland et al, PCT Publication No. WO 96/10392). Long-circulating liposomes are also likely to protect antisense oligomeric compound from nuclease degradation to a greater extent compared to cationic liposomes, based on their ability to avoid accumulation in metabolically aggressive MPS tissues such as the liver and spleen.

Following administration of the antisense oligomeric compound compositions according to the formulations and methods of this disclosure, test subjects will exhibit about a 10% up to about a 99% reduction in one or more symptoms associated with the disease or disorder being treated, as compared to placebo-treated or other suitable control subjects.

EXAMPLES

Example 1

Mutations affecting pre-mRNA splicing are difficult to predict due to the complex mechanism of splicing regulation. A generic approach to systemically detect and characterize effects of sequence variants on splicing would improve current diagnostic practice. Here, we show that such approach is feasible by combining flanking exon RT-PCR, sequence analysis of PCR products, and exon-internal quantitative RT-PCR for all coding exons. It has been applied to uncharacterized mutations in the acid-alpha glucosidase gene causing Pompe disease, a monogenic autosomal recessive disease. Effects on splicing included cryptic splice site usage, intron retention and exon skipping. These differed from in silico predictions, highlighting the need for experimental testing. Quantification of the extent of leaky wild type splicing correlated with disease severity.

Materials and Methods

Patients and Healthy Control

Patients were diagnosed with Pompe disease based on clinical symptoms and GAA enzyme activity. All patients and the healthy control provided informed consent for molecular analysis.

Nomenclature

The positions of the mutations described are aligned against Ensembl GAA cDNA association number ENST00000302262.3. c.1 indicates the first nucleotide of the coding region of GAA mRNA. Further numbering is according to HGVS standards [14].

Cell Culture and cDNA Preparation

Fibroblasts were isolated from skin biopsies of patients and a healthy individual. Cells were cultured in DMEM High Glucose (Lonza)+10% Fetal bovine serum (HyClone, Thermo Scientific)+1% penicillin/streptomycin (Lonza). RNA was isolated using the RNAeasy miniprep kit (Qiagen). 800 ng of RNA was used for generation of cDNA using the iScript cDNA synthesis kit (Biorad). cDNA was diluted 10 times before use.

Flanking Exon PCR Analysis cDNA was amplified using FastStart Taq Polymerase (Roche). Primers were used at a final concentration of 0.333 µM each, dNTPs at 0.333 mM each. The PCR program was performed on a Biorad s1000 thermal cycler (96° C. for 4 min., 35X [96° C. 20 sec., 60° C. 30 sec., 72° C. 1 min.], 72° C. 5 min.) 5 µl of each PCR reaction was run on a 1,5% agarose gel containing ethidium bromide. Gel were photographed on a Typhoon FLA 9000 gel imager (G&E Healthcare). The primers used are listed in FIG. 15.

Exon-Internal qPCR Analysis

To determine the relative concentration of each sample, 4 µl of each cDNA sample (10 times diluted in $H_2O$) was processed in a 15 µl PCR reaction containing IQ Mastermix (Biorad) and 0.333 µM of each primer. To account for the efficiency of each specific primer set, all samples were related to a standard curve from the healthy control sample. All samples were measured in triplicate. The primers used are listed in FIG. 16.

Sanger Sequencing

Genomic DNA mutations were identified at the diagnostic department of Clinical Genetics at the Erasmus MC, Rotterdam, The Netherlands. Direct sequencing of flanking exon PCR products was performed using the Big Dye Terminator kit v3.1 (Applied Biosystems). To obtain pure DNA samples, PCR products visible on gel in the splicing assay were stabbed with a 20 µl pipet tip and DNA on the tip was resuspended in 10 µl H2O. 1 µl was subsequently used in a new PCR (as described in the splicing assay) to obtain DNA from a single template. Excess primers and dNTPs were removed using FastAP Thermosensitive Alkaline Phosphatase (Thermo Scientific), according to the manufacturer's protocol. Samples were purified with sephadex G-50 (GE Healthcare) and the sequence was determined on an AB3130 Genetic Analyzer (Applied Biosystems, Hitachi).

GAA Enzyme Activity

The activity of GAA in fibroblasts was measured with 4-methylumbelliferyl-α-gluocpyranoside (4-MU) or with glycogen as substrate as described [15].

Results

Generic Assay to Detect Splicing Mutations

The approach consists of two parts. First (FIG. 1, left), a generic RT-PCR is performed of the mRNA of interest using standard primers that flank each individual canonical exon (flanking exon PCR). The products are separated by agarose gel electrophoresis. Changes in product size are indicative of alternative/aberrant splicing. Splicing junctions can be precisely determined using sequencing of products isolated from gel or by direct sequencing of the PCR reaction. Second (FIG. 1, right), a standard qPCR is performed to quantify each individual exon (exon-internal qPCR). Primers that anneal within each exon are used. Results are normalized for beta-actin mRNA and for expression in a healthy control. The results quantify exon skipping/inclusion, and may also indicate whether a splicing mutation allows leaky wild type splicing.

Development and Validation of the Assay

Healthy Control

Figure 1C:
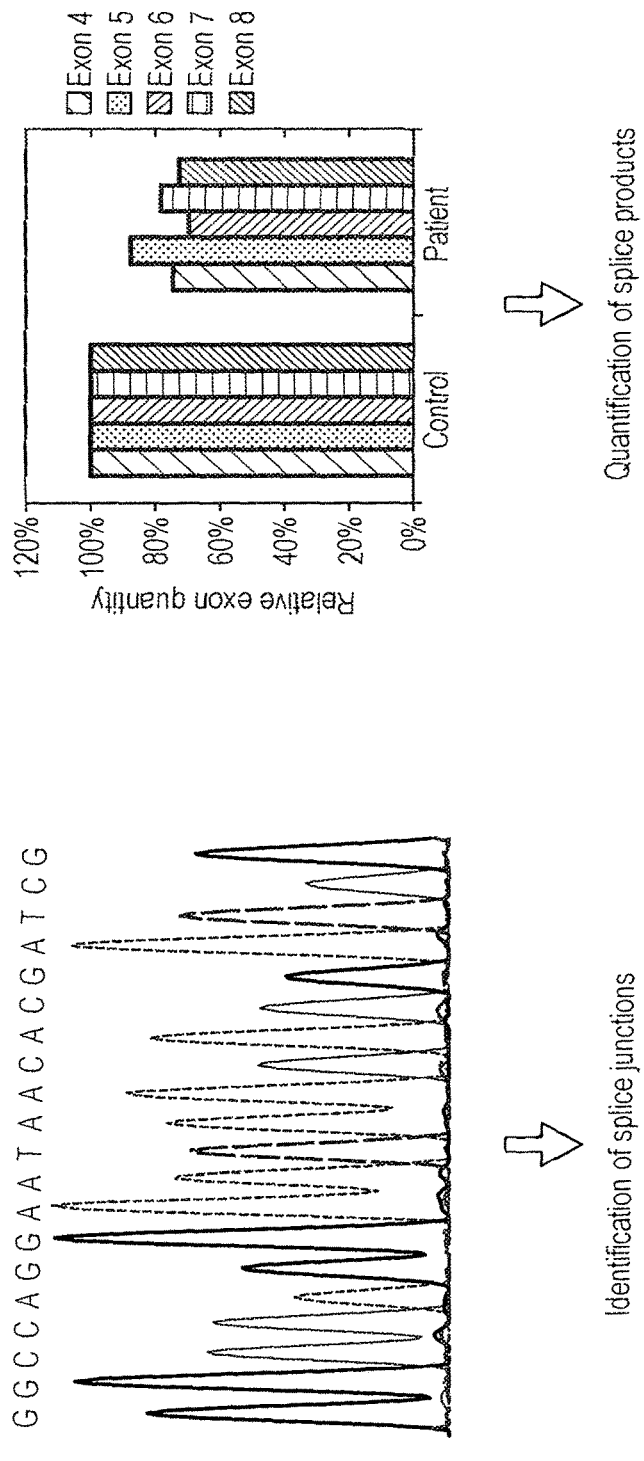
Figure 2A:
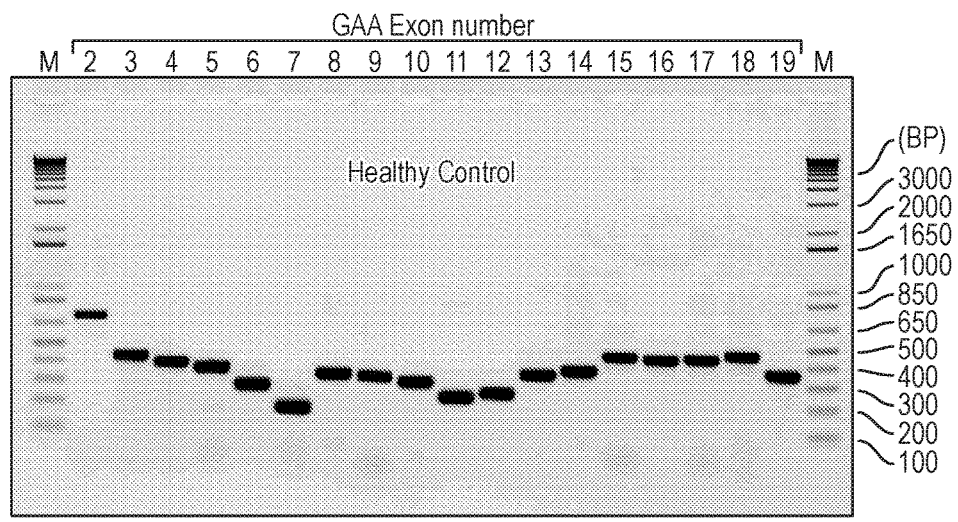
FIG. 2. Splicing analysis of a healthy control and a Pompe patient harboring the common IVS1 splice site mutation. A) Flanking exon PCR analysis of a healthy control. Exon numbers are indicated above the lanes. PCR products were separated by electrophoresis on an agarose gel. B) As A), but for Pompe patient 1 carrying the IVS1 mutation. Numbers besides the bands refer to the products analyzed in further detail (see below). C) Cartoon of the major splicing variants detected for patient 1. The upper cartoon represents the genomic DNA, in which the mutation is indicated. The lower cartoons refer to the splicing variants detected in this study. The translation start site is indicated as c.1. Exons are indicated as boxes. Non-coding exons are in brown, coding exons in green. Introns are depicted as lines. A broken line is used to indicate that the intron is longer than in this drawing. An alternative splice site is indicated. D) Exon-internal qPCR analysis. Beta-actin was used for normalization. Values obtained from the healthy control were set to 100%. Error bars indicate SD (n=3).

The assay was developed using a healthy control. To detect splicing junctions and exon sizes, flanking exon PCR analysis was performed on cDNA prepared from primary fibroblasts using primers that annealed to flanking exons (FIG. 2A). Gel electrophoresis and ethidium bromide staining showed the correct molecular weight products in all cases. This indicated canonical splicing for all exons in these cells. Some additional products were observed in at minor amounts, notably, just above exon 6 and 7. Sequence analysis indicated that these represent products in which intron 6 was retained. The products were observed in this healthy control and in many Pompe patients and may indicate noisy aberrant splicing, which is a known phenomenon [16]. Individual exons were quantified using exon-internal qPCR (FIG. 1B). Values were normalized for 6-actin expression (as measured by qPCR analysis), and were then ready to use for normalization of test samples.

Patient 1

This patient was used to validate whether a well described splicing mutation could be accurately detected in primary fibroblasts using the assay described above. The c.-32-13T>G (IVS1) mutation was chosen because it is a frequent mutation causing juvenile/adult onset of Pompe disease. It is located in intron 1 close to the splice acceptor site of exon 2, and it causes aberrant splicing of exon 2 but also allows leaky wild type splicing [17, 18]. The second allele is known to be expressed at very low levels due to NMD [19]. This is caused by the c.1636+5G>T mutation, which leads to intron 11 inclusion and a premature termination codon. For this reason, the allele containing the IVS1 mutation dominates in the splicing assay described below.

Figure 9:
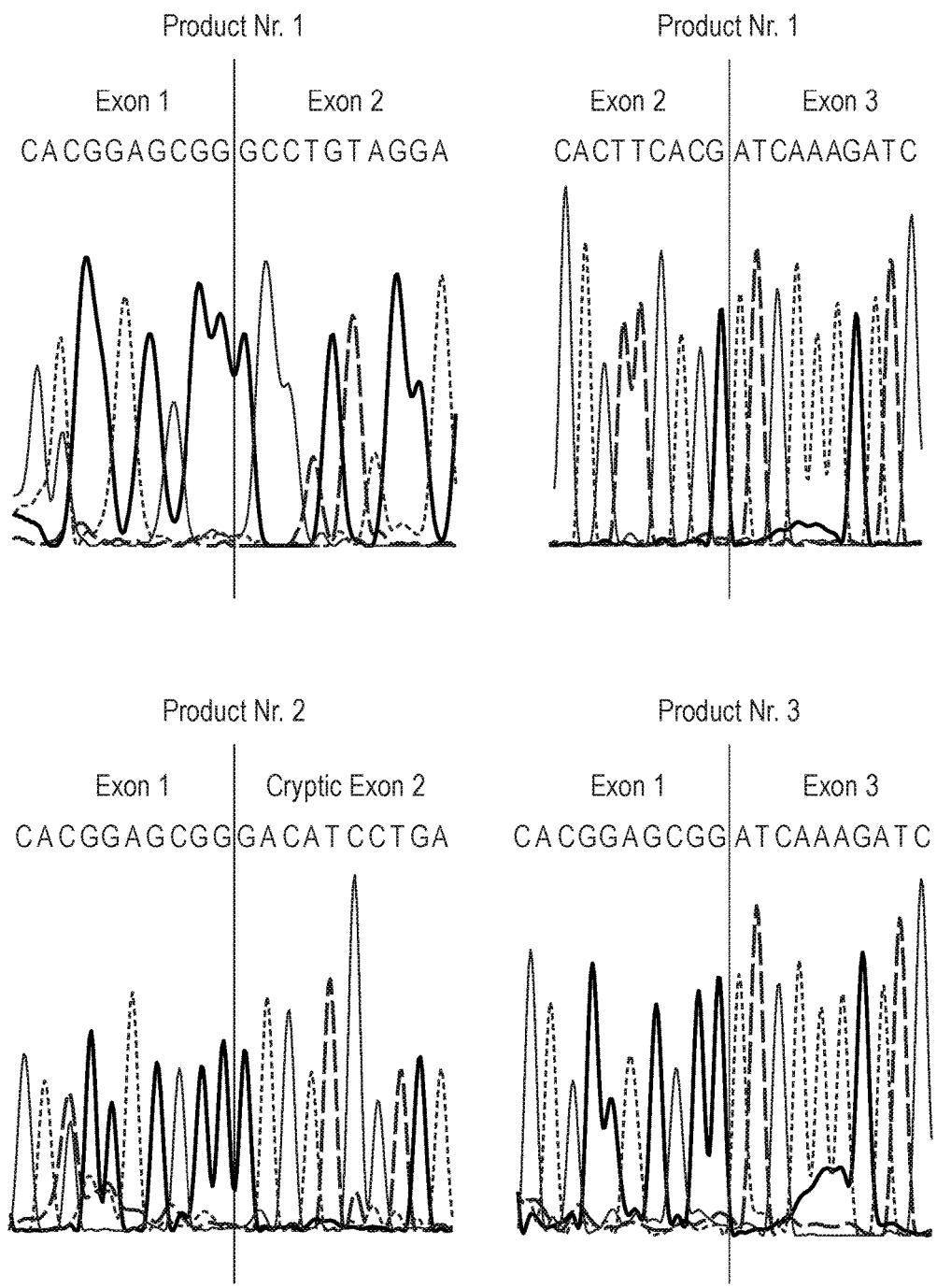
FIG. 9. Sequence analysis of patient 1.

Flanking exon PCR analysis yielded three major products from exon 2 amplification (FIG. 2A). These products were analyzed by DNA sequencing, which indicated that product 1 represented full exon 2 with canonical splicing junctions (FIG. 9). Product 2 contained partially skipped exon 2 due to the utilization of a cryptic splice acceptor site at c.486 while product 3 represented fully skipped exon 2 (FIG. 2A and S2). These products correspond to the major splicing variants reported for the IVS1 mutation, namely normal (N) (product 1), splicing variant (SV) 1 (product 2) and SV2 (product 3) [18].

Figure 2B:
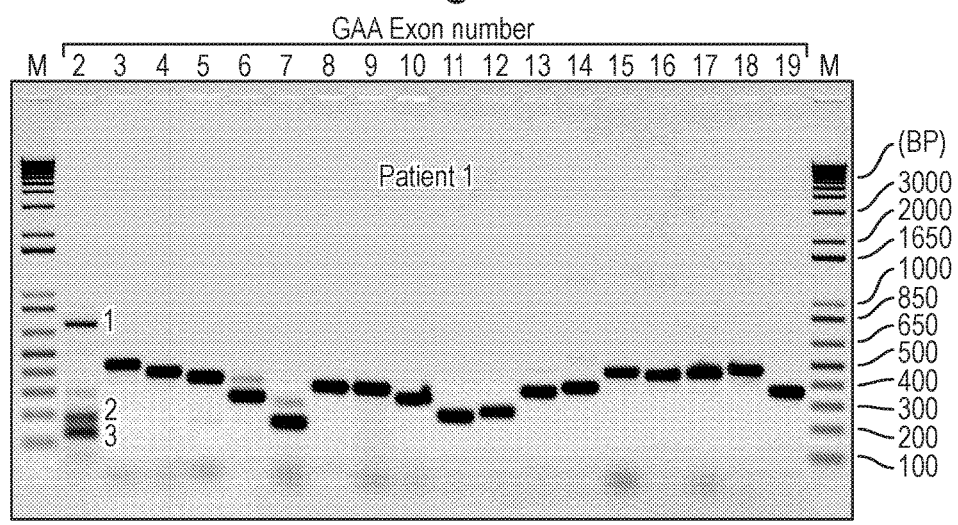
Figure 2C:
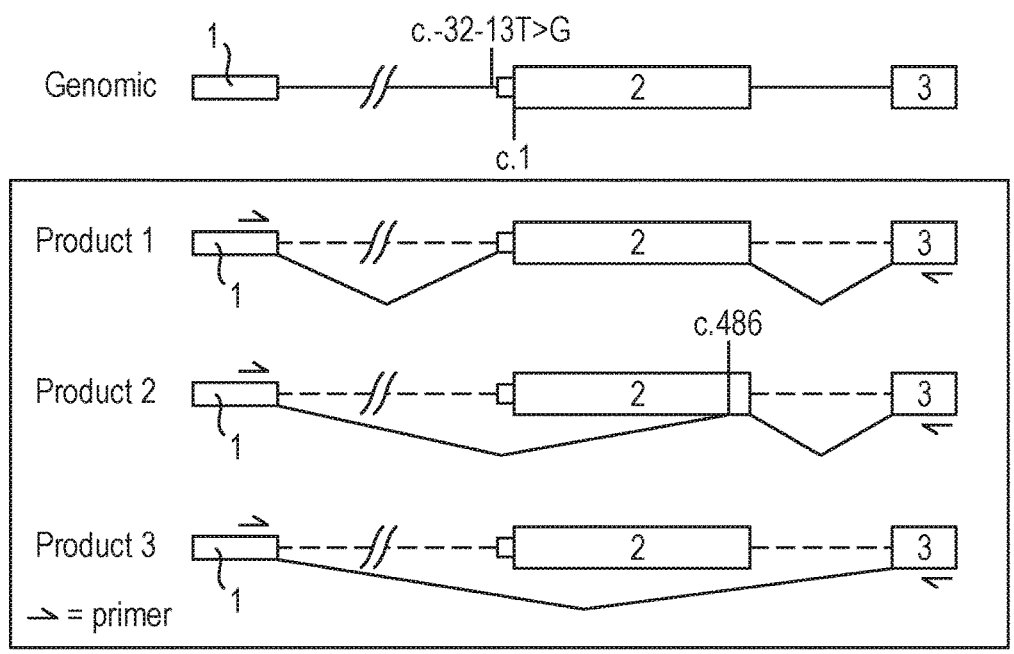

Exon-internal qPCR analysis showed 10-15% expression of exon 2 and all other exons (FIG. 2). This can be explained as follows. The IVS1 mutation allows leaky wild type splicing of exon 2 (product 1 in FIG. 2A) yielding a normal mRNA containing all exons, as noted previously ([18, 20]. The 2 other major products 2 and 3 both result in the deletion of the canonical start of translation, which is located in exon 2. This leads to in mRNA degradation, resulting in minor contribution in the quantitative exon-internal qPCR assay, and predominant detection of the leaky wild type GAA mRNA from the IVS1 allele. In conclusion, the known effects of the IVS1 mutation on splicing were faithfully detected using the generic splicing assay for GAA. Leaky wild type splicing were 10-15% of healthy control levels and explained the juvenile/adult onset of Pompe disease. It is of note that all five splicing prediction programs used here (SpliceSiteFinder-like (SSF), MaxEntScan (MES), NNSplice (NNS), GeneSplicer (GS) and Human Splicing Finder (HSF)) failed to detect an effect of the IVS1 mutation on splicing (FIG. 14A).

Patient 2

Figure 8A:
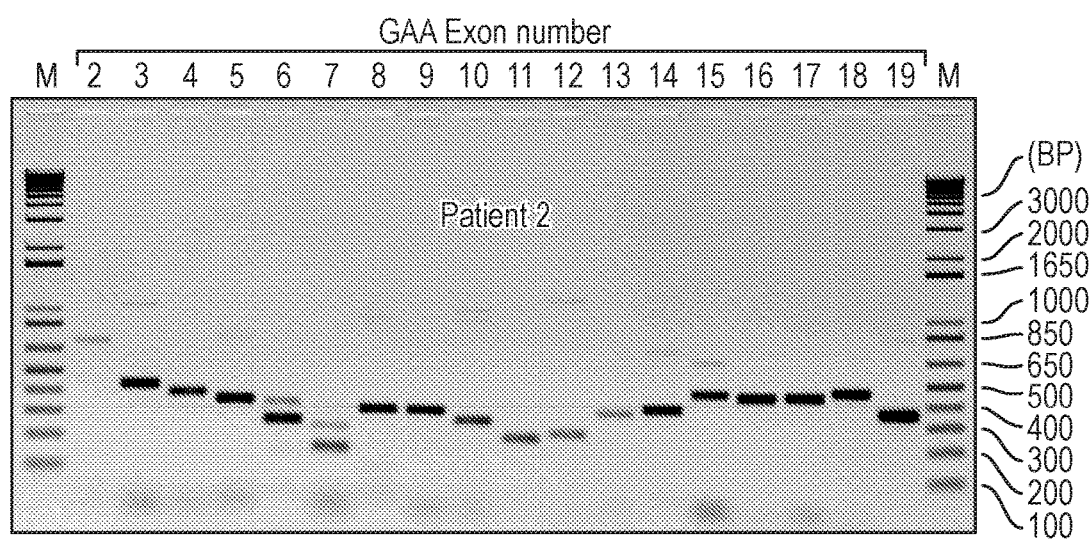
FIG. 8. Splicing analysis of patient 2. A) Flanking exon PCR analysis. B) Exon-internal PCR analysis.

This patient was chosen to test the sensitivity of the assay. Due to a homozygous c.525delT mutation, GAA mRNA expression is very low due to NMD [21]. Surprisingly, flanking exon PCR analysis showed that all exons could still be detected at the correct sizes, although at reduced levels (FIG. 8). Higher molecular weight products were also observed at even lower levels. These may represent unspliced pre-mRNA species, amplified due to the reduced abundance of competing spliced mRNA in the PCR reaction. To quantify the amount of residual mRNA, exon-internal qPCR was performed and showed 5-10% expression of all exons relative to the healthy control (FIG. 8B). In conclusion, the generic splicing assays for GAA allow analysis and quantification of very low mRNA expression. This is particularly relevant for mRNAs that are subject to degradation as the result of reading frame alterations.

Patient 3

A third validation was performed on a patient carrying a well-known deletion removing the entire exon 18 plus its flanking sequences (del ex18, or c.2481+102_2646+31 del) (FIG. 2A). This case is interesting because the splice sites of exon 18 are removed. Previous work has shown that a new mRNA is formed in which exon 17 is neatly spliced to exon 19 via canonical splice sites [17]. The translation reading frame of the resulting mRNA remains intact, suggesting that this mRNA is not susceptible to degradation via the NMD pathway (FIG. 7—Table 2). The second mutation in this patient, c.1548G>A, generates a termination codon in exon 10 [22]. Its effects on mRNA expression have not been reported so far. The premature termination codon is likely to result in low mRNA abundance from this allele.

Figure 3A:
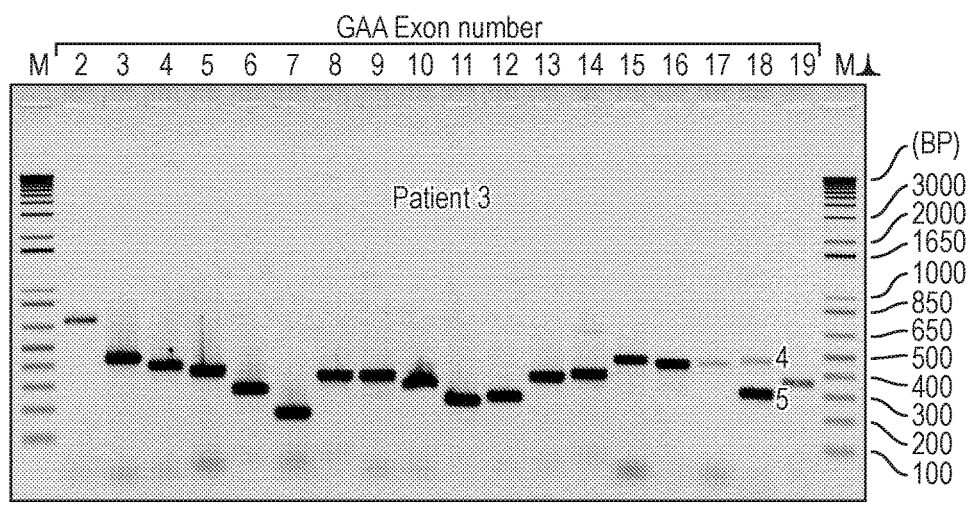
FIG. 3. Splicing analysis of Pompe patients 3 and 4 carrying heterozygous mutations/deletions. A) Flanking exon PCR analysis of patient 3. B) Cartoon of the major splicing variants detected for patient 3. C) Flanking exon PCR analysis of patient 4. D) Cartoon of the major splicing variants detected in patient 4 from allele 1. E) As D) but now for patient 4, allele 2. F) Exon-internal qPCR analysis of patients 3 and 4. Error bars indicate SD (n=3).
Figure 3B:
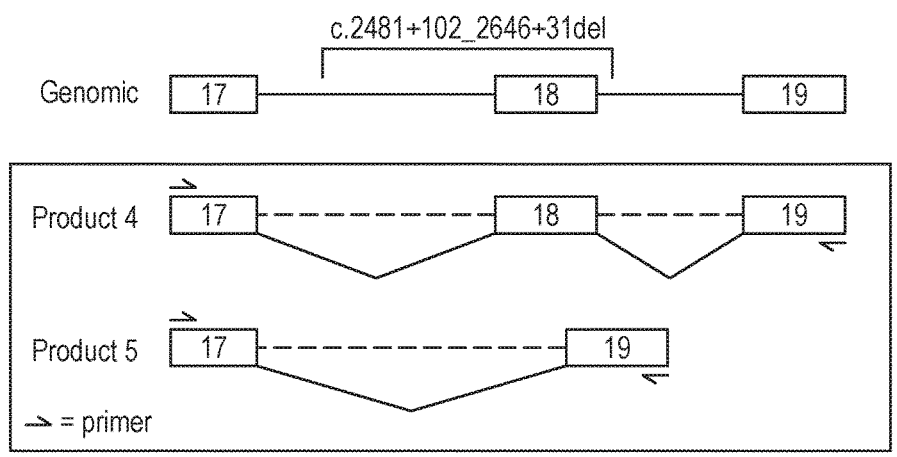

Flanking exon PCR indicated changes for amplification of exons 17, 18, and 19 (FIG. 3A). Exon 18 amplification yielded two products instead of one. Sequence analysis indicated that the highest MW product (number 4) represented wild type spliced exon 18, while the lower MW product (number 5) lacked the entire exon 18, and exon 17 and exon 19 were joined via their canonical splice sites (Fig. S3A). Amplification of exons 17 and 19 yielded lower amounts of the correct products compared to the healthy control. The primers used for their amplification anneal to exon 18, indicating that their detection could not be derived from the delex18 allele but must have come from the c.1548G>A allele. This indicates that the c.1548G>A allele is expressed to some extent, and it explains the detection of moderate levels of wild type spliced exon 18 by flanking exon PCR.

Figure 3C:
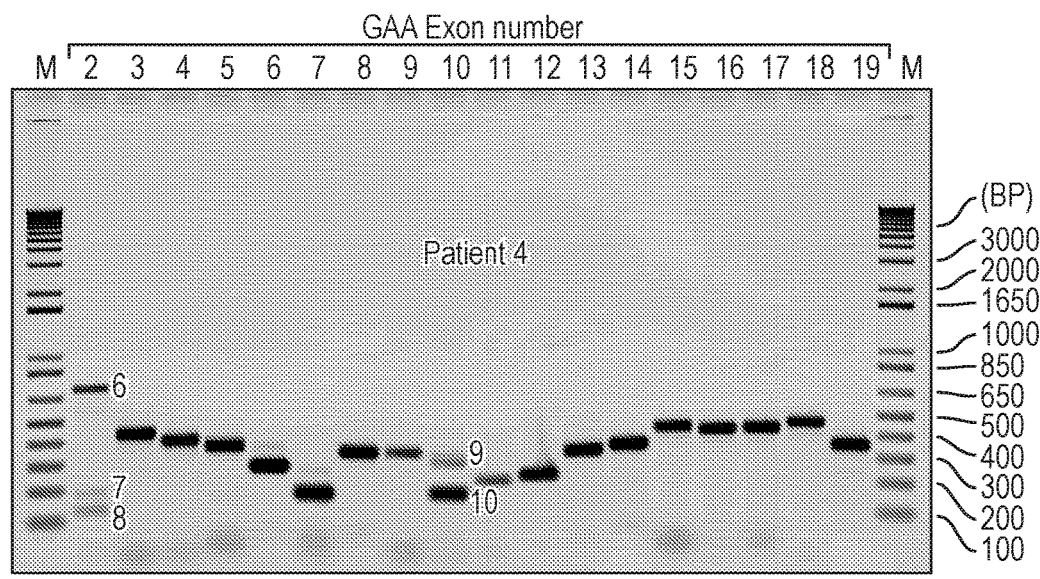
Figure 3D:
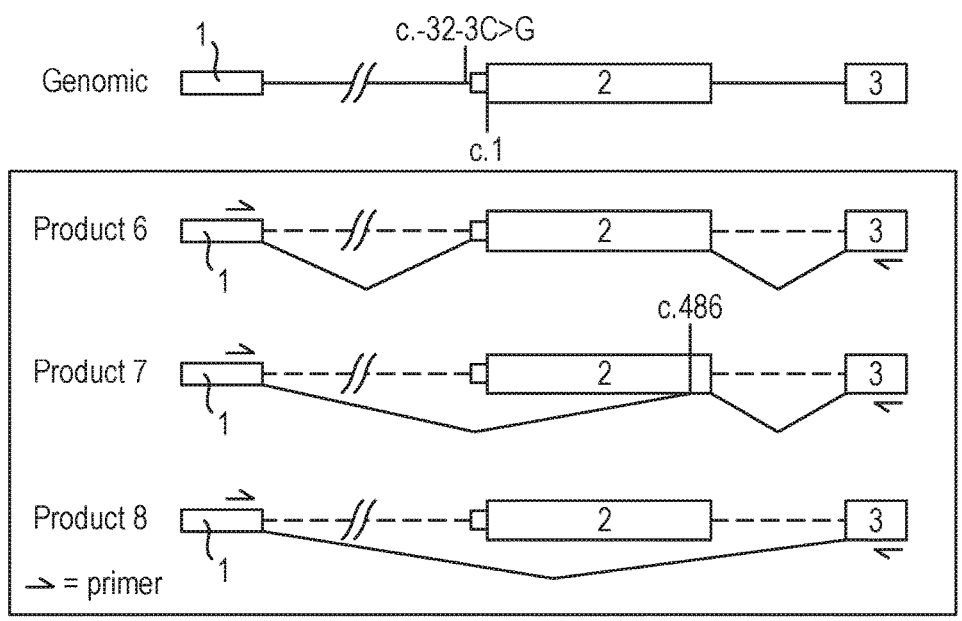
Figure 3E:
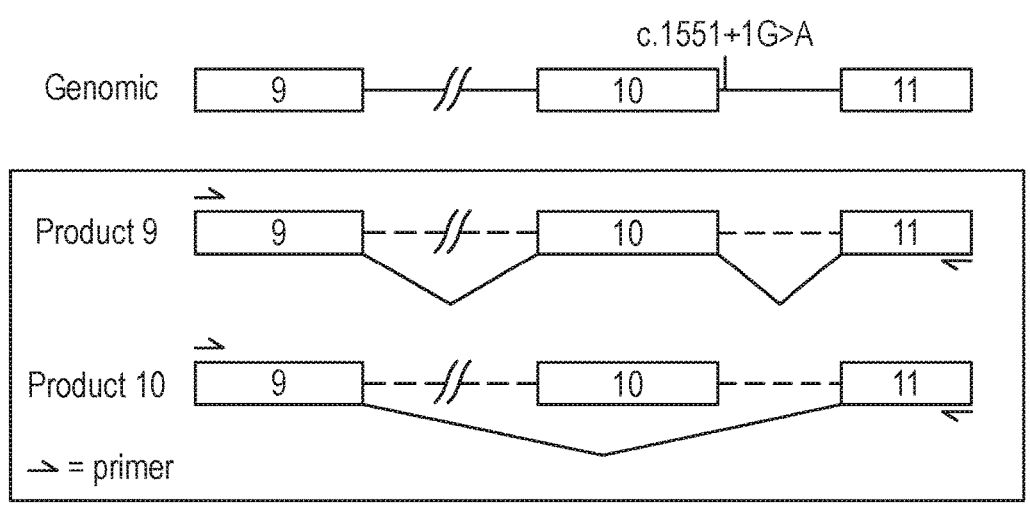
Figure 3F:
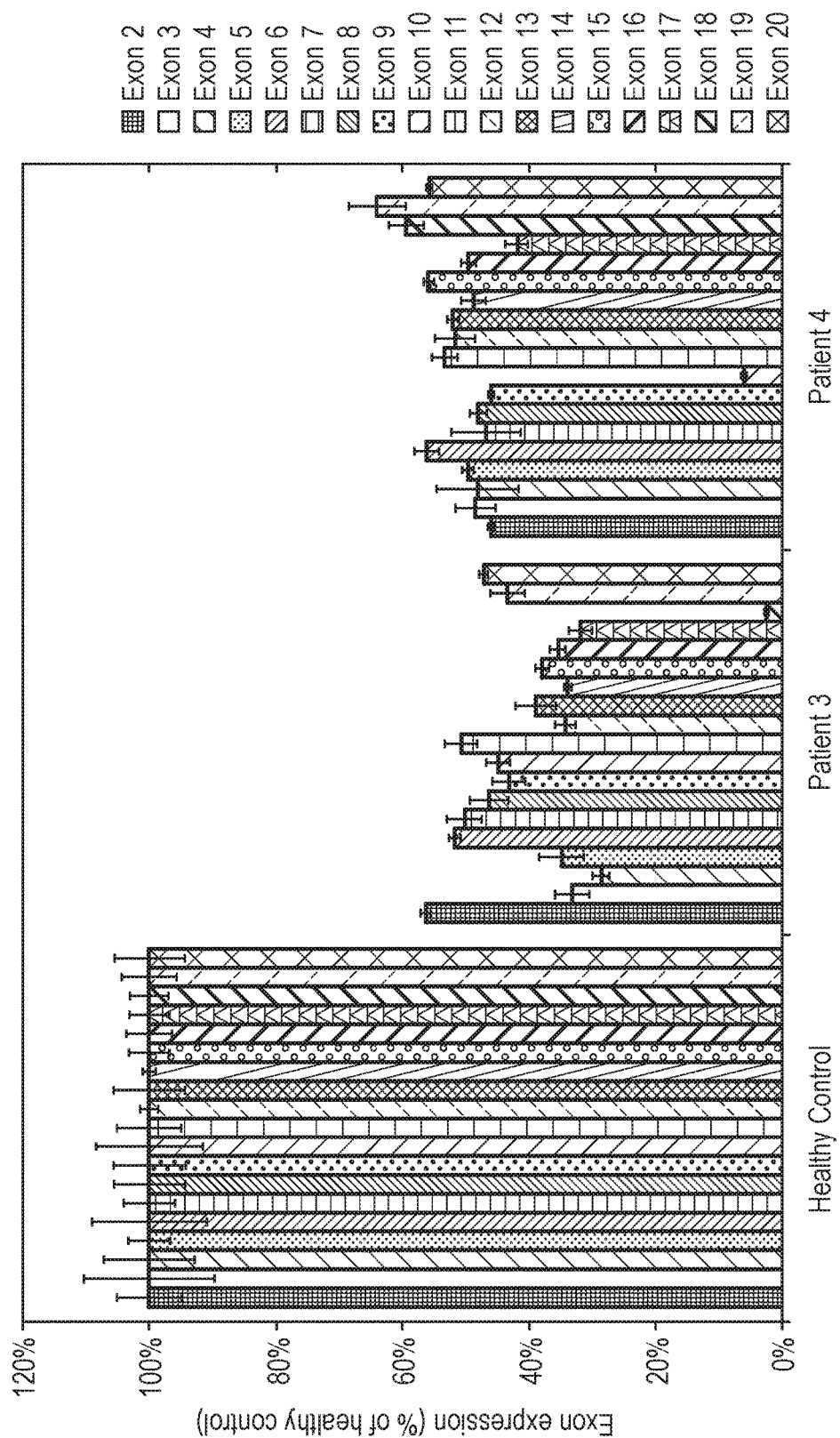

To quantify expression from the c.1548G>A allele, exon-internal qPCR was performed and indicated 3% expression of exon 18, while all other exons were expressed at ~40-50% of healthy control levels (FIG. 3F). This shows that the c.1548G>A mutation results in very low mRNA expression, as measured by the low level of exon 18 detection. Expression of all other exons is derived from the delex18 allele, which produces a stable mRNA in which exon 18 is precisely deleted.

In summary, the generic splicing assay also allows detection and characterization of exonic deletions. A dissection can be made between two alleles by comparing the results of the flanking exon PCR and the exon-internal qPCR assays.

Characterization of Novel Splicing Mutations

Next, a number of patients were analyzed that contained partially characterized or uncharacterized mutations.

Patient 4

Patient 4 contained a novel mutation at c.-32-3C>G located in intron 1 close to the splice acceptor site of exon 2 (FIG. 3D). This mutation is suspected to affect splicing of exon 2 based on its similarity to the published c.-32-3C>A mutation [19]. In this study, a perfect skip of exon 2 was reported. Splicing prediction programs indicated that the c.-32-3C>G mutation weakens the splice acceptor site of exon 2 for some but not all programs (FIG. 14C). The second allele contained a previously reported [23] but uncharacterized mutation at c.1551+1G>A which is located in intron 10 close to the splice donor site of exon 10 (FIG. 3E). Based on the similarity to the published c.1551+1G>C mutation [17, 24], the c.1551+1G>A mutation is suspected to affect exon 10 splicing. Splicing prediction programs indicated loss of the splice donor site of exon 10 (FIG. 14C).

Figure 10B:
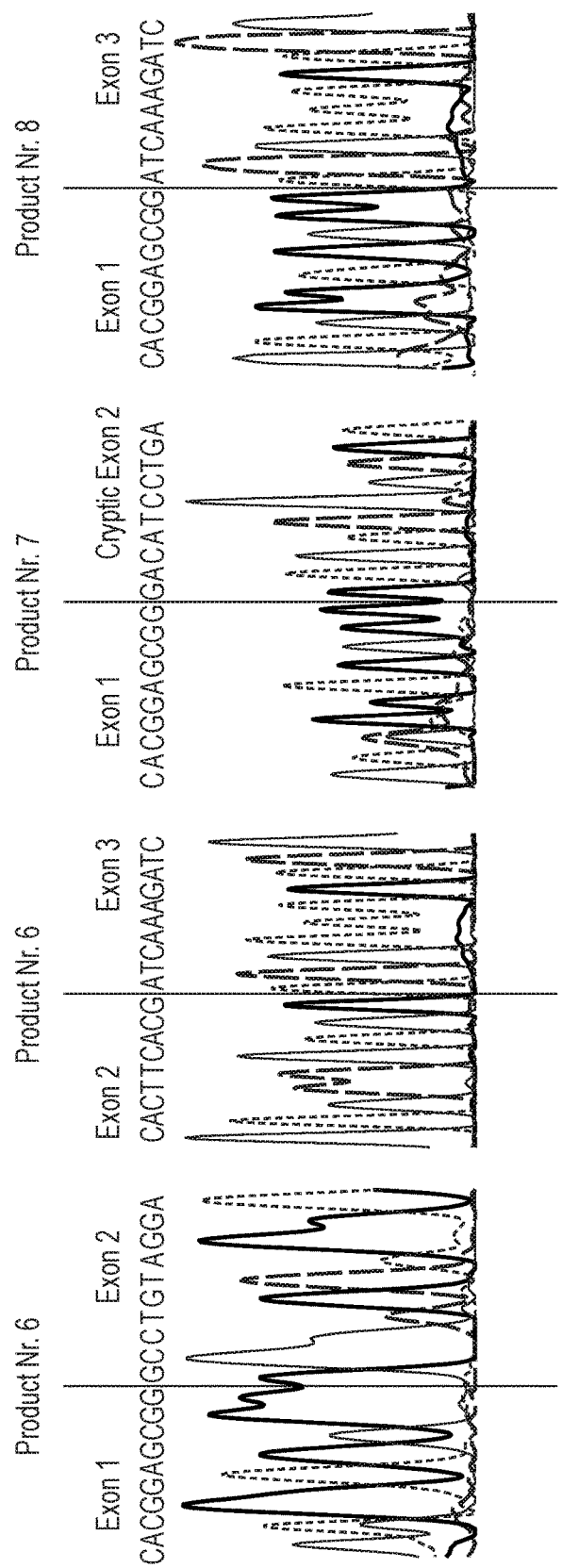
FIG. 10. Sequence analysis of patient 3 (A) and 4 (B-C).
Figure 10C:
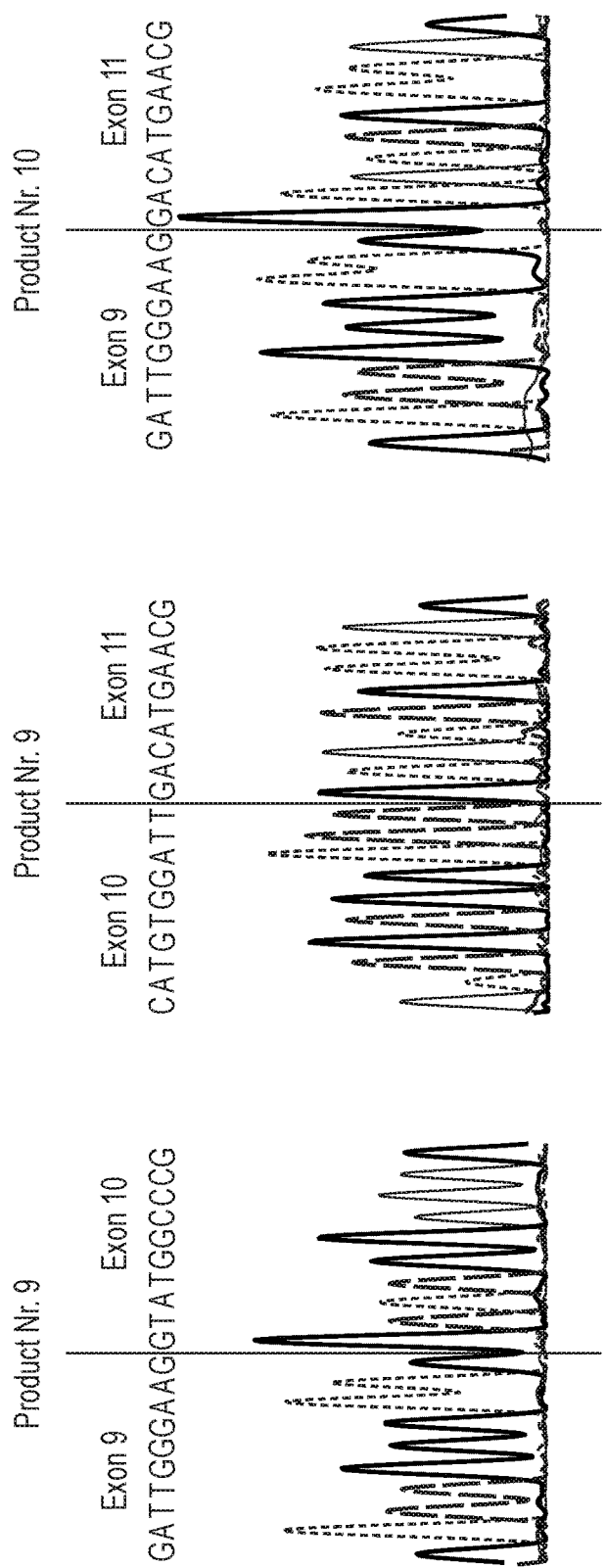

The results of the flanking exon PCR analysis indicated aberrant splicing of two exons: exon 2 and exon 10 (FIG. 3C). Amplification of exon 2 resulted in 3 major products, number 6-8, and sequence analysis indicated that these products included wild type splicing, partial skipping of exon 2 via the cryptic splice acceptor site at c.486 in exon 2, and perfect skipping of exon 2, respectively (FIG. 3D and FIG. 10B). This indicates that two independent mutations in intron 1, namely c.-32-13T>G, which is located in the polypyrimidine tract, and c.-32-3C>G, located near the splice acceptor site, have the same qualitative outcome with respect to exon 2 splicing. Splicing prediction programs were insufficient to accurately predict this outcome. Flanking exon PCR amplification of exon 10 resulted in two major products, 9 and 10 (FIG. 3C). Sequence analysis showed that product 9 contained wild type junctions between exons 9, 10, and 11, and that product 10 represented precise skipping of exon 10 mRNA (FIG. 3E and FIG. 10C) in which the reading frame remains intact. This was surprising because the most straightforward result of a weakening of the splice donor site of exon 10 would be a failure to remove intron 10 rather than a skipping of exon 10.

To determine the extent of splicing defects, exon-internal qPCR was performed. Exon 10 was expressed at ~6%, while all other exons were expressed at ~50% of healthy control levels (FIG. 3F). This is consistent with the idea that the majority of mRNA is derived from the c.1551+1G>A allele in which exon 10 is skipped. The shorter product has an unchanged reading frame and is expected to be stable. In contrast, the c.-32-3C>G allele results in (partial) exon 2 skipping, which is known to result in mRNA degradation analogous to the IVS1 mutation. The c.-32-3C>G allele has only a minor contribution to the exon-internal qPCR results. Its contribution can be judged from exon 10 expression, which can result from leaky wild type splicing of the c.-32-3C>G mutation. However, an alternative source for exon 10 expression is leaky wild type expression of the c.1551+1G>A allele. The very low level of exon 10 expression indicates that both the c.-32-3C>G and the c.1551+1G>A have low or absent levels of leaky wild type expression. This indicates that the c.-32-3C>G mutation may be more severe compared to the IVS1 mutation, as the IVS1 mutation allows a higher level of wild type splicing of 10-15% (FIG. 2D). The clinical course of Pompe disease indicates a juvenile onset for this patient, consistent with a low level of wild type GAA expression and GAA enzyme activity levels that were lower compared to adult onset patients (FIG. 6—Table 1).

Patient 5

Patient 5 was homozygous for c.1075G>A, which is a p.Gly359Arg missense mutation located at the last basepair of exon 6 (FIG. 4B) [25]. This mutation has been classified as presumably nonpathogenic with possible effects on splicing [26]. It is located near the splice donor site of exon 6, and splicing prediction analysis indicated weakening of this site and strengthening of a cryptic splice donor site 4 nucleotides upstream (FIG. 14D).

Figure 4A:
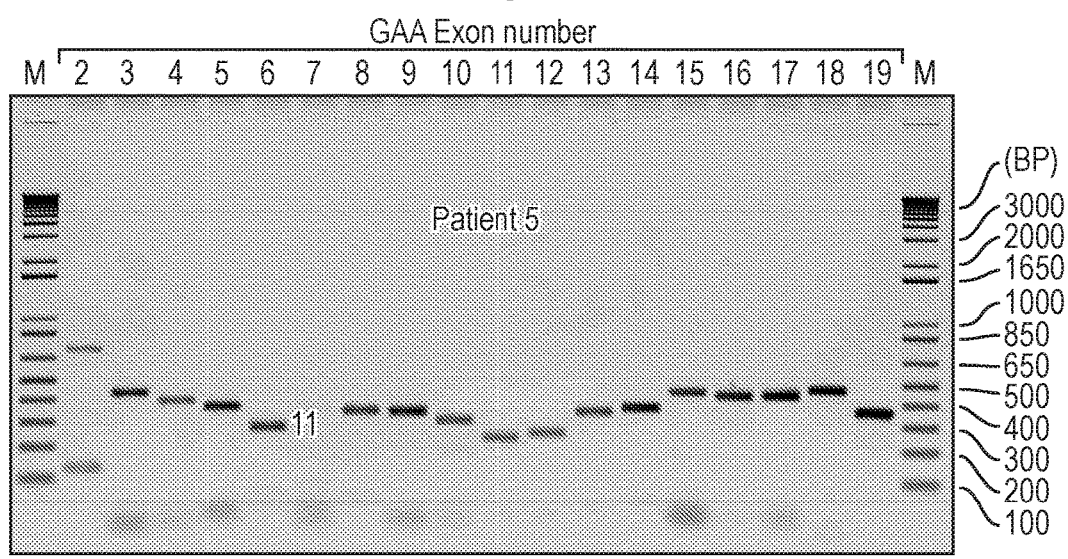
FIG. 4. Splicing analysis of Pompe patients carrying homozygous mutations. A) Flanking exon PCR analysis of patient 5. B) Cartoon of the splicing variant detected for patient 5. C) Flanking exon PCR analysis of patient 6. D) Cartoon of the splicing variants detected for patient 6. E) Flanking exon PCR analysis of patient 7. F) Cartoon of the splicing variant detected for patient 7. G) Exon-internal qPCR analysis of patients 5, 6, and 7. Error bars indicate SD (n=3).
Figure 4B:
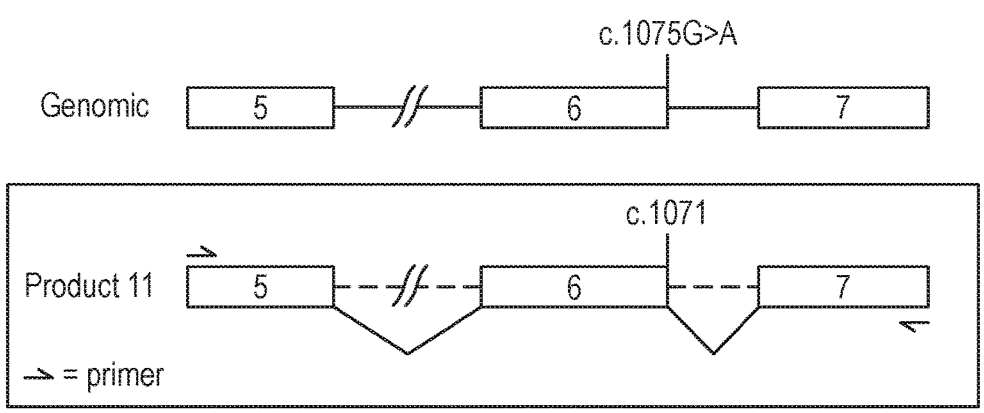
Figure 4C:
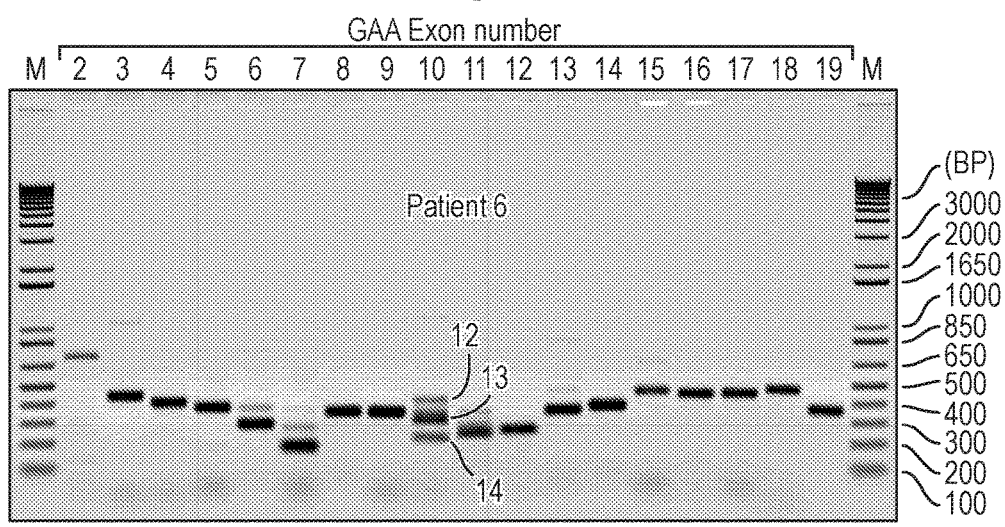
Figure 11A:
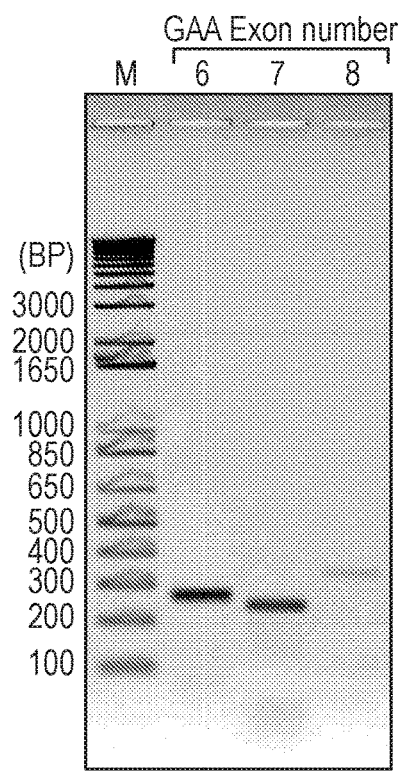
FIG. 11. A) Flanking exon PCR analysis of patient 5 for exon 7 using a forward primer that anneals to exon 5 and a reverse primer that anneals to exon 8. For comparison, standard flanking exon PCR reactions of exons 6 and 8 are shown. Note that GAA mRNA levels in this patient are low due to NMD. B). Sequence analysis of patient 5. C) Sequence analysis of patient 6. D) Sequence analysis of patient 7.
Figure 11B:
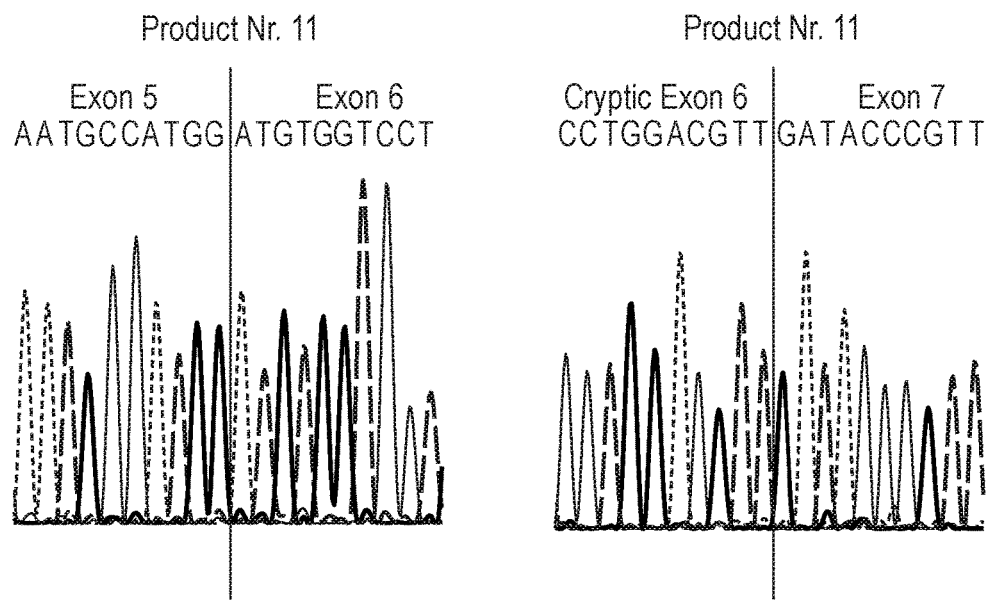

Flanking exon PCR analysis showed absence of a product for exon 7, low levels of the other exons, and a low level of a low MW product for exon 2 (FIG. 4A). Based on the predictions and on the location of this mutation in exon 6, we suspected that splicing junctions around exon 6 and 7 may be altered. In agreement, sequencing of the exon 6 PCR product (product 11) showed that the cryptic splice donor site in exon 6 located 4 nucleotides upstream at c.1071 was used instead (FIG. 4B and Fig. S4B). This explains the absence of a product for exon 7, as the forward primer for exon 7 amplification has 4 mismatches due to the changed splice donor site. Remarkably, the flanking exon PCR assay failed to detect leaky wild type splicing for this mutation. This would have resulted in the presence of a wild type band for exon 7 amplification, which was not observed. To further investigate splicing of exon 7, an alternative forward primer located in exon 5 was used. The expected product was now obtained, and showed splicing from c.1071 in exon 6 to the canonical splice acceptor site of exon 7 (FIG. 11A), as was observed for sequence analysis of product 11. The reading frame of the resulting mRNA has been changed leading to a premature termination codon (Table 2). The low MW product obtained with exon 2 amplification has not been pursued further. It may be caused by a yet unidentified intronic mutation. Alternatively, wild type GAA mRNA is known to have leaky exon 2 skipping, the product of which may be preferentially amplified because of mRNA degradation due to the c.1071 mutation.

Figure 4D:
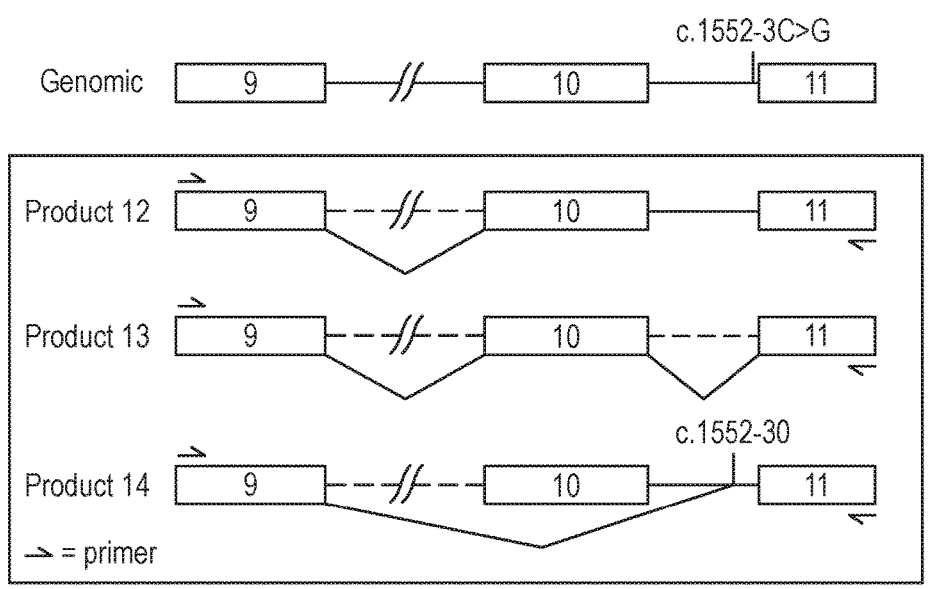
Figure 4E:
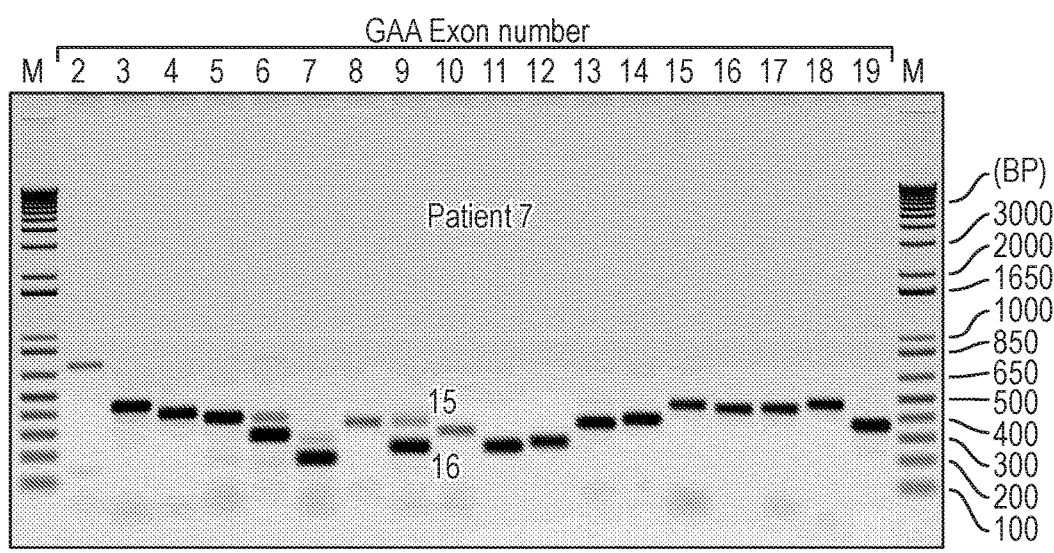
Figure 4F:
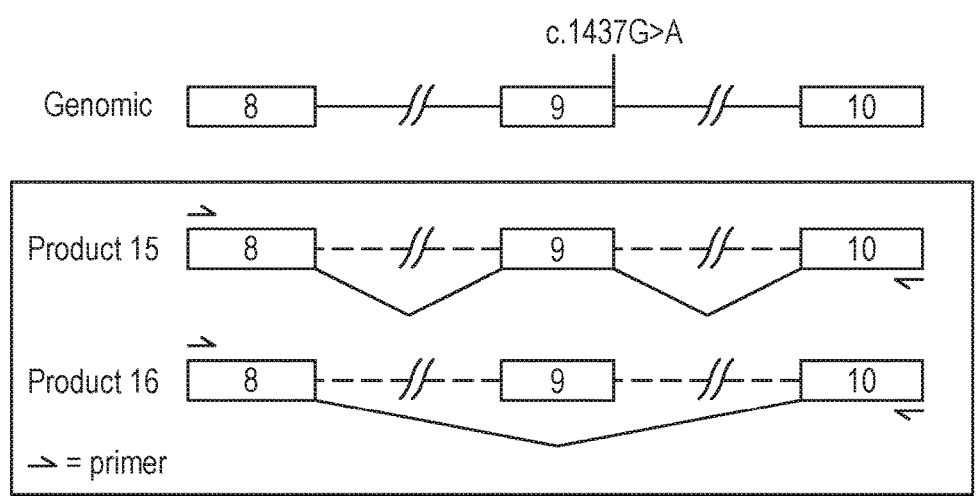
Figure 4G:
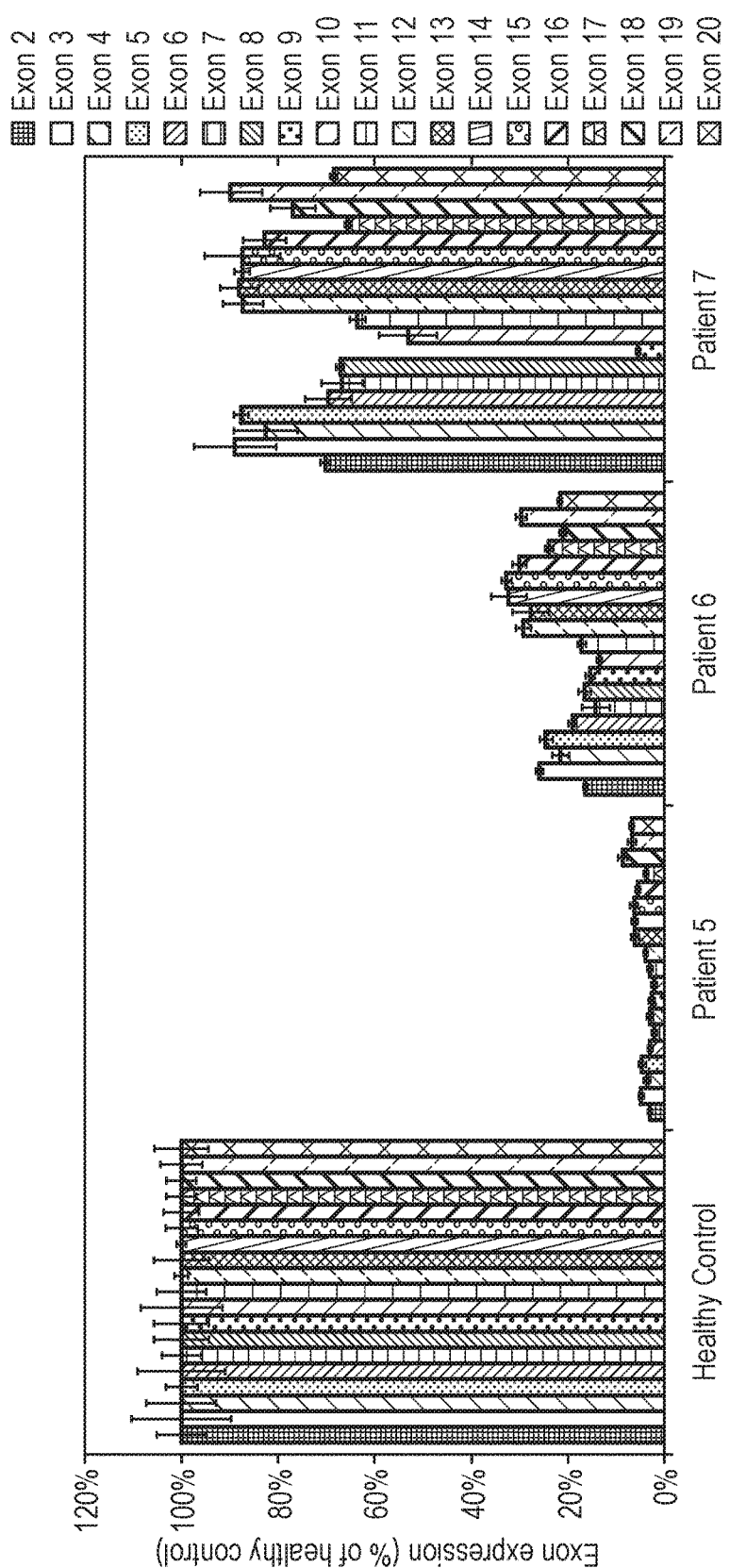

Quantification of GAA mRNA expression using the exon-internal qPCR assay showed that all GAA exons were expressed at very low levels, well below levels observed for the IVS1 mutation but just above the levels observed for the c.525delT mutation (FIG. 4G). This confirmed the notion that leaky wild type splicing levels in this patient are very low or absent, while the majority of the mRNA is unstable. In agreement, very low GAA activity in fibroblasts was measured and the diagnosis of this patient was the most severe classic infantile form of Pompe disease.

Patient 6

Patient 6 carried a homozygous c.1552-3C>G mutation. This mutation is located in intron 10 close to exon 11 (FIG. 4D). Flanking exon PCR analysis showed aberrant splicing of exon 10 with three major products (12-14; FIG. 4E). Sequence analysis indicated that in product 14, exon 10 was completely skipped while a novel splice acceptor site near exon 11 at c.1552-30 was utilized (FIGS. 4D and 11C). This mRNA leaves the reading frame intact (Table 2). Product 13 was identified as wild type spliced mRNA. Product 12 consisted of mRNA in which the complete intron 10 was retained. The reading frame is disrupted in this splicing product. While products 13 and 14 have been detected previously [27], product 12 is novel. Interestingly, splicing prediction programs were ambivalent on predicting the extent of utilization of the canonical or the cryptic splice acceptor sites of exon 11 (FIG. 14F). Moreover, the outcome was unexpected in any case: weakening of the splice acceptor site of exon 11 would not be expected to result in the skipping of exon 10. Instead, two products could be envisioned: one in which the splice donor site of exon 10 splices to the cryptic acceptor at c.1552-30, resulting in extension of exon 11 with a part of intron 10 and further normal splicing. The other expected product would be a perfect skipping of exon 11. The completely different outcome illustrates that experimental validation is required to analyze the molecular consequences of potential splicing mutations.

Quantification of splicing defects was performed with the exon-internal qPCR assay. This showed expression of all exons at ~20% of healthy control levels (FIG. 4G). No extra reduction of exon 10 expression was observed, suggesting that the majority of mRNA included exon 10, favoring products 12 and 13 above 14. The presence of leaky wild type splicing (product 13) is consistent with residual GAA enzyme activity and the milder phenotype with adult onset of Pompe disease in this patient (table 1). In conclusion, c.1552-3C>G results in several splicing defects around exon 10 and intron 10, and it allows leaky wild type splicing compatible with adult disease onset.

Patient 7

Patient 7 was homozygous for c.1437G>A, a silent mutation located at the splice donor site of exon 9 (FIG. 4F). Flanking exon PCR analysis showed two products instead of one for exon 9 amplification, and low yields for exon 8 and exon 10 amplification (FIG. 4E). Sequence analysis indicated that product 15 represented wild type spliced exon 9, while in product 16, exon 9 was perfectly skipped, resulting in a shorter transcript in which the reading frame was unchanged (FIG. 4F and FIG. 11D). As expected from its location, the c.1437G>A mutation was predicted in silico to weaken to splice donor site of exon 9 (FIG. 14E). However, the experimental result was surprising as failure of the splice donor site of exon 9 would be expected to result in inclusion of intron 9 rather than skipping of exon 9. Products of exon 8 and exon 10 amplification had correct sizes but lower yield because exon 9 had reduced availability to serve as template for annealing of the reverse PCR primer (for exon 8) or the forward PCR primer (for exon 10).

Quantification using exon-internal qPCR showed near-normal (70-80% of control) expression levels for all exons except for exon 9, which showed expression of only 5% of healthy control. The juvenile/adult disease onset of this patient is consistent with the leaky nature of the splice site mutation (Table 1). In summary, the c.1437G>A mutation results in precise skipping of exon 9 leaving the reading frame intact, and allows a low level of leaky wild type GAA splicing.

Characterization of a Complex Case: Patient 8

Genotype

Patient 8 contained the missense mutation c.1256A>T on allele 1. It is located in the middle of exon 8, results in p.Asp419Val, and has been classified as mildly pathogenic (FIG. 5B) [26]. The 2nd allele contained a c.1551+1G>T mutation, which is located in intron 10 close to the splice donor site of exon 10[26]. It resembles the c.1551+1G>A mutation described above for patient 4.

Analysis of Splicing Products

Figure 5A:
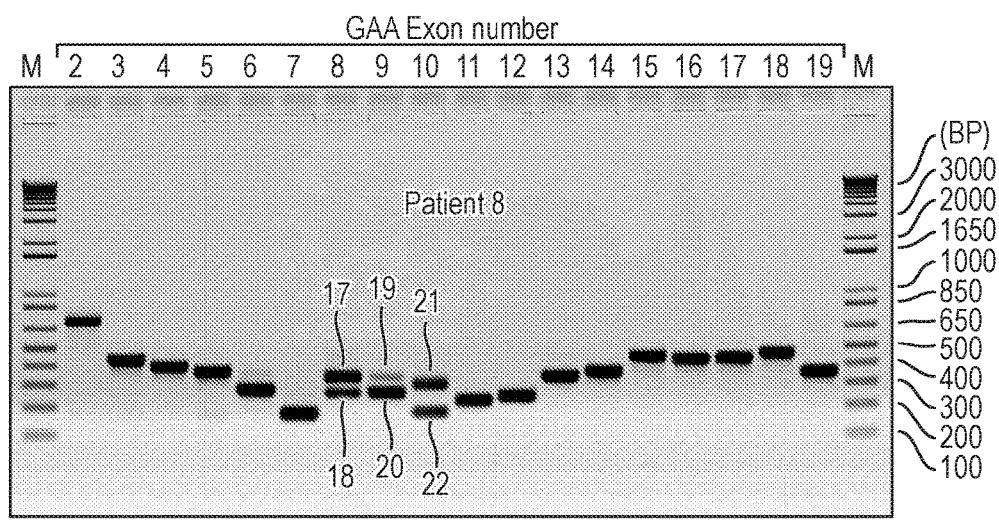
FIG. 5. Analysis of complex splicing changes in Pompe patient 8. A) Flanking exon PCR analysis. B) Cartoon of the splicing variants from allele 1, detected from analysis of exon 8. C) Cartoon of the splicing variants from allele 1, detected from analysis of exon 9. D) Cartoon of the splicing variants from allele 2, detected from analysis of exon 10. E) Exon-internal qPCR analysis. Error bars indicate SD (n=3).
Figure 5B:
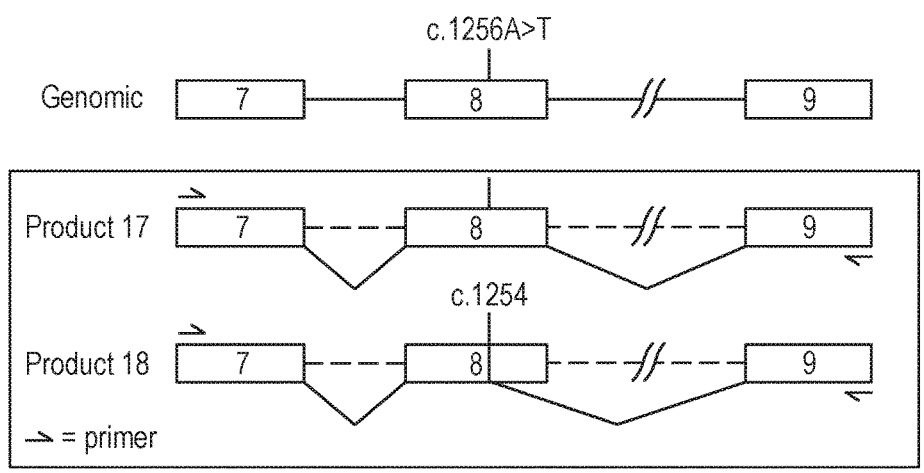
Figure 5C:
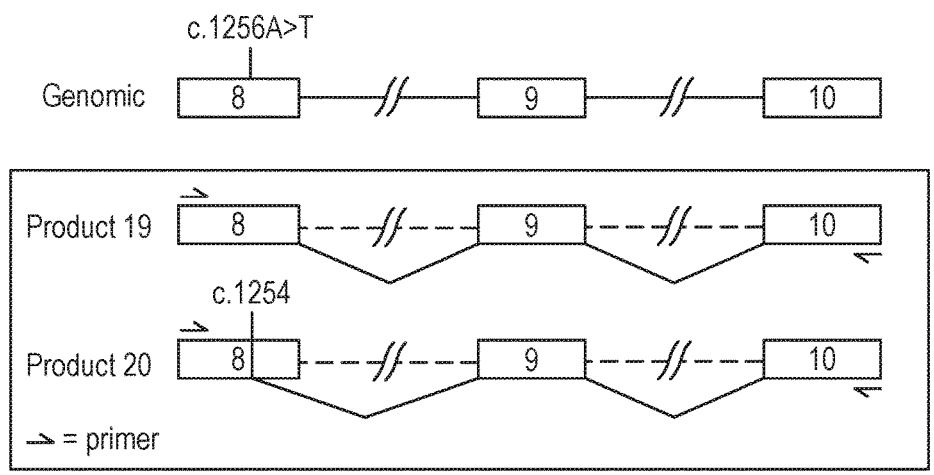
Figure 5D:
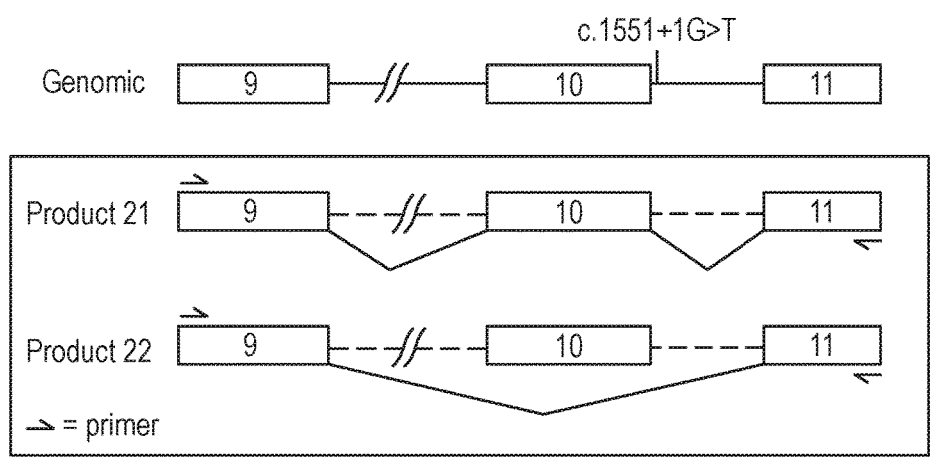
Figure 12:
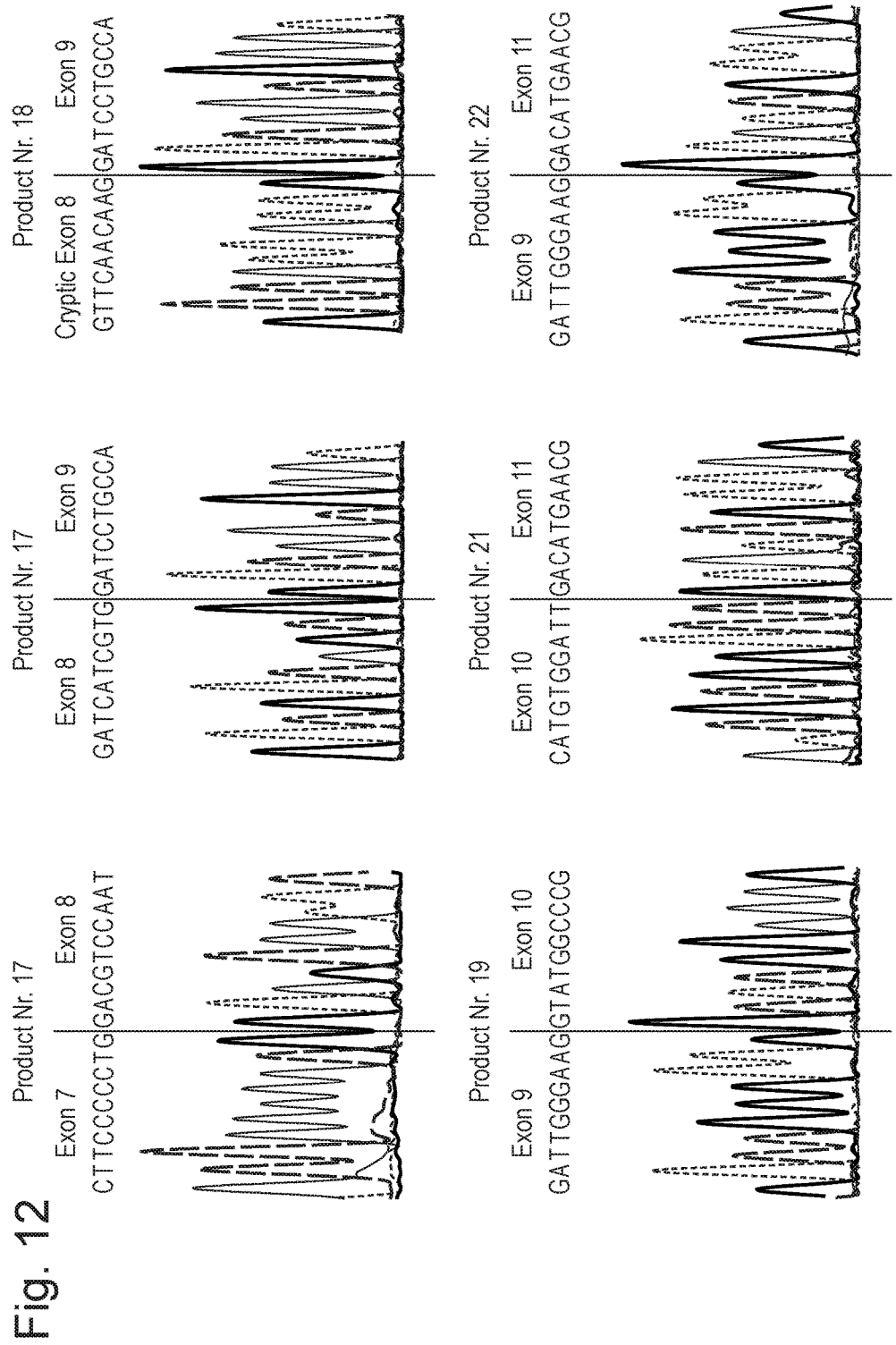
FIG. 12. Sequence analysis of patient 8.
Figure 14G:
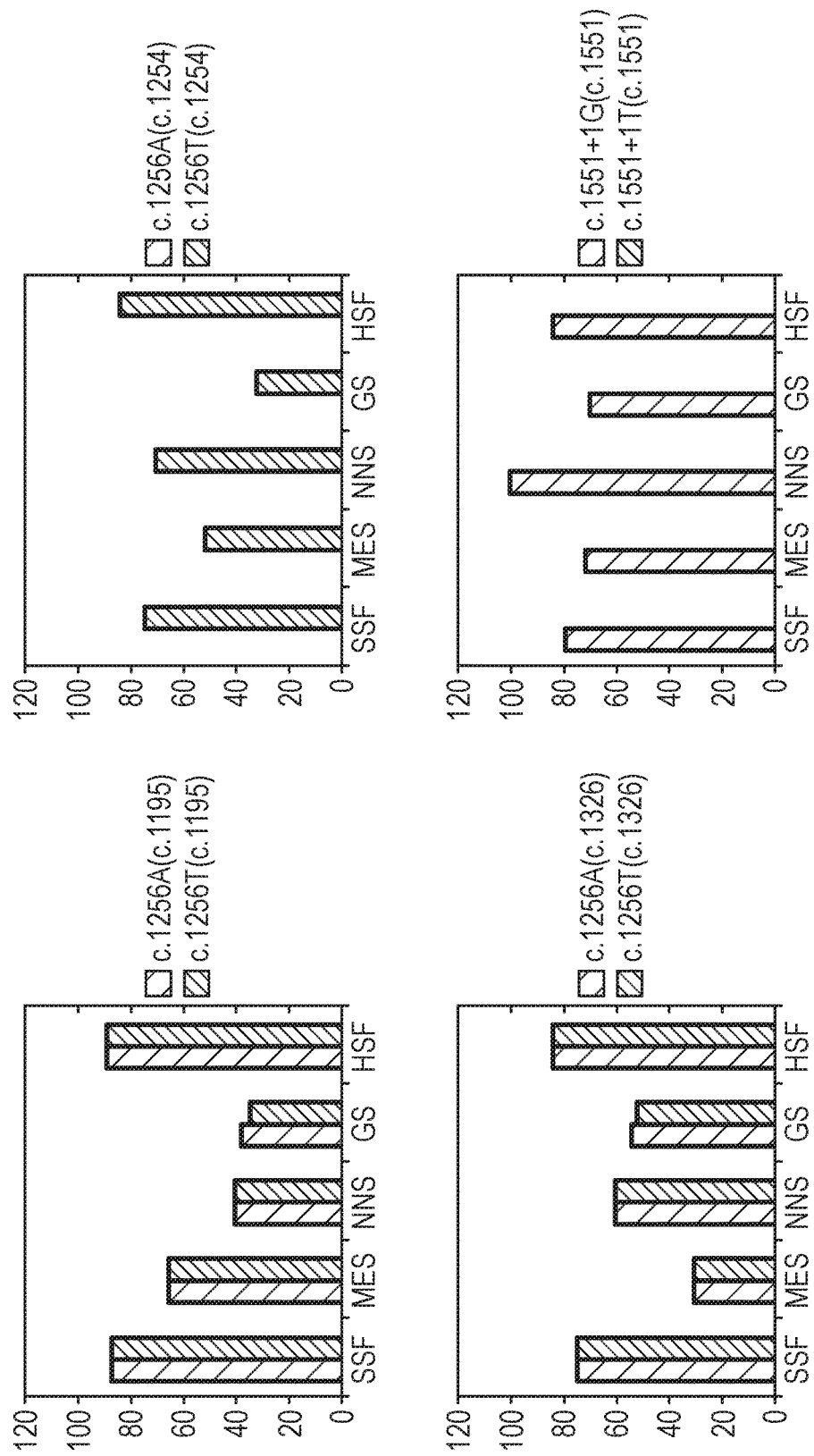
FIG. 14. Splicing predictions using five programs (SpliceSiteFinder-like (SSF), MaxEntScan (MES), NNSplice (NNS), GeneSplicer (GS) and Human Splicing Finder (HSF)) applied to wild type and mutant sequences.
Figure 17:
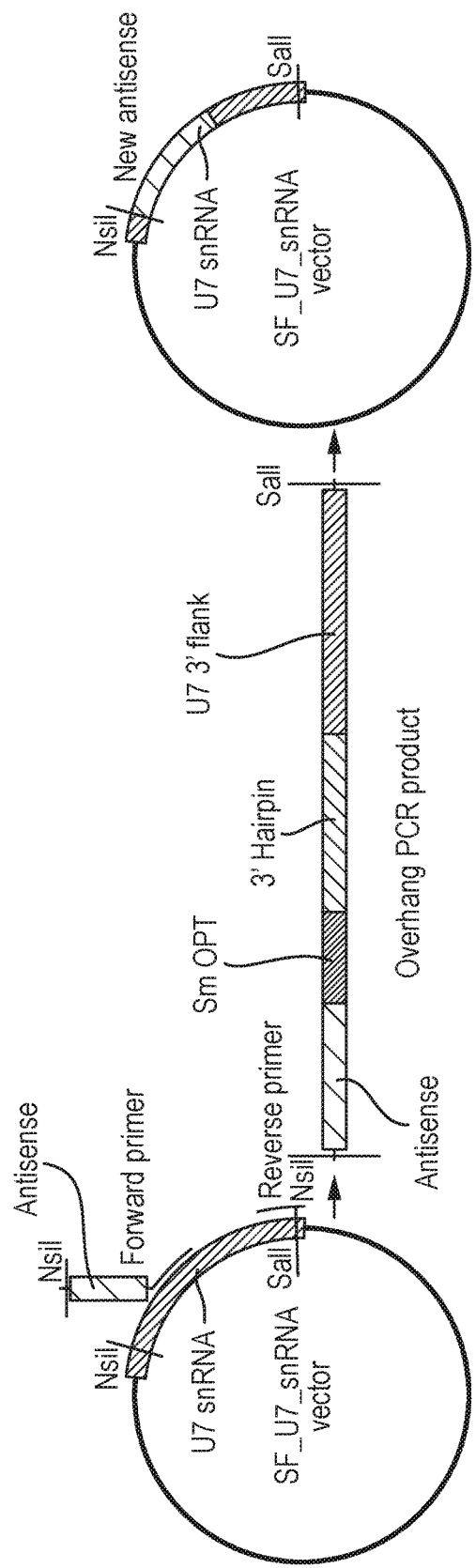
FIG. 17 The modified U7 snRNA which is used with overhang PCR to quickly generate a new U7 snRNA vector with antisense sequence.
Figure 18:
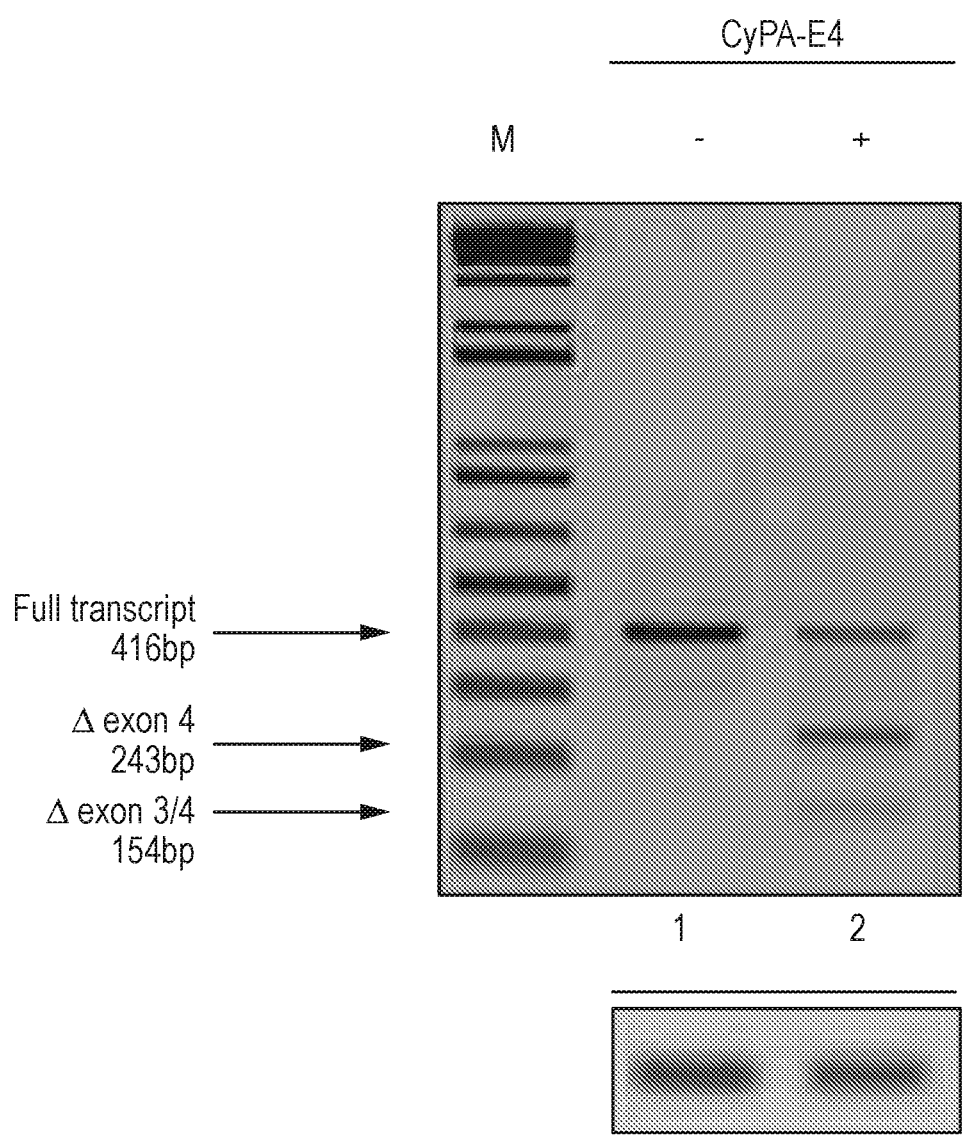
FIG. 18. The modified U7 snRNA lentiviral system is capable of interfering with splicing of CyPA as published previously [Liu, S., et al., Inhibition of HIV-1 multiplication by antisense U7 snRNAs and siRNAs targeting cyclophilin A. Nucleic Acids Res, 2004. 32(12): p. 3752-9]. Upper figure: RT-PCR analysis of exon 4 of cyclophilin A (CyPA-E4). − (lane 1): untransduced HeLa cells. + (lane 2): HeLa cells transduced with modified U7 snRNA lentiviruses (described in FIG. 17) expressing the U7/E4 antisense sequence as described in FIG. 1B of Liu et al. Below: beta actin mRNA. M: molecular weight DNA marker.

Flanking exon PCR analysis indicated multiple PCR products from amplification of exons 8, 9, and 10 (FIG. 5A). All these products were analyzed by sequencing (FIG. 12). This indicated the presence of wild type exon 8 splicing (product 17) and utilization of a novel splice donor site in exon 8 at c.1254, which is located 2 nt upstream of the c.1256A>T mutation (product 18; FIG. 5B-C). This donor spliced to the canonical splicing acceptor site of exon 9 and the resulting reading frame was unchanged (Table 2). Splicing prediction programs indeed showed that c.1254 turned into a splice donor site due to the c.1256A>T mutation (FIG. 14G). The canonical splice donor site of exon 8 remained unchanged, and it was unclear which of the two sites would be preferred from in silico predictions. Product 21 represented wild type splicing of exon 10, while product 22 was the result of perfect exon 10 skipping in which the reading frame remained intact (FIG. 5D and FIG. 12). Loss of the exon 10 splice donor site by the c.1551+1G>T mutation was consistent with splicing predictions (FIG. 14G), but the outcome was not anticipated, as intron 10 inclusion rather than exon 10 skipping seemed the most logical consequence.

Evidence for Low Levels of Leaky Wild Type Splicing

Along with the exon-internal qPCR analysis described below, the flanking exon PCR assay provides information on the severity of the mutations via the relative intensities of the products. These can be explained based on the identification of the splicing products (FIG. 5B-D) and on the locations of the primers used for amplification (FIG. 13).

Exon 7

Detection of exon 7 is performed with a forward primer that anneals to the 3' end of exon 6 and a reverse primer to the 5'end of exon 8 (FIG. 13). The 5'end of exon 8 is retained in all cases while the 3'part is spliced out in the c.1256A>T allele. Flanking exon PCR detection of exon 7 should therefore not be affected in this patient and this was indeed the case (FIG. 5A).

Exon 8

Flanking exon PCR primers used for detection of exon 8 are anneal to exon 7 and 9 (FIG. 13). Both exons are not affected in this patient predicting that all splicing alterations of exon 8 itself should be detected in a semi-quantitative manner. Indeed, a strong wild type product (number 17) was detected, dominated by allele 2, and a slightly weaker smaller product 18 was detected due to the novel cryptic splice donor site at c.1254 in allele 1. Maximal 50% of product 17 is expected to be derived from allele 2 and its stronger abundance compared to product 18 therefore suggests that allele 1 has leaky wild type splicing.

Exon 9

PCR primers for detection of exon 9 by flanking exon PCR anneal to the 5' part of exon 8, which is the part that is not skipped in allele 1, and to exon 10, which is completely skipped in allele 2 (FIG. 12). This complicates detection of exon 9 from these two alleles: a product from allele 1 would be shorter than normal due to the partial skipping of exon 8. A product from allele 2 is not possible due to the precise skipping of exon 10, while this exon is required for primer annealing. The predominant product obtained was the shorter product number 20 which was derived from allele 1. However, a small amount of wild type product number 19 was also observed. This indicates that at least one of the two alleles allows leaky wild type splicing.

Exon 10

Flanking exon PCR analysis of exon 10 is performed with primers annealing in exon 9 and exon 11, both of which are unaffected. The result therefore reflects the splicing alterations of exon 10 in a semi-quantitative way. Product 21 representing wild type splicing was the most abundant, while product 22 in which exon 10 was perfectly skipped was slightly less abundant. Because exon 10 splicing of allele 1 is unaffected and can account for 50% of wild type product, this result suggests that allele 2 also has leaky wild type splicing similar to allele 1.

Quantification Using Exon-Internal qPCR Analysis

Quantification of mRNA expression of each exon revealed that all exons except exons 8 and 10 showed ~2 fold higher abundance compared to the healthy control. Exons 8 and 10 were expressed at 2-fold lower levels with respect to the other exons but still at 80-120% of the levels of the healthy control. This indicates abnormally high mRNA expression in this patient. Allele 1 (1256A>T) suffers from partial skipping of exon 8 resulting in failure in detection of a qPCR product. The residual detection of exon 8 is therefore derived from allele 2 (c.1551+1G>T), expected to contribute 50%, and the remaining expression is likely derived from leaky wild type splicing from allele 1. The same rationale applies to detection of exon 10. In this case, expression was close to 50% relative to other exons, suggesting that the c.1551+1G>T mutation allowed much lower levels of wild type splicing. It should be noted that it is unclear why this patient shows 2-fold higher GAA expression relative to the healthy control, and whether this increase applies to both alleles to similar extents. This patient has a childhood/juvenile disease onset but is clearly less affected compared to classic infantile Pompe patients, consistent with low levels of residual wild type expression of GAA (table 1).

In summary, patient 8 contained two splicing mutations. c.1256A>T is a missense mutation in exon 8 that causes p.Asp419Val and in addition generates a novel splice donor site at c.1254, resulting in partial skipping of exon 8 and in leaky wild type splicing. c.1551+1G>T is located in intron 10 and causes perfect skipping of exon 10 and in leaky wild type splicing. The childhood/juvenile onset of Pompe disease suggests that both mutations are moderately to severely pathogenic. This is consistent with the GAA enzyme activity levels, which are lower compared to adult onset patients.

Mucopolycaccharidosis type VI (Maroteaux-Lamy syndrome) is a autosomal recessive monogenic disorder caused by defects in the gene coding for N-acetylgalactosamine 4-sulfatase (arylsulfatase B; ARSB). To demonstrate the generic nature of the splicing assay, the assay was adapted for MPSVI. To this end, flanking exon primers were designed for all coding exons of the ARSB gene (exons 2-7; the first and the last exons cannot be flanked). The following primer sequences and the expected product sizes (column "WT product size") were used:

| Exon | primer | SEQ ID NO: | WT product | 1142 + 2T > C |
|---|---|---|---|---|
| 2 | Forward GGGTGCTCCTGGACAACTAC | 1590 | 378 | 378 |
|   | Reverse CCTGTTGCAACTTCTTCGCC | 1591 |  |  |
| 3 | Forward ATGGCACCTGGGAATGTACC | 1592 | 444 | 444 |
|   | Reverse GTGTTGTTCCAGAGCCCACT | 1593 |  |  |
| 4 | Forward ACGCTCTGAATGTCACACGA | 1594 | 514 | 514 |
|   | Reverse GTTGGCAGCCAGTCAGAGAT | 1595 |  |  |
| 5 | Forward AAAAAGCAGTGGGCTCTGGA | 1596 | 361 | 117 |
|   | Reverse CGGTGAAGAGTCCACGAAGT | 1597 |  |  |
| 6 | Forward CAGAAGGGCGTGAAGAACCG | 1598 | 314 | 314 |
|   | Reverse CCCGTGAGGAGTTTCCAATTTC | 1599 |  |  |
| 7 | Forward ACTTCGTGGACTCTTCACCG | 1600 | 348 | 348 |
|   | Reverse AGTACACGGGGACTGAGTGT | 1601 |  |  |

Figure 31:
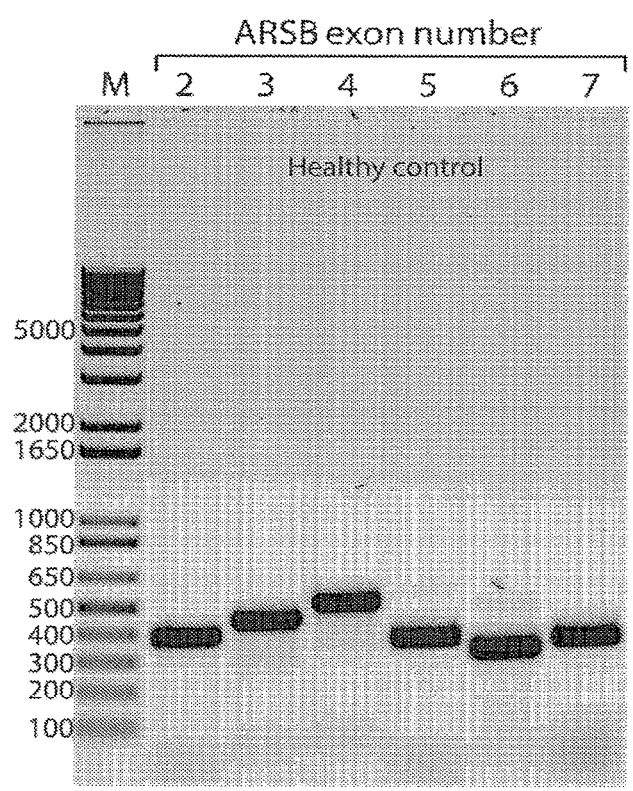
FIG. 31: Splicing assay of healthy person for N-acetylgalactosamine 4-sulfatase (arylsulfatase B; ARSB).
Figure 32:
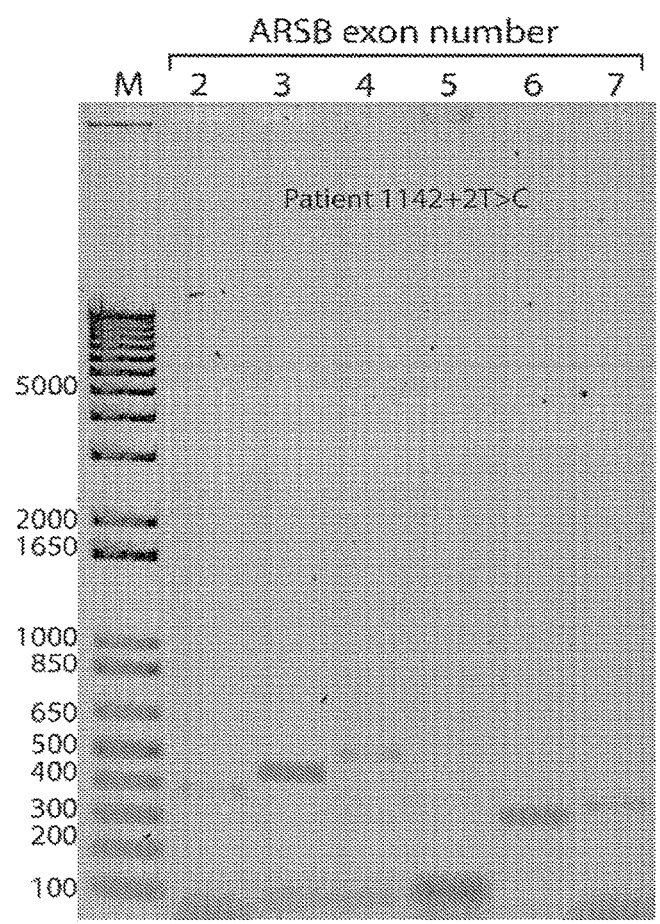
FIG. 32: Splicing assay of patient with Mucopolycaccharidosis type VI (Maroteaux-Lamy syndrome) for N-acetylgalactosamine 4-sulfatase (arylsulfatase B; ARSB).
Figure 33:
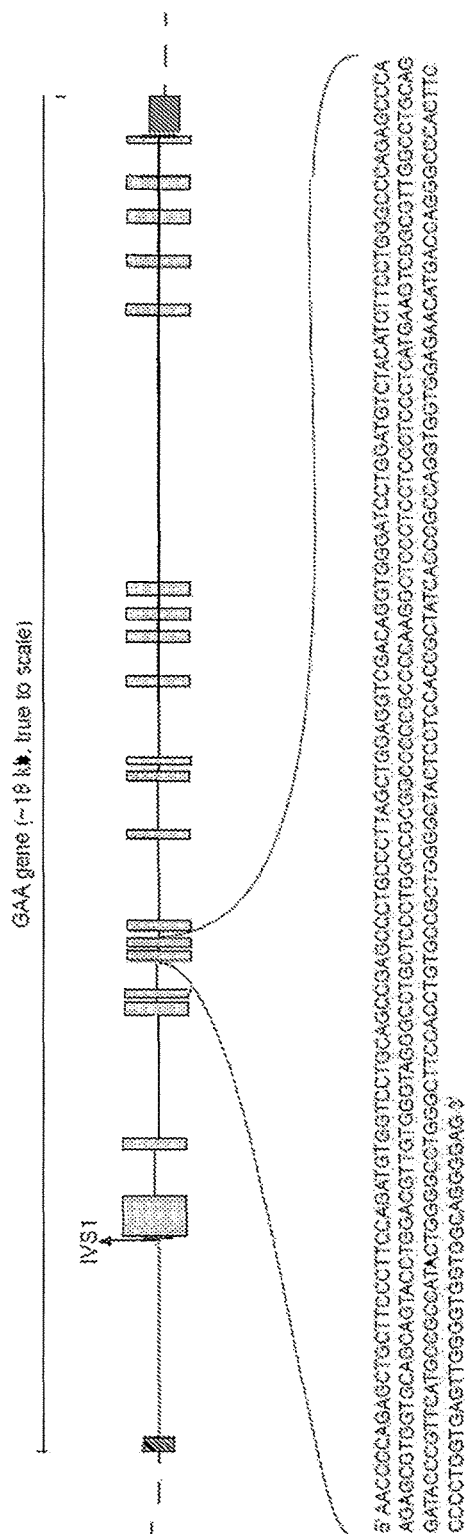
FIG. 33: Target sequence for GAA exon 2 inclusion.

Primary fibroblasts from a healthy control were grown, total RNA was harvested, cDNA was synthesized, and exons 2-7 were amplified by PCR, see FIG. 31. Products were separated on an agarose gel and visualized using ethidium bromide. FIG. 31 shows that all exons gave a predominant single band at the expected size (size markers are indicated on the left and numbers refer to sizes in bp). Next, fibroblasts were grown from a patient homozygous for the ARSB variant c.1142+2T>C. This patient has been described previously in Brands et al. (Orphanet J Rare Dis. 2013 Apr. 4; 8:51). While a splicing defect was suspected, it has not been demonstrated. In addition, it was not known how severe the potential splicing defect may be. Application of the splicing assay to analyze the nature of this variant revealed a severe splicing defect with two major outcomes, as shown in FIG. 32, left part: 1) The product for amplification of exon 5 was lower compared to the healthy control: now a single product of 117 bp instead of 361 bp was obtained, which is consistent with a skipping of exon 5 and a deletion of 244 nucleotides in the mRNA, see above, all products had a lower abundance compared to the healthy control. This is consistent with the idea that the deletion of 244 nucleotides results in a reading frame shift, resulting in activation of the nonsense mediated decay pathway and degradation of the mRNA. Interestingly, no leaky wild type splicing could be detected. This is consistent with the severe and fast disease progression in this patient as described in Brands et al. (Orphanet J Rare Dis. 2013 Apr. 4; 8:51). Taken together, the expression and splicing assay was successfully applied to MPSVI, in which is resulted in the identification of the splicing defect caused by the c.1142+2T>C ARSB variant. The absence of leaky wild type splicing was consistent with the severe phenotype of the patient involved.

Example 2

1 Generation of the SF-U7 snRNA Antisense Vector

The U7snRNA gene with promoter was obtained from female mouse genomic DNA by using Fw-GCGCctgcag-TAACAACATAGGAGCTGTG (SEQ ID NO: 1602) and Rv-GCGCgtcgacCAGATACGCGTTTCCTAGGA (SEQ ID NO: 1603) primers with PstI and SalI overhang (indicated in bold regular letter type) in a PCR amplification. The whole PCR reaction was loaded on a 1% gel and the PCR fragment (425 bp) was cloned into a Topo-II-vector according to the manufacture's manual (Invitrogen). SMopt and StuI sites were generated by using site directed mutagenesis according to an inner and outer primer design with Fw-(GCTCTTT-TAGAATTTTTGGAGCAGGTTTTCTGACTTCG (SEQ ID NO: 1604) and Rv-U7snRNA-SmOPT (CGAAGTCA-GAAAACCTGCTCCAAAAATTCTAAAAGAGC (SEQ ID NO: 1605) or Fw-(CCTGGCTCGCTACAGAGGC CTTTCCGCAAGTGTTACAGC (SEQ ID NO: 1606) and Rv-U7snRNA-StuI (GCTGTAACACTTGCGGAAAGGC CTCTGTAGCGAGCCAGG (SEQ ID NO: 1607) as inner primers and with Fw-M13 (GTAAAACGACGGCCAG) (SEQ ID NO: 1608) and Rv-M13 (CAGGAAACAGCTAT-GAC) (SEQ ID NO: 1609) as outer primers [Heckman, K. L. and L. R. Pease, Gene splicing and mutagenesis by PCR-driven overlap extension. Nat Protoc, 2007. 2(4): p. 924-32]. The modified U7 snRNA sequence was cloned back into pRRL.PPT.SF.pre vector [Warlich E et al., Lentiviral vector design and imaging approaches to visualize the early stages of cellular reprogramming Mol Ther. 2011 April; 19(4):782-9.] by using PstI and SalI sites and replaced the original SFFV promoter. This is the procedure for generating the SF_U7snRNA vector.

2 Optimization of the SF-U7 snRNA Antisense Vector for High Throughput Screening The originally used StuI site is not unique in the lentiviral vector of Warlich et al and was replaced by a NsiI restriction site by site directed mutagenesis by using Fw-cctggctcgc-tacagatgcaTaggaggacggaggacg (SEQ ID NO: 1610) and Rv-cgtcctccgtcctcctAtgcatctgtagcgagccagg (SEQ ID NO: 1611) primers. Capital letters indicate mutated residues.

3 Insertion of Antisense Sequences

New antisense sequences were inserted with an overhang PCR by using overhang forward primers containing the desired antisense sequences (gcgcATGCAT-antisense sequence-ttggagcagg) (SEQ ID NO:1612). Bold capital letters indicate the NsiI restriction site. The reverse primer Rv_ms_U7snRNA_SalI is (GCGCgtcgacCAGA-TACGCGTTTCCTAGGA) (SEQ ID NO: 1613) and was the same for every construct., the small letters indicate the SalI restriction site. Overhang PCR was performed on the modified vector (SF_U7snRNA_NSI) using PfuUltra HF (Agilent Technologies) The PCR program consisted of a 30 second initial denaturation step at 95° C., 35 cycles at 95° C. for 10 seconds, 60° C. for 30 seconds and 72° C. for 10 seconds. Final extension step was at 72° C. for 10 minutes. The PCR reaction containing the desired antisense sequence and U7 snRNA loaded on a 2% agarose gel with 0.2% ethidiumbromide staining Bands were then visualized under a transilluminator (UVP, LLC) excised and extracted using the QIAquick Gel Extraction Kit (Qiagen GmbH, Hilden, Germany).

After gel extraction, 16 µl of purified product was digested using SalI and NsiI (Roche) for 1 hour at 37° C. and purified using the QIAquick PCR Purification Kit (Qiagen GmbH, Hilden, Germany).

Meanwhile the original vector was digested with SalI and NsiI for 1 hour at 37° C., resulting in a vector without antisense sequence. The digested vector was loaded on a 1% agarose gel with ethidiumbromide staining Bands were visualized under a transilluminator and the band corresponding with the digested vector (6358 bp) was excised and purified using the QIAquick Gel Extraction Kit (Qiagen GmbH, Hilden, Germany).

Purified digested vector and digested PCR products were ligated with T4 DNA ligase with ATP (New England Bio-Labs) for 1 hour at room temperature.

The ligation products were transformed in *E. coli* (TOP10) and inoculated on LB agar plates containing 100 µg/ml ampicillin (Sigma). After overnight incubation, four colonies were picked per ligation product for miniprep cultures. Picked colonies were grown overnight in 2 ml LB containing 100 µg/ml ampicillin at 37° C. Purification of the plasmids was carried out using the QIAprep Spin Miniprep Kit (Qiagen GmbH, Hilden, Germany). After extraction, DNA concentration was measured with the Nanovue Spectrophotometer.

Sequences of newly generated constructs were validated with Sanger Sequencing using BigDye Terminator v3.1 (Applied Biosystems) for the sequence reaction and were then purified with Sephadex G-50 (Sigma) according to manufacturer's protocol.

Sequences SEQ ID NO: 41-97 are antisense compounds identified with the U7 screen. The antisense sequence above is depicted as DNA as it is cloned into a vector, however in the cell it is transcribed as a RNA molecule. The skilled person knows then that T is U.

Figure 22:
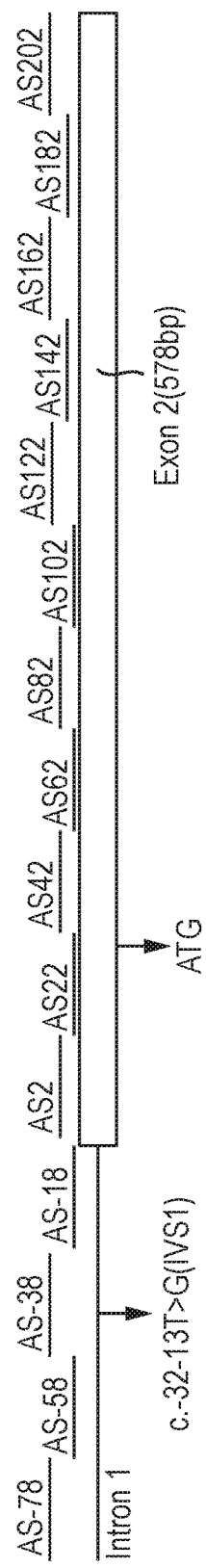
FIG. 22. Examples of positions of antisense sequences targeting GAA for the unbiased intron 1 and exon 2 screen.
Figure 24A:
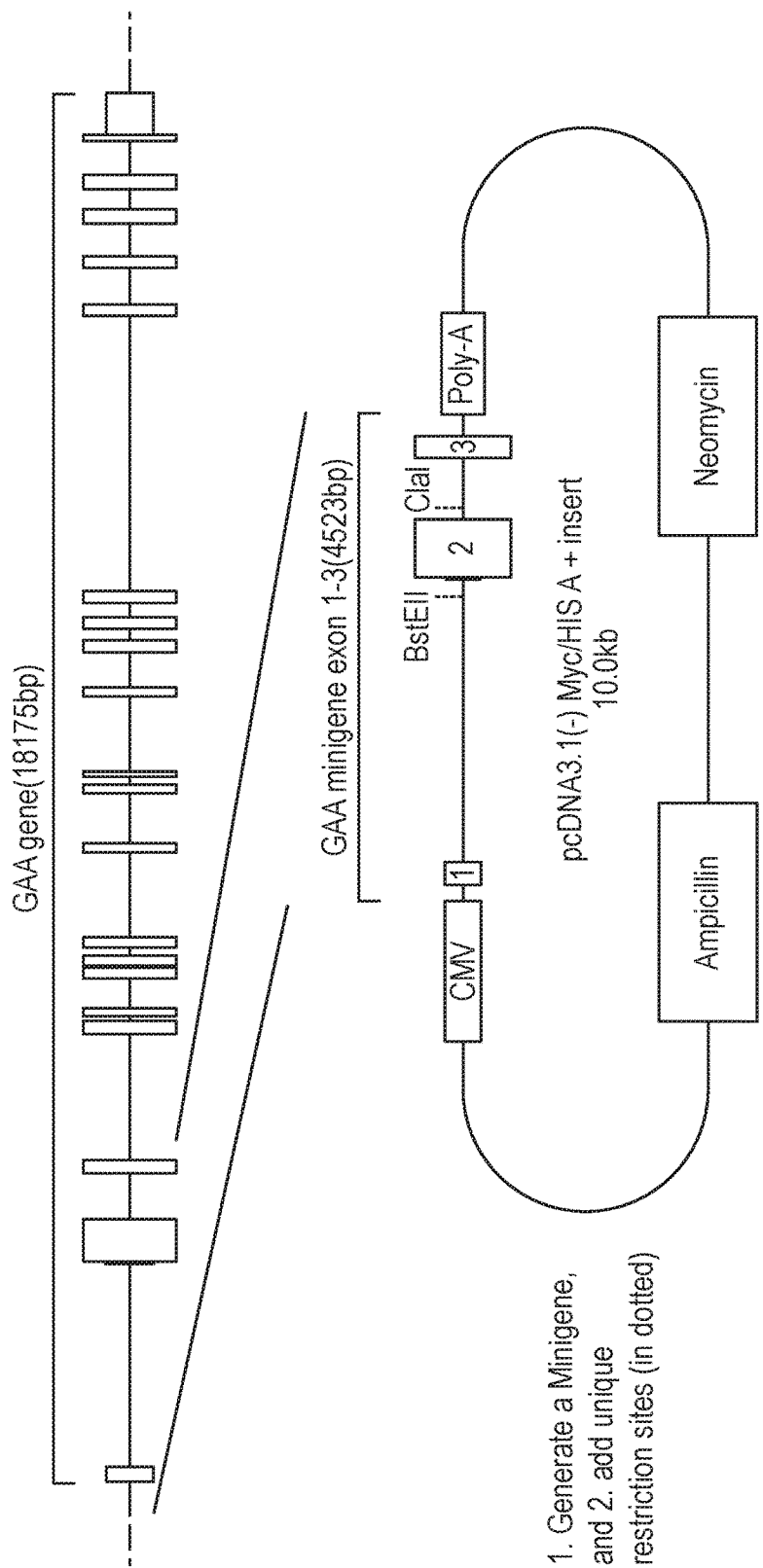
FIG. 24. Minigene construct and method to identify sequences that affect mRNA splicing. A. Generate a Minigene and add unique restriction sites (in red); B Carry out degenerate PCR with minigene as template; C. Ligate PCR products in vector and generate clones; D. Transfect clones in HEK293 cells and analyse RNa for exon 2 inclusion via Exon flanking RT-PCR and exon internal qPCR; E Sequence analysis of clone.
Figure 24B:
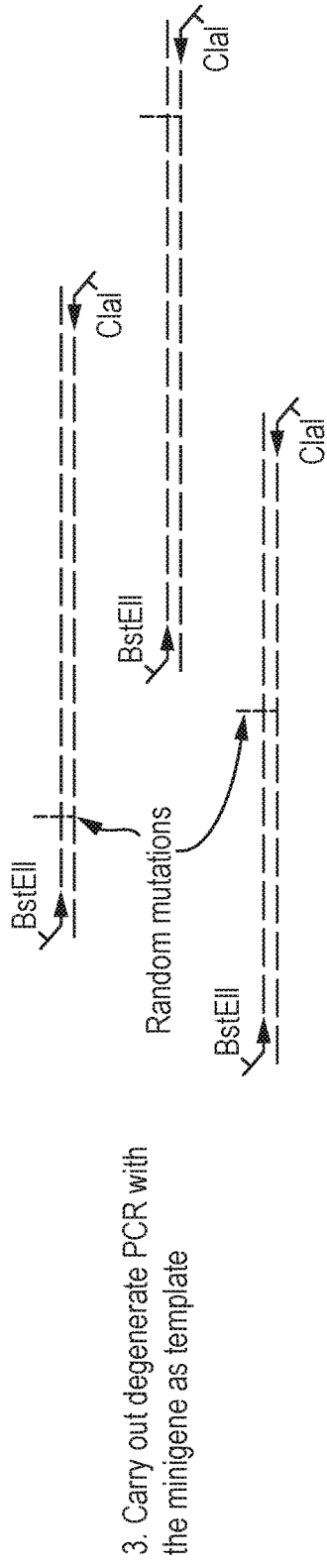
Figure 24C:
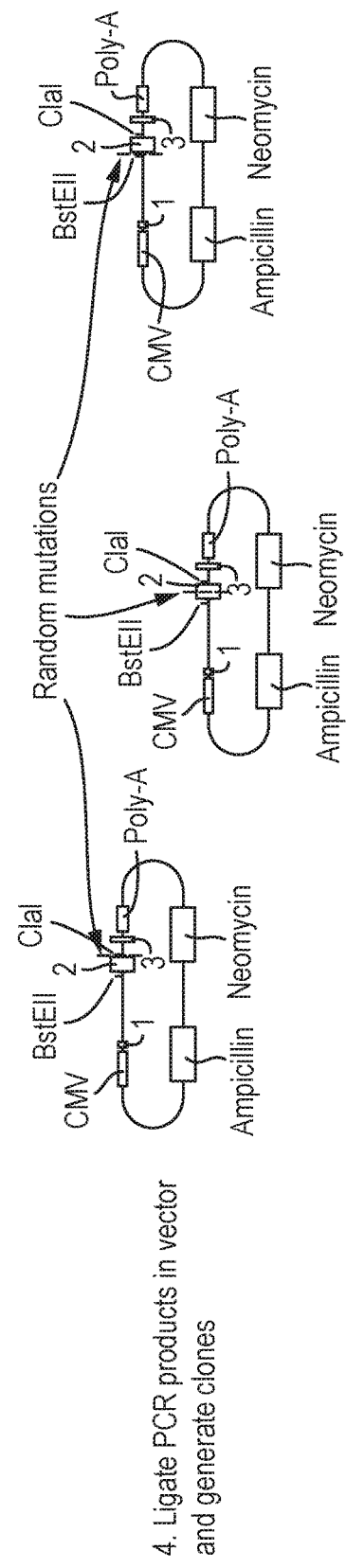
Figure 24D:
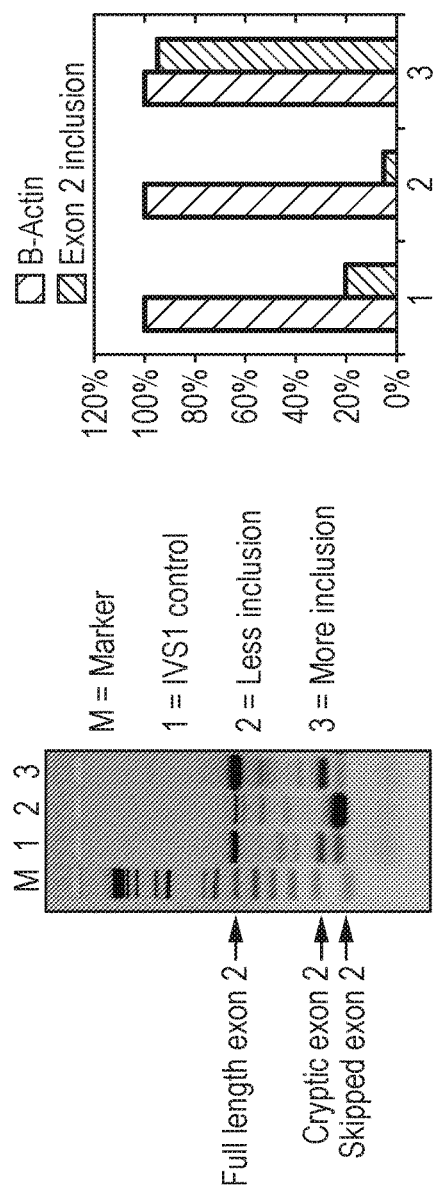
Figure 24E:
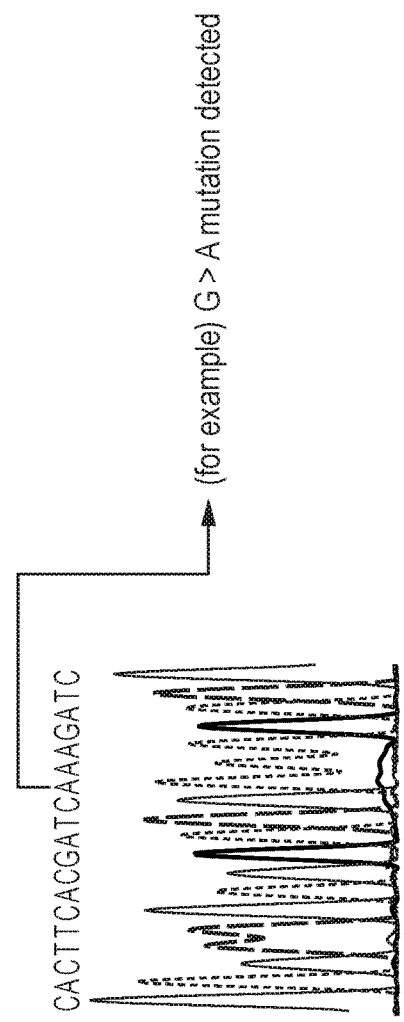

FIG. 22 shows examples of positions of antisense sequences targeting GAA for the unbiased intron 1 and exon 2 screen.

Enzyme Activity Assay

Enzyme activity was measured using the 4-methylumbelliferone assay. Samples were harvested after twelve days of transduction. The lysis buffer consisted of 50 mM Tris (pH 7.5), 100 mM NaCl, 50 mM NaF, 1% Tx-100 and one tablet protease inhibitor with EDTA (Roche). Lysis buffer was incubated on transduced fibroblasts for 5 minutes on ice before harvesting. Samples were either directly used or snap-freezed using liquid nitrogen and stored at −80° C. Otherwise, samples were kept on ice for further use in 4-methylumbelliferone assay.

GAA activity was measured using the substrate 4-methylumbelliferyl-α-D-glucopyranoside, which is fluorogenic in nature. Protein concentrations of the samples was determined by the Lowry protein method using the BCA Protein Assay Kit (Pierce, Thermo Scientific). Bovine serum albumin (BSA) standards consisted of 0, 0.1, 0.2, 0.4, 0.5, 0.6, 1.0, 2.0 mg/ml. Absorbance was measured at 562 nm for the BCA Protein Assay, and for the 4-methylumbelliferone assay excitation was at 365 nm and emission at 448 nm, using the Varioskan (Thermo Scientific) microplate reader. GAA enzyme activity was expressed as nanomoles of substrate hydrolyzed per hour per milligram of total protein.

Lentiviral Vector Production

For lentiviral vector production, 293T cells 90% confluent growing on 10 cm culture dishes were seeded 1/8 on 10 cm culture dishes. After 16-24 hours, a total of 3 µg U7 snRNA construct, 2 µg Pax2 and 1 µg VSV were cotransfected using Fugene 6 Transfection Agent (Promega). Viral supernatants (9 ml) were harvested 72 hours post-transfection, filtered over 0.45 µm filters (MillexHV, Millipore) and concentrated by ultra-centrifugation in a Beckman Ultracentrifuge (Beckman Coulter) at 20.000 rpm, 4° C. for 2 hours. Viral pellets were resuspended in 100 µl Dulbecco's modified Eagle's medium Low Glucose (Gibco, Paisley, UK), aliquoted in CryoTubes (Thermo Scientific) and stored at −80° C. Lentiviral titers were determined after concentration by ultra-centrifugation with the HIV p24 Antigen ELISA Kit (Retrotek, ZeptroMetrix Corporation). The assay was measured with a Varioskan microplate reader (Thermo Scientific)

Transduction of Cells

Culture media was replaced with new culture media containing 6 ng/ml protamine sulphate (sigma) 24 hours after seeding. The cells were transduced with equal titers of lentiviruses (see above).

Figure 19:
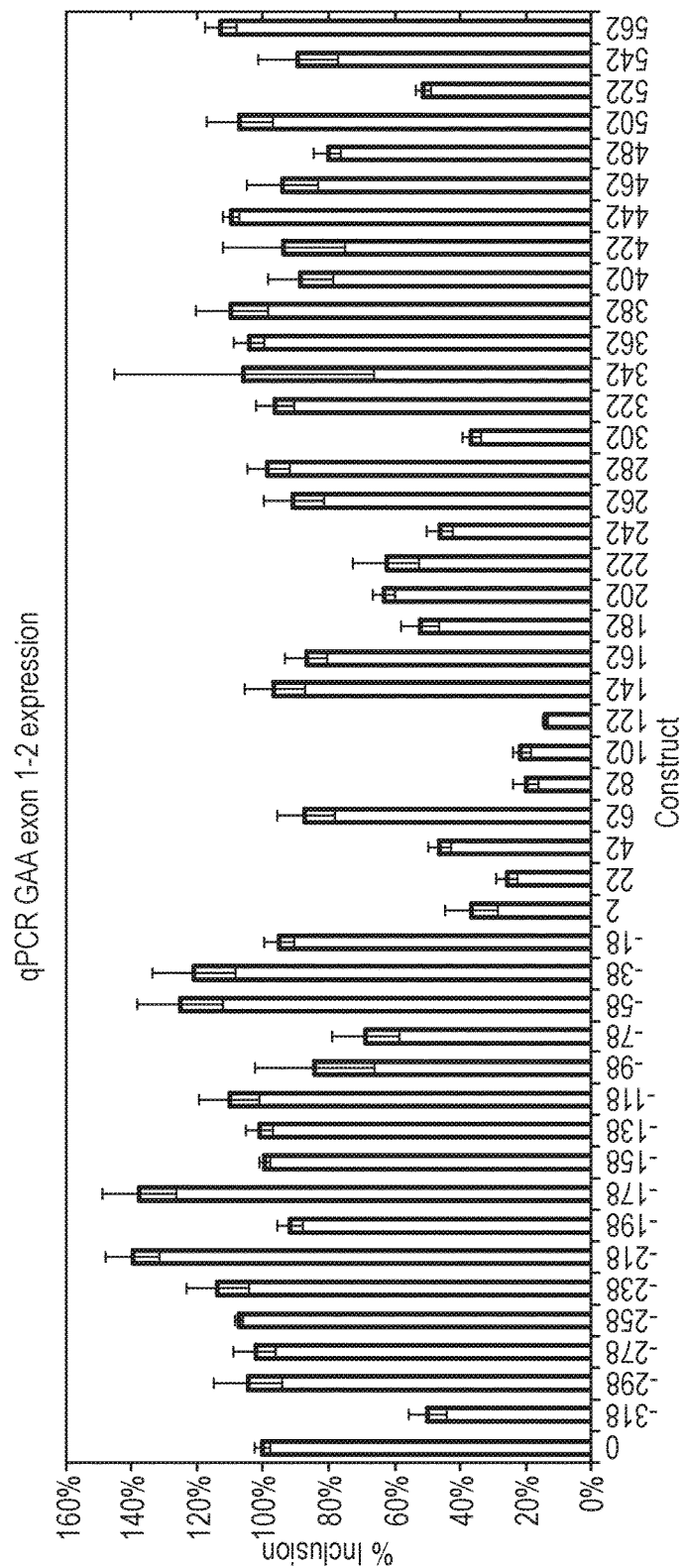
FIG. 19. RNA expression analysis using RT-qPCR of a screen performed for sequences in intron 1 and exon 2 of the GAA pre-mRNA with antisense sequences using the U7 small nuclear RNA system. Numbers indicate antisense sequence positions according to table 1.

Primary fibroblasts from patient were transduced, see above with lentivirus containing the U7snRNA AON construct and splicing was allowed to occur. The screen on fibroblasts was performed by infection of individual wells containing primary fibroblasts with lentiviruses expressing a single type of U7 snRNA AONs. RNA was analysed 5 days after infection. Splicing products were analysed with RT-qPCR. GAA enzyme activity was analysed 12 days after infection (see above: enzyme activity assay). FIG. 19 shows changes in exon 2 inclusion by different AONs. RNA expression analysis using RT-qPCR of a screen on intron 1 and exon 2 of GAA with antisense sequences with the use of the U7 small nuclear RNA system. Numbers indicate antisense sequence positions according to table 1. The control is the patient fibroblast without added AON vector.

Figure 20:
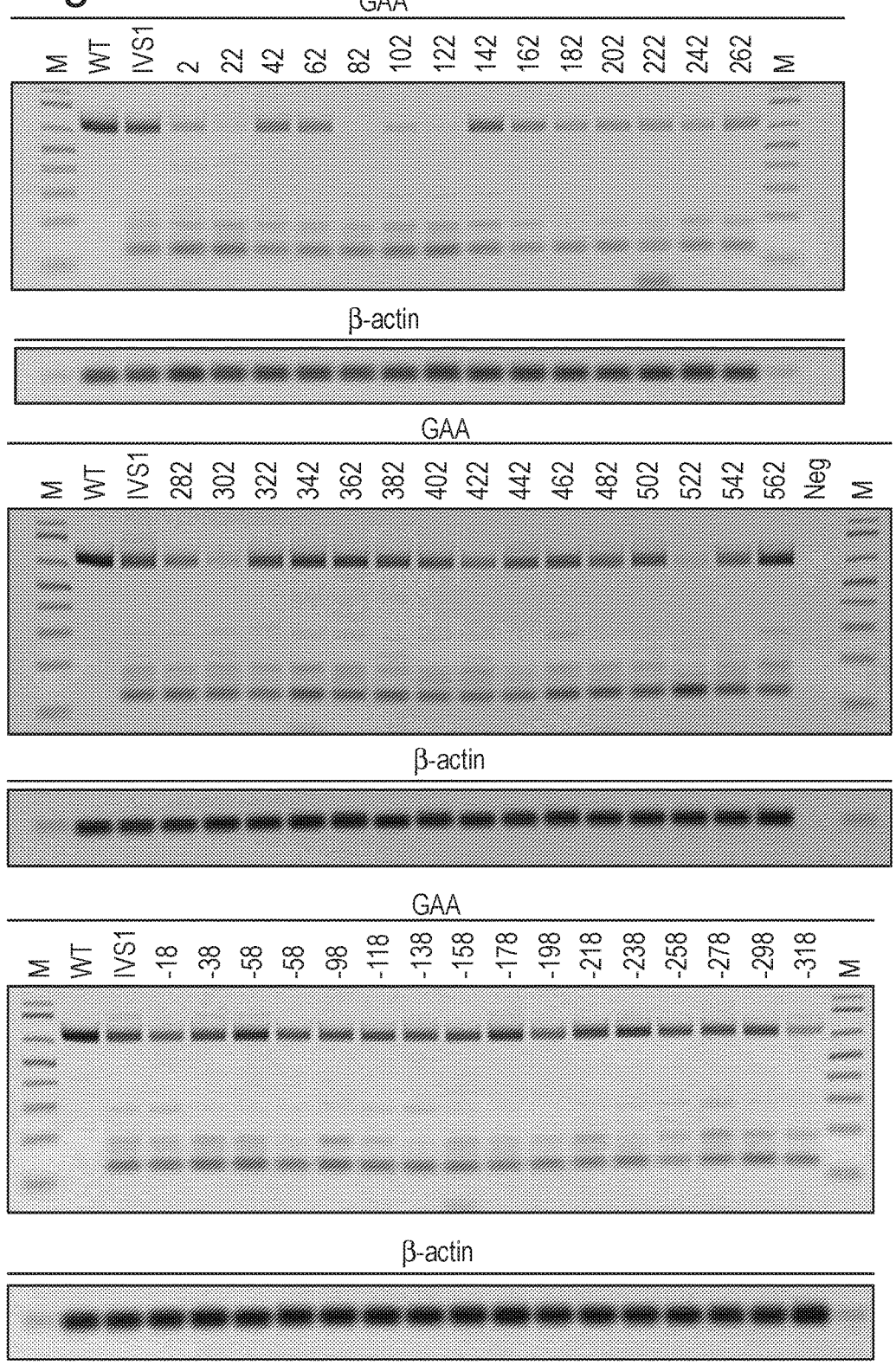
FIG. 20 RNA expression analysis using RT-PCR of a screen performed for sequences in intron 1 and exon 2 of the GAA pre-mRNA with antisense sequences using the U7 small nuclear RNA system. Numbers indicate antisense sequence positions according to table 1. In the GAA RT-PCR, three major products are observed. The upper product represents exon 2 inclusion, the lower doublet represents partial skipping of exon 2 (upper band of the doublet) and complete skipping of exon 2 (lower band of the doublet). Beta-actin RT-PCR was used as loading control.

FIG. 20 shows RNA analysis with RT-PCR of a screen on intron 1 and exon 2 of GAA with antisense sequences used in the U7 small nuclear RNA system. Numbers indicate antisense sequence positions according to table 1. In the GAA RT-PCR, three major products are observed. The upper product represents exon 2 inclusion, the lower doublet represents partial skipping of exon 2 (upper band of the doublet) and complete skipping of exon 2 (lower band of the doublet. Beta-actin RT-PCR was used as loading control.

Figure 21:
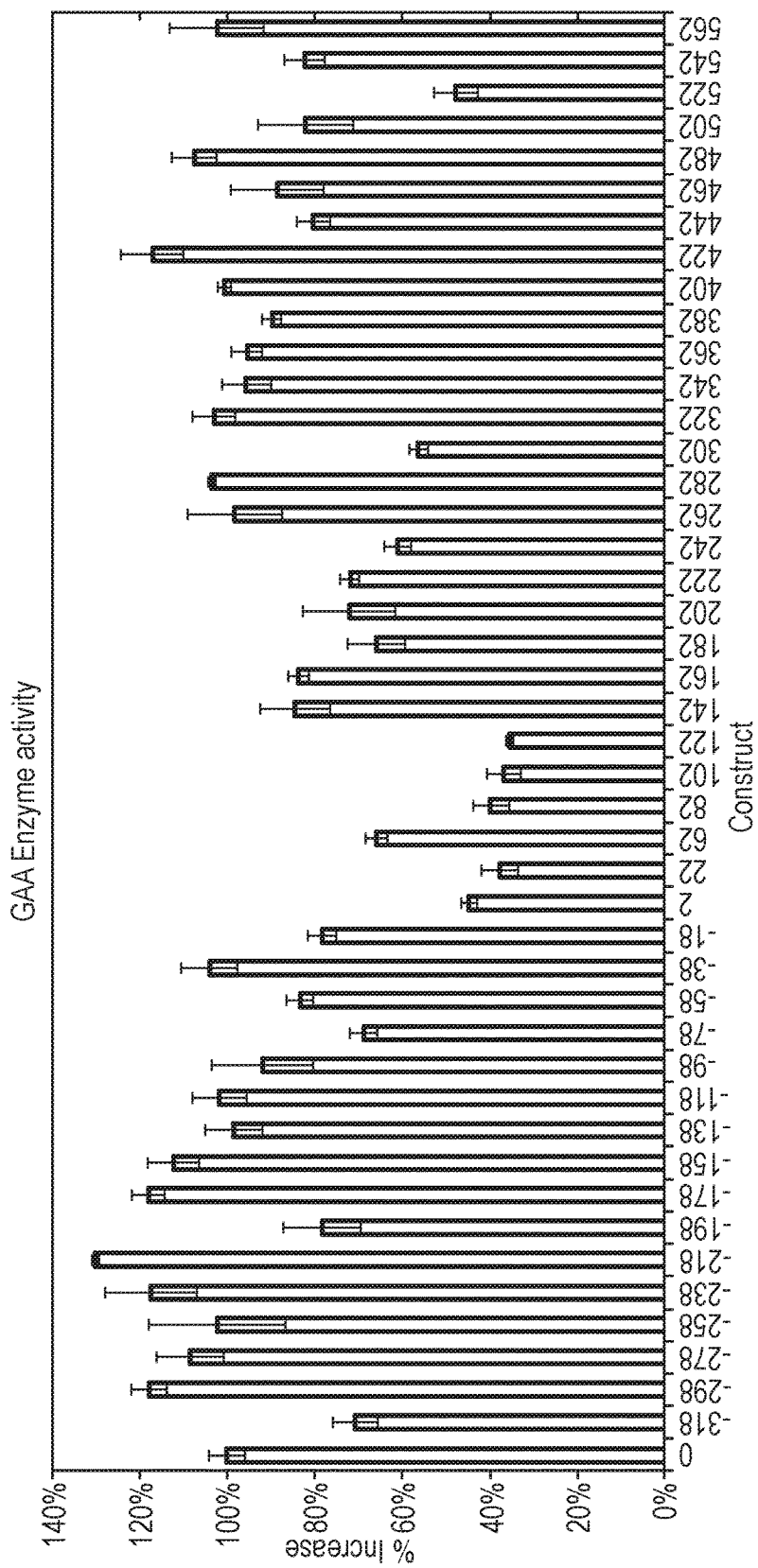
FIG. 21. Enzyme activity of GAA of a screen performed for sequences in intron 1 and exon 2 of the GAA pre-mRNA with antisense sequences using the U7 small nuclear RNA system. Numbers indicate antisense sequence positions according to table 1.

FIG. 21 shows GAA enzyme activity of the screen on intron 1 and exon 2 of GAA with antisense sequences in the U7 small nuclear RNA system. Numbers indicate antisense sequence positions according to table 1. The control is the patient fibroblast without added AON vector.

It is clear that some clones significantly increase the inclusion of exon 2 and thereby provide potential candidates for a therapy for pompe patients having the IVS1 mutation. FIG. 23 shows an example illustrating that the identified sequence could not be predicted as the identified sequence was identified both as enhancer and as silencer motif.

Example 3

By far the most common mutation causing Pompe disease is the c.-32-13T>G (IVS1) mutation. This mutation in the GAA gene is located in an intron 13 basebairs upstream of exon 2, the exon that contains the start codon for translation of the GAA mRNA. The IVS1 mutation causes miss-splicing of exon 2 in approximately 90% of GAA transcripts because it disrupts the polypyrimidine tract which reduces the strength of the exon 2 splice acceptor site.

To counteract this reduced strength of the splice site, we want to identify sequences that bind splicing factors that have a negative effect on splicing of GAA exon 2. By integration of random mutations in and around exon 2 we could be able to find these sequences.

For quick screening of a large number of mutations we generated a minigene containing GAA exon 1, intron 1, exon 2, intron 2, exon 3 and a part of intron 3 (FIG. 24, part 1). By integration of 2 unique restriction sites, we are able to quickly exchange part of the minigene surrounding exon 2 with mutant sequences (FIG. 24, part 2). A PCR is carried out at suboptimal conditions to integrate random mutations in the PCR products (FIG. 24, part 3). These PCR products, which also contain the restriction sites located around exon 2, can then be ligated directly into the destination vector. After transformation of the ligated products, clones can be picked and the plasmid can be isolated from the clone, containing a random mutation (FIG. 24, part 4). Separate transfection of these clones into HEK293 cells generate RNA-transcripts from the GAA minigene that result in differential splicing compared to the control. An example is shown in figure part 5, were a flanking exon RT-PCR and an exon internal qPCR is carried out against cDNA generated from 3 clones (indicated in FIG. 24, part 5). Sequencing of the plasmids that yield a higher inclusion of exon 2 results in identification on an important sequence that influences splicing in a negative manner. These sequences can sequentially be used to test as a potential target for antisense therapy or to screen for compounds that bind to this area.

Figure 25B:
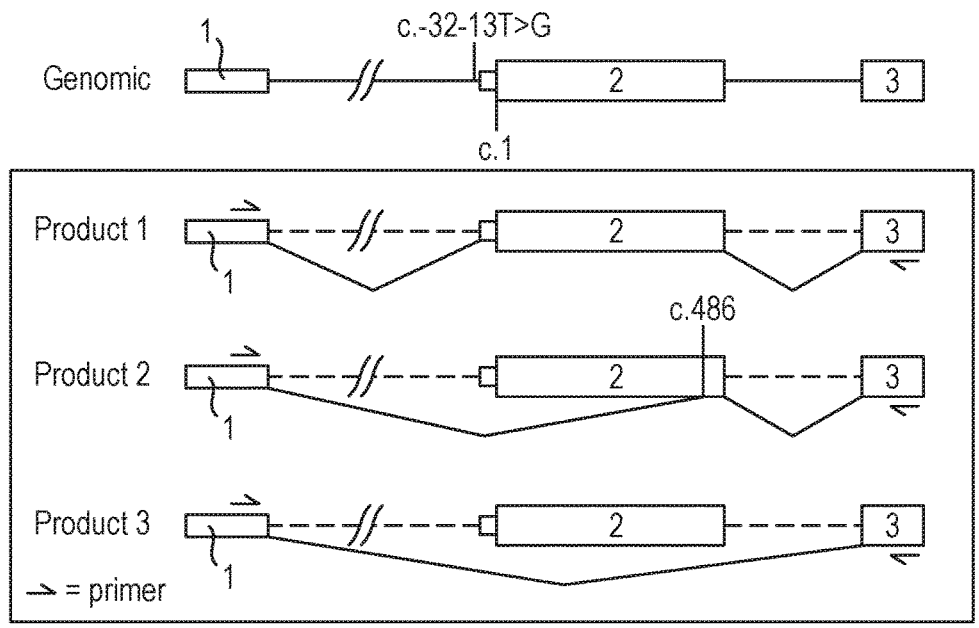
FIG. 25. Examples of mutations identified in the IVS1 minigene screen. HEK293 cells were transfected with minigene constructs and splicing was analysed after 24 hrs. A. RT-PCR analysis of the wild type minigene (WT), the minigene containing the IVS1 mutation (IVS1), and clones 115 and 97, which were identified in the unbiased minigene-based screen. Product 1: wild type mRNA, product 2: partially skipped exon 2 mRNA, product 3: fully skipped mRNA. B. Cartoon of the splice products. C. RT-qPCR analysis. Values were normalized for transfection efficiency by RT-qPCR analysis of neomycin (expressed from the same plasmid backbone from a separate promoter) and for cell numbers using beta-actin RT-qPCR analysis.
Figure 25C:
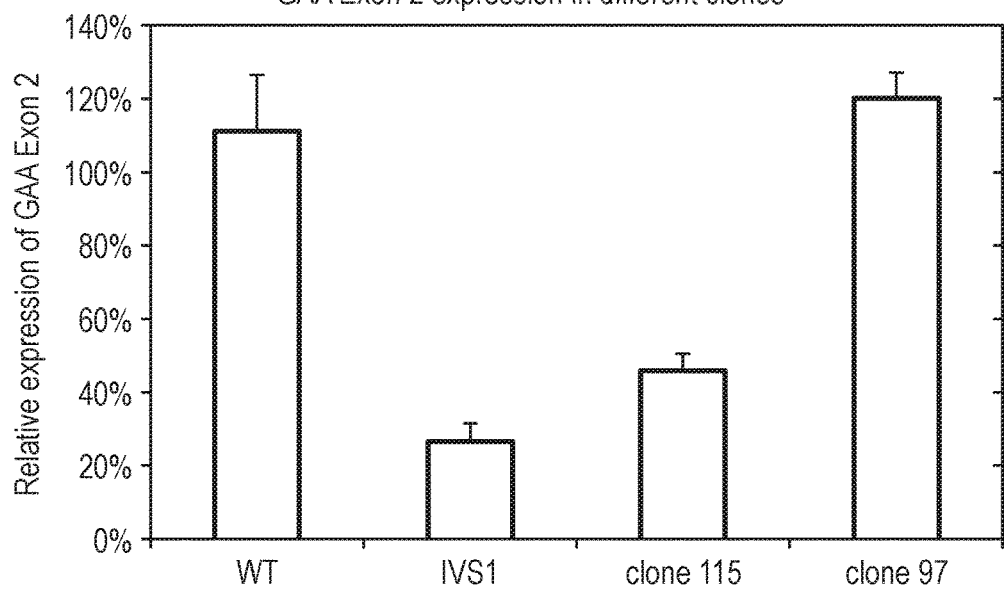

FIG. 25 provides the results of two of the clones. Clone 115 and clone 97 demonstrate a 118% and a 297% increase of exon 2 inclusion, respectively, in comparison to the IVS1 mutation. Clone 115 contains the mutations: c.17C>T, c.469C>T, and c.546+23C>A. It results in increased wild type splicing (band 1) and decreased perfect skipping (band 3). Clone 97 contains the mutations: c.-32-102T>C, c.-32-56C>T, c.11G>A, c.112G>A, and c.137C>T. This clone also misses c.-32-553 to c.-32-122, however, this does not affect exon 2 exclusion (as determined by us by comparing splicing from minigene constructs that do or do not contain this region). Wild type splicing (band 3) is strongly increased, while both partial (band 2) and perfect (band 3) skipping are decreased.

Apart from the minigene for Exon 1-Exon 3, we also generated a minigene containing the genomic region from GAA exon 5 to GAA exon 8. With this minigene we can test other mutations that influence splicing much like the IVS1 mutation.

Figure 34:
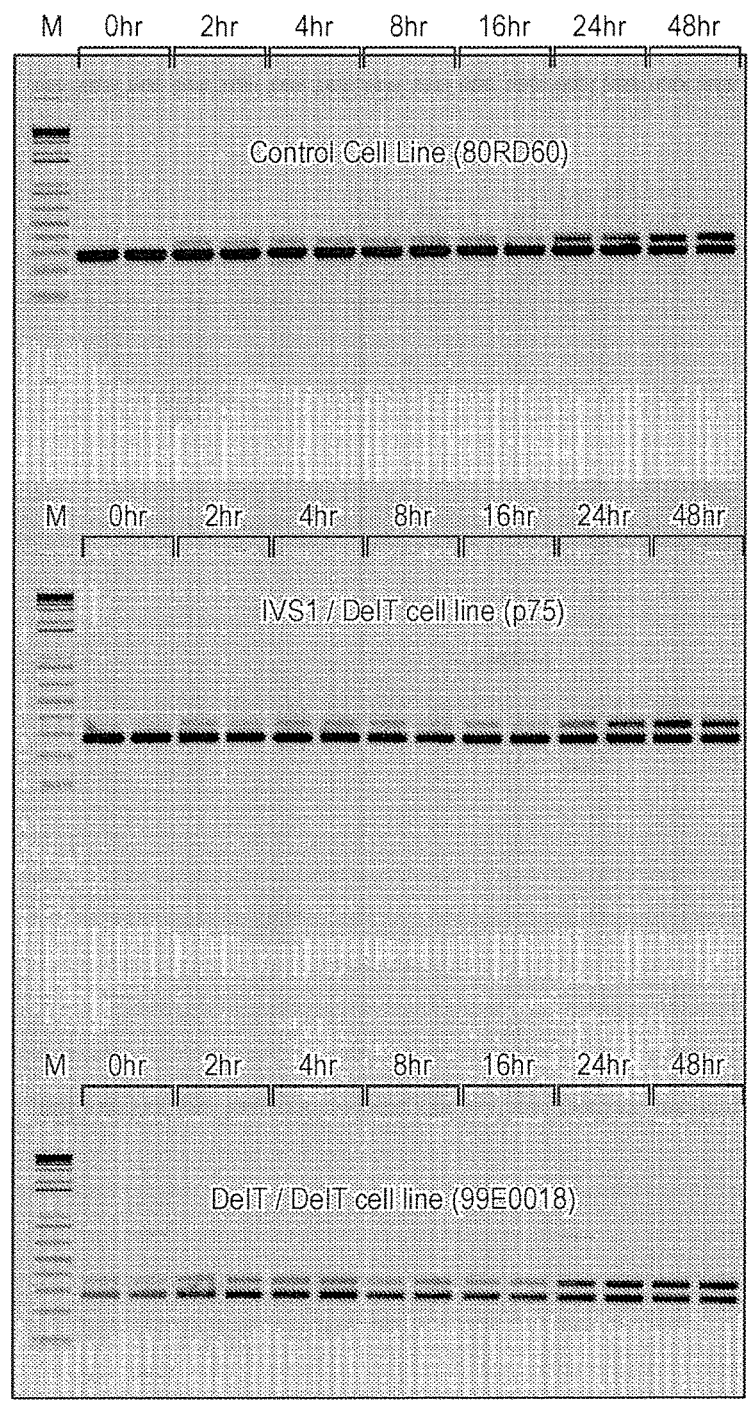
FIG. 34: Result of inhibition of the nonsense mediated decay (NMD) pathway on inclusion of intron 6 of the GAA mRNA.

FIG. 34 shows the result of inhibition of the nonsense mediated decay (NMD) pathway on inclusion of intron 6 of the GAA mRNA. Cyclohexamide treatment of primary fibroblasts from a healthy control (upper gel), a Pompe patient with the genotype c.-32-13T>G, c.525delT (middle gel), and a Pompe patient with the genotype c.525delT, c.525delT (lower gel) was performed. Without inhibition of the NMD pathway (lanes labelled with 0 hr), a strong band was detected using RT-PCR representing canonical splicing of exon 6 and exon 7. A faint band just above the canonical band was observed. This band was determined by DNA sequence analysis to represent inclusion of intron 6. Because such product changes the reading frame resulting in activation of the NMD pathway, we speculated that intron 6 inclusion may in fact be a frequent event that escapes proper detection. This idea was confirmed by inhibition of the NMD pathway: this resulted in the detection of a strong band representing intron 6 inclusion. This indicated that many GAA pre-mRNA species escape canonical splicing in both healthy controls and in Pompe patients. The minigene containing GAA exon 5-8 mentioned above and the U7 snRNA screen will be used to identify sequences that can prevent inclusion of intron 6 in the final mRNA by blocking a repressor of exon 6/7 splicing. This would represent a generic therapy for all splicing mutations with leaky wild type splicing causing Pompe disease, because correct splicing of exons 6/7 will be enhanced thereby also enhancing the levels of leaky wild type splicing.

The following mutations give an increased RNA expression: c.17C>T, c.469C>T, and c.546+23C>A., c.-32-102T>C, c.-32-56C>T, c.11G>A, c.112G>A, and c.137C>T. AONs that target mRNA sequences where these mutations are located may be useful for treating patients. SEQ ID NO: 98-540 are exemplary sequences found with the minigene approach. The table above shows SEQ ID NO: 98-540 and the mutation or genomic sequence it targets.

Figure 26:
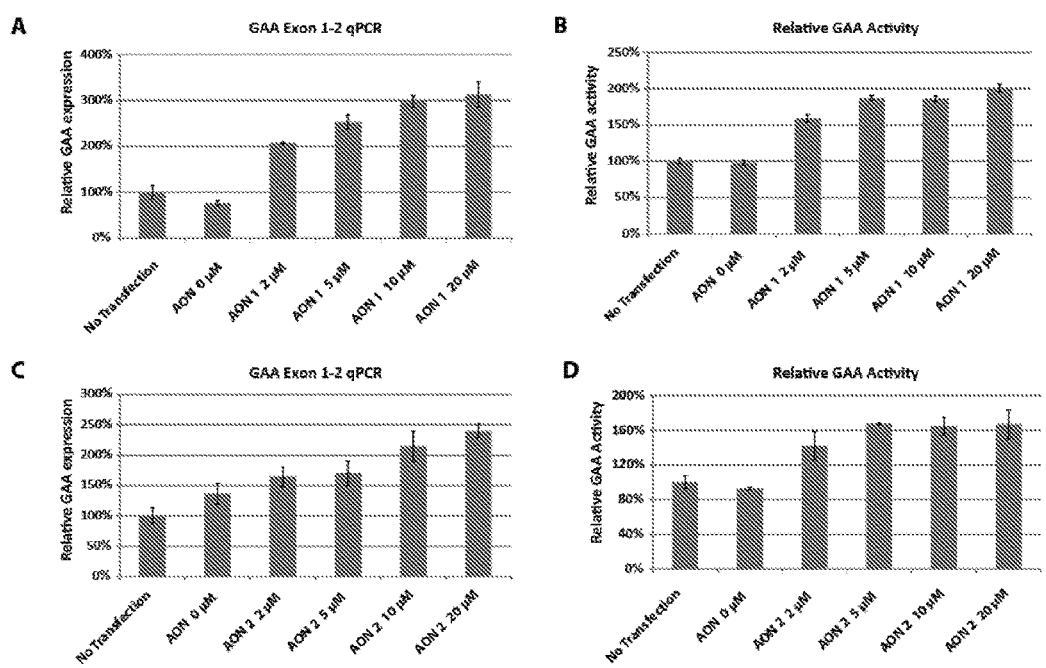
FIG. 26: Correction of aberrant splicing of GAA exon 2 using antisense oligonucleotides in patient 1.

The FIG. 26 shows a dose-response curve for SEQ ID NO: 12 (AON 1) (upper panels) and SEQ ID NO: 33 (AON 2) (lower panels). Patient-derived fibroblasts with the genotype c.-32-13T>G (IVS1) on one allele and c.525delT on the other allele were either untreated ('no transfection') or incubated with antisense oligomeric compound at 0-20 µM. Please note that the c.525delT undergoes nonsense-mediated decay, which explains why the effects at the RNA level are derived primarily from the IVS1 allele. Cells were harvested for RNA analysis after 3 days (A, C), and for protein analysis after 5 days (B, D). Both SEQ ID NO: 12 AON 1 and SEQ ID NO: 33 (AON 2) bind to a sequence present in intron 1 of the GAA pre-mRNA, which was identified using the U7 snRNA assay. This results in promotion of exon 2 inclusion, yielding higher expression of wild type GAA mRNA. This is measured at the mRNA level (using primers that specifically detect wild type GAA) and at the protein level (using an assay for GAA enzymatic activity).

RNA analysis: total RNA was isolated, cDNA was synthesized, and RT-qPCR analysis was performed to detect GAA exon 2 inclusion (using a forward primer specific for exon 1 and a reverse primer specific for exon 2).

Protein analysis: GAA enzyme activity was measured using the 4-MU assay. Activities were normalized for total protein as measured using the BCA assay.

Antisense oligomeric compound treatment: Antisense oligomeric compound used herein are morpholino's obtained from gene tools. Antisense oligomeric compound were transfected into the cells using endoporter (gene tools) according to the manufactor's instructions.

Figure 27:
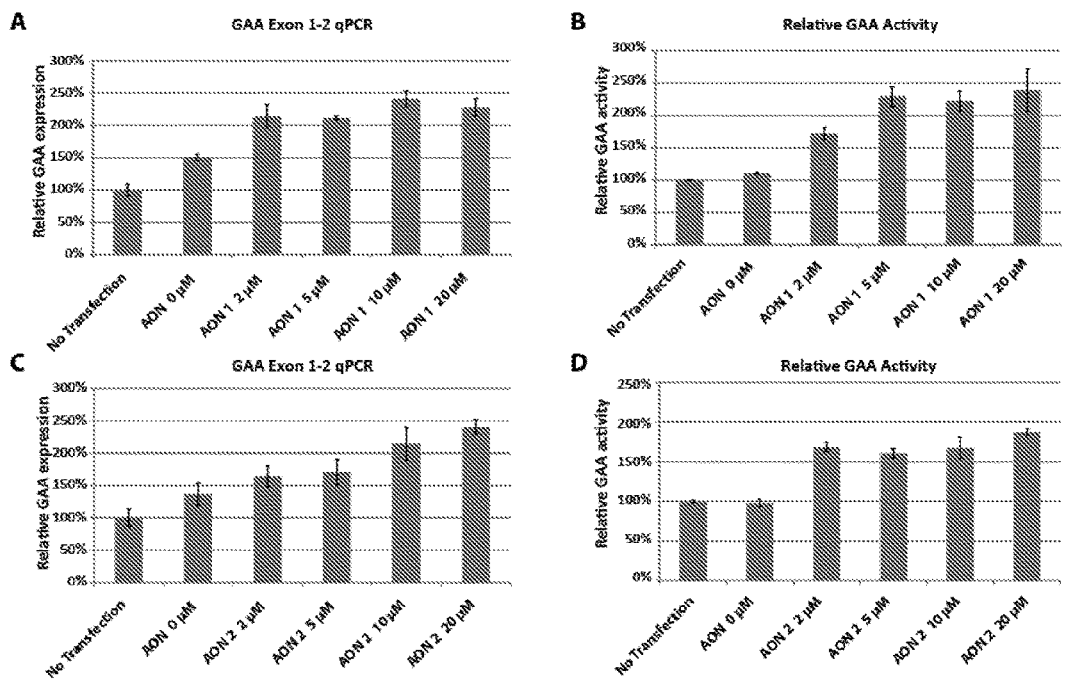
FIG. 27. Correction of aberrant splicing of GAA exon 2 using antisense oligonucleotides in patient 2.

This following experiment is similar to that of patient fibroblast line 1 (FIG. 26) and served to demonstrate that the antisense oligomeric compounds also work in an independent cell line 2 from another patient. In this case, the genotype was IVS1 on one allele and a missense variant (c.923A>C) on the other allele. Please note that the c.923A>C allele does not undergo nonsense-mediated decay, and mRNA levels represent a mix of both alleles, making the effects on the IVS1 allele less pronounced compared to patient 1. The FIG. 27 shows a dose-response curve for SEQ ID NO: 12 (AON 1) (upper panels) and SEQ ID NO: 33 (AON 2) (lower panels).

FIG. 28 shows the specificity of antisense oligomeric compounds SEQ ID NO: 12 (AON 1) and SEQ ID NO: 33 (AON 2) for promoting exon 2 inclusion.

SEQ ID NO: 35 (control AON 2) and SEQ ID NO: 36 (control AON 3) target another region in intron 1 of GAA but is ineffective in promoting exon 2 inclusion. An unrelated AON targeting the CypA mRNA (control AON 1; SEQ ID NO: 34) does not affect GAA exon 2 inclusion. SEQ ID NO: 12 (AON 1) and SEQ ID NO: 33 (AON 2) efficiently promote inclusion of GAA exon 2 as shown by RT-qPCR analysis (A) and concomitant GAA enzyme activity assay (B). This shows that only when the in the U7 snRNA assay identified intronic splice silencing (ISS) sequence is targeted, as with SEQ ID NO: 12 (AON 1) and SEQ ID NO: 33 (AON 2), GAA exon 2 inclusion is promoted.

| Sequence number | Target Gene | Sequence in cDNA to which AON anneals | sequence of AON (5'→3'): | Seq ID |
|---|---|---|---|---|
| Control AON 1 | CypA | c.354_362 + 11* | TGTACCCTTACCACTCAGTC | 34 |
| Control AON 2 | GAA | c.-32-224_ - 200** | GAGTGCAGAGCACTTGCACAGTCTG | 35 |
| Control AON 3 | GAA | c.-32-219_ - 200** | GAGTGCAGAGCACTTGCACAGTCTG | 36 |

*CypA cDNA sequence is Refseq entry NM_021130.4
**GAA cDNA sequence is Refseq entry NM_000152.3

Figure 29:
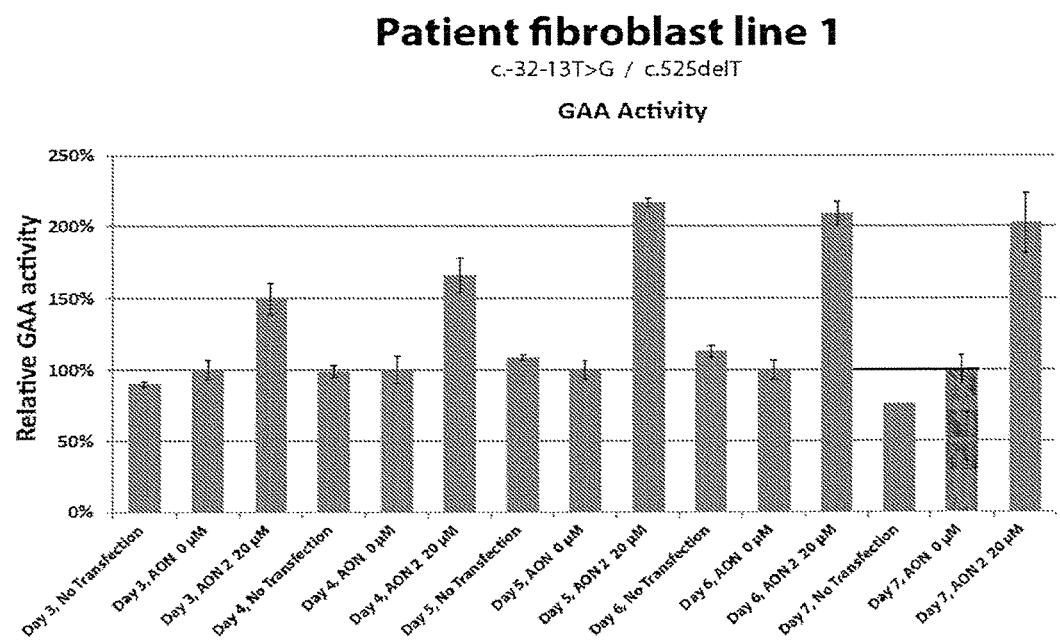
FIG. 29: Time course of the effect of the SEQ ID NO 33 (AON 2) on patient fibroblast line 1.
Figure 30:
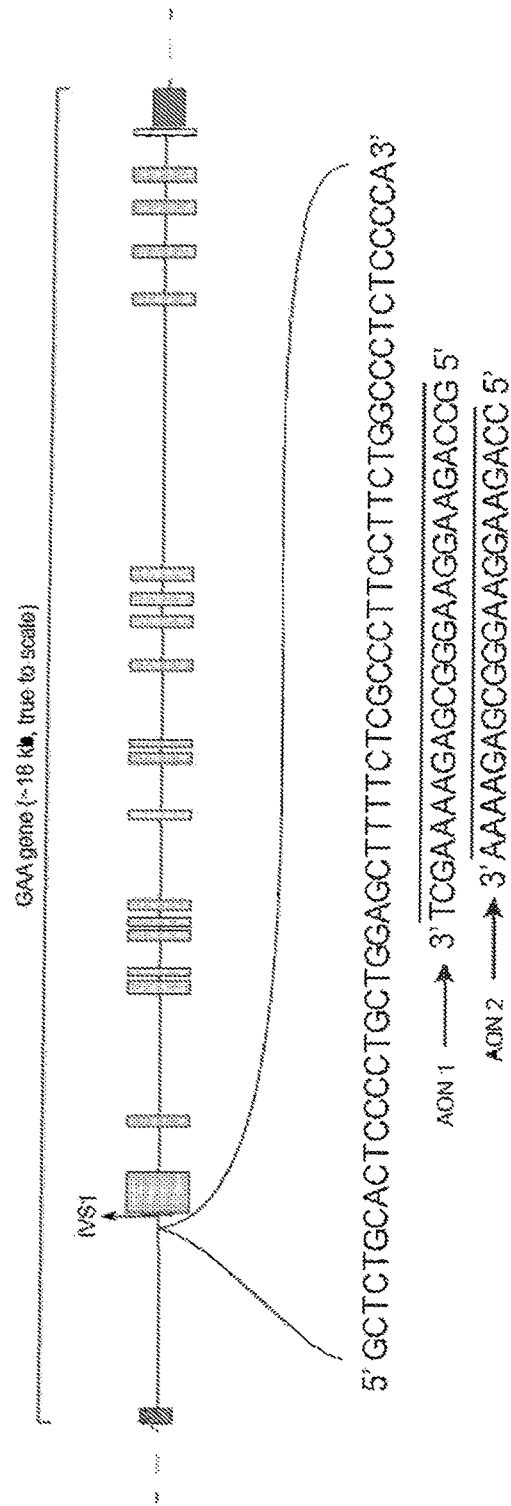
FIG. 30: Genomic target sequence for GAA exon inclusion

FIG. 29 shows the time course of the effect of the SEQ ID NO: 33 (AON 2) on patient fibroblast line 1. Cells were assayed for GAA activity at 3-7 days after the addition of antisense oligomeric compound. Antisense oligomeric compound was continuously present in the medium throughout the experiment.

The figure shows that the effect on GAA activity starts after 3 days and reaches a maximum at 5 days after AON addition.

REFERENCES

1. Boycott, K. M., et al., Rare-disease genetics in the era of next-generation sequencing: discovery to translation. Nat Rev Genet, 2013. 14(10): p. 681-91.
2. Havens, M. A., D. M. Duelli, and M. L. Hastings, Targeting RNA splicing for disease therapy. Wiley Interdiscip Rev RNA, 2013. 4(3): p. 247-66.
3. Desmet, F. O., et al., Human Splicing Finder: an online bioinformatics tool to predict splicing signals. Nucleic Acids Res, 2009. 37(9): p. e67.
4. Yeo, G. and C. B. Burge, Maximum entropy modeling of short sequence motifs with applications to RNA splicing signals. J Comput Biol, 2004. 11(2-3): p. 377-94.
5. Reese, M. G., et al., Improved splice site detection in Genie. J Comput Biol, 1997. 4(3): p. 311-23.
6. Pertea, M., X. Lin, and S. L. Salzberg, GeneSplicer: a new computational method for splice site prediction. Nucleic Acids Res, 2001. 29(5): p. 1185-90.
7. Palacios, I. M., Nonsense-mediated mRNA decay: from mechanistic insights to impacts on human health. Brief Funct Genomics, 2013. 12(1): p. 25-36.
8. van der Ploeg, A. T. and A. J. Reuser, Pompe's disease. Lancet, 2008. 372(9646): p. 1342-53.
9. Umapathysivam, K., J. J. Hopwood, and P. J. Meikle, Correlation of acid alpha-glucosidase and glycogen content in skin fibroblasts with age of onset in Pompe disease. Clin Chim Acta, 2005. 361(1-2): p. 191-8.
10. Van den Hout, H., et al., Recombinant human alpha-glucosidase from rabbit milk in Pompe patients. Lancet, 2000. 356(9227): p. 397-8.
11. Kishnani, P., et al., Enzyme replacement therapy with recombinant human acid alpha glucosidase (rhGAA) in infantile Pompe disease (IPD): Results from a Phase 2 study. Pediatric Research, 2003. 53(4): p. 259a-259a.
12. Kishnani, P. S., et al., Recombinant human acid alpha-glucosidase—Major clinical benefits in infantile-onset Pompe disease. Neurology, 2007. 68(2): p. 99-109.
13. Gungor, D., et al., Impact of enzyme replacement therapy on survival in adults with Pompe disease: results from a prospective international observational study. Orphanet Journal of Rare Diseases, 2013. 8.
14. den Dunnen, J. T. and S. E. Antonarakis, Mutation nomenclature extensions and suggestions to describe complex mutations: A discussion. Human Mutation, 2000. 15(1): p. 7-12.
15. Butterworth, J. and D. M. Droadhead, Diagnosis of Pompe's disease in cultured skin fibroblasts and primary amniotic fluid cells using 4-methylumbelliferyl-alpha-D-glucopyranoside as substrate. Clin Chim Acta, 1977. 78(2): p. 335-42.
16. Pickrell, J. K., et al., Noisy splicing drives mRNA isoform diversity in human cells. PLoS Genet, 2010. 6(12): p. e1001236.
17. Huie, M. L., et al., Aberrant splicing in adult onset glycogen storage disease type II (GSDII): molecular identification of an IVS1 (−13T→G) mutation in a majority of patients and a novel IVS10 (+1GT→CT) mutation. Hum Mol Genet, 1994. 3(12): p. 2231-6.
18. Boerkoel, C. F., et al., Leaky splicing mutation in the acid maltase gene is associated with delayed onset of glycogenosis type II. Am J Hum Genet, 1995. 56(4): p. 887-97.
19. Pittis, M. G., et al., Molecular and functional characterization of eight novel GAA mutations in Italian infants with Pompe disease. Hum Mutat, 2008. 29(6): p. E27-36.
20. Dardis, A., et al., Functional characterization of the common c.-32-13T>G mutation of GAA gene: identification of potential therapeutic agents. Nucleic Acids Res, 2014. 42(2): p. 1291-302.
21. Hermans, M. M., et al., The effect of a single base pair deletion (delta T525) and a C1634T missense mutation (pro545leu) on the expression of lysosomal alpha-glucosidase in patients with glycogen storage disease type II. Hum Mol Genet, 1994. 3(12): p. 2213-8.
22. Hermans, M. M., et al., Twenty-two novel mutations in the lysosomal alpha-glucosidase gene (GAA) underscore the genotype-phenotype correlation in glycogen storage disease type II. Hum Mutat, 2004. 23(1): p. 47-56.
23. Orlikowski, D., et al., Recombinant human acid alpha-glucosidase (rhGAA) in adult patients with severe respiratory failure due to Pompe disease. Neuromuscul Disord, 2011. 21(7): p. 477-82.
24. Stroppiano, M., et al., Aberrant splicing at catalytic site as cause of infantile onset glycogen storage disease type II (GSDII): molecular identification of a novel IVS9

(+2GT→GC) in combination with rare IVS10 (+1GT→CT). Am J Med Genet, 2001. 101(1): p. 55-8.
25. Muller-Felber, W., et al., Late onset Pompe disease: clinical and neurophysiological spectrum of 38 patients including long-term follow-up in 18 patients. Neuromuscul Disord, 2007. 17(9-10): p. 698-706.
26. Kroos, M., et al., Update of the pompe disease mutation database with 60 novel GAA sequence variants and additional studies on the functional effect of 34 previously reported variants. Hum Mutat, 2012. 33(8): p. 1161-5.
27. Kroos, M., et al., Seven cases of Pompe disease from Greece. J Inherit Metab Dis, 2006. 29(4): p. 556-63.
28. Barbosa-Morais, N. L., et al., The evolutionary landscape of alternative splicing in vertebrate species. Science, 2012. 338(6114): p. 1587-93.
29. Wang, G. S. and T. A. Cooper, Splicing in disease: disruption of the splicing code and the decoding machinery. Nat Rev Genet, 2007. 8(10): p. 749-61.
30. Kwan, T., et al., Genome-wide analysis of transcript isoform variation in humans. Nat Genet, 2008. 40(2): p. 225-31.
31. Castle, J. C., et al., Expression of 24,426 human alternative splicing events and predicted cis regulation in 48 tissues and cell lines. Nat Genet, 2008. 40(12): p. 1416-25.
32. Wang, E. T., et al., Alternative isoform regulation in human tissue transcriptomes. Nature, 2008. 456(7221): p. 470-6.
33. Lappalainen, T., et al., Transcriptome and genome sequencing uncovers functional variation in humans. Nature, 2013. 501(7468): p. 506-11.
34. Lalonde, E., et al., RNA sequencing reveals the role of splicing polymorphisms in regulating human gene expression. Genome Res, 2011. 21(4): p. 545-54.
35. Wokke, J. H., et al., Genotype-phenotype correlation in adult-onset acid maltase deficiency. Ann Neurol, 1995. 38(3): p. 450-4.
36. Kishnani, P. S., et al., Cross-reactive immunologic material status affects treatment outcomes in Pompe disease infants. Mol Genet Metab, 2010. 99(1): p. 26-33.
37. Lim, K. H., et al., Using positional distribution to identify splicing elements and predict pre-mRNA processing defects in human genes. Proc Natl Acad Sci USA, 2011. 108(27): p. 11093-8.
38. Fan, L., et al., Sudemycins, novel small molecule analogues of FR901464, induce alternative gene splicing. ACS Chem Biol, 2011. 6(6): p. 582-9.
39. Webb, T. R., A. S. Joyner, and P. M. Potter, The development and application of small molecule modulators of SF3b as therapeutic agents for cancer. Drug Discov Today, 2013. 18(1-2): p. 43-9.
40. Warlich, E., et al., *Lentiviral vector design and imaging approaches to visualize the early stages of cellular reprogramming*. Mol Ther, 2011. 19(4): p. 782-9.

The invention claimed is:

1. A method of modulating splicing of GAA pre-mRNA in a cell comprising: contacting the cell with an antisense oligomeric compound targeting SEQ ID NO:1 or a single nucleotide polymorphism of SEQ ID NO:1, wherein the antisense oligomeric compound comprises a nucleic acid sequence selected from the group consisting of SEQ ID Nos: 2-33, 38-40, 47 and 92-97 or a sequence having at least 95% sequence identity thereto.

2. A method for treating Pompe disease in a patient comprising administering an effective amount of an antisense oligmeric compound targeting SEQ ID NO:1 or a single nucleotide polymorphism of SEQ ID NO:1, wherein the antisense oligomeric compound comprises a nucleic acid sequence selected from the group consisting of SEQ ID Nos: 2-33, 38-40, 47 and 92-97 or a sequence having at least 95% sequence identity thereto.

3. A method to restore the function of GAA in a cell wherein said method comprises the administration of an antisense oligmeric compound targeting SEQ ID NO:1 or a single nucleotide polymorphism of SEQ ID NO:1, wherein the antisense oligomeric compound comprises a nucleic acid sequence selected from the group consisting of SEQ ID Nos: 2-33, 38-40, 47 and 92-97 or a sequence having at least 95% sequence identity thereto.

4. A method of correcting abnormal gene expression in a cell, preferably a muscular cell, of a subject, the method comprising administering to the subject an antisense oligomeric compound targeting SEQ ID NO:1 or a single nucleotide polymorphism of SEQ ID NO:1, wherein the antisense oligomeric compound comprises a nucleic acid sequence selected from the group consisting of SEQ ID Nos: 2-33, 38-40, 47 and 92-97 or a sequence having at least 95% sequence identity thereto.

5. The method according to claim 1 wherein the cell comprises at least one mutation selected from the group consisting of c.-32-13T>G, c.-32-3C>G, c.547-6, c.1071, c.1254, and c.1552 30.

6. The method of claim 1 wherein exon inclusion is accomplished.

7. The method according to claim 5, wherein the cell comprises mutation c.-32-3C>G or c.-32-13T>G.

\* \* \* \* \*

SEQUENCE LISTING

<160> NUMBER OF SEQ ID NOS: 1727

<210> SEQ ID NO 1
<211> LENGTH: 55
<212> TYPE: DNA
<213> ORGANISM: Artificial Sequence
<220> FEATURE:
<223> OTHER INFORMATION: target sequence

<400> SEQUENCE: 1
gctctgcact cccctgctgg agcttttctc gcccttcctt ctggccctct cccca     55

<210> SEQ ID NO 2
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 2
tggggagagg gccagaagga agggc     25

<210> SEQ ID NO 3
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 3
ggggagaggg ccagaaggaa gggcg     25

<210> SEQ ID NO 4
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 4
gggagagggc cagaaggaag ggcga                                    25

<210> SEQ ID NO 5
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 5
ggagagggcc agaaggaagg gcgag                                    25

<210> SEQ ID NO 6
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 6
gagagggcca gaaggaaggg cgaga                                    25

<210> SEQ ID NO 7
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 7
agagggccag aaggaagggc gagaa                                    25

<210> SEQ ID NO 8
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 8
gagggccaga aggaagggcg agaaa                                    25

<210> SEQ ID NO 9
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 9
agggccagaa ggaagggcga gaaaa                                    25

<210> SEQ ID NO 10
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 10
gggccagaag gaagggcgag aaaag                                    25

```
<210> SEQ ID NO 11
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 11
ggccagaagg aagggcgaga aaagc                                              25

<210> SEQ ID NO 12
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 12
gccagaagga agggcgagaa aagct                                              25

<210> SEQ ID NO 13
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 13
ccagaaggaa gggcgagaaa agctc                                              25

<210> SEQ ID NO 14
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 14
cagaaggaag ggcgagaaaa gctcc                                              25

<210> SEQ ID NO 15
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 15
agaaggaagg gcgagaaaag ctcca                                              25

<210> SEQ ID NO 16
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 16
gaaggaaggg cgagaaaagc tccag                                              25

<210> SEQ ID NO 17
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 17
aaggaagggc gagaaaagct ccagc                                   25

<210> SEQ ID NO 18
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 18
aggaagggcg agaaaagctc cagca                                   25

<210> SEQ ID NO 19
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 19
ggaagggcga gaaaagctcc agcag                                   25

<210> SEQ ID NO 20
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 20
gaagggcgag aaaagctcca gcagg                                   25

<210> SEQ ID NO 21
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 21
aagggcgaga aaagctccag caggg                                   25

<210> SEQ ID NO 22
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 22
agggcgagaa aagctccagc agggg                                   25

<210> SEQ ID NO 23
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 23
gggcgagaaa agctccagca gggga                                   25

<210> SEQ ID NO 24
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 24
ggcgagaaaa gctccagcag gggag                                              25

<210> SEQ ID NO 25
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 25
gcgagaaaag ctccagcagg ggagt                                              25

<210> SEQ ID NO 26
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 26
cgagaaaagc tccagcaggg gagtg                                              25

<210> SEQ ID NO 27
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 27
gagaaaagct ccagcagggg agtgc                                              25

<210> SEQ ID NO 28
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 28
agaaaagctc cagcagggga gtgca                                              25

<210> SEQ ID NO 29
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 29
gaaaagctcc agcaggggag tgcag                                              25

<210> SEQ ID NO 30
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 30
```
aaaagctcca gcagggagt gcaga                                          25

<210> SEQ ID NO 31
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 31
aaagctccag cagggagtg cagag                                          25

<210> SEQ ID NO 32
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 32
aagctccagc aggggagtgc agagc                                         25

<210> SEQ ID NO 33
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 33
ccagaaggaa gggcgagaaa a                                             21

<210> SEQ ID NO 34
<211> LENGTH: 20
<212> TYPE: DNA
<213> ORGANISM: Artificial Sequence
<220> FEATURE:
<223> OTHER INFORMATION: control AON1

<400> SEQUENCE: 34 tgtacccta ccactcagtc                                                20

<210> SEQ ID NO 35
<211> LENGTH: 25
<212> TYPE: DNA
<213> ORGANISM: Artificial Sequence
<220> FEATURE:
<223> OTHER INFORMATION: control AON2

<400> SEQUENCE: 35
gagtgcagag cacttgcaca gtctg                                         25

<210> SEQ ID NO 36
<211> LENGTH: 25
<212> TYPE: DNA
<213> ORGANISM: Artificial Sequence
<220> FEATURE:
<223> OTHER INFORMATION: control AON3

<400> SEQUENCE: 36
gagtgcagag cacttgcaca gtctg                                         25

<210> SEQ ID NO 37
<211> LENGTH: 45
<212> TYPE: DNA
<213> ORGANISM: Artificial Sequence

```
<220> FEATURE:
<223> OTHER INFORMATION: target sequence

<400> SEQUENCE: 37
gctctgcact cccctgctgg agcttttctc gcccttcctt ctggc        45

<210> SEQ ID NO 38
<211> LENGTH: 31
<212> TYPE: DNA
<213> ORGANISM: Artificial Sequence
<220> FEATURE:
<223> OTHER INFORMATION: target sequence

<400> SEQUENCE: 38
tgcactcccc tgctggagct tttctcgccc t                        31

<210> SEQ ID NO 39
<211> LENGTH: 36
<212> TYPE: DNA
<213> ORGANISM: Artificial Sequence
<220> FEATURE:
<223> OTHER INFORMATION: target sequence

<400> SEQUENCE: 39
tgcactcccc tgctggagct tttctcgccc ttcctt                   36

<210> SEQ ID NO 40
<211> LENGTH: 31
<212> TYPE: DNA
<213> ORGANISM: Artificial Sequence
<220> FEATURE:
<223> OTHER INFORMATION: target sequence

<400> SEQUENCE: 40 tccctgctg gagcttttct cgcccttcct t                         31

<210> SEQ ID NO 41
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 41
ccaaacagct gtcgcctggg                                     20

<210> SEQ ID NO 42
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 42
aggtagacac ttgaaacagg                                     20

<210> SEQ ID NO 43
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 43
cccaggaaga ccagcaaggc                                     20
```

<210> SEQ ID NO 44
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 44
tcaaacacgc ttagaatgtc				20

<210> SEQ ID NO 45
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 45
gtctgctaaa atgttacaaa				20

<210> SEQ ID NO 46
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 46
gagtgcagag cacttgcaca				20

<210> SEQ ID NO 47
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 47
cgagaaaagc tccagcaggg				20

<210> SEQ ID NO 48
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 48
gagagggcca gaaggaaggg				20

<210> SEQ ID NO 49
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 49
gccctgctgt ctagactggg				20

<210> SEQ ID NO 50
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 50
aggtggccag ggtgggtgtt                                               20

<210> SEQ ID NO 51
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 51
gcacccaggc aggtggggta                                               20

<210> SEQ ID NO 52
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 52
caaccgcggc tggcactgca                                               20

<210> SEQ ID NO 53
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 53
tcaaagcagc tctgagacat                                               20

<210> SEQ ID NO 54
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 54
gggcggcact cacggggctc                                               20

<210> SEQ ID NO 55
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 55
gctcagcagg gaggcgggag                                               20

<210> SEQ ID NO 56
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 56
cctgcgggag aagaaagcgg                                               20

<210> SEQ ID NO 57

-continued

```
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 57
gcctggacag ctcctacagg                                               20

<210> SEQ ID NO 58
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 58
cactcccatg gttggagatg                                               20

<210> SEQ ID NO 59
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 59
tgggagcagg gcgggtgcct                                               20

<210> SEQ ID NO 60
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 60
cgcagacggc caggagccgg                                               20

<210> SEQ ID NO 61
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 61
ggttgccaag gacacgaggg                                               20

<210> SEQ ID NO 62
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 62
atgtgcccca ggagtgcagc                                               20

<210> SEQ ID NO 63
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 63
```
gcaggaaatc atggagtagg                                              20

<210> SEQ ID NO 64
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 64
actcagctct cggggaacca                                              20

<210> SEQ ID NO 65
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 65
tccaggactg gggaggagcc                                              20

<210> SEQ ID NO 66
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 66
ggtgagctgg gtgagtctcc                                              20

<210> SEQ ID NO 67
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 67
tggtctgctg gctccctgct                                              20

<210> SEQ ID NO 68
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 68
gcctgggcat cccggggccc                                              20

<210> SEQ ID NO 69
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 69
ctctgggacg gccggggtgt                                              20

<210> SEQ ID NO 70
<211> LENGTH: 20
<212> TYPE: DNA

```
<213> ORGANISM: Artificial Sequence
<220> FEATURE:
<223> OTHER INFORMATION: antisense oligomeric compound

<400> SEQUENCE: 70
gtcgcactgt gtgggcactg                                                    20

<210> SEQ ID NO 71
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 71
aagcggctgt tgggggggac                                                    20

<210> SEQ ID NO 72
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 72
ccttgtcagg ggcgcaatcg                                                    20

<210> SEQ ID NO 73
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 73
gcactgttcc tgggtgatgg                                                    20

<210> SEQ ID NO 74
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 74
tagcaacagc cgcgggcctc                                                    20

<210> SEQ ID NO 75
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 75
gcccctgctt tgcagggatg                                                    20

<210> SEQ ID NO 76
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 76
ccccatctgg gctccctgca                                                    20
```

<210> SEQ ID NO 77
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 77
gggaagaagc accagggctg                                                  20

<210> SEQ ID NO 78
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 78
tgtagctggg gtagctgggt                                                  20

<210> SEQ ID NO 79
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 79
ggagctcagg ttctccagct                                                  20

<210> SEQ ID NO 80
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 80
gccgtgtagc ccatttcaga                                                  20

<210> SEQ ID NO 81
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 81
gggtggtacg ggtcagggtg                                                  20

<210> SEQ ID NO 82
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 82
gtccttgggg aagaaggtgg                                                  20

<210> SEQ ID NO 83
<211> LENGTH: 20
<212> TYPE: DNA
<213> ORGANISM: Artificial Sequence
<220> FEATURE:

<223> OTHER INFORMATION: antisense oligomeric compound

<400> SEQUENCE: 83
tccagccgca gggtcaggat                                       20

<210> SEQ ID NO 84
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 84
tctcagtctc catcatcacg                                       20

<210> SEQ ID NO 85
<211> LENGTH: 16
<212> TYPE: DNA
<213> ORGANISM: Artificial Sequence
<220> FEATURE:
<223> OTHER INFORMATION: antisense oligomeric compound

<400> SEQUENCE: 85
gtgaagtgga ggcggt                                           16

<210> SEQ ID NO 86
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 86
agagcacttg cacagtctgc                                       20

<210> SEQ ID NO 87
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 87
gcagagcact tgcacagtct                                       20

<210> SEQ ID NO 88
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 88
gtgcagagca cttgcacagt                                       20

<210> SEQ ID NO 89
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 89
gggagtgcag agcacttgca                                       20

```
<210> SEQ ID NO 90
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 90
aggggagtgc agagcacttg                                                  20

<210> SEQ ID NO 91
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 91
gcaggggagt gcagagcact                                                  20

<210> SEQ ID NO 92
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 92
gccagaagga agggcgagaa                                                  20

<210> SEQ ID NO 93
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 93
gggccagaag gaagggcgag                                                  20

<210> SEQ ID NO 94
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 94
gagggccaga aggaagggcg                                                  20

<210> SEQ ID NO 95
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 95
gggagagggc cagaaggaag                                                  20

<210> SEQ ID NO 96
<211> LENGTH: 20
<212> TYPE: DNA
<213> ORGANISM: Artificial Sequence
<220> FEATURE:
<223> OTHER INFORMATION: antisense oligomeric compound
```

```
<400> SEQUENCE: 96
tggggagagg gccagaagga                                              20

<210> SEQ ID NO 97
<211> LENGTH: 20
<212> TYPE: DNA
<213> ORGANISM: Artificial Sequence
<220> FEATURE:
<223> OTHER INFORMATION: antisense oligomeric compound

<400> SEQUENCE: 97
actggggaga gggccagaag                                              20

<210> SEQ ID NO 98
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 98
cacccaggca ggtggggtaa ggtgg                                        25

<210> SEQ ID NO 99
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 99
agcacccagg caggtgggt aaggt                                         25

<210> SEQ ID NO 100
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 100
gcagcaccca ggcaggtggg gtaag                                        25

<210> SEQ ID NO 101
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 101
ctgcagcacc caggcaggtg gggta                                        25

<210> SEQ ID NO 102
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 102
cactgcagca cccaggcagg tgggg                                        25

<210> SEQ ID NO 103
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 103
ggcactgcag cacccaggca ggtgg                                              25

<210> SEQ ID NO 104
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 104
ctggcactgc agcacccagg caggt                                              25

<210> SEQ ID NO 105
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 105
ggctggcact gcagcaccca ggcag                                              25

<210> SEQ ID NO 106
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 106
gcggctggca ctgcagcacc caggc                                              25

<210> SEQ ID NO 107
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 107
ccgcggctgg cactgcagca cccag                                              25

<210> SEQ ID NO 108
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 108
tcaaccgcgg ctggcactgc agcac                                              25

<210> SEQ ID NO 109
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 109
```

```
acccaggcag gtggggtaag gtggc                                          25

<210> SEQ ID NO 110
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 110
gcacccaggc aggtggggta aggtg                                          25

<210> SEQ ID NO 111
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 111
cagcacccag gcaggtgggg taagg                                          25

<210> SEQ ID NO 112
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 112
tgcagcaccc aggcaggtgg ggtaa                                          25

<210> SEQ ID NO 113
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 113
actgcagcac ccaggcaggt ggggt                                          25

<210> SEQ ID NO 114
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 114
gcactgcagc acccaggcag gtggg                                          25

<210> SEQ ID NO 115
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 115
tggcactgca gcacccaggc aggtg                                          25

<210> SEQ ID NO 116
<211> LENGTH: 25
<212> TYPE: DNA
<213> ORGANISM: Artificial Sequence
```

```
<220> FEATURE:
<223> OTHER INFORMATION: antisense oligomeric compound

<400> SEQUENCE: 116
gctggcactg cagcacccag gcagg                                          25

<210> SEQ ID NO 117
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 117
cggctggcac tgcagcaccc aggca                                          25

<210> SEQ ID NO 118
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 118
cgcggctggc actgcagcac ccagg                                          25

<210> SEQ ID NO 119
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 119
accgcggctg gcactgcagc accca                                          25

<210> SEQ ID NO 120
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 120
caaccgcggc tggcactgca gcacc                                          25

<210> SEQ ID NO 121
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 121
atcaaccgcg gctggcactg cagca                                          25

<210> SEQ ID NO 122
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 122
ggctctcaaa gcagctctga gacat                                          25
```

<210> SEQ ID NO 123
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 123
ggggctctca aagcagctct gagac                                              25

<210> SEQ ID NO 124
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 124
acggggctct caaagcagct ctgag                                              25

<210> SEQ ID NO 125
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 125
tcacggggct ctcaaagcag ctctg                                              25

<210> SEQ ID NO 126
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 126
actcacgggg ctctcaaagc agctc                                              25

<210> SEQ ID NO 127
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 127
gcactcacgg ggctctcaaa gcagc                                              25

<210> SEQ ID NO 128
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 128
cggcactcac ggggctctca aagca                                              25

<210> SEQ ID NO 129
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 129
ggcggcactc acggggctct caaag                                          25

<210> SEQ ID NO 130
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 130
ggggcggcac tcacggggct ctcaa                                          25

<210> SEQ ID NO 131
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 131
gaggggcggc actcacgggg ctctc                                          25

<210> SEQ ID NO 132
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 132
gggaggggcg gcactcacgg ggctc                                          25

<210> SEQ ID NO 133
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 133
gcgggagggg cggcactcac ggggc                                          25

<210> SEQ ID NO 134
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 134
aggcgggagg ggcggcactc acggg                                          25

<210> SEQ ID NO 135
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 135
ggaggcggga ggggcggcac tcacg                                          25

<210> SEQ ID NO 136
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 136
agggaggcgg gagggcggc actca                                      25

<210> SEQ ID NO 137
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 137
gcagggaggc gggaggggcg gcact                                     25

<210> SEQ ID NO 138
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 138
cagcagggag gcgggagggg cggca                                     25

<210> SEQ ID NO 139
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 139
ctcagcaggg aggcgggagg ggcgg                                     25

<210> SEQ ID NO 140
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 140
ggctcagcag ggaggcggga ggggc                                     25

<210> SEQ ID NO 141
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 141
cgggctcagc agggaggcgg gaggg                                     25

<210> SEQ ID NO 142
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 142
```
agcgggctca gcaggaggc gggag                                              25

<210> SEQ ID NO 143
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 143
aaagcgggct cagcagggag gcggg                                             25

<210> SEQ ID NO 144
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 144
agaaagcggg ctcagcaggg aggcg                                             25

<210> SEQ ID NO 145
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 145
gaagaaagcg ggctcagcag ggagg                                             25

<210> SEQ ID NO 146
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 146
gagaagaaag cgggctcagc aggga                                             25

<210> SEQ ID NO 147
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 147
gggagaagaa agcgggctca gcagg                                             25

<210> SEQ ID NO 148
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 148
gcgggagaag aaagcgggct cagca                                             25

<210> SEQ ID NO 149
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 149
ctgcgggaga agaaagcggg ctcag                                       25

<210> SEQ ID NO 150
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 150
gcctgcggga gaagaaagcg ggctc                                       25

<210> SEQ ID NO 151
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 151
aggcctgcgg gagaagaaag cgggc                                       25

<210> SEQ ID NO 152
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 152
actcccatgg ttggagatgg cctgg                                       25

<210> SEQ ID NO 153
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 153
tcactcccat ggttggagat ggcct                                       25

<210> SEQ ID NO 154
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 154
cctcactccc atggttggag atggc                                       25

<210> SEQ ID NO 155
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 155
tgcctcactc ccatggttgg agatg                                       25
```

<210> SEQ ID NO 156
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 156
ggtgcctcac tcccatggtt ggaga                                25

<210> SEQ ID NO 157
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 157
cgggtgcctc actcccatgg ttgga                                25

<210> SEQ ID NO 158
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 158
ggcgggtgcc tcactcccat ggttg                                25

<210> SEQ ID NO 159
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 159
agggcgggtg cctcactccc atggt                                25

<210> SEQ ID NO 160
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 160
gcagggcggg tgcctcactc ccatg                                25

<210> SEQ ID NO 161
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 161
gagcagggcg ggtgcctcac tccca                                25

<210> SEQ ID NO 162
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 162
gggagcaggg cgggtgcctc actcc                                    25

<210> SEQ ID NO 163
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 163
gtgggagcag ggcgggtgcc tcact                                    25

<210> SEQ ID NO 164
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 164
cggtgggagc agggcgggtg cctca                                    25

<210> SEQ ID NO 165
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 165
gccggtggga gcagggcggg tgcct                                    25

<210> SEQ ID NO 166
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 166
gagccggtgg gagcagggcg ggtgc                                    25

<210> SEQ ID NO 167
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 167
aggagccggt gggagcaggg cgggt                                    25

<210> SEQ ID NO 168
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 168
ccaggagccg gtgggagcag ggcgg                                    25

```
<210> SEQ ID NO 169
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 169
ggccaggagc cggtgggagc agggc                                          25

<210> SEQ ID NO 170
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 170
acggccagga gccggtggga gcagg                                          25

<210> SEQ ID NO 171
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 171
agacggccag gagccggtgg gagca                                          25

<210> SEQ ID NO 172
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 172
gcagacggcc aggagccggt gggag                                          25

<210> SEQ ID NO 173
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 173
gcgcagacgg ccaggagccg gtggg                                          25

<210> SEQ ID NO 174
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 174
gggcgcagac ggccaggagc cggtg                                          25

<210> SEQ ID NO 175
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 175
gagggcgcag acggccagga gccgg                                          25

<210> SEQ ID NO 176
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 176
acgagggcgc agacggccag gagcc                                          25

<210> SEQ ID NO 177
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 177
acacgagggc gcagacggcc aggag                                          25

<210> SEQ ID NO 178
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 178
ggacacgagg gcgcagacgg ccagg                                          25

<210> SEQ ID NO 179
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 179
aaggacacga gggcgcagac ggcca                                          25

<210> SEQ ID NO 180
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 180
ccaaggacac gagggcgcag acggc                                          25

<210> SEQ ID NO 181
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 181
tgccaaggac acgagggcgc agacg                                          25

<210> SEQ ID NO 182
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 182
gctctcaaag cagctctgag acatc                                       25

<210> SEQ ID NO 183
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 183
gggctctcaa agcagctctg agaca                                       25

<210> SEQ ID NO 184
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 184
ctcacggggc tctcaaagca gctct                                       25

<210> SEQ ID NO 185
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 185
cactcacggg gctctcaaag cagct                                       25

<210> SEQ ID NO 186
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 186
ggcactcacg ggctctcaa agcag                                        25

<210> SEQ ID NO 187
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 187
gcggcactca cggggctctc aaagc                                       25

<210> SEQ ID NO 188
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 188
```
gggcggcact cacggggctc tcaaa                                              25

<210> SEQ ID NO 189
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 189
aggggcggca ctcacggggc tctca                                              25

<210> SEQ ID NO 190
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 190
ggaggggcgg cactcacggg gctct                                              25

<210> SEQ ID NO 191
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 191
cgggaggggc ggcactcacg gggct                                              25

<210> SEQ ID NO 192
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 192
ggcgggaggg gcggcactca cgggg                                              25

<210> SEQ ID NO 193
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 193
gaggcgggag gggcggcact cacgg                                              25

<210> SEQ ID NO 194
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 194
gggaggcggg aggggcggca ctcac                                              25

<210> SEQ ID NO 195
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 195
cagggaggcg ggagggcgg cactc                                      25

<210> SEQ ID NO 196
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 196
agcagggagg cgggaggggc ggcac                                     25

<210> SEQ ID NO 197
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 197
tcagcaggga ggcgggaggg gcggc                                     25

<210> SEQ ID NO 198
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 198
gctcagcagg gaggcgggag gggcg                                     25

<210> SEQ ID NO 199
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 199
gggctcagca gggaggcggg agggg                                     25

<210> SEQ ID NO 200
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 200
gcgggctcag cagggaggcg ggagg                                     25

<210> SEQ ID NO 201
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 201
aagcgggctc agcagggagg cggga                                     25

```
<210> SEQ ID NO 202
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 202
gaaagcgggc tcagcaggga ggcgg                                         25

<210> SEQ ID NO 203
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 203
aagaaagcgg gctcagcagg gaggc                                         25

<210> SEQ ID NO 204
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 204
agaagaaagc gggctcagca gggag                                         25

<210> SEQ ID NO 205
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 205
ggagaagaaa gcgggctcag caggg                                         25

<210> SEQ ID NO 206
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 206
cgggagaaga aagcgggctc agcag                                         25

<210> SEQ ID NO 207
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 207
tgcgggagaa gaaagcgggc tcagc                                         25

<210> SEQ ID NO 208
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 208
cctgcgggag aagaaagcgg gctca                                           25

<210> SEQ ID NO 209
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 209
ggcctgcggg agaagaaagc gggct                                           25

<210> SEQ ID NO 210
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 210
caggcctgcg ggagaagaaa gcggg                                           25

<210> SEQ ID NO 211
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 211
cggggctctc aaagcagctc tgaga                                           25

<210> SEQ ID NO 212
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 212
cacggggctc tcaaagcagc tctga                                           25

<210> SEQ ID NO 213
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 213
ctcccatggt tggagatggc ctgga                                           25

<210> SEQ ID NO 214
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 214
cactcccatg gttggagatg gcctg                                           25

<210> SEQ ID NO 215
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 215
ctcactccca tggttggaga tggcc                                              25

<210> SEQ ID NO 216
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 216
gcctcactcc catggttgga gatgg                                              25

<210> SEQ ID NO 217
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 217
gtgcctcact cccatggttg gagat                                              25

<210> SEQ ID NO 218
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 218
gggtgcctca ctcccatggt tggag                                              25

<210> SEQ ID NO 219
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 219
gcgggtgcct cactcccatg gttgg                                              25

<210> SEQ ID NO 220
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 220
gggcgggtgc ctcactccca tggtt                                              25

<210> SEQ ID NO 221
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 221
```
cagggcgggt gcctcactcc catgg                                              25

<210> SEQ ID NO 222
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 222
agcagggcgg gtgcctcact cccat                                              25

<210> SEQ ID NO 223
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 223
ggagcagggc gggtgcctca ctccc                                              25

<210> SEQ ID NO 224
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 224
tgggagcagg gcgggtgcct cactc                                              25

<210> SEQ ID NO 225
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 225
ggtgggagca gggcgggtgc ctcac                                              25

<210> SEQ ID NO 226
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 226
ccggtgggag cagggcgggt gcctc                                              25

<210> SEQ ID NO 227
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 227
agccggtggg agcagggcgg gtgcc                                              25

<210> SEQ ID NO 228
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 228
ggagccggtg ggagcagggc gggtg                                    25

<210> SEQ ID NO 229
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 229
caggagccgg tgggagcagg gcggg                                    25

<210> SEQ ID NO 230
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 230
gccaggagcc ggtgggagca gggcg                                    25

<210> SEQ ID NO 231
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 231
cggccaggag ccggtgggag caggg                                    25

<210> SEQ ID NO 232
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 232
gacggccagg agccggtggg agcag                                    25

<210> SEQ ID NO 233
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 233
cagacggcca ggagccggtg ggagc                                    25

<210> SEQ ID NO 234
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 234
cgcagacggc caggagccgg tggga                                    25
```

```
<210> SEQ ID NO 235
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 235
ggcgcagacg gccaggagcc ggtgg                                    25

<210> SEQ ID NO 236
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 236
agggcgcaga cggccaggag ccggt                                    25

<210> SEQ ID NO 237
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 237
cgagggcgca gacggccagg agccg                                    25

<210> SEQ ID NO 238
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 238
cacgagggcg cagacggcca ggagc                                    25

<210> SEQ ID NO 239
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 239
gacacgaggg cgcagacggc cagga                                    25

<210> SEQ ID NO 240
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 240
aggacacgag ggcgcagacg gccag                                    25

<210> SEQ ID NO 241
<211> LENGTH: 25
<212> TYPE: DNA
<213> ORGANISM: Artificial Sequence
<220> FEATURE:
```

<223> OTHER INFORMATION: antisense oligomeric compound

<400> SEQUENCE: 241
caaggacacg agggcgcaga cggcc                               25

<210> SEQ ID NO 242
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 242
gccaaggaca cgagggcgca gacgg                               25

<210> SEQ ID NO 243
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 243
ttgccaagga cacgagggcg cagac                               25

<210> SEQ ID NO 244
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 244
ggatgtgccc caggagtgca gcggt                               25

<210> SEQ ID NO 245
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 245
taggatgtgc cccaggagtg cagcg                               25

<210> SEQ ID NO 246
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 246
agtaggatgt gccccaggag tgcag                               25

<210> SEQ ID NO 247
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 247
ggagtaggat gtgccccagg agtgc                               25

```
<210> SEQ ID NO 248
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 248
atggagtagg atgtgcccca ggagt                                              25

<210> SEQ ID NO 249
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 249
tcatggagta ggatgtgccc cagga                                              25

<210> SEQ ID NO 250
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 250
aatcatggag taggatgtgc cccag                                              25

<210> SEQ ID NO 251
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 251
gaaatcatgg agtaggatgt gcccc                                              25

<210> SEQ ID NO 252
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 252
aggaaatcat ggagtaggat gtgcc                                              25

<210> SEQ ID NO 253
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 253
gcaggaaatc atggagtagg atgtg                                              25

<210> SEQ ID NO 254
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 254
cagcaggaaa tcatggagta ggatg    25

<210> SEQ ID NO 255
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 255
accagcagga aatcatggag tagga    25

<210> SEQ ID NO 256
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 256
gaaccagcag gaaatcatgg agtag    25

<210> SEQ ID NO 257
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 257
gggaaccagc aggaaatcat ggagt    25

<210> SEQ ID NO 258
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 258
cggggaacca gcaggaaatc atgga    25

<210> SEQ ID NO 259
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 259
ctcggggaac cagcaggaaa tcatg    25

<210> SEQ ID NO 260
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 260
ctctcgggga accagcagga aatca    25

<210> SEQ ID NO 261
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 261
agctctcggg gaaccagcag gaaat                                        25

<210> SEQ ID NO 262
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 262
tcagctctcg gggaaccagc aggaa                                        25

<210> SEQ ID NO 263
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 263
actcagctct cggggaacca gcagg                                        25

<210> SEQ ID NO 264
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 264
ccactcagct ctcggggaac cagca                                        25

<210> SEQ ID NO 265
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 265
agccactcag ctctcgggga accag                                        25

<210> SEQ ID NO 266
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 266
ggagccactc agctctcggg gaacc                                        25

<210> SEQ ID NO 267
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 267
```
gaggagccac tcagctctcg gggaa       25

<210> SEQ ID NO 268
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 268
gggaggagcc actcagctct cgggg       25

<210> SEQ ID NO 269
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 269
tggggaggag ccactcagct ctcgg       25

<210> SEQ ID NO 270
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 270
actggggagg agccactcag ctctc       25

<210> SEQ ID NO 271
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 271
ggactgggga ggagccactc agctc       25

<210> SEQ ID NO 272
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 272
caggactggg gaggagccac tcagc       25

<210> SEQ ID NO 273
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 273
tccaggactg gggaggagcc actca       25

<210> SEQ ID NO 274
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 274
cctccaggac tggggaggag ccact                                              25

<210> SEQ ID NO 275
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 275
ctcctccagg actggggagg agcca                                              25

<210> SEQ ID NO 276
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 276
gtctcctcca ggactgggga ggagc                                              25

<210> SEQ ID NO 277
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 277
gagtctcctc caggactggg gagga                                              25

<210> SEQ ID NO 278
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 278
gtgagtctcc tccaggactg gggag                                              25

<210> SEQ ID NO 279
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 279
gggtgagtct cctccaggac tgggg                                              25

<210> SEQ ID NO 280
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 280
ctgggtgagt ctcctccagg actgg                                              25
```

<210> SEQ ID NO 281
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 281
agctgggtga gtctcctcca ggact                                              25

<210> SEQ ID NO 282
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 282
tgagctgggt gagtctcctc cagga                                              25

<210> SEQ ID NO 283
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 283
ggtgagctgg gtgagtctcc tccag                                              25

<210> SEQ ID NO 284
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 284
ctggtgagct gggtgagtct cctcc                                              25

<210> SEQ ID NO 285
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 285
tgctggtgag ctgggtgagt ctcct                                              25

<210> SEQ ID NO 286
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 286
cctgctggtg agctgggtga gtctc                                              25

<210> SEQ ID NO 287
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 287
tccctgctgg tgagctgggt gagtc                                     25

<210> SEQ ID NO 288
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 288
gctccctgct ggtgagctgg gtgag                                     25

<210> SEQ ID NO 289
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 289
tggctccctg ctggtgagct gggtg                                     25

<210> SEQ ID NO 290
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 290
gctggctccc tgctggtgag ctggg                                     25

<210> SEQ ID NO 291
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 291
ctgctggctc cctgctggtg agctg                                     25

<210> SEQ ID NO 292
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 292
gtctgctggc tccctgctgg tgagc                                     25

<210> SEQ ID NO 293
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 293
gatgtgcccc aggagtgcag cggtt                                     25

<210> SEQ ID NO 294
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 294
aggatgtgcc ccaggagtgc agcgg                                      25

<210> SEQ ID NO 295
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 295
gtaggatgtg ccccaggagt gcagc                                      25

<210> SEQ ID NO 296
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 296
gagtaggatg tgccccagga gtgca                                      25

<210> SEQ ID NO 297
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 297
tggagtagga tgtgcccag gagtg                                       25

<210> SEQ ID NO 298
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 298
catggagtag gatgtgcccc aggag                                      25

<210> SEQ ID NO 299
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 299
atcatggagt aggatgtgcc ccagg                                      25

<210> SEQ ID NO 300
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 300
```
aaatcatgga gtaggatgtg cccca                                           25

<210> SEQ ID NO 301
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 301
ggaaatcatg gagtaggatg tgccc                                           25

<210> SEQ ID NO 302
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 302
caggaaatca tggagtagga tgtgc                                           25

<210> SEQ ID NO 303
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 303
agcaggaaat catggagtag gatgt                                           25

<210> SEQ ID NO 304
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 304
ccagcaggaa atcatggagt aggat                                           25

<210> SEQ ID NO 305
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 305
aaccagcagg aaatcatgga gtagg                                           25

<210> SEQ ID NO 306
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 306
ggaaccagca ggaaatcatg gagta                                           25

<210> SEQ ID NO 307
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 307
ggggaaccag caggaaatca tggag                                         25

<210> SEQ ID NO 308
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 308
tcggggaacc agcaggaaat catgg                                         25

<210> SEQ ID NO 309
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 309
tctcggggaa ccagcaggaa atcat                                         25

<210> SEQ ID NO 310
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 310
gctctcgggg aaccagcagg aaatc                                         25

<210> SEQ ID NO 311
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 311
cagctctcgg ggaaccagca ggaaa                                         25

<210> SEQ ID NO 312
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 312
ctcagctctc ggggaaccag cagga                                         25

<210> SEQ ID NO 313
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 313
cactcagctc tcggggaacc agcag                                         25
```

```
<210> SEQ ID NO 314
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 314
gccactcagc tctcggggaa ccagc                                           25

<210> SEQ ID NO 315
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 315
gagccactca gctctcgggg aacca                                           25

<210> SEQ ID NO 316
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 316
aggagccact cagctctcgg ggaac                                           25

<210> SEQ ID NO 317
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 317
ggaggagcca ctcagctctc gggga                                           25

<210> SEQ ID NO 318
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 318
ggggaggagc cactcagctc tcggg                                           25

<210> SEQ ID NO 319
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 319
ctggggagga gccactcagc tctcg                                           25

<210> SEQ ID NO 320
<211> LENGTH: 25
<212> TYPE: DNA
<213> ORGANISM: Artificial Sequence
<220> FEATURE:
```

```
<223> OTHER INFORMATION: antisense oligomeric compound

<400> SEQUENCE: 320
gactggggag gagccactca gctct                                            25

<210> SEQ ID NO 321
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 321
aggactgggg aggagccact cagct                                            25

<210> SEQ ID NO 322
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 322
ccaggactgg ggaggagcca ctcag                                            25

<210> SEQ ID NO 323
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 323
ctccaggact ggggaggagc cactc                                            25

<210> SEQ ID NO 324
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 324
tcctccagga ctggggagga gccac                                            25

<210> SEQ ID NO 325
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 325
tctcctccag gactggggag gagcc                                            25

<210> SEQ ID NO 326
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 326
agtctcctcc aggactgggg aggag                                            25
```

```
<210> SEQ ID NO 327
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 327
tgagtctcct ccaggactgg ggagg                                    25

<210> SEQ ID NO 328
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 328
ggtgagtctc tccaggact gggga                                     25

<210> SEQ ID NO 329
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 329
tgggtgagtc tcctccagga ctggg                                    25

<210> SEQ ID NO 330
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 330
gctgggtgag tctcctccag gactg                                    25

<210> SEQ ID NO 331
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 331
gagctgggtg agtctcctcc aggac                                    25

<210> SEQ ID NO 332
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 332
gtgagctggg tgagtctcct ccagg                                    25

<210> SEQ ID NO 333
<211> LENGTH: 25
<212> TYPE: DNA
<213> ORGANISM: Artificial Sequence
<220> FEATURE:
<223> OTHER INFORMATION: antisense oligomeric compound
```

-continued

```
<400> SEQUENCE: 333
tggtgagctg ggtgagtctc ctcca                                        25

<210> SEQ ID NO 334
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 334
gctggtgagc tgggtgagtc tcctc                                        25

<210> SEQ ID NO 335
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 335
ctgctggtga gctgggtgag tctcc                                        25

<210> SEQ ID NO 336
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 336
ccctgctggt gagctgggtg agtct                                        25

<210> SEQ ID NO 337
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 337
ctccctgctg gtgagctggg tgagt                                        25

<210> SEQ ID NO 338
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 338
ggctccctgc tggtgagctg ggtga                                        25

<210> SEQ ID NO 339
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 339
ctggctccct gctggtgagc tgggt                                        25

<210> SEQ ID NO 340
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 340
tgctggctcc ctgctggtga gctgg                                              25

<210> SEQ ID NO 341
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 341
tctgctggct ccctgctggt gagct                                              25

<210> SEQ ID NO 342
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 342
ggtctgctgg ctccctgctg gtgag                                              25

<210> SEQ ID NO 343
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 343
agcccctgct ttgcagggat gtagc                                              25

<210> SEQ ID NO 344
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 344
gcagcccctg ctttgcaggg atgta                                              25

<210> SEQ ID NO 345
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 345
ctgcagcccc tgctttgcag ggatg                                              25

<210> SEQ ID NO 346
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 346
```
ccctgcagcc cctgctttgc aggga                                              25

<210> SEQ ID NO 347
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 347
ctccctgcag ccctgctttt gcagg                                              25

<210> SEQ ID NO 348
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 348
ggctccctgc agccctgct ttgca                                               25

<210> SEQ ID NO 349
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 349
tgggctccct gcagccctg ctttg                                               25

<210> SEQ ID NO 350
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 350
tctgggctcc ctgcagcccc tgctt                                              25

<210> SEQ ID NO 351
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 351
catctgggct ccctgcagcc cctgc                                              25

<210> SEQ ID NO 352
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 352
cccatctggg ctccctgcag ccct                                               25

<210> SEQ ID NO 353
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 353
gccccatctg ggctccctgc agccc                                              25

<210> SEQ ID NO 354
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 354
ctgccccatc tgggctccct gcagc                                              25

<210> SEQ ID NO 355
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 355
ggctgcccca tctgggctcc ctgca                                              25

<210> SEQ ID NO 356
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 356
agggctgccc catctgggct ccctg                                              25

<210> SEQ ID NO 357
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 357
ccagggctgc cccatctggg ctccc                                              25

<210> SEQ ID NO 358
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 358
caccagggct gccccatctg ggctc                                              25

<210> SEQ ID NO 359
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 359
agcaccaggg ctgccccatc tgggc                                              25
```

```
<210> SEQ ID NO 360
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 360
gaagcaccag ggctgcccca tctgg                                          25

<210> SEQ ID NO 361
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 361
aagaagcacc agggctgccc catct                                          25

<210> SEQ ID NO 362
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 362
ggaagaagca ccagggctgc cccat                                          25

<210> SEQ ID NO 363
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 363
tgggaagaag caccagggct gcccc                                          25

<210> SEQ ID NO 364
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 364
ggtgggaaga agcaccaggg ctgcc                                          25

<210> SEQ ID NO 365
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 365
tgggtgggaa gaagcaccag ggctg                                          25

<210> SEQ ID NO 366
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 366
gctgggtggg aagaagcacc agggc                                              25

<210> SEQ ID NO 367
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 367
gcccctgctt tgcagggatg tagca                                              25

<210> SEQ ID NO 368
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 368
cagcccctgc tttgcaggga tgtag                                              25

<210> SEQ ID NO 369
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 369
tgcagcccct gctttgcagg gatgt                                              25

<210> SEQ ID NO 370
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 370
cctgcagccc ctgctttgca gggat                                              25

<210> SEQ ID NO 371
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 371
tccctgcagc ccctgctttg caggg                                              25

<210> SEQ ID NO 372
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 372
gctccctgca gccctgctt tgcag                                               25

<210> SEQ ID NO 373
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 373
gggctccctg cagcccctgc tttgc                               25

<210> SEQ ID NO 374
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 374
ctgggctccc tgcagcccct gcttt                               25

<210> SEQ ID NO 375
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 375
atctgggctc cctgcagccc ctgct                               25

<210> SEQ ID NO 376
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 376
ccatctgggc tccctgcagc ccctg                               25

<210> SEQ ID NO 377
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 377
ccccatctgg gctccctgca gcccc                               25

<210> SEQ ID NO 378
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 378
tgccccatct gggctccctg cagcc                               25

<210> SEQ ID NO 379
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 379
```
gctgccccat ctgggctccc tgcag                                         25

<210> SEQ ID NO 380
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 380
gggctgcccc atctgggctc cctgc                                         25

<210> SEQ ID NO 381
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 381
cagggctgcc ccatctgggc tccct                                         25

<210> SEQ ID NO 382
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 382
accagggctg ccccatctgg gctcc                                         25

<210> SEQ ID NO 383
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 383
gcaccagggc tgccccatct gggct                                         25

<210> SEQ ID NO 384
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 384
aagcaccagg gctgccccat ctggg                                         25

<210> SEQ ID NO 385
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 385
agaagcacca gggctgcccc atctg                                         25

<210> SEQ ID NO 386
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 386
gaagaagcac cagggctgcc ccatc                                              25

<210> SEQ ID NO 387
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 387
gggaagaagc accagggctg cccca                                              25

<210> SEQ ID NO 388
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 388
gtgggaagaa gcaccagggc tgccc                                              25

<210> SEQ ID NO 389
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 389
gggtgggaag aagcaccagg gctgc                                              25

<210> SEQ ID NO 390
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 390
ctgggtggga agaagcacca gggct                                              25

<210> SEQ ID NO 391
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 391
agctgggtgg gaagaagcac caggg                                              25

<210> SEQ ID NO 392
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 392
cagcttgtag ctggggtagc tgggt                                              25
```

<210> SEQ ID NO 393
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 393
tccagcttgt agctggggta gctgg         25

<210> SEQ ID NO 394
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 394
tctccagctt gtagctgggg tagct         25

<210> SEQ ID NO 395
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 395
gttctccagc ttgtagctgg ggtag         25

<210> SEQ ID NO 396
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 396
aggttctcca gcttgtagct ggggt         25

<210> SEQ ID NO 397
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 397
tcaggttctc cagcttgtag ctggg         25

<210> SEQ ID NO 398
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 398
gctcaggttc tccagcttgt agctg         25

<210> SEQ ID NO 399
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 399
gagctcaggt tctccagctt gtagc          25

<210> SEQ ID NO 400
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 400
aggagctcag gttctccagc ttgta          25

<210> SEQ ID NO 401
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 401
agaggagctc aggttctcca gcttg          25

<210> SEQ ID NO 402
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 402
tcagaggagc tcaggttctc cagct          25

<210> SEQ ID NO 403
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 403
tttcagagga gctcaggttc tccag          25

<210> SEQ ID NO 404
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 404
agcttgtagc tggggtagct gggtg          25

<210> SEQ ID NO 405
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 405
ccagcttgta gctggggtag ctggg          25

<210> SEQ ID NO 406
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 406
ctccagcttg tagctggggt agctg					25

<210> SEQ ID NO 407
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 407
ttctccagct tgtagctggg gtagc					25

<210> SEQ ID NO 408
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 408
ggttctccag cttgtagctg gggta					25

<210> SEQ ID NO 409
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 409
caggttctcc agcttgtagc tgggg					25

<210> SEQ ID NO 410
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 410
ctcaggttct ccagcttgta gctgg					25

<210> SEQ ID NO 411
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 411
agctcaggtt ctccagcttg tagct					25

<210> SEQ ID NO 412
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 412
ggagctcagg ttctccagct tgtag                                       25

<210> SEQ ID NO 413
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 413
gaggagctca ggttctccag cttgt                                       25

<210> SEQ ID NO 414
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 414
cagaggagct caggttctcc agctt                                       25

<210> SEQ ID NO 415
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 415
ttcagaggag ctcaggttct ccagc                                       25

<210> SEQ ID NO 416
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 416
atttcagagg agctcaggtt ctcca                                       25

<210> SEQ ID NO 417
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 417
ggggtggtac gggtcagggt ggccg                                       25

<210> SEQ ID NO 418
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 418
tgggggtggt acgggtcagg gtggc                                       25

<210> SEQ ID NO 419
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 419
ggtgggggtg gtacgggtca gggtg                                              25

<210> SEQ ID NO 420
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 420
aaggtggggg tggtacgggt caggg                                              25

<210> SEQ ID NO 421
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 421
agaaggtggg ggtggtacgg gtcag                                              25

<210> SEQ ID NO 422
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 422
gaagaaggtg ggggtggtac gggtc                                              25

<210> SEQ ID NO 423
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 423
gggaagaagg tgggggtggt acggg                                              25

<210> SEQ ID NO 424
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 424
tggggaagaa ggtgggggtg gtacg                                              25

<210> SEQ ID NO 425
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 425
```
cttggggaag aaggtggggg tggta                                                 25

<210> SEQ ID NO 426
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 426
tccttgggga agaaggtggg ggtgg                                                 25

<210> SEQ ID NO 427
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 427
tgtccttggg gaagaaggtg ggggt                                                 25

<210> SEQ ID NO 428
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 428
gatgtccttg gggaagaagg tgggg                                                 25

<210> SEQ ID NO 429
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 429
aggatgtcct tggggaagaa ggtgg                                                 25

<210> SEQ ID NO 430
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 430
tcaggatgtc cttggggaag aaggt                                                 25

<210> SEQ ID NO 431
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 431
ggtcaggatg tccttgggga agaag                                                 25

<210> SEQ ID NO 432
<211> LENGTH: 25
<212> TYPE: DNA
<213> ORGANISM: Artificial Sequence -continued

```
<220> FEATURE:
<223> OTHER INFORMATION: antisense oligomeric compound

<400> SEQUENCE: 432
agggtcagga tgtccttggg gaaga                                         25

<210> SEQ ID NO 433
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 433
gcagggtcag gatgtccttg gggaa                                         25

<210> SEQ ID NO 434
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 434
ccgcagggtc aggatgtcct tgggg                                         25

<210> SEQ ID NO 435
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 435
agccgcaggg tcaggatgtc cttgg                                         25

<210> SEQ ID NO 436
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 436
gggtggtacg ggtcagggtg gccgt                                         25

<210> SEQ ID NO 437
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 437 ggggtggta cgggtcaggg tggcc                                          25

<210> SEQ ID NO 438
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 438
gtgggggtgg tacgggtcag ggtgg                                         25
```

```
<210> SEQ ID NO 439
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 439
aggtgggggt ggtacgggtc agggt                                             25

<210> SEQ ID NO 440
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 440
gaaggtgggg gtggtacggg tcagg                                             25

<210> SEQ ID NO 441
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 441
aagaaggtgg gggtggtacg ggtca                                             25

<210> SEQ ID NO 442
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 442
ggaagaaggt gggggtggta cgggt                                             25

<210> SEQ ID NO 443
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 443
ggggaagaag gtgggggtgg tacgg                                             25

<210> SEQ ID NO 444
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 444
ttggggaaga aggtgggggt ggtac                                             25

<210> SEQ ID NO 445
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 445
ccttggggaa gaaggtgggg gtggt                                          25

<210> SEQ ID NO 446
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 446
gtccttgggg aagaaggtgg gggtg                                          25

<210> SEQ ID NO 447
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 447
atgtccttgg ggaagaaggt ggggg                                          25

<210> SEQ ID NO 448
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 448
ggatgtcctt ggggaagaag gtggg                                          25

<210> SEQ ID NO 449
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 449
caggatgtcc ttggggaaga aggtg                                          25

<210> SEQ ID NO 450
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 450
gtcaggatgt ccttggggaa gaagg                                          25

<210> SEQ ID NO 451
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 451
gggtcaggat gtccttgggg aagaa                                          25

<210> SEQ ID NO 452
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 452
cagggtcagg atgtccttgg ggaag                                          25

<210> SEQ ID NO 453
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 453
cgcagggtca ggatgtcctt gggga                                          25

<210> SEQ ID NO 454
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 454
gccgcagggt caggatgtcc ttggg                                          25

<210> SEQ ID NO 455
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 455
cagccgcagg gtcaggatgt ccttg                                          25

<210> SEQ ID NO 456
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 456
cgtccagccg cagggtcagg atgtc                                          25

<210> SEQ ID NO 457
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 457
cacgtccagc cgcagggtca ggatg                                          25

<210> SEQ ID NO 458
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 458
```
atcacgtcca gccgcagggt cagga                                            25

<210> SEQ ID NO 459
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 459
tcatcacgtc cagccgcagg gtcag                                            25

<210> SEQ ID NO 460
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 460
catcatcacg tccagccgca gggtc                                            25

<210> SEQ ID NO 461
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 461
tccatcatca cgtccagccg caggg                                            25

<210> SEQ ID NO 462
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 462
tctccatcat cacgtccagc cgcag                                            25

<210> SEQ ID NO 463
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 463
agtctccatc atcacgtcca gccgc                                            25

<210> SEQ ID NO 464
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 464
tcagtctcca tcatcacgtc cagcc                                            25

<210> SEQ ID NO 465
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 465
tctcagtctc catcatcacg tccag                                              25

<210> SEQ ID NO 466
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 466
gttctcagtc tccatcatca cgtcc                                              25

<210> SEQ ID NO 467
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 467
cggttctcag tctccatcat cacgt                                              25

<210> SEQ ID NO 468
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 468
ggcggttctc agtctccatc atcac                                              25

<210> SEQ ID NO 469
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 469
gaggcggttc tcagtctcca tcatc                                              25

<210> SEQ ID NO 470
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 470
tggaggcggt tctcagtctc catca                                              25

<210> SEQ ID NO 471
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 471
agtggaggcg gttctcagtc tccat                                              25
```

<210> SEQ ID NO 472
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 472
gaagtggagg cggttctcag tctcc                                          25

<210> SEQ ID NO 473
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 473
gtccagccgc agggtcagga tgtcc                                          25

<210> SEQ ID NO 474
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 474
acgtccagcc gcagggtcag gatgt                                          25

<210> SEQ ID NO 475
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 475
tcacgtccag ccgcagggtc aggat                                          25

<210> SEQ ID NO 476
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 476
catcacgtcc agccgcaggg tcagg                                          25

<210> SEQ ID NO 477
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 477
atcatcacgt ccagccgcag ggtca                                          25

<210> SEQ ID NO 478
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 478
ccatcatcac gtccagccgc agggt                                    25

<210> SEQ ID NO 479
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 479
ctccatcatc acgtccagcc gcagg                                    25

<210> SEQ ID NO 480
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 480
gtctccatca tcacgtccag ccgca                                    25

<210> SEQ ID NO 481
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 481
cagtctccat catcacgtcc agccg                                    25

<210> SEQ ID NO 482
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 482
ctcagtctcc atcatcacgt ccagc                                    25

<210> SEQ ID NO 483
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 483
ttctcagtct ccatcatcac gtcca                                    25

<210> SEQ ID NO 484
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 484
ggttctcagt ctccatcatc acgtc                                    25

```
<210> SEQ ID NO 485
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 485
gcggttctca gtctccatca tcacg                                          25

<210> SEQ ID NO 486
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 486
aggcggttct cagtctccat catca                                          25

<210> SEQ ID NO 487
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 487
ggaggcggtt ctcagtctcc atcat                                          25

<210> SEQ ID NO 488
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 488
gtggaggcgg ttctcagtct ccatc                                          25

<210> SEQ ID NO 489
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 489
aagtggaggc ggttctcagt ctcca                                          25

<210> SEQ ID NO 490
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 490
tgaagtggag gcggttctca gtctc                                          25

<210> SEQ ID NO 491
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 491
tgccctgccc accgtgaagt ggagg                                              25

<210> SEQ ID NO 492
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 492
cctgccctgc ccaccgtgaa gtgga                                              25

<210> SEQ ID NO 493
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 493
cccctgccct gcccaccgtg aagtg                                              25

<210> SEQ ID NO 494
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 494
cgcccctgcc ctgcccaccg tgaag                                              25

<210> SEQ ID NO 495
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 495
cccgcccctg ccctgcccac cgtga                                              25

<210> SEQ ID NO 496
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 496
gccctgccca ccgtgaagtg gaggc                                              25

<210> SEQ ID NO 497
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 497
ctgccctgcc caccgtgaag tggag                                              25

<210> SEQ ID NO 498
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 498
ccctgccctg cccaccgtga agtgg                                             25

<210> SEQ ID NO 499
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 499
gcccctgccc tgcccaccgt gaagt                                             25

<210> SEQ ID NO 500
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 500
ccgcccctgc cctgcccacc gtgaa                                             25

<210> SEQ ID NO 501
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 501
ccccgcccct gccctgccca ccgtg                                             25

<210> SEQ ID NO 502
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 502 gccccgccc ctgccctgcc caccg                                              25

<210> SEQ ID NO 503
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 503 ccgccccgc ccctgccctg cccac                                              25

<210> SEQ ID NO 504
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 504
```
cgccgccccc gccctgccc tgccc         25

<210> SEQ ID NO 505
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 505
gccgccgccc ccgcccctgc cctgc         25

<210> SEQ ID NO 506
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 506
tggccgccgc cccgcccct gccct         25

<210> SEQ ID NO 507
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 507
cctggccgcc gccccgccc ctgcc         25

<210> SEQ ID NO 508
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 508
gccctggccg ccgccccgc ccctg         25

<210> SEQ ID NO 509
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 509
ctgccctggc cgccgccccc gcccc         25

<210> SEQ ID NO 510
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 510
ctctgccctg gccgccgccc ccgcc         25

<210> SEQ ID NO 511
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 511
ccctctgccc tggccgccgc ccccg                                    25

<210> SEQ ID NO 512
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 512
caccctctgc cctggccgcc gcccc                                    25

<210> SEQ ID NO 513
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 513
cgcaccctct gccctggccg ccgcc                                    25

<210> SEQ ID NO 514
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 514
cgcgcaccct ctgccctggc cgccg                                    25

<210> SEQ ID NO 515
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 515
cccccgcccc tgccctgccc accgt                                    25

<210> SEQ ID NO 516
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 516
cgcccccgcc cctgccctgc ccacc                                    25

<210> SEQ ID NO 517
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 517
gccgcccccg ccctgccct gccca                                     25
```

<210> SEQ ID NO 518
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 518
ccgccgcccc cgcccctgcc ctgcc                                    25

<210> SEQ ID NO 519
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 519
ggccgccgcc cccgcccctg ccctg                                    25

<210> SEQ ID NO 520
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 520
ctggccgccg ccccgcccc tgccc                                     25

<210> SEQ ID NO 521
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 521
ccctggccgc cgcccccgcc cctgc                                    25

<210> SEQ ID NO 522
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 522
tgccctggcc gccgccccg ccct                                      25

<210> SEQ ID NO 523
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 523
tctgccctgg ccgccgcccc cgccc                                    25

<210> SEQ ID NO 524
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 524
cctctgccct ggccgccgcc cccgc                                              25

<210> SEQ ID NO 525
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 525
accctctgcc ctggccgccg ccccc                                              25

<210> SEQ ID NO 526
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 526
gcaccctctg ccctggccgc cgccc                                              25

<210> SEQ ID NO 527
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 527
gcgcaccctc tgccctggcc gccgc                                              25

<210> SEQ ID NO 528
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 528
agagatgggg gtttattgat gttcc                                              25

<210> SEQ ID NO 529
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 529
gaagagatgg gggtttattg atgtt                                              25

<210> SEQ ID NO 530
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 530
tagaagagat gggggtttat tgatg                                              25

<210> SEQ ID NO 531
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 531
tctagaagag atgggggttt attga                                          25

<210> SEQ ID NO 532
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 532
gatctagaag agatgggggt ttatt                                          25

<210> SEQ ID NO 533
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 533
ttgatctaga agagatgggg gttta                                          25

<210> SEQ ID NO 534
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 534
ctttgatcta gaagagatgg gggtt                                          25

<210> SEQ ID NO 535
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 535
atctttgatc tagaagagat ggggg                                          25

<210> SEQ ID NO 536
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 536
ggatctttga tctagaagag atggg                                          25

<210> SEQ ID NO 537
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 537
```
ctggatcttt gatctagaag agatg                                              25

<210> SEQ ID NO 538
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 538
agctggatct ttgatctaga agaga                                              25

<210> SEQ ID NO 539
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 539
ttagctggat ctttgatcta gaaga                                              25

<210> SEQ ID NO 540
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 540
tgttagctgg atctttgatc tagaa                                              25

<210> SEQ ID NO 541
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 541
ctggaaggga agcagctctg gggtt                                              25

<210> SEQ ID NO 542
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 542
tctggaaggg aagcagctct ggggt                                              25

<210> SEQ ID NO 543
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 543
atctggaagg gaagcagctc tgggg                                              25

<210> SEQ ID NO 544
<211> LENGTH: 25
<212> TYPE: DNA

<213> ORGANISM: Artificial Sequence
<220> FEATURE:
<223> OTHER INFORMATION: antisense oligomeric compound

<400> SEQUENCE: 544
catctggaag ggaagcagct ctggg                                    25

<210> SEQ ID NO 545
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 545
acatctggaa gggaagcagc tctgg                                    25

<210> SEQ ID NO 546
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 546
cacatctgga agggaagcag ctctg                                    25

<210> SEQ ID NO 547
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 547
ccacatctgg aagggaagca gctct                                    25

<210> SEQ ID NO 548
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 548
accacatctg gaagggaagc agctc                                    25

<210> SEQ ID NO 549
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 549
gaccacatct ggaagggaag cagct                                    25

<210> SEQ ID NO 550
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 550
ggaccacatc tggaagggaa gcagc                                    25

```
<210> SEQ ID NO 551
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 551
aggaccacat ctggaaggga agcag                                       25

<210> SEQ ID NO 552
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 552
caggaccaca tctggaaggg aagca                                       25

<210> SEQ ID NO 553
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 553
gcaggaccac atctggaagg gaagc                                       25

<210> SEQ ID NO 554
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 554
tgcaggacca catctggaag ggaag                                       25

<210> SEQ ID NO 555
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 555
ctgcaggacc acatctggaa gggaa                                       25

<210> SEQ ID NO 556
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 556
gctgcaggac cacatctgga aggga                                       25

<210> SEQ ID NO 557
<211> LENGTH: 25
<212> TYPE: DNA
<213> ORGANISM: Artificial Sequence
<220> FEATURE:
```

<223> OTHER INFORMATION: antisense oligomeric compound

<400> SEQUENCE: 557
ggctgcagga ccacatctgg aaggg                               25

<210> SEQ ID NO 558
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 558
cggctgcagg accacatctg gaagg                               25

<210> SEQ ID NO 559
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 559
tcggctgcag gaccacatct ggaag                               25

<210> SEQ ID NO 560
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 560
ctcggctgca ggaccacatc tggaa                               25

<210> SEQ ID NO 561
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 561
gctcggctgc aggaccacat ctgga                               25

<210> SEQ ID NO 562
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 562
ggctcggctg caggaccaca tctgg                               25

<210> SEQ ID NO 563
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 563
gggctcggct gcaggaccac atctg                               25

```
<210> SEQ ID NO 564
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 564
agggctcggc tgcaggacca catct                                           25

<210> SEQ ID NO 565
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 565
cagggctcgg ctgcaggacc acatc                                           25

<210> SEQ ID NO 566
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 566
gcagggctcg gctgcaggac cacat                                           25

<210> SEQ ID NO 567
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 567
ggcagggctc ggctgcagga ccaca                                           25

<210> SEQ ID NO 568
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 568
gggcagggct cggctgcagg accac                                           25

<210> SEQ ID NO 569
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 569
agggcagggc tcggctgcag gacca                                           25

<210> SEQ ID NO 570
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 570
aagggcaggg ctcggctgca ggacc                                          25

<210> SEQ ID NO 571
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 571
taagggcagg gctcggctgc aggac                                          25

<210> SEQ ID NO 572
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 572
ctaagggcag ggctcggctg cagga                                          25

<210> SEQ ID NO 573
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 573
gctaagggca gggctcggct gcagg                                          25

<210> SEQ ID NO 574
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 574
agctaagggc agggctcggc tgcag                                          25

<210> SEQ ID NO 575
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 575
cagctaaggg cagggctcgg ctgca                                          25

<210> SEQ ID NO 576
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 576
ccagctaagg gcagggctcg gctgc                                          25

<210> SEQ ID NO 577
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 577
tccagctaag ggcagggctc ggctg                                    25

<210> SEQ ID NO 578
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 578
ctccagctaa gggcagggct cggct                                    25

<210> SEQ ID NO 579
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 579
cctccagcta agggcagggc tcggc                                    25

<210> SEQ ID NO 580
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 580
acctccagct aagggcaggg ctcgg                                    25

<210> SEQ ID NO 581
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 581
gacctccagc taagggcagg gctcg                                    25

<210> SEQ ID NO 582
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 582
cgacctccag ctaagggcag ggctc                                    25

<210> SEQ ID NO 583
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 583
```
tcgacctcca gctaagggca gggct                                              25

<210> SEQ ID NO 584
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 584
gtcgacctcc agctaagggc agggc                                              25

<210> SEQ ID NO 585
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 585
tgtcgacctc cagctaaggg caggg                                              25

<210> SEQ ID NO 586
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 586
ctgtcgacct ccagctaagg gcagg                                              25

<210> SEQ ID NO 587
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 587
cctgtcgacc tccagctaag ggcag                                              25

<210> SEQ ID NO 588
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 588
acctgtcgac ctccagctaa gggca                                              25

<210> SEQ ID NO 589
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 589
cacctgtcga cctccagcta agggc                                              25

<210> SEQ ID NO 590
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 590
ccacctgtcg acctccagct aaggg                                              25

<210> SEQ ID NO 591
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 591
cccacctgtc gacctccagc taagg                                              25

<210> SEQ ID NO 592
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 592
tcccacctgt cgacctccag ctaag                                              25

<210> SEQ ID NO 593
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 593
atcccacctg tcgacctcca gctaa                                              25

<210> SEQ ID NO 594
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 594
gatcccacct gtcgacctcc agcta                                              25

<210> SEQ ID NO 595
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 595
ggatcccacc tgtcgacctc cagct                                              25

<210> SEQ ID NO 596
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 596
aggatcccac ctgtcgacct ccagc                                              25
```

<210> SEQ ID NO 597
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 597
caggatccca cctgtcgacc tccag                                  25

<210> SEQ ID NO 598
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 598
ccaggatccc acctgtcgac ctcca                                  25

<210> SEQ ID NO 599
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 599
tccaggatcc cacctgtcga cctcc                                  25

<210> SEQ ID NO 600
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 600
atccaggatc ccacctgtcg acctc                                  25

<210> SEQ ID NO 601
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 601
catccaggat cccacctgtc gacct                                  25

<210> SEQ ID NO 602
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 602
acatccagga tcccacctgt cgacc                                  25

<210> SEQ ID NO 603
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 603
gacatccagg atcccacctg tcgac                                          25

<210> SEQ ID NO 604
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 604
agacatccag gatcccacct gtcga                                          25

<210> SEQ ID NO 605
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 605
tagacatcca ggatcccacc tgtcg                                          25

<210> SEQ ID NO 606
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 606
gtagacatcc aggatcccac ctgtc                                          25

<210> SEQ ID NO 607
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 607
tgtagacatc caggatccca cctgt                                          25

<210> SEQ ID NO 608
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 608
atgtagacat ccaggatccc acctg                                          25

<210> SEQ ID NO 609
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 609
gatgtagaca tccaggatcc cacct                                          25

<210> SEQ ID NO 610
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 610
agatgtagac atccaggatc ccacc                                              25

<210> SEQ ID NO 611
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 611
aagatgtaga catccaggat cccac                                              25

<210> SEQ ID NO 612
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 612
gaagatgtag acatccagga tccca                                              25

<210> SEQ ID NO 613
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 613
ggaagatgta gacatccagg atccc                                              25

<210> SEQ ID NO 614
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 614
aggaagatgt agacatccag gatcc                                              25

<210> SEQ ID NO 615
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 615
caggaagatg tagacatcca ggatc                                              25

<210> SEQ ID NO 616
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 616
```
ccaggaagat gtagacatcc aggat                                              25

<210> SEQ ID NO 617
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 617
cccaggaaga tgtagacatc cagga                                              25

<210> SEQ ID NO 618
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 618
gcccaggaag atgtagacat ccagg                                              25

<210> SEQ ID NO 619
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 619
ggcccaggaa gatgtagaca tccag                                              25

<210> SEQ ID NO 620
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 620
gggcccagga agatgtagac atcca                                              25

<210> SEQ ID NO 621
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 621
tgggcccagg aagatgtaga catcc                                              25

<210> SEQ ID NO 622
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 622
ctgggcccag gaagatgtag acatc                                              25

<210> SEQ ID NO 623
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 623
tctgggccca ggaagatgta gacat                                              25

<210> SEQ ID NO 624
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 624
ctctgggccc aggaagatgt agaca                                              25

<210> SEQ ID NO 625
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 625
gctctgggcc caggaagatg tagac                                              25

<210> SEQ ID NO 626
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 626
ggctctgggc ccaggaagat gtaga                                              25

<210> SEQ ID NO 627
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 627
gggctctggg cccaggaaga tgtag                                              25

<210> SEQ ID NO 628
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 628
tgggctctgg gcccaggaag atgta                                              25

<210> SEQ ID NO 629
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 629
ttgggctctg ggcccaggaa gatgt                                              25
```

```
<210> SEQ ID NO 630
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 630
cttgggctct gggcccagga agatg                                          25

<210> SEQ ID NO 631
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 631
tcttgggctc tgggcccagg aagat                                          25

<210> SEQ ID NO 632
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 632
ctcttgggct ctgggcccag gaaga                                          25

<210> SEQ ID NO 633
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 633
gctcttgggc tctgggccca ggaag                                          25

<210> SEQ ID NO 634
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 634
cgctcttggg ctctgggccc aggaa                                          25

<210> SEQ ID NO 635
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 635
acgctcttgg gctctgggcc cagga                                          25

<210> SEQ ID NO 636
<211> LENGTH: 25
<212> TYPE: DNA
<213> ORGANISM: Artificial Sequence
<220> FEATURE:
```

```
<223> OTHER INFORMATION: antisense oligomeric compound

<400> SEQUENCE: 636
cacgctcttg ggctctgggc ccagg                                              25

<210> SEQ ID NO 637
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 637
ccacgctctt gggctctggg cccag                                              25

<210> SEQ ID NO 638
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 638
accacgctct tgggctctgg gccca                                              25

<210> SEQ ID NO 639
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 639
caccacgctc ttgggctctg ggccc                                              25

<210> SEQ ID NO 640
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 640
gcaccacgct cttgggctct gggcc                                              25

<210> SEQ ID NO 641
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 641
tgcaccacgc tcttgggctc tgggc                                              25

<210> SEQ ID NO 642
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 642
ctgcaccacg ctcttgggct ctggg                                              25
```

```
<210> SEQ ID NO 643
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 643
gctgcaccac gctcttgggc tctgg                                       25

<210> SEQ ID NO 644
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 644
tgctgcacca cgctcttggg ctctg                                       25

<210> SEQ ID NO 645
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 645
ctgctgcacc acgctcttgg gctct                                       25

<210> SEQ ID NO 646
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 646
actgctgcac cacgctcttg ggctc                                       25

<210> SEQ ID NO 647
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 647
tactgctgca ccacgctctt gggct                                       25

<210> SEQ ID NO 648
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 648
gtactgctgc accacgctct tgggc                                       25

<210> SEQ ID NO 649
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 649
ggtactgctg caccacgctc ttggg                                          25

<210> SEQ ID NO 650
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 650
aggtactgct gcaccacgct cttgg                                          25

<210> SEQ ID NO 651
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 651
caggtactgc tgcaccacgc tcttg                                          25

<210> SEQ ID NO 652
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 652
ccaggtactg ctgcaccacg ctctt                                          25

<210> SEQ ID NO 653
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 653
tccaggtact gctgcaccac gctct                                          25

<210> SEQ ID NO 654
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 654
gtccaggtac tgctgcacca cgctc                                          25

<210> SEQ ID NO 655
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 655
cgtccaggta ctgctgcacc acgct                                          25

<210> SEQ ID NO 656
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 656
acgtccaggt actgctgcac cacgc                                       25

<210> SEQ ID NO 657
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 657
aacgtccagg tactgctgca ccacg                                       25

<210> SEQ ID NO 658
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 658
caacgtccag gtactgctgc accac                                       25

<210> SEQ ID NO 659
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 659
acaacgtcca ggtactgctg cacca                                       25

<210> SEQ ID NO 660
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 660
cacaacgtcc aggtactgct gcacc                                       25

<210> SEQ ID NO 661
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 661
ccacaacgtc caggtactgc tgcac                                       25

<210> SEQ ID NO 662
<211> LENGTH: 50
<212> TYPE: DNA
<213> ORGANISM: Artificial Sequence
<220> FEATURE:
<223> OTHER INFORMATION: antisense oligomeric compound

<400> SEQUENCE: 662
```

```
cccacaacgt ccaggtactg ctgcaaccca caacgtccag gtactgctgc                50
```

<210> SEQ ID NO 663
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 663

```
tacccacaac gtccaggtac tgctg                                           25
```

<210> SEQ ID NO 664
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 664

```
ctacccacaa cgtccaggta ctgct                                           25
```

<210> SEQ ID NO 665
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 665

```
cctacccaca acgtccaggt actgc                                           25
```

<210> SEQ ID NO 666
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 666

```
cctacccaca acgtccaggt actgc                                           25
```

<210> SEQ ID NO 667
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 667

```
ccctacccac aacgtccagg tactg                                           25
```

<210> SEQ ID NO 668
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 668

```
gccctaccca caacgtccag gtact                                           25
```

<210> SEQ ID NO 669
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 669
ggccctaccc acaacgtcca ggtac                                       25

<210> SEQ ID NO 670
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 670
aggccctacc cacaacgtcc aggta                                       25

<210> SEQ ID NO 671
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 671
caggccctac ccacaacgtc caggt                                       25

<210> SEQ ID NO 672
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 672
gcaggcccta cccacaacgt ccagg                                       25

<210> SEQ ID NO 673
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 673
agcaggccct acccacaacg tccag                                       25

<210> SEQ ID NO 674
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 674
gagcaggccc tacccacaac gtcca                                       25

<210> SEQ ID NO 675
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 675
ggagcaggcc ctacccacaa cgtcc                                       25
```

```
<210> SEQ ID NO 676
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 676
gggagcaggc cctacccaca acgtc                                               25

<210> SEQ ID NO 677
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 677
agggagcagg ccctacccac aacgt                                               25

<210> SEQ ID NO 678
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 678
cagggagcag gccctaccca caacg                                               25

<210> SEQ ID NO 679
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 679
ccagggagca ggccctaccc acaac                                               25

<210> SEQ ID NO 680
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 680
gccagggagc aggccctacc cacaa                                               25

<210> SEQ ID NO 681
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 681
ggccagggag caggccctac ccaca                                               25

<210> SEQ ID NO 682
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 682
cggccaggga gcaggcccta cccac                                              25

<210> SEQ ID NO 683
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 683
gcggccaggg agcaggccct accca                                              25

<210> SEQ ID NO 684
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 684
cgcggccagg gagcagggcc taccc                                              25

<210> SEQ ID NO 685
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 685
ccgcggccag ggagcaggcc ctacc                                              25

<210> SEQ ID NO 686
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 686
gccgcggcca gggagcaggc cctac                                              25

<210> SEQ ID NO 687
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 687
ggccgcggcc agggagcagg cccta                                              25

<210> SEQ ID NO 688
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 688
gggccgcggc cagggagcag gccct                                              25

<210> SEQ ID NO 689
```

-continued

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 689
ggggccgcgg ccagggagca ggccc                                        25

<210> SEQ ID NO 690
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 690
gggggccgcg gccagggagc aggcc                                        25

<210> SEQ ID NO 691
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 691
cgggggccgc ggccagggag caggc                                        25

<210> SEQ ID NO 692
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 692
gcgggggccg cggccaggga gcagg                                        25

<210> SEQ ID NO 693
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 693
ggcgggggcc gcggccaggg agcag                                        25

<210> SEQ ID NO 694
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 694 gggcggggc cgcggccagg gagca                                         25

<210> SEQ ID NO 695
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 695
```
ggggcggggg ccgcggccag ggagc                                                25

<210> SEQ ID NO 696
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 696
tggggcgggg gccgcggcca gggag                                                25

<210> SEQ ID NO 697
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 697
ttggggcggg ggccgcggcc aggga                                                25

<210> SEQ ID NO 698
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 698
cttggggcgg gggccgcggc caggg                                                25

<210> SEQ ID NO 699
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 699
ccttggggcg ggggccgcgg ccagg                                                25

<210> SEQ ID NO 700
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 700
gccttggggc ggggccgcg gccag                                                 25

<210> SEQ ID NO 701
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 701
agccttgggg cggggccgc ggcca                                                 25

<210> SEQ ID NO 702
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 702
gagccttggg gcggggccg cggcc                                          25

<210> SEQ ID NO 703
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 703
ggagccttgg ggcggggcc gcggc                                          25

<210> SEQ ID NO 704
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 704
gggagccttg gggcggggc cgcgg                                          25

<210> SEQ ID NO 705
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 705
agggagcctt ggggcggggg ccgcg                                         25

<210> SEQ ID NO 706
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 706
gagggagcct tggggcgggg gccgc                                         25

<210> SEQ ID NO 707
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 707
ggagggagcc ttggggcggg ggccg                                         25

<210> SEQ ID NO 708
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 708
aggagggagc cttggggcgg gggcc                                         25
```

<210> SEQ ID NO 709
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 709
gaggagggag ccttggggcg ggggc                                          25

<210> SEQ ID NO 710
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 710
ggaggaggga gccttggggc ggggg                                          25

<210> SEQ ID NO 711
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 711
gggaggaggg agccttgggg cgggg                                          25

<210> SEQ ID NO 712
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 712
agggaggagg gagccttggg gcggg                                          25

<210> SEQ ID NO 713
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 713
gagggaggag ggagccttgg ggcgg                                          25

<210> SEQ ID NO 714
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 714
ggagggagga gggagccttg gggcg                                          25

<210> SEQ ID NO 715
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 715
gggagggagg agggagcctt ggggc        25

<210> SEQ ID NO 716
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 716
agggagggag gagggagcct tgggg        25

<210> SEQ ID NO 717
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 717
gagggaggga ggagggagcc ttggg        25

<210> SEQ ID NO 718
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 718
tgagggaggg aggagggagc cttgg        25

<210> SEQ ID NO 719
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 719
atgagggagg gaggagggag ccttg        25

<210> SEQ ID NO 720
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 720
catgagggag ggaggaggga gcctt        25

<210> SEQ ID NO 721
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 721
tcatgaggga gggaggaggg agcct        25

```
<210> SEQ ID NO 722
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 722
ttcatgaggg agggaggagg gagcc                                          25

<210> SEQ ID NO 723
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 723
cttcatgagg gagggaggag ggagc                                          25

<210> SEQ ID NO 724
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 724
acttcatgag ggagggagga gggag                                          25

<210> SEQ ID NO 725
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 725
gacttcatga gggagggagg aggga                                          25

<210> SEQ ID NO 726
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 726
cgacttcatg agggagggag gaggg                                          25

<210> SEQ ID NO 727
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 727
ccgacttcat gagggaggga ggagg                                          25

<210> SEQ ID NO 728
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 728
gccgacttca tgagggaggg aggag                                        25

<210> SEQ ID NO 729
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 729
cgccgacttc atgagggagg gagga                                        25

<210> SEQ ID NO 730
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 730
acgccgactt catgagggag ggagg                                        25

<210> SEQ ID NO 731
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 731
aacgccgact tcatgaggga gggag                                        25

<210> SEQ ID NO 732
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 732
caacgccgac ttcatgaggg aggga                                        25

<210> SEQ ID NO 733
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 733
ccaacgccga cttcatgagg gaggg                                        25

<210> SEQ ID NO 734
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 734
gccaacgccg acttcatgag ggagg                                        25

<210> SEQ ID NO 735
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 735
ggccaacgcc gacttcatga gggag                                  25

<210> SEQ ID NO 736
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 736
aggccaacgc cgacttcatg aggga                                  25

<210> SEQ ID NO 737
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 737
caggccaacg ccgacttcat gaggg                                  25

<210> SEQ ID NO 738
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 738
gcaggccaac gccgacttca tgagg                                  25

<210> SEQ ID NO 739
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 739
tgcaggccaa cgccgacttc atgag                                  25

<210> SEQ ID NO 740
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 740
ctgcaggcca acgccgactt catga                                  25

<210> SEQ ID NO 741
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 741
```
cctgcaggcc aacgccgact tcatg                                          25

<210> SEQ ID NO 742
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 742
tcctgcaggc caacgccgac ttcat                                          25

<210> SEQ ID NO 743
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 743
atcctgcagg ccaacgccga cttca                                          25

<210> SEQ ID NO 744
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 744
tatcctgcag gccaacgccg acttc                                          25

<210> SEQ ID NO 745
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 745
gtatcctgca ggccaacgcc gactt                                          25

<210> SEQ ID NO 746
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 746
ggtatcctgc aggccaacgc cgact                                          25

<210> SEQ ID NO 747
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 747
gggtatcctg caggccaacg ccgac                                          25

<210> SEQ ID NO 748
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 748
cgggtatcct gcaggccaac gccga                                           25

<210> SEQ ID NO 749
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 749
acgggtatcc tgcaggccaa cgccg                                           25

<210> SEQ ID NO 750
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 750
aacgggtatc ctgcaggcca acgcc                                           25

<210> SEQ ID NO 751
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 751
gaacgggtat cctgcaggcc aacgc                                           25

<210> SEQ ID NO 752
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 752
tgaacgggta tcctgcaggc caacg                                           25

<210> SEQ ID NO 753
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 753
atgaacgggt atcctgcagg ccaac                                           25

<210> SEQ ID NO 754
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 754
catgaacggg tatcctgcag gccaa                                           25
```

<210> SEQ ID NO 755
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 755
gcatgaacgg gtatcctgca ggcca                                  25

<210> SEQ ID NO 756
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 756
ggcatgaacg ggtatcctgc aggcc                                  25

<210> SEQ ID NO 757
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 757
cggcatgaac gggtatcctg caggc                                  25

<210> SEQ ID NO 758
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 758
gcggcatgaa cgggtatcct gcagg                                  25

<210> SEQ ID NO 759
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 759
ggcggcatga acgggtatcc tgcag                                  25

<210> SEQ ID NO 760
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 760
tggcggcatg aacgggtatc ctgca                                  25

<210> SEQ ID NO 761
<211> LENGTH: 25
<212> TYPE: DNA
<213> ORGANISM: Artificial Sequence
<220> FEATURE:
<223> OTHER INFORMATION: antisense oligomeric compound -continued

```
<400> SEQUENCE: 761
atggcggcat gaacgggtat cctgc                                              25

<210> SEQ ID NO 762
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 762
tatggcggca tgaacgggta tcctg                                              25

<210> SEQ ID NO 763
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 763
gtatggcggc atgaacgggt atcct                                              25

<210> SEQ ID NO 764
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 764
agtatggcgg catgaacggg tatcc                                              25

<210> SEQ ID NO 765
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 765
cagtatggcg gcatgaacgg gtatc                                              25

<210> SEQ ID NO 766
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 766
ccagtatggc ggcatgaacg ggtat                                              25

<210> SEQ ID NO 767
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 767
cccagtatgg cggcatgaac gggta                                              25

<210> SEQ ID NO 768
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 768
ccccagtatg gcggcatgaa cgggt                                            25

<210> SEQ ID NO 769
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 769
gccccagtat ggcggcatga acggg                                            25

<210> SEQ ID NO 770
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 770
ggccccagta tggcggcatg aacgg                                            25

<210> SEQ ID NO 771
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 771
aggccccagt atggcggcat gaacg                                            25

<210> SEQ ID NO 772
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 772
caggccccag tatggcggca tgaac                                            25

<210> SEQ ID NO 773
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 773
ccaggcccca gtatggcggc atgaa                                            25

<210> SEQ ID NO 774
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 774
```
cccaggcccc agtatggcgg catga                                    25

<210> SEQ ID NO 775
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 775
gcccaggccc cagtatggcg gcatg                                    25

<210> SEQ ID NO 776
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 776
agcccaggcc ccagtatggc ggcat                                    25

<210> SEQ ID NO 777
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 777
aagcccaggc cccagtatgg cggca                                    25

<210> SEQ ID NO 778
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 778
gaagcccagg ccccagtatg gcggc                                    25

<210> SEQ ID NO 779
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 779
ggaagcccag gccccagtat ggcgg                                    25

<210> SEQ ID NO 780
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 780
tggaagccca ggccccagta tggcg                                    25

<210> SEQ ID NO 781
<211> LENGTH: 25
<212> TYPE: DNA

<213> ORGANISM: Artificial Sequence
<220> FEATURE:
<223> OTHER INFORMATION: antisense oligomeric compound

<400> SEQUENCE: 781
gtggaagccc aggccccagt atggc                                              25

<210> SEQ ID NO 782
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 782
ggtggaagcc caggccccag tatgg                                              25

<210> SEQ ID NO 783
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 783
aggtggaagc ccaggcccca gtatg                                              25

<210> SEQ ID NO 784
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 784
caggtggaag cccaggcccc agtat                                              25

<210> SEQ ID NO 785
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 785
acaggtggaa gcccaggccc cagta                                              25

<210> SEQ ID NO 786
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 786
cacaggtgga agcccaggcc ccagt                                              25

<210> SEQ ID NO 787
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 787
gcacaggtgg aagcccaggc ccag                                               25

<210> SEQ ID NO 788
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 788
ggcacaggtg gaagcccagg cccca                                          25

<210> SEQ ID NO 789
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 789
cggcacaggt ggaagcccag gcccc                                          25

<210> SEQ ID NO 790
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 790
gcggcacagg tggaagccca ggccc                                          25

<210> SEQ ID NO 791
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 791
agcggcacag gtggaagccc aggcc                                          25

<210> SEQ ID NO 792
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 792
cagcggcaca ggtggaagcc caggc                                          25

<210> SEQ ID NO 793
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 793
ccagcggcac aggtggaagc ccagg                                          25

<210> SEQ ID NO 794
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 794
cccagcggca caggtggaag cccag                                          25

<210> SEQ ID NO 795
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 795
ccccagcggc acaggtggaa gccca                                          25

<210> SEQ ID NO 796
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 796
gccccagcgg cacaggtgga agccc                                          25

<210> SEQ ID NO 797
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 797
agccccagcg gcacaggtgg aagcc                                          25

<210> SEQ ID NO 798
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 798
tagccccagc ggcacaggtg gaagc                                          25

<210> SEQ ID NO 799
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 799
gtagccccag cggcacaggt ggaag                                          25

<210> SEQ ID NO 800
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 800
agtagcccca gcggcacagg tggaa                                          25

```
<210> SEQ ID NO 801
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 801
gagtagcccc agcggcacag gtgga                                     25

<210> SEQ ID NO 802
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 802
ggagtagccc cagcggcaca ggtgg                                     25

<210> SEQ ID NO 803
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 803
aggagtagcc ccagcggcac aggtg                                     25

<210> SEQ ID NO 804
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 804
gaggagtagc cccagcggca caggt                                     25

<210> SEQ ID NO 805
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 805
ggaggagtag ccccagcggc acagg                                     25

<210> SEQ ID NO 806
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 806
tggaggagta gccccagcgg cacag                                     25

<210> SEQ ID NO 807
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 807
gtggaggagt agccccagcg gcaca                                          25

<210> SEQ ID NO 808
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 808
ggtggaggag tagccccagc ggcac                                          25

<210> SEQ ID NO 809
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 809
cggtggagga gtagccccag cggca                                          25

<210> SEQ ID NO 810
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 810
gcggtggagg agtagcccca gcggc                                          25

<210> SEQ ID NO 811
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 811
agcggtggag gagtagcccc agcgg                                          25

<210> SEQ ID NO 812
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 812
tagcggtgga ggagtagccc cagcg                                          25

<210> SEQ ID NO 813
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 813
atagcggtgg aggagtagcc ccagc                                          25

<210> SEQ ID NO 814
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 814
gatagcggtg gaggagtagc cccag                                              25

<210> SEQ ID NO 815
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 815
tgatagcggt ggaggagtag cccca                                              25

<210> SEQ ID NO 816
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 816
gtgatagcgg tggaggagta gcccc                                              25

<210> SEQ ID NO 817
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 817
ggtgatagcg gtggaggagt agccc                                              25

<210> SEQ ID NO 818
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 818
gggtgatagc ggtggaggag tagcc                                              25

<210> SEQ ID NO 819
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 819
cgggtgatag cggtggagga gtagc                                              25

<210> SEQ ID NO 820
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 820
```
gcgggtgata gcggtggagg agtag 25

<210> SEQ ID NO 821
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 821
ggcgggtgat agcggtggag gagta 25

<210> SEQ ID NO 822
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 822
tggcgggtga tagcggtgga ggagt 25

<210> SEQ ID NO 823
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 823
ctggcgggtg atagcggtgg aggag 25

<210> SEQ ID NO 824
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 824
cctggcgggt gatagcggtg gagga 25

<210> SEQ ID NO 825
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 825
acctggcggg tgatagcggt ggagg 25

<210> SEQ ID NO 826
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 826
cacctggcgg gtgatagcgg tggag 25

<210> SEQ ID NO 827
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 827
ccacctggcg ggtgatagcg gtgga                                              25

<210> SEQ ID NO 828
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 828
accacctggc gggtgatagc ggtgg                                              25

<210> SEQ ID NO 829
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 829
caccacctgg cgggtgatag cggtg                                              25

<210> SEQ ID NO 830
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 830
ccaccacctg gcgggtgata gcggt                                              25

<210> SEQ ID NO 831
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 831
tccaccacct ggcgggtgat agcgg                                              25

<210> SEQ ID NO 832
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 832
ctccaccacc tggcgggtga tagcg                                              25

<210> SEQ ID NO 833
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 833
tctccaccac ctggcgggtg atagc                                              25
```

```
<210> SEQ ID NO 834
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 834
ttctccacca cctggcgggt gatag                                              25

<210> SEQ ID NO 835
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 835
gttctccacc acctggcggg tgata                                              25

<210> SEQ ID NO 836
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 836
tgttctccac cacctggcgg gtgat                                              25

<210> SEQ ID NO 837
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 837
atgttctcca ccacctggcg ggtga                                              25

<210> SEQ ID NO 838
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 838
catgttctcc accacctggc gggtg                                              25

<210> SEQ ID NO 839
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 839
tcatgttctc caccacctgg cgggt                                              25

<210> SEQ ID NO 840
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 840
gtcatgttct ccaccacctg gcggg                                           25

<210> SEQ ID NO 841
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 841
ggtcatgttc tccaccacct ggcgg                                           25

<210> SEQ ID NO 842
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 842
tggtcatgtt ctccaccacc tggcg                                           25

<210> SEQ ID NO 843
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 843
ctggtcatgt tctccaccac ctggc                                           25

<210> SEQ ID NO 844
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 844
cctggtcatg ttctccacca cctgg                                           25

<210> SEQ ID NO 845
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 845
ccctggtcat gttctccacc acctg                                           25

<210> SEQ ID NO 846
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 846
gccctggtca tgttctccac cacct                                           25

<210> SEQ ID NO 847
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 847
ggccctggtc atgttctcca ccacc                                         25

<210> SEQ ID NO 848
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 848
gggccctggt catgttctcc accac                                         25

<210> SEQ ID NO 849
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 849
tgggccctgg tcatgttctc cacca                                         25

<210> SEQ ID NO 850
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 850
gtgggccctg gtcatgttct ccacc                                         25

<210> SEQ ID NO 851
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 851
agtgggccct ggtcatgttc tccac                                         25

<210> SEQ ID NO 852
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 852
aagtgggccc tggtcatgtt ctcca                                         25

<210> SEQ ID NO 853
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 853
```
gaagtgggcc ctggtcatgt tctcc                                              25

<210> SEQ ID NO 854
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 854
ggaagtgggc cctggtcatg ttctc                                              25

<210> SEQ ID NO 855
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 855
gggaagtggg ccctggtcat gttct                                              25

<210> SEQ ID NO 856
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 856
ggggaagtgg gccctggtca tgttc                                              25

<210> SEQ ID NO 857
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 857
gggggaagtg ggccctggtc atgtt                                              25

<210> SEQ ID NO 858
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 858
agggggaagt gggccctggt catgt                                              25

<210> SEQ ID NO 859
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 859 caggggaag tgggccctgg tcatg                                               25

<210> SEQ ID NO 860
<211> LENGTH: 25
<212> TYPE: DNA

<213> ORGANISM: Artificial Sequence
<220> FEATURE:
<223> OTHER INFORMATION: antisense oligomeric compound

<400> SEQUENCE: 860 ccaggggaa gtgggccctg gtcat                                      25

<210> SEQ ID NO 861
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 861
accaggggga agtgggccct ggtca                                     25

<210> SEQ ID NO 862
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 862
caccaggggg aagtgggccc tggtc                                     25

<210> SEQ ID NO 863
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 863
tcaccagggg gaagtgggcc ctggt                                     25

<210> SEQ ID NO 864
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 864
ctcaccaggg ggaagtgggc cctgg                                     25

<210> SEQ ID NO 865
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 865
actcaccagg gggaagtggg ccctg                                     25

<210> SEQ ID NO 866
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 866
aactcaccag ggggaagtgg gccct                                     25

<210> SEQ ID NO 867
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 867
caactcacca gggggaagtg ggccc                                           25

<210> SEQ ID NO 868
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 868
ccaactcacc aggggaagt gggcc                                            25

<210> SEQ ID NO 869
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 869
cccaactcac caggggaag tgggc                                            25

<210> SEQ ID NO 870
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 870
ccccaactca ccaggggaa gtggg                                            25

<210> SEQ ID NO 871
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 871
accccaactc accaggggga agtgg                                           25

<210> SEQ ID NO 872
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 872
caccccaact caccaggggg aagtg                                           25

<210> SEQ ID NO 873
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 873
ccaccccaac tcaccagggg gaagt                                         25

<210> SEQ ID NO 874
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 874
accaccccaa ctcaccaggg ggaag                                         25

<210> SEQ ID NO 875
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 875 caccaccccca actcaccagg gggaa                                        25

<210> SEQ ID NO 876
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 876
ccaccacccc aactcaccag gggga                                         25

<210> SEQ ID NO 877
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 877
gccaccaccc caactcacca ggggg                                         25

<210> SEQ ID NO 878
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 878
tgccaccacc ccaactcacc agggg                                         25

<210> SEQ ID NO 879
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 879
ctgccaccac cccaactcac caggg                                         25

```
<210> SEQ ID NO 880
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 880
cctgccacca ccccaactca ccagg                                              25

<210> SEQ ID NO 881
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 881
ccctgccacc accccaactc accag                                              25

<210> SEQ ID NO 882
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 882
cccctgccac accccaact cacca                                               25

<210> SEQ ID NO 883
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 883
tcccctgcca ccaccccaac tcacc                                              25

<210> SEQ ID NO 884
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 884 ctccccctgcc accaccccaa ctcac                                             25

<210> SEQ ID NO 885
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 885
aagggaagca gctctggggt t                                                  21

<210> SEQ ID NO 886
<211> LENGTH: 21
<212> TYPE: DNA
<213> ORGANISM: Artificial Sequence
<220> FEATURE:
<223> OTHER INFORMATION: antisense oligomeric compound
```

<400> SEQUENCE: 886
gaagggaagc agctctgggg t                                              21

<210> SEQ ID NO 887
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 887
ggaagggaag cagctctggg g                                              21

<210> SEQ ID NO 888
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 888
tggaagggaa gcagctctgg g                                              21

<210> SEQ ID NO 889
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 889
ctggaaggga agcagctctg g                                              21

<210> SEQ ID NO 890
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 890
tctggaaggg aagcagctct g                                              21

<210> SEQ ID NO 891
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 891
atctggaagg gaagcagctc t                                              21

<210> SEQ ID NO 892
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 892
catctggaag ggaagcagct c                                              21

<210> SEQ ID NO 893
<211> LENGTH: 21

```
<212> TYPE: DNA
<213> ORGANISM: Artificial Sequence
<220> FEATURE:
<223> OTHER INFORMATION: antisense oligomeric compound

<400> SEQUENCE: 893
acatctggaa gggaagcagc t                                              21

<210> SEQ ID NO 894
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 894
cacatctgga agggaagcag c                                              21

<210> SEQ ID NO 895
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 895
ccacatctgg aagggaagca g                                              21

<210> SEQ ID NO 896
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 896
accacatctg gaagggaagc a                                              21

<210> SEQ ID NO 897
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 897
gaccacatct ggaagggaag c                                              21

<210> SEQ ID NO 898
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 898
ggaccacatc tggaagggaa g                                              21

<210> SEQ ID NO 899
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 899
```
aggaccacat ctggaaggga a                                             21

<210> SEQ ID NO 900
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 900
caggaccaca tctggaaggg a                                             21

<210> SEQ ID NO 901
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 901
gcaggaccac atctggaagg g                                             21

<210> SEQ ID NO 902
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 902
tgcaggacca catctggaag g                                             21

<210> SEQ ID NO 903
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 903
ctgcaggacc acatctggaa g                                             21

<210> SEQ ID NO 904
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 904
gctgcaggac cacatctgga a                                             21

<210> SEQ ID NO 905
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 905
ggctgcagga ccacatctgg a                                             21

<210> SEQ ID NO 906
<211> LENGTH: 21
<212> TYPE: DNA
<213> ORGANISM: Artificial Sequence

```
<220> FEATURE:
<223> OTHER INFORMATION: antisense oligomeric compound

<400> SEQUENCE: 906
cggctgcagg accacatctg g                                               21

<210> SEQ ID NO 907
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 907
tcggctgcag gaccacatct g                                               21

<210> SEQ ID NO 908
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 908
ctcggctgca ggaccacatc t                                               21

<210> SEQ ID NO 909
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 909
gctcggctgc aggaccacat c                                               21

<210> SEQ ID NO 910
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 910
ggctcggctg caggaccaca t                                               21

<210> SEQ ID NO 911
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 911
gggctcggct gcaggaccac a                                               21

<210> SEQ ID NO 912
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 912
agggctcggc tgcaggacca c                                               21
```

<210> SEQ ID NO 913
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 913
cagggctcgg ctgcaggacc a                                              21

<210> SEQ ID NO 914
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 914
gcagggctcg gctgcaggac c                                              21

<210> SEQ ID NO 915
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 915
ggcagggctc ggctgcagga c                                              21

<210> SEQ ID NO 916
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 916
gggcagggct cggctgcagg a                                              21

<210> SEQ ID NO 917
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 917
agggcagggc tcggctgcag g                                              21

<210> SEQ ID NO 918
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 918
aagggcaggg ctcggctgca g                                              21

<210> SEQ ID NO 919
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 919
taagggcagg gctcggctgc a                                              21

<210> SEQ ID NO 920
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 920
ctaagggcag ggctcggctg c                                              21

<210> SEQ ID NO 921
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 921
gctaagggca gggctcggct g                                              21

<210> SEQ ID NO 922
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 922
agctaagggc agggctcggc t                                              21

<210> SEQ ID NO 923
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 923
cagctaaggg cagggctcgg c                                              21

<210> SEQ ID NO 924
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 924
ccagctaagg gcagggctcg g                                              21

<210> SEQ ID NO 925
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 925
tccagctaag gcagggctc g                                               21

<210> SEQ ID NO 926

```
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 926
ctccagctaa gggcagggct c                                              21

<210> SEQ ID NO 927
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 927
cctccagcta agggcagggc t                                              21

<210> SEQ ID NO 928
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 928
acctccagct aagggcaggg c                                              21

<210> SEQ ID NO 929
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 929
gacctccagc taagggcagg g                                              21

<210> SEQ ID NO 930
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 930
cgacctccag ctaagggcag g                                              21

<210> SEQ ID NO 931
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 931
tcgacctcca gctaagggca g                                              21

<210> SEQ ID NO 932
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 932
```
gtcgacctcc agctaagggc a                                              21

<210> SEQ ID NO 933
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 933
tgtcgacctc cagctaaggg c                                              21

<210> SEQ ID NO 934
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 934
ctgtcgacct ccagctaagg g                                              21

<210> SEQ ID NO 935
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 935
cctgtcgacc tccagctaag g                                              21

<210> SEQ ID NO 936
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 936
acctgtcgac ctccagctaa g                                              21

<210> SEQ ID NO 937
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 937
cacctgtcga cctccagcta a                                              21

<210> SEQ ID NO 938
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 938
ccacctgtcg acctccagct a                                              21

<210> SEQ ID NO 939
<211> LENGTH: 21
<212> TYPE: DNA

```
<213> ORGANISM: Artificial Sequence
<220> FEATURE:
<223> OTHER INFORMATION: antisense oligomeric compound

<400> SEQUENCE: 939
cccacctgtc gacctccagc t                                              21

<210> SEQ ID NO 940
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 940
tcccacctgt cgacctccag c                                              21

<210> SEQ ID NO 941
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 941
atcccacctg tcgacctcca g                                              21

<210> SEQ ID NO 942
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 942
gatcccacct gtcgacctcc a                                              21

<210> SEQ ID NO 943
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 943
ggatcccacc tgtcgacctc c                                              21

<210> SEQ ID NO 944
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 944
aggatcccac ctgtcgacct c                                              21

<210> SEQ ID NO 945
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 945
caggatccca cctgtcgacc t                                              21
```

<210> SEQ ID NO 946
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 946
ccaggatccc acctgtcgac c                                              21

<210> SEQ ID NO 947
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 947
tccaggatcc cacctgtcga c                                              21

<210> SEQ ID NO 948
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 948
atccaggatc ccacctgtcg a                                              21

<210> SEQ ID NO 949
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 949
catccaggat cccacctgtc g                                              21

<210> SEQ ID NO 950
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 950
acatccagga tcccacctgt c                                              21

<210> SEQ ID NO 951
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 951
gacatccagg atcccacctg t                                              21

<210> SEQ ID NO 952
<211> LENGTH: 21
<212> TYPE: DNA
<213> ORGANISM: Artificial Sequence
<220> FEATURE:

<223> OTHER INFORMATION: antisense oligomeric compound

<400> SEQUENCE: 952
agacatccag gatcccacct g                                              21

<210> SEQ ID NO 953
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 953
tagacatcca ggatcccacc t                                              21

<210> SEQ ID NO 954
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 954
gtagacatcc aggatcccac c                                              21

<210> SEQ ID NO 955
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 955
tgtagacatc caggatccca c                                              21

<210> SEQ ID NO 956
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 956
atgtagacat ccaggatccc a                                              21

<210> SEQ ID NO 957
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 957
gatgtagaca tccaggatcc c                                              21

<210> SEQ ID NO 958
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 958
agatgtagac atccaggatc c                                              21

```
<210> SEQ ID NO 959
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 959
aagatgtaga catccaggat c                                               21

<210> SEQ ID NO 960
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 960
gaagatgtag acatccagga t                                               21

<210> SEQ ID NO 961
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 961
ggaagatgta gacatccagg a                                               21

<210> SEQ ID NO 962
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 962
aggaagatgt agacatccag g                                               21

<210> SEQ ID NO 963
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 963
caggaagatg tagacatcca g                                               21

<210> SEQ ID NO 964
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 964
ccaggaagat gtagacatcc a                                               21

<210> SEQ ID NO 965
<211> LENGTH: 21
<212> TYPE: DNA
<213> ORGANISM: Artificial Sequence
<220> FEATURE:
<223> OTHER INFORMATION: antisense oligomeric compound
```

```
<400> SEQUENCE: 965
cccaggaaga tgtagacatc c                                              21

<210> SEQ ID NO 966
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 966
gcccaggaag atgtagacat c                                              21

<210> SEQ ID NO 967
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 967
ggcccaggaa gatgtagaca t                                              21

<210> SEQ ID NO 968
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 968
gggcccagga agatgtagac a                                              21

<210> SEQ ID NO 969
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 969
tgggcccagg aagatgtaga c                                              21

<210> SEQ ID NO 970
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 970
ctgggcccag gaagatgtag a                                              21

<210> SEQ ID NO 971
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 971
tctgggccca ggaagatgta g                                              21

<210> SEQ ID NO 972
<211> LENGTH: 21
```

```
<212> TYPE: DNA
<213> ORGANISM: Artificial Sequence
<220> FEATURE:
<223> OTHER INFORMATION: antisense oligomeric compound

<400> SEQUENCE: 972
ctctgggccc aggaagatgt a                                             21

<210> SEQ ID NO 973
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 973
gctctgggcc caggaagatg t                                             21

<210> SEQ ID NO 974
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 974
ggctctgggc ccaggaagat g                                             21

<210> SEQ ID NO 975
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 975
gggctctggg cccaggaaga t                                             21

<210> SEQ ID NO 976
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 976
tgggctctgg gcccaggaag a                                             21

<210> SEQ ID NO 977
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 977
ttgggctctg ggcccaggaa g                                             21

<210> SEQ ID NO 978
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 978
```
cttgggctct gggcccagga a         21

<210> SEQ ID NO 979
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 979
tcttgggctc tgggcccagg a         21

<210> SEQ ID NO 980
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 980
ctcttgggct ctgggcccag g         21

<210> SEQ ID NO 981
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 981
gctcttgggc tctgggccca g         21

<210> SEQ ID NO 982
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 982
cgctcttggg ctctgggccc a         21

<210> SEQ ID NO 983
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 983
acgctcttgg gctctgggcc c         21

<210> SEQ ID NO 984
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 984
cacgctcttg ggctctgggc c         21

<210> SEQ ID NO 985
<211> LENGTH: 21
<212> TYPE: DNA
<213> ORGANISM: Artificial Sequence

```
<220> FEATURE:
<223> OTHER INFORMATION: antisense oligomeric compound

<400> SEQUENCE: 985
ccacgctctt gggctctggg c                                              21

<210> SEQ ID NO 986
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 986
accacgctct tgggctctgg g                                              21

<210> SEQ ID NO 987
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 987
caccacgctc ttgggctctg g                                              21

<210> SEQ ID NO 988
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 988
gcaccacgct cttgggctct g                                              21

<210> SEQ ID NO 989
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 989
tgcaccacgc tcttgggctc t                                              21

<210> SEQ ID NO 990
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 990
ctgcaccacg ctcttgggct c                                              21

<210> SEQ ID NO 991
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 991
gctgcaccac gctcttgggc t                                              21
```

```
<210> SEQ ID NO 992
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 992
tgctgcacca cgctcttggg c                                          21

<210> SEQ ID NO 993
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 993
ctgctgcacc acgctcttgg g                                          21

<210> SEQ ID NO 994
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 994
actgctgcac cacgctcttg g                                          21

<210> SEQ ID NO 995
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 995
tactgctgca ccacgctctt g                                          21

<210> SEQ ID NO 996
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 996
gtactgctgc accacgctct t                                          21

<210> SEQ ID NO 997
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 997
ggtactgctg caccacgctc t                                          21

<210> SEQ ID NO 998
<211> LENGTH: 21
<212> TYPE: DNA
<213> ORGANISM: Artificial Sequence
<220> FEATURE:
<223> OTHER INFORMATION: antisense oligomeric compound
```

<400> SEQUENCE: 998
aggtactgct gcaccacgct c    21

<210> SEQ ID NO 999
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 999
caggtactgc tgcaccacgc t    21

<210> SEQ ID NO 1000
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1000
ccaggtactg ctgcaccacg c    21

<210> SEQ ID NO 1001
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1001
tccaggtact gctgcaccac g    21

<210> SEQ ID NO 1002
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1002
gtccaggtac tgctgcacca c    21

<210> SEQ ID NO 1003
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1003
cgtccaggta ctgctgcacc a    21

<210> SEQ ID NO 1004
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1004
acgtccaggt actgctgcac c    21

<210> SEQ ID NO 1005

```
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1005
aacgtccagg tactgctgca c                                              21

<210> SEQ ID NO 1006
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1006
caacgtccag gtactgctgc a                                              21

<210> SEQ ID NO 1007
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1007
acaacgtcca ggtactgctg c                                              21

<210> SEQ ID NO 1008
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1008
cacaacgtcc aggtactgct g                                              21

<210> SEQ ID NO 1009
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1009
ccacaacgtc caggtactgc t                                              21

<210> SEQ ID NO 1010
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1010
cccacaacgt ccaggtactg c                                              21

<210> SEQ ID NO 1011
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1011
```
acccacaacg tccaggtact g                                      21

<210> SEQ ID NO 1012
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1012
tacccacaac gtccaggtac t                                      21

<210> SEQ ID NO 1013
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1013
ctacccacaa cgtccaggta c                                      21

<210> SEQ ID NO 1014
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1014
cctacccaca acgtccaggt a                                      21

<210> SEQ ID NO 1015
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1015
ccctacccac aacgtccagg t                                      21

<210> SEQ ID NO 1016
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1016
gccctaccca caacgtccag g                                      21

<210> SEQ ID NO 1017
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1017
ggccctaccc acaacgtcca g                                      21

<210> SEQ ID NO 1018
<211> LENGTH: 21
<212> TYPE: DNA

```
<213> ORGANISM: Artificial Sequence
<220> FEATURE:
<223> OTHER INFORMATION: antisense oligomeric compound

<400> SEQUENCE: 1018
aggccctacc cacaacgtcc a                                              21

<210> SEQ ID NO 1019
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1019
caggccctac ccacaacgtc c                                              21

<210> SEQ ID NO 1020
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1020
gcaggcccta cccacaacgt c                                              21

<210> SEQ ID NO 1021
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1021
agcaggccct acccacaacg t                                              21

<210> SEQ ID NO 1022
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1022
gagcaggccc tacccacaac g                                              21

<210> SEQ ID NO 1023
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1023
ggagcaggcc ctacccacaa c                                              21

<210> SEQ ID NO 1024
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1024
gggagcaggc cctacccaca a                                              21
```

<210> SEQ ID NO 1025
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1025
agggagcagg ccctacccac a                                    21

<210> SEQ ID NO 1026
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1026
cagggagcag gccctaccca c                                    21

<210> SEQ ID NO 1027
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1027
ccagggagca ggccctaccc a                                    21

<210> SEQ ID NO 1028
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1028
gccagggagc aggccctacc c                                    21

<210> SEQ ID NO 1029
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1029
ggccagggag caggccctac c                                    21

<210> SEQ ID NO 1030
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1030
cggccaggga gcaggcccta c                                    21

<210> SEQ ID NO 1031
<211> LENGTH: 21
<212> TYPE: DNA
<213> ORGANISM: Artificial Sequence
<220> FEATURE:

<223> OTHER INFORMATION: antisense oligomeric compound

<400> SEQUENCE: 1031
gcggccaggg agcaggccct a    21

<210> SEQ ID NO 1032
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1032
cgcggccagg gagcaggccc t    21

<210> SEQ ID NO 1033
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1033
ccgcggccag ggagcaggcc c    21

<210> SEQ ID NO 1034
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1034
gccgcggcca gggagcaggc c    21

<210> SEQ ID NO 1035
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1035
ggccgcggcc agggagcagg c    21

<210> SEQ ID NO 1036
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1036
gggccgcggc cagggagcag g    21

<210> SEQ ID NO 1037
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1037
ggggccgcgg ccagggagca g    21

```
<210> SEQ ID NO 1038
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1038
gggggccgcg gccagggagc a                                              21

<210> SEQ ID NO 1039
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1039
cgggggccgc ggccagggag c                                              21

<210> SEQ ID NO 1040
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1040 gcggggccg cggccaggga g                                               21

<210> SEQ ID NO 1041
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1041 ggcggggcc gcggccaggg a                                               21

<210> SEQ ID NO 1042
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1042 gggcggggc cgcggccagg g                                               21

<210> SEQ ID NO 1043
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1043
ggggcggggg ccgcggccag g                                              21

<210> SEQ ID NO 1044
<211> LENGTH: 21
<212> TYPE: DNA
<213> ORGANISM: Artificial Sequence
<220> FEATURE:
<223> OTHER INFORMATION: antisense oligomeric compound
```

```
<400> SEQUENCE: 1044
tggggcgggg gccgcggcca g                                              21

<210> SEQ ID NO 1045
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1045
ttggggcggg ggccgcggcc a                                              21

<210> SEQ ID NO 1046
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1046
cttggggcgg gggccgcggc c                                              21

<210> SEQ ID NO 1047
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1047
ccttggggcg ggggccgcgg c                                              21

<210> SEQ ID NO 1048
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1048
gccttggggc ggggggccgcg g                                             21

<210> SEQ ID NO 1049
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1049
agccttgggg cggggccgc g                                               21

<210> SEQ ID NO 1050
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1050
gagccttggg gcggggggccg c                                             21

<210> SEQ ID NO 1051
<211> LENGTH: 21
```

```
<212> TYPE: DNA
<213> ORGANISM: Artificial Sequence
<220> FEATURE:
<223> OTHER INFORMATION: antisense oligomeric compound

<400> SEQUENCE: 1051
ggagccttgg ggcgggggcc g                                              21

<210> SEQ ID NO 1052
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1052
gggagccttg gggcgggggc c                                              21

<210> SEQ ID NO 1053
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1053
agggagcctt ggggcggggg c                                              21

<210> SEQ ID NO 1054
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1054
gagggagcct tggggcgggg g                                              21

<210> SEQ ID NO 1055
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1055
ggagggagcc ttggggcggg g                                              21

<210> SEQ ID NO 1056
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1056
aggagggagc cttggggcgg g                                              21

<210> SEQ ID NO 1057
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1057
```
gaggagggag ccttggggcg g                                               21

<210> SEQ ID NO 1058
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1058
ggaggaggga gccttggggc g                                               21

<210> SEQ ID NO 1059
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1059
gggaggaggg agccttgggg c                                               21

<210> SEQ ID NO 1060
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1060
agggaggagg gagccttggg g                                               21

<210> SEQ ID NO 1061
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1061
gagggaggag ggagccttgg g                                               21

<210> SEQ ID NO 1062
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1062
ggagggagga gggagccttg g                                               21

<210> SEQ ID NO 1063
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1063
gggagggagg agggagcctt g                                               21

<210> SEQ ID NO 1064
<211> LENGTH: 21
<212> TYPE: DNA
<213> ORGANISM: Artificial Sequence

```
<220> FEATURE:
<223> OTHER INFORMATION: antisense oligomeric compound

<400> SEQUENCE: 1064
agggagggag gagggagcct t                                              21

<210> SEQ ID NO 1065
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1065
gagggaggga ggagggagcc t                                              21

<210> SEQ ID NO 1066
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1066
tgagggaggg aggagggagc c                                              21

<210> SEQ ID NO 1067
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1067
atgagggagg gaggagggag c                                              21

<210> SEQ ID NO 1068
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1068
catgagggag ggaggaggga g                                              21

<210> SEQ ID NO 1069
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1069
tcatgaggga gggaggaggg a                                              21

<210> SEQ ID NO 1070
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1070
ttcatgaggg agggaggagg g                                              21
```

<210> SEQ ID NO 1071
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1071
cttcatgagg gagggaggag g                                             21

<210> SEQ ID NO 1072
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1072
acttcatgag ggagggagga g                                             21

<210> SEQ ID NO 1073
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1073
gacttcatga gggagggagg a                                             21

<210> SEQ ID NO 1074
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1074
cgacttcatg agggagggag g                                             21

<210> SEQ ID NO 1075
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1075
ccgacttcat gagggaggga g                                             21

<210> SEQ ID NO 1076
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1076
gccgacttca tgagggaggg a                                             21

<210> SEQ ID NO 1077
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1077
cgccgacttc atgagggagg g                                              21

<210> SEQ ID NO 1078
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1078
acgccgactt catgagggag g                                              21

<210> SEQ ID NO 1079
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1079
aacgccgact tcatgaggga g                                              21

<210> SEQ ID NO 1080
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1080
caacgccgac ttcatgaggg a                                              21

<210> SEQ ID NO 1081
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1081
ccaacgccga cttcatgagg g                                              21

<210> SEQ ID NO 1082
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1082
gccaacgccg acttcatgag g                                              21

<210> SEQ ID NO 1083
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1083
ggccaacgcc gacttcatga g                                              21

<210> SEQ ID NO 1084

```
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1084
aggccaacgc cgacttcatg a                                              21

<210> SEQ ID NO 1085
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1085
caggccaacg ccgacttcat g                                              21

<210> SEQ ID NO 1086
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1086
gcaggccaac gccgacttca t                                              21

<210> SEQ ID NO 1087
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1087
tgcaggccaa cgccgacttc a                                              21

<210> SEQ ID NO 1088
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1088
ctgcaggcca acgccgactt c                                              21

<210> SEQ ID NO 1089
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1089
cctgcaggcc aacgccgact t                                              21

<210> SEQ ID NO 1090
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1090
```
tcctgcaggc aacgccgac t                                              21

<210> SEQ ID NO 1091
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1091
atcctgcagg ccaacgccga c                                             21

<210> SEQ ID NO 1092
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1092
tatcctgcag gccaacgccg a                                             21

<210> SEQ ID NO 1093
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1093
gtatcctgca ggccaacgcc g                                             21

<210> SEQ ID NO 1094
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1094
ggtatcctgc aggccaacgc c                                             21

<210> SEQ ID NO 1095
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1095
gggtatcctg caggccaacg c                                             21

<210> SEQ ID NO 1096
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1096
cgggtatcct gcaggccaac g                                             21

<210> SEQ ID NO 1097
<211> LENGTH: 21
<212> TYPE: DNA

```
<213> ORGANISM: Artificial Sequence
<220> FEATURE:
<223> OTHER INFORMATION: antisense oligomeric compound

<400> SEQUENCE: 1097
acgggtatcc tgcaggccaa c                                              21

<210> SEQ ID NO 1098
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1098
aacgggtatc ctgcaggcca a                                              21

<210> SEQ ID NO 1099
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1099
gaacgggtat cctgcaggcc a                                              21

<210> SEQ ID NO 1100
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1100
tgaacgggta tcctgcaggc c                                              21

<210> SEQ ID NO 1101
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1101
atgaacgggt atcctgcagg c                                              21

<210> SEQ ID NO 1102
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1102
catgaacggg tatcctgcag g                                              21

<210> SEQ ID NO 1103
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1103
gcatgaacgg gtatcctgca g                                              21
```

<210> SEQ ID NO 1104
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1104
ggcatgaacg ggtatcctgc a                                         21

<210> SEQ ID NO 1105
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1105
cggcatgaac gggtatcctg c                                         21

<210> SEQ ID NO 1106
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1106
gcggcatgaa cgggtatcct g                                         21

<210> SEQ ID NO 1107
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1107
ggcggcatga acgggtatcc t                                         21

<210> SEQ ID NO 1108
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1108
tggcggcatg aacgggtatc c                                         21

<210> SEQ ID NO 1109
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1109
atggcggcat gaacgggtat c                                         21

<210> SEQ ID NO 1110
<211> LENGTH: 21
<212> TYPE: DNA
<213> ORGANISM: Artificial Sequence
<220> FEATURE:

<223> OTHER INFORMATION: antisense oligomeric compound

<400> SEQUENCE: 1110
tatggcggca tgaacgggta t                                              21

<210> SEQ ID NO 1111
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1111
gtatggcggc atgaacgggt a                                              21

<210> SEQ ID NO 1112
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1112
agtatggcgg catgaacggg t                                              21

<210> SEQ ID NO 1113
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1113
cagtatggcg gcatgaacgg g                                              21

<210> SEQ ID NO 1114
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1114
ccagtatggc ggcatgaacg g                                              21

<210> SEQ ID NO 1115
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1115
cccagtatgg cggcatgaac g                                              21

<210> SEQ ID NO 1116
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1116
ccccagtatg gcggcatgaa c                                              21

```
<210> SEQ ID NO 1117
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1117
gccccagtat ggcggcatga a                                              21

<210> SEQ ID NO 1118
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1118
ggccccagta tggcggcatg a                                              21

<210> SEQ ID NO 1119
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1119
aggccccagt atggcggcat g                                              21

<210> SEQ ID NO 1120
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1120
caggccccag tatggcggca t                                              21

<210> SEQ ID NO 1121
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1121
ccaggcccca gtatggcggc a                                              21

<210> SEQ ID NO 1122
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1122
cccaggcccc agtatggcgg c                                              21

<210> SEQ ID NO 1123
<211> LENGTH: 21
<212> TYPE: DNA
<213> ORGANISM: Artificial Sequence
<220> FEATURE:
<223> OTHER INFORMATION: antisense oligomeric compound
```

<400> SEQUENCE: 1123
gcccaggccc cagtatggcg g                                          21

<210> SEQ ID NO 1124
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1124
agcccaggcc ccagtatggc g                                          21

<210> SEQ ID NO 1125
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1125
aagcccaggc cccagtatgg c                                          21

<210> SEQ ID NO 1126
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1126
gaagcccagg ccccagtatg g                                          21

<210> SEQ ID NO 1127
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1127
ggaagcccag gccccagtat g                                          21

<210> SEQ ID NO 1128
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1128
tggaagccca ggccccagta t                                          21

<210> SEQ ID NO 1129
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1129
gtggaagccc aggccccagt a                                          21

<210> SEQ ID NO 1130
<211> LENGTH: 21

```
<212> TYPE: DNA
<213> ORGANISM: Artificial Sequence
<220> FEATURE:
<223> OTHER INFORMATION: antisense oligomeric compound

<400> SEQUENCE: 1130
ggtggaagcc caggccccag t                                              21

<210> SEQ ID NO 1131
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1131
aggtggaagc ccaggcccca g                                              21

<210> SEQ ID NO 1132
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1132
caggtggaag cccaggcccc a                                              21

<210> SEQ ID NO 1133
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1133
acaggtggaa gcccaggccc c                                              21

<210> SEQ ID NO 1134
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1134
cacaggtgga agcccaggcc c                                              21

<210> SEQ ID NO 1135
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1135
gcacaggtgg aagcccaggc c                                              21

<210> SEQ ID NO 1136
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1136
```
ggcacaggtg aagcccagg c                      21

<210> SEQ ID NO 1137
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1137
cggcacaggt ggaagcccag g                     21

<210> SEQ ID NO 1138
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1138
gcggcacagg tggaagccca g                     21

<210> SEQ ID NO 1139
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1139
agcggcacag gtggaagccc a                     21

<210> SEQ ID NO 1140
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1140
cagcggcaca ggtggaagcc c                     21

<210> SEQ ID NO 1141
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1141
ccagcggcac aggtggaagc c                     21

<210> SEQ ID NO 1142
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1142
cccagcggca caggtggaag c                     21

<210> SEQ ID NO 1143
<211> LENGTH: 21
<212> TYPE: DNA
<213> ORGANISM: Artificial Sequence -continued

```
<220> FEATURE:
<223> OTHER INFORMATION: antisense oligomeric compound

<400> SEQUENCE: 1143
ccccagcggc acaggtggaa g                                              21

<210> SEQ ID NO 1144
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1144
gccccagcgg cacaggtgga a                                              21

<210> SEQ ID NO 1145
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1145
agccccagcg gcacaggtgg a                                              21

<210> SEQ ID NO 1146
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1146
tagccccagc ggcacaggtg g                                              21

<210> SEQ ID NO 1147
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1147
gtagccccag cggcacaggt g                                              21

<210> SEQ ID NO 1148
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1148
agtagcccca gcggcacagg t                                              21

<210> SEQ ID NO 1149
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1149
gagtagcccc agcggcacag g                                              21
```

<210> SEQ ID NO 1150
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1150
ggagtagccc cagcggcaca g                                              21

<210> SEQ ID NO 1151
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1151
aggagtagcc ccagcggcac a                                              21

<210> SEQ ID NO 1152
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1152
gaggagtagc cccagcggca c                                              21

<210> SEQ ID NO 1153
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1153
ggaggagtag ccccagcggc a                                              21

<210> SEQ ID NO 1154
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1154
tggaggagta gccccagcgg c                                              21

<210> SEQ ID NO 1155
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1155
gtggaggagt agccccagcg g                                              21

<210> SEQ ID NO 1156
<211> LENGTH: 21
<212> TYPE: DNA
<213> ORGANISM: Artificial Sequence
<220> FEATURE:
<223> OTHER INFORMATION: antisense oligomeric compound -continued

```
<400> SEQUENCE: 1156
ggtggaggag tagccccagc g                                              21

<210> SEQ ID NO 1157
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1157
cggtggagga gtagccccag c                                              21

<210> SEQ ID NO 1158
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1158
gcggtggagg agtagcccca g                                              21

<210> SEQ ID NO 1159
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1159
agcggtggag gagtagcccc a                                              21

<210> SEQ ID NO 1160
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1160
tagcggtgga ggagtagccc c                                              21

<210> SEQ ID NO 1161
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1161
atagcggtgg aggagtagcc c                                              21

<210> SEQ ID NO 1162
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1162
gatagcggtg gaggagtagc c                                              21

<210> SEQ ID NO 1163
```

```
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1163
tgatagcggt ggaggagtag c                                              21

<210> SEQ ID NO 1164
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1164
gtgatagcgg tggaggagta g                                              21

<210> SEQ ID NO 1165
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1165
ggtgatagcg gtggaggagt a                                              21

<210> SEQ ID NO 1166
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1166
gggtgatagc ggtggaggag t                                              21

<210> SEQ ID NO 1167
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1167
cgggtgatag cggtggagga g                                              21

<210> SEQ ID NO 1168
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1168
gcgggtgata gcggtggagg a                                              21

<210> SEQ ID NO 1169
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1169
```
ggcgggtgat agcggtggag g                                              21

<210> SEQ ID NO 1170
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1170
tggcgggtga tagcggtgga g                                              21

<210> SEQ ID NO 1171
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1171
ctggcgggtg atagcggtgg a                                              21

<210> SEQ ID NO 1172
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1172
cctggcgggt gatagcggtg g                                              21

<210> SEQ ID NO 1173
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1173
acctggcggg tgatagcggt g                                              21

<210> SEQ ID NO 1174
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1174
cacctggcgg gtgatagcgg t                                              21

<210> SEQ ID NO 1175
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1175
ccacctggcg ggtgatagcg g                                              21

<210> SEQ ID NO 1176
<211> LENGTH: 21
<212> TYPE: DNA

<213> ORGANISM: Artificial Sequence
<220> FEATURE:
<223> OTHER INFORMATION: antisense oligomeric compound

<400> SEQUENCE: 1176
accacctggc gggtgatagc g					21

<210> SEQ ID NO 1177
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1177
caccacctgg cgggtgatag c					21

<210> SEQ ID NO 1178
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1178
ccaccacctg gcgggtgata g					21

<210> SEQ ID NO 1179
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1179
tccaccacct ggcgggtgat a					21

<210> SEQ ID NO 1180
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1180
ctccaccacc tggcgggtga t					21

<210> SEQ ID NO 1181
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1181
tctccaccac ctggcgggtg a					21

<210> SEQ ID NO 1182
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1182
ttctccacca cctggcgggt g					21

<210> SEQ ID NO 1183
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1183
gttctccacc acctggcggg t                                              21

<210> SEQ ID NO 1184
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1184
tgttctccac cacctggcgg g                                              21

<210> SEQ ID NO 1185
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1185
atgttctcca ccacctggcg g                                              21

<210> SEQ ID NO 1186
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1186
catgttctcc accacctggc g                                              21

<210> SEQ ID NO 1187
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1187
tcatgttctc caccacctgg c                                              21

<210> SEQ ID NO 1188
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1188
gtcatgttct ccaccacctg g                                              21

<210> SEQ ID NO 1189
<211> LENGTH: 21
<212> TYPE: DNA
<213> ORGANISM: Artificial Sequence
<220> FEATURE:

<223> OTHER INFORMATION: antisense oligomeric compound

<400> SEQUENCE: 1189
ggtcatgttc tccaccacct g                                    21

<210> SEQ ID NO 1190
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1190
tggtcatgtt ctccaccacc t                                    21

<210> SEQ ID NO 1191
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1191
ctggtcatgt tctccaccac c                                    21

<210> SEQ ID NO 1192
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1192
cctggtcatg ttctccacca c                                    21

<210> SEQ ID NO 1193
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1193
ccctggtcat gttctccacc a                                    21

<210> SEQ ID NO 1194
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1194
gccctggtca tgttctccac c                                    21

<210> SEQ ID NO 1195
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1195
ggccctggtc atgttctcca c                                    21

```
<210> SEQ ID NO 1196
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1196
gggccctggt catgttctcc a                                              21

<210> SEQ ID NO 1197
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1197
tgggccctgg tcatgttctc c                                              21

<210> SEQ ID NO 1198
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1198
gtgggccctg gtcatgttct c                                              21

<210> SEQ ID NO 1199
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1199
agtgggccct ggtcatgttc t                                              21

<210> SEQ ID NO 1200
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1200
aagtgggccc tggtcatgtt c                                              21

<210> SEQ ID NO 1201
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1201
gaagtgggcc ctggtcatgt t                                              21

<210> SEQ ID NO 1202
<211> LENGTH: 21
<212> TYPE: DNA
<213> ORGANISM: Artificial Sequence
<220> FEATURE:
<223> OTHER INFORMATION: antisense oligomeric compound
```

```
<400> SEQUENCE: 1202
ggaagtgggc cctggtcatg t                                              21

<210> SEQ ID NO 1203
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1203
gggaagtggg ccctggtcat g                                              21

<210> SEQ ID NO 1204
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1204
ggggaagtgg gccctggtca t                                              21

<210> SEQ ID NO 1205
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1205
gggggaagtg ggccctggtc a                                              21

<210> SEQ ID NO 1206
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1206
agggggaagt gggccctggt c                                              21

<210> SEQ ID NO 1207
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1207 caggggggaag tgggccctgg t                                             21

<210> SEQ ID NO 1208
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1208 ccaggggggaa gtgggccctg g                                             21

<210> SEQ ID NO 1209
<211> LENGTH: 21
```

```
<212> TYPE: DNA
<213> ORGANISM: Artificial Sequence
<220> FEATURE:
<223> OTHER INFORMATION: antisense oligomeric compound

<400> SEQUENCE: 1209
accaggggga agtgggccct g                                              21

<210> SEQ ID NO 1210
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1210
caccaggggg aagtgggccc t                                              21

<210> SEQ ID NO 1211
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1211
tcaccagggg gaagtgggcc c                                              21

<210> SEQ ID NO 1212
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1212
ctcaccaggg ggaagtgggc c                                              21

<210> SEQ ID NO 1213
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1213
actcaccagg gggaagtggg c                                              21

<210> SEQ ID NO 1214
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1214
aactcaccag ggggaagtgg g                                              21

<210> SEQ ID NO 1215
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1215
```

```
caactcacca gggggaagtg g                                              21

<210> SEQ ID NO 1216
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1216
ccaactcacc aggggaagt g                                               21

<210> SEQ ID NO 1217
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1217
cccaactcac caggggggaag t                                             21

<210> SEQ ID NO 1218
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1218
ccccaactca ccaggggggaa g                                             21

<210> SEQ ID NO 1219
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1219
accccaactc accaggggga a                                              21

<210> SEQ ID NO 1220
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1220
caccccaact caccaggggg a                                              21

<210> SEQ ID NO 1221
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1221
ccaccccaac tcaccagggg g                                              21

<210> SEQ ID NO 1222
<211> LENGTH: 21
<212> TYPE: DNA
<213> ORGANISM: Artificial Sequence
```

```
<220> FEATURE:
<223> OTHER INFORMATION: antisense oligomeric compound

<400> SEQUENCE: 1222
accaccccaa ctcaccaggg g                                              21

<210> SEQ ID NO 1223
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1223
caccacccca actcaccagg g                                              21

<210> SEQ ID NO 1224
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1224
ccaccacccc aactcaccag g                                              21

<210> SEQ ID NO 1225
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1225
gccaccaccc caactcacca g                                              21

<210> SEQ ID NO 1226
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1226
tgccaccacc ccaactcacc a                                              21

<210> SEQ ID NO 1227
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1227
ctgccaccac cccaactcac c                                              21

<210> SEQ ID NO 1228
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1228
cctgccacca ccccaactca c                                              21
```

<210> SEQ ID NO 1229
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1229
ccctgccacc accccaactc a                                              21

<210> SEQ ID NO 1230
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1230
cccctgccac caccccaact c                                              21

<210> SEQ ID NO 1231
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1231
tcccctgcca ccaccccaac t                                              21

<210> SEQ ID NO 1232
<211> LENGTH: 21
<212> TYPE: DNA
<213> ORGANISM: Artificial Sequence
<220> FEATURE:
<223> OTHER INFORMATION: antisense oligomeric compound

<400> SEQUENCE: 1232
ctcccctgcc accaccccaa c                                              21

<210> SEQ ID NO 1233
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1233
ggaagcagct ctggggtt                                                  18

<210> SEQ ID NO 1234
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1234
gggaagcagc tctggggt                                                  18

<210> SEQ ID NO 1235
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1235
agggaagcag ctctgggg                                                 18

<210> SEQ ID NO 1236
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1236
aagggaagca gctctggg                                                 18

<210> SEQ ID NO 1237
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1237
gaagggaagc agctctgg                                                 18

<210> SEQ ID NO 1238
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1238
ggaagggaag cagctctg                                                 18

<210> SEQ ID NO 1239
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1239
tggaagggaa gcagctct                                                 18

<210> SEQ ID NO 1240
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1240
ctggaaggga agcagctc                                                 18

<210> SEQ ID NO 1241
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1241
tctggaaggg aagcagct                                                 18

<210> SEQ ID NO 1242

```
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1242
atctggaagg gaagcagc                                                 18

<210> SEQ ID NO 1243
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1243
catctggaag ggaagcag                                                 18

<210> SEQ ID NO 1244
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1244
acatctggaa gggaagca                                                 18

<210> SEQ ID NO 1245
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1245
cacatctgga agggaagc                                                 18

<210> SEQ ID NO 1246
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1246
ccacatctgg aagggaag                                                 18

<210> SEQ ID NO 1247
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1247
accacatctg gaagggaa                                                 18

<210> SEQ ID NO 1248
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1248
```

```
gaccacatct ggaaggga                                              18

<210> SEQ ID NO 1249
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1249
ggaccacatc tggaaggg                                              18

<210> SEQ ID NO 1250
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1250
aggaccacat ctggaagg                                              18

<210> SEQ ID NO 1251
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1251
caggaccaca tctggaag                                              18

<210> SEQ ID NO 1252
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1252
gcaggaccac atctggaa                                              18

<210> SEQ ID NO 1253
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1253
tgcaggacca catctgga                                              18

<210> SEQ ID NO 1254
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1254
ctgcaggacc acatctgg                                              18

<210> SEQ ID NO 1255
<211> LENGTH: 18
<212> TYPE: DNA
```

```
<213> ORGANISM: Artificial Sequence
<220> FEATURE:
<223> OTHER INFORMATION: antisense oligomeric compound

<400> SEQUENCE: 1255
gctgcaggac cacatctg                                                 18

<210> SEQ ID NO 1256
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1256
ggctgcagga ccacatct                                                 18

<210> SEQ ID NO 1257
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1257
cggctgcagg accacatc                                                 18

<210> SEQ ID NO 1258
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1258
tcggctgcag gaccacat                                                 18

<210> SEQ ID NO 1259
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1259
ctcggctgca ggaccaca                                                 18

<210> SEQ ID NO 1260
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1260
gctcggctgc aggaccac                                                 18

<210> SEQ ID NO 1261
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1261
ggctcggctg caggacca                                                 18
```

<210> SEQ ID NO 1262
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1262
gggctcggct gcaggacc                                                 18

<210> SEQ ID NO 1263
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1263
agggctcggc tgcaggac                                                 18

<210> SEQ ID NO 1264
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1264
cagggctcgg ctgcagga                                                 18

<210> SEQ ID NO 1265
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1265
gcagggctcg gctgcagg                                                 18

<210> SEQ ID NO 1266
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1266
ggcagggctc ggctgcag                                                 18

<210> SEQ ID NO 1267
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1267
gggcagggct cggctgca                                                 18

<210> SEQ ID NO 1268
<211> LENGTH: 18
<212> TYPE: DNA
<213> ORGANISM: Artificial Sequence
<220> FEATURE:

```
<223> OTHER INFORMATION: antisense oligomeric compound

<400> SEQUENCE: 1268
agggcagggc tcggctgc                                              18

<210> SEQ ID NO 1269
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1269
aagggcaggg ctcggctg                                              18

<210> SEQ ID NO 1270
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1270
taagggcagg gctcggct                                              18

<210> SEQ ID NO 1271
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1271
ctaagggcag ggctcggc                                              18

<210> SEQ ID NO 1272
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1272
gctaagggca gggctcgg                                              18

<210> SEQ ID NO 1273
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1273
agctaagggc agggctcg                                              18

<210> SEQ ID NO 1274
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1274
cagctaaggg cagggctc                                              18
```

```
<210> SEQ ID NO 1275
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1275
ccagctaagg gcagggct                                                 18

<210> SEQ ID NO 1276
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1276
tccagctaag ggcagggc                                                 18

<210> SEQ ID NO 1277
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1277
ctccagctaa gggcaggg                                                 18

<210> SEQ ID NO 1278
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1278
cctccagcta agggcagg                                                 18

<210> SEQ ID NO 1279
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1279
acctccagct aagggcag                                                 18

<210> SEQ ID NO 1280
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1280
gacctccagc taagggca                                                 18

<210> SEQ ID NO 1281
<211> LENGTH: 18
<212> TYPE: DNA
<213> ORGANISM: Artificial Sequence
<220> FEATURE:
<223> OTHER INFORMATION: antisense oligomeric compound
```

<400> SEQUENCE: 1281
cgacctccag ctaagggc                                                 18

<210> SEQ ID NO 1282
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1282
tcgacctcca gctaaggg                                                 18

<210> SEQ ID NO 1283
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1283
gtcgacctcc agctaagg                                                 18

<210> SEQ ID NO 1284
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1284
tgtcgacctc cagctaag                                                 18

<210> SEQ ID NO 1285
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1285
ctgtcgacct ccagctaa                                                 18

<210> SEQ ID NO 1286
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1286
cctgtcgacc tccagcta                                                 18

<210> SEQ ID NO 1287
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1287
acctgtcgac ctccagct                                                 18

<210> SEQ ID NO 1288
<211> LENGTH: 18

```
<212> TYPE: DNA
<213> ORGANISM: Artificial Sequence
<220> FEATURE:
<223> OTHER INFORMATION: antisense oligomeric compound

<400> SEQUENCE: 1288
cacctgtcga cctccagc                                                18

<210> SEQ ID NO 1289
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1289
ccacctgtcg acctccag                                                18

<210> SEQ ID NO 1290
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1290
cccacctgtc gacctcca                                                18

<210> SEQ ID NO 1291
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1291
tcccacctgt cgacctcc                                                18

<210> SEQ ID NO 1292
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1292
atcccacctg tcgacctc                                                18

<210> SEQ ID NO 1293
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1293
gatcccacct gtcgacct                                                18

<210> SEQ ID NO 1294
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1294
```

```
ggatcccacc tgtcgacc                                              18

<210> SEQ ID NO 1295
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1295
aggatcccac ctgtcgac                                              18

<210> SEQ ID NO 1296
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1296
caggatccca cctgtcga                                              18

<210> SEQ ID NO 1297
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1297
ccaggatccc acctgtcg                                              18

<210> SEQ ID NO 1298
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1298
tccaggatcc cacctgtc                                              18

<210> SEQ ID NO 1299
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1299
atccaggatc ccacctgt                                              18

<210> SEQ ID NO 1300
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1300
catccaggat cccacctg                                              18

<210> SEQ ID NO 1301
<211> LENGTH: 18
<212> TYPE: DNA
<213> ORGANISM: Artificial Sequence
```

```
<220> FEATURE:
<223> OTHER INFORMATION: antisense oligomeric compound

<400> SEQUENCE: 1301
acatccagga tcccacct                                                   18

<210> SEQ ID NO 1302
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1302
gacatccagg atcccacc                                                   18

<210> SEQ ID NO 1303
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1303
agacatccag gatcccac                                                   18

<210> SEQ ID NO 1304
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1304
tagacatcca ggatccca                                                   18

<210> SEQ ID NO 1305
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1305
gtagacatcc aggatccc                                                   18

<210> SEQ ID NO 1306
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1306
tgtagacatc caggatcc                                                   18

<210> SEQ ID NO 1307
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1307
atgtagacat ccaggatc                                                   18
```

<210> SEQ ID NO 1308
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1308
gatgtagaca tccaggat                                                 18

<210> SEQ ID NO 1309
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1309
agatgtagac atccagga                                                 18

<210> SEQ ID NO 1310
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1310
aagatgtaga catccagg                                                 18

<210> SEQ ID NO 1311
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1311
gaagatgtag acatccag                                                 18

<210> SEQ ID NO 1312
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1312
ggaagatgta gacatcca                                                 18

<210> SEQ ID NO 1313
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1313
aggaagatgt agacatcc                                                 18

<210> SEQ ID NO 1314
<211> LENGTH: 18
<212> TYPE: DNA
<213> ORGANISM: Artificial Sequence
<220> FEATURE:
<223> OTHER INFORMATION: antisense oligomeric compound -continued

<400> SEQUENCE: 1314
caggaagatg tagacatc                                                        18

<210> SEQ ID NO 1315
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1315
ccaggaagat gtagacat                                                        18

<210> SEQ ID NO 1316
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1316
cccaggaaga tgtagaca                                                        18

<210> SEQ ID NO 1317
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1317
gcccaggaag atgtagac                                                        18

<210> SEQ ID NO 1318
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1318
ggcccaggaa gatgtaga                                                        18

<210> SEQ ID NO 1319
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1319
gggcccagga agatgtag                                                        18

<210> SEQ ID NO 1320
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1320
tgggcccagg aagatgta                                                        18

<210> SEQ ID NO 1321

```
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1321
ctgggcccag gaagatgt                                                  18

<210> SEQ ID NO 1322
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1322
tctgggccca ggaagatg                                                  18

<210> SEQ ID NO 1323
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1323
ctctgggccc aggaagat                                                  18

<210> SEQ ID NO 1324
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1324
gctctgggcc caggaaga                                                  18

<210> SEQ ID NO 1325
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1325
ggctctgggc ccaggaag                                                  18

<210> SEQ ID NO 1326
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1326
gggctctggg cccaggaa                                                  18

<210> SEQ ID NO 1327
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1327
```
tgggctctgg gcccagga                                                18

<210> SEQ ID NO 1328
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1328
ttgggctctg ggcccagg                                                18

<210> SEQ ID NO 1329
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1329
cttgggctct gggcccag                                                18

<210> SEQ ID NO 1330
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1330
tcttgggctc tgggccca                                                18

<210> SEQ ID NO 1331
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1331
ctcttgggct ctgggccc                                                18

<210> SEQ ID NO 1332
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1332
gctcttgggc tctgggcc                                                18

<210> SEQ ID NO 1333
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1333
cgctcttggg ctctgggc                                                18

<210> SEQ ID NO 1334
<211> LENGTH: 18
<212> TYPE: DNA

```
<213> ORGANISM: Artificial Sequence
<220> FEATURE:
<223> OTHER INFORMATION: antisense oligomeric compound

<400> SEQUENCE: 1334
acgctcttgg gctctggg                                              18

<210> SEQ ID NO 1335
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1335
cacgctcttg ggctctgg                                              18

<210> SEQ ID NO 1336
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1336
ccacgctctt gggctctg                                              18

<210> SEQ ID NO 1337
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1337
accacgctct tgggctct                                              18

<210> SEQ ID NO 1338
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1338
caccacgctc ttgggctc                                              18

<210> SEQ ID NO 1339
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1339
gcaccacgct cttgggct                                              18

<210> SEQ ID NO 1340
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1340
tgcaccacgc tcttgggc                                              18
```

<210> SEQ ID NO 1341
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1341
ctgcaccacg ctcttggg                                                 18

<210> SEQ ID NO 1342
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1342
gctgcaccac gctcttgg                                                 18

<210> SEQ ID NO 1343
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1343
tgctgcacca cgctcttg                                                 18

<210> SEQ ID NO 1344
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1344
ctgctgcacc acgctctt                                                 18

<210> SEQ ID NO 1345
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1345
actgctgcac cacgctct                                                 18

<210> SEQ ID NO 1346
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1346
tactgctgca ccacgctc                                                 18

<210> SEQ ID NO 1347
<211> LENGTH: 18
<212> TYPE: DNA
<213> ORGANISM: Artificial Sequence
<220> FEATURE:

<223> OTHER INFORMATION: antisense oligomeric compound

<400> SEQUENCE: 1347
gtactgctgc accacgct                                                    18

<210> SEQ ID NO 1348
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1348
ggtactgctg caccacgc                                                    18

<210> SEQ ID NO 1349
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1349
aggtactgct gcaccacg                                                    18

<210> SEQ ID NO 1350
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1350
caggtactgc tgcaccac                                                    18

<210> SEQ ID NO 1351
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1351
ccaggtactg ctgcacca                                                    18

<210> SEQ ID NO 1352
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1352
tccaggtact gctgcacc                                                    18

<210> SEQ ID NO 1353
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1353
gtccaggtac tgctgcac                                                    18

```
<210> SEQ ID NO 1354
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1354
cgtccaggta ctgctgca                                                 18

<210> SEQ ID NO 1355
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1355
acgtccaggt actgctgc                                                 18

<210> SEQ ID NO 1356
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1356
aacgtccagg tactgctg                                                 18

<210> SEQ ID NO 1357
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1357
caacgtccag gtactgct                                                 18

<210> SEQ ID NO 1358
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1358
acaacgtcca ggtactgc                                                 18

<210> SEQ ID NO 1359
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1359
cacaacgtcc aggtactg                                                 18

<210> SEQ ID NO 1360
<211> LENGTH: 18
<212> TYPE: DNA
<213> ORGANISM: Artificial Sequence
<220> FEATURE:
<223> OTHER INFORMATION: antisense oligomeric compound
```

```
<400> SEQUENCE: 1360
ccacaacgtc caggtact                                               18

<210> SEQ ID NO 1361
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1361
cccacaacgt ccaggtac                                               18

<210> SEQ ID NO 1362
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1362
acccacaacg tccaggta                                               18

<210> SEQ ID NO 1363
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1363
tacccacaac gtccaggt                                               18

<210> SEQ ID NO 1364
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1364
ctacccacaa cgtccagg                                               18

<210> SEQ ID NO 1365
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1365
cctacccaca acgtccag                                               18

<210> SEQ ID NO 1366
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1366
ccctacccac aacgtcca                                               18

<210> SEQ ID NO 1367
<211> LENGTH: 18
```

```
<212> TYPE: DNA
<213> ORGANISM: Artificial Sequence
<220> FEATURE:
<223> OTHER INFORMATION: antisense oligomeric compound

<400> SEQUENCE: 1367
gccctaccca caacgtcc                                                  18

<210> SEQ ID NO 1368
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1368
ggccctaccc acaacgtc                                                  18

<210> SEQ ID NO 1369
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1369
aggccctacc cacaacgt                                                  18

<210> SEQ ID NO 1370
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1370
caggccctac ccacaacg                                                  18

<210> SEQ ID NO 1371
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1371
gcaggcccta cccacaac                                                  18

<210> SEQ ID NO 1372
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1372
agcaggccct acccacaa                                                  18

<210> SEQ ID NO 1373
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1373
```
gagcaggccc tacccaca         18

<210> SEQ ID NO 1374
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1374
ggagcaggcc ctacccac         18

<210> SEQ ID NO 1375
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1375
gggagcaggc cctaccca         18

<210> SEQ ID NO 1376
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1376
agggagcagg ccctaccc         18

<210> SEQ ID NO 1377
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1377
cagggagcag gccctacc         18

<210> SEQ ID NO 1378
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1378
ccagggagca ggccctac         18

<210> SEQ ID NO 1379
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1379
gccagggagc aggcccta         18

<210> SEQ ID NO 1380
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1380
ggccagggag caggccct                                                    18

<210> SEQ ID NO 1381
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1381
cggccaggga gcaggccc                                                    18

<210> SEQ ID NO 1382
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1382
gcggccaggg agcaggcc                                                    18

<210> SEQ ID NO 1383
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1383
cgcggccagg gagcaggc                                                    18

<210> SEQ ID NO 1384
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1384
ccgcggccag ggagcagg                                                    18

<210> SEQ ID NO 1385
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1385
gccgcggcca gggagcag                                                    18

<210> SEQ ID NO 1386
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1386
ggccgcggcc agggagca                                                    18

<210> SEQ ID NO 1387
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1387
gggccgcggc cagggagc                                                  18

<210> SEQ ID NO 1388
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1388
ggggccgcgg ccagggag                                                  18

<210> SEQ ID NO 1389
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1389
gggggccgcg gccaggga                                                  18

<210> SEQ ID NO 1390
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1390 cggggggccgc ggccaggg                                                 18

<210> SEQ ID NO 1391
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1391 gcggggggccg cggccagg                                                 18

<210> SEQ ID NO 1392
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1392 ggcggggggcc gcggccag                                                 18

<210> SEQ ID NO 1393
<211> LENGTH: 18
<212> TYPE: DNA
<213> ORGANISM: Artificial Sequence
<220> FEATURE:
<223> OTHER INFORMATION: antisense oligomeric compound

```
<400> SEQUENCE: 1393
gggcgggggc cgcggcca                                                  18

<210> SEQ ID NO 1394
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1394
ggggcggggg ccgcggcc                                                  18

<210> SEQ ID NO 1395
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1395
tggggcgggg gccgcggc                                                  18

<210> SEQ ID NO 1396
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1396
ttggggcggg ggccgcgg                                                  18

<210> SEQ ID NO 1397
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1397
cttggggcgg gggccgcg                                                  18

<210> SEQ ID NO 1398
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1398
ccttggggcg ggggccgc                                                  18

<210> SEQ ID NO 1399
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1399
gccttggggc gggggccg                                                  18

<210> SEQ ID NO 1400
```

```
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1400
agccttgggg cgggggcc                                                  18

<210> SEQ ID NO 1401
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1401
gagccttggg gcgggggc                                                  18

<210> SEQ ID NO 1402
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1402
ggagccttgg ggcggggg                                                  18

<210> SEQ ID NO 1403
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1403
gggagccttg gggcgggg                                                  18

<210> SEQ ID NO 1404
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1404
agggagcctt ggggcggg                                                  18

<210> SEQ ID NO 1405
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1405
gagggagcct tggggcgg                                                  18

<210> SEQ ID NO 1406
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1406
```
ggagggagcc ttggggcg                                            18

<210> SEQ ID NO 1407
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1407
aggagggagc cttggggc                                            18

<210> SEQ ID NO 1408
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1408
gaggagggag ccttgggg                                            18

<210> SEQ ID NO 1409
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1409
ggaggaggga gccttggg                                            18

<210> SEQ ID NO 1410
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1410
gggaggaggg agccttgg                                            18

<210> SEQ ID NO 1411
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1411
agggaggagg gagccttg                                            18

<210> SEQ ID NO 1412
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1412
gagggaggag ggagcctt                                            18

<210> SEQ ID NO 1413
<211> LENGTH: 18
<212> TYPE: DNA

```
<213> ORGANISM: Artificial Sequence
<220> FEATURE:
<223> OTHER INFORMATION: antisense oligomeric compound

<400> SEQUENCE: 1413
ggagggagga gggagcct                                              18

<210> SEQ ID NO 1414
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1414
gggagggagg agggagcc                                              18

<210> SEQ ID NO 1415
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1415
agggagggag gagggagc                                              18

<210> SEQ ID NO 1416
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1416
gagggaggga ggagggag                                              18

<210> SEQ ID NO 1417
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1417
tgagggaggg aggaggga                                              18

<210> SEQ ID NO 1418
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1418
atgagggagg gaggaggg                                              18

<210> SEQ ID NO 1419
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1419
catgagggag ggaggagg                                              18
```

<210> SEQ ID NO 1420
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1420
tcatgaggga gggaggag                                                 18

<210> SEQ ID NO 1421
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1421
ttcatgaggg agggagga                                                 18

<210> SEQ ID NO 1422
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1422
cttcatgagg gagggagg                                                 18

<210> SEQ ID NO 1423
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1423
acttcatgag ggagggag                                                 18

<210> SEQ ID NO 1424
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1424
gacttcatga gggaggga                                                 18

<210> SEQ ID NO 1425
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1425
cgacttcatg agggaggg                                                 18

<210> SEQ ID NO 1426
<211> LENGTH: 18
<212> TYPE: DNA
<213> ORGANISM: Artificial Sequence
<220> FEATURE:

<223> OTHER INFORMATION: antisense oligomeric compound

<400> SEQUENCE: 1426
ccgacttcat gagggagg                                                    18

<210> SEQ ID NO 1427
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1427
gccgacttca tgagggag                                                    18

<210> SEQ ID NO 1428
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1428
cgccgacttc atgaggga                                                    18

<210> SEQ ID NO 1429
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1429
acgccgactt catgaggg                                                    18

<210> SEQ ID NO 1430
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1430
aacgccgact tcatgagg                                                    18

<210> SEQ ID NO 1431
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1431
caacgccgac ttcatgag                                                    18

<210> SEQ ID NO 1432
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1432
ccaacgccga cttcatga                                                    18

<210> SEQ ID NO 1433
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1433
gccaacgccg acttcatg                                             18

<210> SEQ ID NO 1434
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1434
ggccaacgcc gacttcat                                             18

<210> SEQ ID NO 1435
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1435
aggccaacgc cgacttca                                             18

<210> SEQ ID NO 1436
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1436
caggccaacg ccgacttc                                             18

<210> SEQ ID NO 1437
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1437
gcaggccaac gccgactt                                             18

<210> SEQ ID NO 1438
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1438
tgcaggccaa cgccgact                                             18

<210> SEQ ID NO 1439
<211> LENGTH: 18
<212> TYPE: DNA
<213> ORGANISM: Artificial Sequence
<220> FEATURE:
<223> OTHER INFORMATION: antisense oligomeric compound

```
<400> SEQUENCE: 1439
ctgcaggcca acgccgac                                                  18

<210> SEQ ID NO 1440
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1440
cctgcaggcc aacgccga                                                  18

<210> SEQ ID NO 1441
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1441
tcctgcaggc caacgccg                                                  18

<210> SEQ ID NO 1442
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1442
atcctgcagg ccaacgcc                                                  18

<210> SEQ ID NO 1443
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1443
tatcctgcag gccaacgc                                                  18

<210> SEQ ID NO 1444
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1444
gtatcctgca ggccaacg                                                  18

<210> SEQ ID NO 1445
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1445
ggtatcctgc aggccaac                                                  18

<210> SEQ ID NO 1446
<211> LENGTH: 18
```

```
<212> TYPE: DNA
<213> ORGANISM: Artificial Sequence
<220> FEATURE:
<223> OTHER INFORMATION: antisense oligomeric compound

<400> SEQUENCE: 1446
gggtatcctg caggccaa                                                 18

<210> SEQ ID NO 1447
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1447
cgggtatcct gcaggcca                                                 18

<210> SEQ ID NO 1448
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1448
acgggtatcc tgcaggcc                                                 18

<210> SEQ ID NO 1449
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1449
aacgggtatc ctgcaggc                                                 18

<210> SEQ ID NO 1450
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1450
gaacgggtat cctgcagg                                                 18

<210> SEQ ID NO 1451
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1451
tgaacgggta tcctgcag                                                 18

<210> SEQ ID NO 1452
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1452
```

```
atgaacgggt atcctgca                                                18
```

<210> SEQ ID NO 1453
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1453

```
catgaacggg tatcctgc                                                18
```

<210> SEQ ID NO 1454
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1454

```
gcatgaacgg gtatcctg                                                18
```

<210> SEQ ID NO 1455
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1455

```
ggcatgaacg ggtatcct                                                18
```

<210> SEQ ID NO 1456
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1456

```
cggcatgaac gggtatcc                                                18
```

<210> SEQ ID NO 1457
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1457

```
gcggcatgaa cgggtatc                                                18
```

<210> SEQ ID NO 1458
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1458

```
ggcggcatga acgggtat                                                18
```

<210> SEQ ID NO 1459
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1459
tggcggcatg aacgggta                                                 18

<210> SEQ ID NO 1460
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1460
atggcggcat gaacgggt                                                 18

<210> SEQ ID NO 1461
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1461
tatggcggca tgaacggg                                                 18

<210> SEQ ID NO 1462
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1462
gtatggcggc atgaacgg                                                 18

<210> SEQ ID NO 1463
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1463
agtatggcgg catgaacg                                                 18

<210> SEQ ID NO 1464
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1464
cagtatggcg gcatgaac                                                 18

<210> SEQ ID NO 1465
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1465
ccagtatggc ggcatgaa                                                 18

<210> SEQ ID NO 1466
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1466
cccagtatgg cggcatga                                                 18

<210> SEQ ID NO 1467
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1467
ccccagtatg gcggcatg                                                 18

<210> SEQ ID NO 1468
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1468
gccccagtat ggcggcat                                                 18

<210> SEQ ID NO 1469
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1469
ggccccagta tggcggca                                                 18

<210> SEQ ID NO 1470
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1470
aggccccagt atggcggc                                                 18

<210> SEQ ID NO 1471
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1471
caggccccag tatggcgg                                                 18

<210> SEQ ID NO 1472
<211> LENGTH: 18
<212> TYPE: DNA
<213> ORGANISM: Artificial Sequence
<220> FEATURE:
<223> OTHER INFORMATION: antisense oligomeric compound

```
<400> SEQUENCE: 1472
ccaggcccca gtatggcg                                                 18

<210> SEQ ID NO 1473
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1473
cccaggcccc agtatggc                                                 18

<210> SEQ ID NO 1474
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1474
gcccaggccc cagtatgg                                                 18

<210> SEQ ID NO 1475
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1475
agcccaggcc ccagtatg                                                 18

<210> SEQ ID NO 1476
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1476
aagcccaggc cccagtat                                                 18

<210> SEQ ID NO 1477
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1477
gaagcccagg ccccagta                                                 18

<210> SEQ ID NO 1478
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1478
ggaagcccag gccccagt                                                 18

<210> SEQ ID NO 1479
```

```
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1479
tggaagccca ggccccag                                                 18

<210> SEQ ID NO 1480
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1480
gtggaagccc aggccca                                                  18

<210> SEQ ID NO 1481
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1481
ggtggaagcc caggcccc                                                 18

<210> SEQ ID NO 1482
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1482
aggtggaagc ccaggccc                                                 18

<210> SEQ ID NO 1483
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1483
caggtggaag cccaggcc                                                 18

<210> SEQ ID NO 1484
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1484
acaggtggaa gcccaggc                                                 18

<210> SEQ ID NO 1485
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1485
```
cacaggtgga agcccagg                                                      18

<210> SEQ ID NO 1486
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1486
gcacaggtgg aagcccag                                                      18

<210> SEQ ID NO 1487
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1487
ggcacaggtg gaagccca                                                      18

<210> SEQ ID NO 1488
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1488
cggcacaggt ggaagccc                                                      18

<210> SEQ ID NO 1489
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1489
gcggcacagg tggaagcc                                                      18

<210> SEQ ID NO 1490
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1490
agcggcacag gtggaagc                                                      18

<210> SEQ ID NO 1491
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1491
cagcggcaca ggtggaag                                                      18

<210> SEQ ID NO 1492
<211> LENGTH: 18
<212> TYPE: DNA

```
<213> ORGANISM: Artificial Sequence
<220> FEATURE:
<223> OTHER INFORMATION: antisense oligomeric compound

<400> SEQUENCE: 1492
ccagcggcac aggtggaa                                                 18

<210> SEQ ID NO 1493
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1493
cccagcggca caggtgga                                                 18

<210> SEQ ID NO 1494
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1494
ccccagcggc acaggtgg                                                 18

<210> SEQ ID NO 1495
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1495
gccccagcgg cacaggtg                                                 18

<210> SEQ ID NO 1496
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1496
agccccagcg gcacaggt                                                 18

<210> SEQ ID NO 1497
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1497
tagccccagc ggcacagg                                                 18

<210> SEQ ID NO 1498
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1498
gtagccccag cggcacag                                                 18
```

<210> SEQ ID NO 1499
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1499
agtagcccca gcggcaca                                                 18

<210> SEQ ID NO 1500
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1500
gagtagcccc agcggcac                                                 18

<210> SEQ ID NO 1501
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1501
ggagtagccc cagcggca                                                 18

<210> SEQ ID NO 1502
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1502
aggagtagcc ccagcggc                                                 18

<210> SEQ ID NO 1503
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1503
gaggagtagc cccagcgg                                                 18

<210> SEQ ID NO 1504
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1504
ggaggagtag ccccagcg                                                 18

<210> SEQ ID NO 1505
<211> LENGTH: 18
<212> TYPE: DNA
<213> ORGANISM: Artificial Sequence
<220> FEATURE:

<223> OTHER INFORMATION: antisense oligomeric compound

<400> SEQUENCE: 1505
tggaggagta gccccagc                18

<210> SEQ ID NO 1506
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1506
gtggaggagt agccccag                18

<210> SEQ ID NO 1507
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1507
ggtggaggag tagcccca                18

<210> SEQ ID NO 1508
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1508
cggtggagga gtagcccc                18

<210> SEQ ID NO 1509
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1509
gcggtggagg agtagccc                18

<210> SEQ ID NO 1510
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1510
agcggtggag gagtagcc                18

<210> SEQ ID NO 1511
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1511
tagcggtgga ggagtagc                18

```
<210> SEQ ID NO 1512
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1512
atagcggtgg aggagtag                                                18

<210> SEQ ID NO 1513
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1513
gatagcggtg gaggagta                                                18

<210> SEQ ID NO 1514
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1514
tgatagcggt ggaggagt                                                18

<210> SEQ ID NO 1515
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1515
gtgatagcgg tggaggag                                                18

<210> SEQ ID NO 1516
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1516
ggtgatagcg gtggagga                                                18

<210> SEQ ID NO 1517
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1517
gggtgatagc ggtggagg                                                18

<210> SEQ ID NO 1518
<211> LENGTH: 18
<212> TYPE: DNA
<213> ORGANISM: Artificial Sequence
<220> FEATURE:
<223> OTHER INFORMATION: antisense oligomeric compound
```

```
<400> SEQUENCE: 1518
cgggtgatag cggtggag                                          18

<210> SEQ ID NO 1519
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1519
gcgggtgata gcggtgga                                          18

<210> SEQ ID NO 1520
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1520
ggcgggtgat agcggtgg                                          18

<210> SEQ ID NO 1521
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1521
tggcgggtga tagcggtg                                          18

<210> SEQ ID NO 1522
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1522
ctggcgggtg atagcggt                                          18

<210> SEQ ID NO 1523
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1523
cctggcgggt gatagcgg                                          18

<210> SEQ ID NO 1524
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1524
acctggcggg tgatagcg                                          18

<210> SEQ ID NO 1525
<211> LENGTH: 18
```

```
<212> TYPE: DNA
<213> ORGANISM: Artificial Sequence
<220> FEATURE:
<223> OTHER INFORMATION: antisense oligomeric compound

<400> SEQUENCE: 1525
cacctggcgg gtgatagc                                                 18

<210> SEQ ID NO 1526
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1526
ccacctggcg ggtgatag                                                 18

<210> SEQ ID NO 1527
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1527
accacctggc gggtgata                                                 18

<210> SEQ ID NO 1528
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1528
caccacctgg cgggtgat                                                 18

<210> SEQ ID NO 1529
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1529
ccaccacctg gcgggtga                                                 18

<210> SEQ ID NO 1530
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1530
tccaccacct ggcgggtg                                                 18

<210> SEQ ID NO 1531
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1531
```
ctccaccacc tggcgggt                                          18

<210> SEQ ID NO 1532
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1532
tctccaccac ctggcggg                                          18

<210> SEQ ID NO 1533
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1533
ttctccacca cctggcgg                                          18

<210> SEQ ID NO 1534
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1534
gttctccacc acctggcg                                          18

<210> SEQ ID NO 1535
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1535
tgttctccac cacctggc                                          18

<210> SEQ ID NO 1536
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1536
atgttctcca ccacctgg                                          18

<210> SEQ ID NO 1537
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1537
catgttctcc accacctg                                          18

<210> SEQ ID NO 1538
<211> LENGTH: 18
<212> TYPE: DNA
<213> ORGANISM: Artificial Sequence

```
<220> FEATURE:
<223> OTHER INFORMATION: antisense oligomeric compound

<400> SEQUENCE: 1538
tcatgttctc caccacct                                                 18

<210> SEQ ID NO 1539
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1539
gtcatgttct ccaccacc                                                 18

<210> SEQ ID NO 1540
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1540
ggtcatgttc tccaccac                                                 18

<210> SEQ ID NO 1541
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1541
tggtcatgtt ctccacca                                                 18

<210> SEQ ID NO 1542
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1542
ctggtcatgt tctccacc                                                 18

<210> SEQ ID NO 1543
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1543
cctggtcatg ttctccac                                                 18

<210> SEQ ID NO 1544
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1544
ccctggtcat gttctcca                                                 18
```

<210> SEQ ID NO 1545
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1545
gccctggtca tgttctcc                                               18

<210> SEQ ID NO 1546
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1546
ggccctggtc atgttctc                                               18

<210> SEQ ID NO 1547
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1547
gggccctggt catgttct                                               18

<210> SEQ ID NO 1548
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1548
tgggccctgg tcatgttc                                               18

<210> SEQ ID NO 1549
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1549
gtgggccctg gtcatgtt                                               18

<210> SEQ ID NO 1550
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1550
agtgggccct ggtcatgt                                               18

<210> SEQ ID NO 1551
<211> LENGTH: 18
<212> TYPE: DNA
<213> ORGANISM: Artificial Sequence
<220> FEATURE:
<223> OTHER INFORMATION: antisense oligomeric compound

```
<400> SEQUENCE: 1551
aagtgggccc tggtcatg                                                    18

<210> SEQ ID NO 1552
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1552
gaagtgggcc ctggtcat                                                    18

<210> SEQ ID NO 1553
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1553
ggaagtgggc cctggtca                                                    18

<210> SEQ ID NO 1554
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1554
gggaagtggg ccctggtc                                                    18

<210> SEQ ID NO 1555
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1555
ggggaagtgg gccctggt                                                    18

<210> SEQ ID NO 1556
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1556
gggggaagtg ggccctgg                                                    18

<210> SEQ ID NO 1557
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1557 aggggggaagt gggccctg                                                   18

<210> SEQ ID NO 1558
```

```
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1558
cagggggaag tgggccct                                                 18

<210> SEQ ID NO 1559
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1559
ccagggggaa gtgggccc                                                 18

<210> SEQ ID NO 1560
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1560
accaggggga agtgggcc                                                 18

<210> SEQ ID NO 1561
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1561
caccaggggg aagtgggc                                                 18

<210> SEQ ID NO 1562
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1562
tcaccagggg gaagtggg                                                 18

<210> SEQ ID NO 1563
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1563
ctcaccaggg ggaagtgg                                                 18

<210> SEQ ID NO 1564
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1564
```
actcaccagg gggaagtg                                                 18

<210> SEQ ID NO 1565
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1565
aactcaccag ggggaagt                                                 18

<210> SEQ ID NO 1566
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1566
caactcacca gggggaag                                                 18

<210> SEQ ID NO 1567
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1567
ccaactcacc aggggggaa                                                18

<210> SEQ ID NO 1568
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1568
cccaactcac caggggga                                                 18

<210> SEQ ID NO 1569
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1569
ccccaactca ccaggggg                                                 18

<210> SEQ ID NO 1570
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1570
accccaactc accagggg                                                 18

<210> SEQ ID NO 1571
<211> LENGTH: 18
<212> TYPE: DNA

```
<213> ORGANISM: Artificial Sequence
<220> FEATURE:
<223> OTHER INFORMATION: antisense oligomeric compound

<400> SEQUENCE: 1571
caccccaact caccaggg                                                 18

<210> SEQ ID NO 1572
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1572
ccaccccaac tcaccagg                                                 18

<210> SEQ ID NO 1573
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1573
accaccccaa ctcaccag                                                 18

<210> SEQ ID NO 1574
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1574
caccacccca actcacca                                                 18

<210> SEQ ID NO 1575
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1575
ccaccacccc aactcacc                                                 18

<210> SEQ ID NO 1576
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1576
gccaccaccc caactcac                                                 18

<210> SEQ ID NO 1577
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1577
tgccaccacc ccaactca                                                 18
```

```
<210> SEQ ID NO 1578
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1578
ctgccaccac cccaactc                                              18

<210> SEQ ID NO 1579
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1579
cctgccacca ccccaact                                              18

<210> SEQ ID NO 1580
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1580
ccctgccacc accccaac                                              18

<210> SEQ ID NO 1581
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1581
cccctgccac caccccaa                                              18

<210> SEQ ID NO 1582
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1582
tcccctgcca ccacccca                                              18

<210> SEQ ID NO 1583
<211> LENGTH: 18
<212> TYPE: DNA
<213> ORGANISM: Artificial Sequence
<220> FEATURE:
<223> OTHER INFORMATION: antisense oligomeric compound

<400> SEQUENCE: 1583
ctcccctgcc accacccc                                              18

<210> SEQ ID NO 1584
<211> LENGTH: 368
<212> TYPE: DNA
<213> ORGANISM: Artificial Sequence
<220> FEATURE:
```

<223> OTHER INFORMATION: target sequence

<400> SEQUENCE: 1584

| aaccccagag ctgcttccct tccagatgtg gtcctgcagc cgagccctgc ccttagctgg | 60 |
| aggtcgacag gtgggatcct ggatgtctac atcttcctgg gcccagagcc caagagcgtg | 120 |
| gtgcagcagt acctggacgt tgtgggtagg gcctgctccc tggccgcggc ccccgcccca | 180 |
| aggctccctc ctccctccct catgaagtcg gcgttggcct gcaggatacc cgttcatgcc | 240 |
| gccatactgg ggcctgggct tccacctgtg ccgctggggc tactcctcca ccgctatcac | 300 |
| ccgccaggtg gtggagaaca tgaccagggc ccacttcccc ctggtgagtt ggggtggtgg | 360 |
| cagggagg | 368 |

<210> SEQ ID NO 1585
<211> LENGTH: 74
<212> TYPE: DNA
<213> ORGANISM: Artificial Sequence
<220> FEATURE:
<223> OTHER INFORMATION: target sequence

<400> SEQUENCE: 1585

| aaccccagag ctgcttccct tccagatgtg gtcctgcagc cgagccctgc ccttagctgg | 60 |
| aggtcgacag gtgg | 74 |

<210> SEQ ID NO 1586
<211> LENGTH: 74
<212> TYPE: DNA
<213> ORGANISM: Artificial Sequence
<220> FEATURE:
<223> OTHER INFORMATION: target sequence

<400> SEQUENCE: 1586

| gatcctggat gtctacatct tcctgggccc agagcccaag agcgtggtgc agcagtacct | 60 |
| ggacgttgtg ggta | 74 |

<210> SEQ ID NO 1587
<211> LENGTH: 74
<212> TYPE: DNA
<213> ORGANISM: Artificial Sequence
<220> FEATURE:
<223> OTHER INFORMATION: target sequence

<400> SEQUENCE: 1587

| gggcctgctc cctggccgcg gccccgccc caaggctccc tcctccctcc ctcatgaagt | 60 |
| cggcgttggc ctgc | 74 |

<210> SEQ ID NO 1588
<211> LENGTH: 74
<212> TYPE: DNA
<213> ORGANISM: Artificial Sequence
<220> FEATURE:
<223> OTHER INFORMATION: target sequence

<400> SEQUENCE: 1588

| aggatacccg ttcatgccgc catactgggg cctgggcttc cacctgtgcc gctggggcta | 60 |
| ctcctccacc gcta | 74 |

<210> SEQ ID NO 1589
<211> LENGTH: 72
<212> TYPE: DNA
<213> ORGANISM: Artificial Sequence

```
<220> FEATURE:
<223> OTHER INFORMATION: target sequence

<400> SEQUENCE: 1589
tcacccgcca ggtggtggag aacatgacca gggcccactt cccctggtg agttggggtg        60 gtggcagggg ag                                                           72

<210> SEQ ID NO 1590
<211> LENGTH: 20
<212> TYPE: DNA
<213> ORGANISM: Artificial Sequence
<220> FEATURE:
<223> OTHER INFORMATION: primer

<400> SEQUENCE: 1590
gggtgctcct ggacaactac                                                   20

<210> SEQ ID NO 1591
<211> LENGTH: 20
<212> TYPE: DNA
<213> ORGANISM: Artificial Sequence
<220> FEATURE:
<223> OTHER INFORMATION: primer

<400> SEQUENCE: 1591
cctgttgcaa cttcttcgcc                                                   20

<210> SEQ ID NO 1592
<211> LENGTH: 20
<212> TYPE: DNA
<213> ORGANISM: Artificial Sequence
<220> FEATURE:
<223> OTHER INFORMATION: primer

<400> SEQUENCE: 1592
atggcacctg ggaatgtacc                                                   20

<210> SEQ ID NO 1593
<211> LENGTH: 20
<212> TYPE: DNA
<213> ORGANISM: Artificial Sequence
<220> FEATURE:
<223> OTHER INFORMATION: primer

<400> SEQUENCE: 1593
gtgttgttcc agagcccact                                                   20

<210> SEQ ID NO 1594
<211> LENGTH: 20
<212> TYPE: DNA
<213> ORGANISM: Artificial Sequence
<220> FEATURE:
<223> OTHER INFORMATION: primer

<400> SEQUENCE: 1594
acgctctgaa tgtcacacga                                                   20

<210> SEQ ID NO 1595
<211> LENGTH: 20
<212> TYPE: DNA
<213> ORGANISM: Artificial Sequence
<220> FEATURE:
<223> OTHER INFORMATION: primer

<400> SEQUENCE: 1595
```

```
gttggcagcc agtcagagat                                              20

<210> SEQ ID NO 1596
<211> LENGTH: 20
<212> TYPE: DNA
<213> ORGANISM: Artificial Sequence
<220> FEATURE:
<223> OTHER INFORMATION: primer

<400> SEQUENCE: 1596
aaaaagcagt gggctctgga                                              20

<210> SEQ ID NO 1597
<211> LENGTH: 20
<212> TYPE: DNA
<213> ORGANISM: Artificial Sequence
<220> FEATURE:
<223> OTHER INFORMATION: primer

<400> SEQUENCE: 1597
cggtgaagag tccacgaagt                                              20

<210> SEQ ID NO 1598
<211> LENGTH: 20
<212> TYPE: DNA
<213> ORGANISM: Artificial Sequence
<220> FEATURE:
<223> OTHER INFORMATION: primer

<400> SEQUENCE: 1598
cagaagggcg tgaagaaccg                                              20

<210> SEQ ID NO 1599
<211> LENGTH: 22
<212> TYPE: DNA
<213> ORGANISM: Artificial Sequence
<220> FEATURE:
<223> OTHER INFORMATION: primer

<400> SEQUENCE: 1599
cccgtgagga gtttccaatt tc                                           22

<210> SEQ ID NO 1600
<211> LENGTH: 20
<212> TYPE: DNA
<213> ORGANISM: Artificial Sequence
<220> FEATURE:
<223> OTHER INFORMATION: primer

<400> SEQUENCE: 1600
acttcgtgga ctcttcaccg                                              20

<210> SEQ ID NO 1601
<211> LENGTH: 20
<212> TYPE: DNA
<213> ORGANISM: Artificial Sequence
<220> FEATURE:
<223> OTHER INFORMATION: primer

<400> SEQUENCE: 1601
agtacacggg gactgagtgt                                              20

<210> SEQ ID NO 1602
<211> LENGTH: 29
<212> TYPE: DNA
<213> ORGANISM: Artificial Sequence
```

<220> FEATURE:
<223> OTHER INFORMATION: primer

<400> SEQUENCE: 1602
gcgcctgcag taacaacata ggagctgtg        29

<210> SEQ ID NO 1603
<211> LENGTH: 30
<212> TYPE: DNA
<213> ORGANISM: Artificial Sequence
<220> FEATURE:
<223> OTHER INFORMATION: primer

<400> SEQUENCE: 1603
gcgcgtcgac cagatacgcg tttcctagga        30

<210> SEQ ID NO 1604
<211> LENGTH: 38
<212> TYPE: DNA
<213> ORGANISM: Artificial Sequence
<220> FEATURE:
<223> OTHER INFORMATION: primer

<400> SEQUENCE: 1604
gctcttttag aatttttgga gcaggttttc tgacttcg        38

<210> SEQ ID NO 1605
<211> LENGTH: 38
<212> TYPE: DNA
<213> ORGANISM: Artificial Sequence
<220> FEATURE:
<223> OTHER INFORMATION: primer

<400> SEQUENCE: 1605
cgaagtcaga aaacctgctc caaaaattct aaaagagc        38

<210> SEQ ID NO 1606
<211> LENGTH: 39
<212> TYPE: DNA
<213> ORGANISM: Artificial Sequence
<220> FEATURE:
<223> OTHER INFORMATION: primer

<400> SEQUENCE: 1606
cctggctcgc tacagaggcc tttccgcaag tgttacagc        39

<210> SEQ ID NO 1607
<211> LENGTH: 39
<212> TYPE: DNA
<213> ORGANISM: Artificial Sequence
<220> FEATURE:
<223> OTHER INFORMATION: primer

<400> SEQUENCE: 1607
gctgtaacac ttgcggaaag gcctctgtag cgagccagg        39

<210> SEQ ID NO 1608
<211> LENGTH: 16
<212> TYPE: DNA
<213> ORGANISM: Artificial Sequence
<220> FEATURE:
<223> OTHER INFORMATION: primer

<400> SEQUENCE: 1608
gtaaaacgac ggccag        16

<210> SEQ ID NO 1609
<211> LENGTH: 17
<212> TYPE: DNA
<213> ORGANISM: Artificial Sequence
<220> FEATURE:
<223> OTHER INFORMATION: primer

<400> SEQUENCE: 1609
caggaaacag ctatgac                                                        17

<210> SEQ ID NO 1610
<211> LENGTH: 37
<212> TYPE: DNA
<213> ORGANISM: Artificial Sequence
<220> FEATURE:
<223> OTHER INFORMATION: primer

<400> SEQUENCE: 1610
cctggctcgc tacagatgca taggaggacg gaggacg                                  37

<210> SEQ ID NO 1611
<211> LENGTH: 37
<212> TYPE: DNA
<213> ORGANISM: Artificial Sequence
<220> FEATURE:
<223> OTHER INFORMATION: primer

<400> SEQUENCE: 1611
cgtcctccgt cctcctatgc atctgtagcg agccagg                                  37

<210> SEQ ID NO 1612
<211> LENGTH: 10
<212> TYPE: DNA
<213> ORGANISM: Artificial Sequence
<220> FEATURE:
<223> OTHER INFORMATION: primer - first part befiore antisense

<400> SEQUENCE: 1612
gcgcatgcat                                                                10

<210> SEQ ID NO 1613
<211> LENGTH: 30
<212> TYPE: DNA
<213> ORGANISM: Artificial Sequence
<220> FEATURE:
<223> OTHER INFORMATION: primer

<400> SEQUENCE: 1613
gcgcgtcgac cagatacgcg tttcctagga                                          30

<210> SEQ ID NO 1614
<211> LENGTH: 10
<212> TYPE: DNA
<213> ORGANISM: Artificial Sequence
<220> FEATURE:
<223> OTHER INFORMATION: primer second part after antisense sequence

<400> SEQUENCE: 1614
ttggagcagg                                                                10

<210> SEQ ID NO 1615
<211> LENGTH: 12
<212> TYPE: PRT
<213> ORGANISM: Artificial Sequence
<220> FEATURE:
<223> OTHER INFORMATION: TAT sequence

<400> SEQUENCE: 1615

Cys Tyr Gly Arg Lys Arg Arg Gln Arg Arg Arg
1               5                   10

<210> SEQ ID NO 1616
<211> LENGTH: 20
<212> TYPE: DNA
<213> ORGANISM: Homo sapiens

<400> SEQUENCE: 1616
ggccaggaat aacacgatcg                                           20

<210> SEQ ID NO 1617
<211> LENGTH: 20
<212> TYPE: DNA
<213> ORGANISM: Homo sapiens

<400> SEQUENCE: 1617
cacggagcgg gcctgtagga                                           20

<210> SEQ ID NO 1618
<211> LENGTH: 19
<212> TYPE: DNA
<213> ORGANISM: Homo sapiens

<400> SEQUENCE: 1618
cacttcacga tcaaagatc                                            19

<210> SEQ ID NO 1619
<211> LENGTH: 19
<212> TYPE: DNA
<213> ORGANISM: Homo sapiens

<400> SEQUENCE: 1619
cacggacggg acatcctga                                            19

<210> SEQ ID NO 1620
<211> LENGTH: 20
<212> TYPE: DNA
<213> ORGANISM: Homo sapiens

<400> SEQUENCE: 1620
cacggagcgg atcaaagatc                                           20

<210> SEQ ID NO 1621
<211> LENGTH: 20
<212> TYPE: DNA
<213> ORGANISM: Homo sapiens

<400> SEQUENCE: 1621 cccccctgcag ggccctggcc                                          20

<210> SEQ ID NO 1622
<211> LENGTH: 20
<212> TYPE: DNA
<213> ORGANISM: Homo sapiens

<400> SEQUENCE: 1622
ggccaggaat aacacgatcg                                           20

<210> SEQ ID NO 1623
<211> LENGTH: 20

```
<212> TYPE: DNA
<213> ORGANISM: Homo sapiens

<400> SEQUENCE: 1623 cccctgcag aacacgatcg                                              20

<210> SEQ ID NO 1624
<211> LENGTH: 20
<212> TYPE: DNA
<213> ORGANISM: Homo sapiens

<400> SEQUENCE: 1624
cacggagcgg gcctgtagga                                             20

<210> SEQ ID NO 1625
<211> LENGTH: 19
<212> TYPE: DNA
<213> ORGANISM: Homo sapiens

<400> SEQUENCE: 1625
cacttcacga tcaaagatc                                              19

<210> SEQ ID NO 1626
<211> LENGTH: 20
<212> TYPE: DNA
<213> ORGANISM: Homo sapiens

<400> SEQUENCE: 1626
cacggagcgg gacatcctga                                             20

<210> SEQ ID NO 1627
<211> LENGTH: 20
<212> TYPE: DNA
<213> ORGANISM: Homo sapiens

<400> SEQUENCE: 1627
cacggagcgg atcaaagatc                                             20

<210> SEQ ID NO 1628
<211> LENGTH: 21
<212> TYPE: DNA
<213> ORGANISM: Homo sapiens

<400> SEQUENCE: 1628
gattgggaaa ggtatggccc g                                           21

<210> SEQ ID NO 1629
<211> LENGTH: 20
<212> TYPE: DNA
<213> ORGANISM: Homo sapiens

<400> SEQUENCE: 1629
catgtggatt gacatgaacg                                             20

<210> SEQ ID NO 1630
<211> LENGTH: 20
<212> TYPE: DNA
<213> ORGANISM: Homo sapiens

<400> SEQUENCE: 1630
gattgggaag gacatgaacg                                             20

<210> SEQ ID NO 1631
```

```
<211> LENGTH: 20
<212> TYPE: DNA
<213> ORGANISM: Homo sapiens

<400> SEQUENCE: 1631
aatgccatgg atgtggtcct                                                 20

<210> SEQ ID NO 1632
<211> LENGTH: 20
<212> TYPE: DNA
<213> ORGANISM: Homo sapiens

<400> SEQUENCE: 1632
cctggacgtt gatacccgtt                                                 20

<210> SEQ ID NO 1633
<211> LENGTH: 20
<212> TYPE: DNA
<213> ORGANISM: Homo sapiens

<400> SEQUENCE: 1633
gattgggaag gtatggcccg                                                 20

<210> SEQ ID NO 1634
<211> LENGTH: 20
<212> TYPE: DNA
<213> ORGANISM: Homo sapiens

<400> SEQUENCE: 1634
catgtggatt gtaagtgtgg                                                 20

<210> SEQ ID NO 1635
<211> LENGTH: 20
<212> TYPE: DNA
<213> ORGANISM: Homo sapiens

<400> SEQUENCE: 1635
tctcttggag gacatgaacg                                                 20

<210> SEQ ID NO 1636
<211> LENGTH: 20
<212> TYPE: DNA
<213> ORGANISM: Homo sapiens

<400> SEQUENCE: 1636
catgtggatt gacatgaacg                                                 20

<210> SEQ ID NO 1637
<211> LENGTH: 20
<212> TYPE: DNA
<213> ORGANISM: Homo sapiens

<400> SEQUENCE: 1637
gattgggaag agtcacctac                                                 20

<210> SEQ ID NO 1638
<211> LENGTH: 20
<212> TYPE: DNA
<213> ORGANISM: Homo sapiens

<400> SEQUENCE: 1638
gatcatcgtg gatcctgcca                                                 20
```

```
<210> SEQ ID NO 1639
<211> LENGTH: 20
<212> TYPE: DNA
<213> ORGANISM: Homo sapiens

<400> SEQUENCE: 1639
gattgggaag gtatggcccg                                               20

<210> SEQ ID NO 1640
<211> LENGTH: 20
<212> TYPE: DNA
<213> ORGANISM: Homo sapiens

<400> SEQUENCE: 1640
gatcatcgtg gtatggcccg                                               20

<210> SEQ ID NO 1641
<211> LENGTH: 20
<212> TYPE: DNA
<213> ORGANISM: Homo sapiens

<400> SEQUENCE: 1641 cttcccctg gacgtccaat                                                20

<210> SEQ ID NO 1642
<211> LENGTH: 20
<212> TYPE: DNA
<213> ORGANISM: Homo sapiens

<400> SEQUENCE: 1642
gatcatcgtg gatcctgcca                                               20

<210> SEQ ID NO 1643
<211> LENGTH: 20
<212> TYPE: DNA
<213> ORGANISM: Homo sapiens

<400> SEQUENCE: 1643
gttcaacaag gatcctgcca                                               20

<210> SEQ ID NO 1644
<211> LENGTH: 20
<212> TYPE: DNA
<213> ORGANISM: Homo sapiens

<400> SEQUENCE: 1644
gattgggaag gtatggcccg                                               20

<210> SEQ ID NO 1645
<211> LENGTH: 20
<212> TYPE: DNA
<213> ORGANISM: Homo sapiens

<400> SEQUENCE: 1645
catgtggatt gacatgaacg                                               20

<210> SEQ ID NO 1646
<211> LENGTH: 20
<212> TYPE: DNA
<213> ORGANISM: Homo sapiens

<400> SEQUENCE: 1646
gattgggaag gacatgaacg                                               20
```

```
<210> SEQ ID NO 1647
<211> LENGTH: 18
<212> TYPE: DNA
<213> ORGANISM: Artificial Sequence
<220> FEATURE:
<223> OTHER INFORMATION: primer

<400> SEQUENCE: 1647
aaactgaggc acggagcg                                                 18

<210> SEQ ID NO 1648
<211> LENGTH: 18
<212> TYPE: DNA
<213> ORGANISM: Artificial Sequence
<220> FEATURE:
<223> OTHER INFORMATION: primer

<400> SEQUENCE: 1648
gaagggctcc tcggagaa                                                 18

<210> SEQ ID NO 1649
<211> LENGTH: 22
<212> TYPE: DNA
<213> ORGANISM: Artificial Sequence
<220> FEATURE:
<223> OTHER INFORMATION: primer

<400> SEQUENCE: 1649
agctcctctg aaatgggcta ca                                            22

<210> SEQ ID NO 1650
<211> LENGTH: 19
<212> TYPE: DNA
<213> ORGANISM: Artificial Sequence
<220> FEATURE:
<223> OTHER INFORMATION: primer

<400> SEQUENCE: 1650
gcaaggtccc ggttccaca                                                19

<210> SEQ ID NO 1651
<211> LENGTH: 20
<212> TYPE: DNA
<213> ORGANISM: Artificial Sequence
<220> FEATURE:
<223> OTHER INFORMATION: primer

<400> SEQUENCE: 1651
gctaacaggc gctacgaggt                                               20

<210> SEQ ID NO 1652
<211> LENGTH: 21
<212> TYPE: DNA
<213> ORGANISM: Artificial Sequence
<220> FEATURE:
<223> OTHER INFORMATION: primer

<400> SEQUENCE: 1652
tgctgtttag caggaacacc c                                             21

<210> SEQ ID NO 1653
<211> LENGTH: 21
<212> TYPE: DNA
<213> ORGANISM: Artificial Sequence
<220> FEATURE:
<223> OTHER INFORMATION: primer
```

<400> SEQUENCE: 1653
ctgttctttg cggaccagtt c                                              21

<210> SEQ ID NO 1654
<211> LENGTH: 21
<212> TYPE: DNA
<213> ORGANISM: Artificial Sequence
<220> FEATURE:
<223> OTHER INFORMATION: primer

<400> SEQUENCE: 1654
ccacaacgtc caggtactgc t                                              21

<210> SEQ ID NO 1655
<211> LENGTH: 21
<212> TYPE: DNA
<213> ORGANISM: Artificial Sequence
<220> FEATURE:
<223> OTHER INFORMATION: primer

<400> SEQUENCE: 1655
ggtctcaccc tttctacctg g                                              21

<210> SEQ ID NO 1656
<211> LENGTH: 21
<212> TYPE: DNA
<213> ORGANISM: Artificial Sequence
<220> FEATURE:
<223> OTHER INFORMATION: primer

<400> SEQUENCE: 1656
gtgatagcgg tggaggagta g                                              21

<210> SEQ ID NO 1657
<211> LENGTH: 21
<212> TYPE: DNA
<213> ORGANISM: Artificial Sequence
<220> FEATURE:
<223> OTHER INFORMATION: primer

<400> SEQUENCE: 1657
cagcagtacc tggacgttgt g                                              21

<210> SEQ ID NO 1658
<211> LENGTH: 22
<212> TYPE: DNA
<213> ORGANISM: Artificial Sequence
<220> FEATURE:
<223> OTHER INFORMATION: primer

<400> SEQUENCE: 1658
agtccatgta gtccaggtcg tt                                             22

<210> SEQ ID NO 1659
<211> LENGTH: 18
<212> TYPE: DNA
<213> ORGANISM: Artificial Sequence
<220> FEATURE:
<223> OTHER INFORMATION: primer

<400> SEQUENCE: 1659
cgttcatgcc gccatact                                                  18

<210> SEQ ID NO 1660

```
<211> LENGTH: 21
<212> TYPE: DNA
<213> ORGANISM: Artificial Sequence
<220> FEATURE:
<223> OTHER INFORMATION: primer

<400> SEQUENCE: 1660
ggtctcgttg gtgatgaaaa c                                              21

<210> SEQ ID NO 1661
<211> LENGTH: 20
<212> TYPE: DNA
<213> ORGANISM: Artificial Sequence
<220> FEATURE:
<223> OTHER INFORMATION: primer

<400> SEQUENCE: 1661
gacgtccagt ggaacgacct                                                20

<210> SEQ ID NO 1662
<211> LENGTH: 20
<212> TYPE: DNA
<213> ORGANISM: Artificial Sequence
<220> FEATURE:
<223> OTHER INFORMATION: primer

<400> SEQUENCE: 1662
acctggtcat ggaactcagc                                                20

<210> SEQ ID NO 1663
<211> LENGTH: 19
<212> TYPE: DNA
<213> ORGANISM: Artificial Sequence
<220> FEATURE:
<223> OTHER INFORMATION: primer

<400> SEQUENCE: 1663
gatcctgcca tcagcagct                                                 19

<210> SEQ ID NO 1664
<211> LENGTH: 20
<212> TYPE: DNA
<213> ORGANISM: Artificial Sequence
<220> FEATURE:
<223> OTHER INFORMATION: primer

<400> SEQUENCE: 1664
tgggttctcc agctcattgt                                                20

<210> SEQ ID NO 1665
<211> LENGTH: 20
<212> TYPE: DNA
<213> ORGANISM: Artificial Sequence
<220> FEATURE:
<223> OTHER INFORMATION: primer

<400> SEQUENCE: 1665
aggacatggt ggctgagttc                                                20

<210> SEQ ID NO 1666
<211> LENGTH: 22
<212> TYPE: DNA
<213> ORGANISM: Artificial Sequence
<220> FEATURE:
<223> OTHER INFORMATION: primer

<400> SEQUENCE: 1666
```
cgtagaggtt gtgcaggttg ta                                            22

<210> SEQ ID NO 1667
<211> LENGTH: 21
<212> TYPE: DNA
<213> ORGANISM: Artificial Sequence
<220> FEATURE:
<223> OTHER INFORMATION: primer

<400> SEQUENCE: 1667
aacgagcctt ccaacttcat c                                             21

<210> SEQ ID NO 1668
<211> LENGTH: 20
<212> TYPE: DNA
<213> ORGANISM: Artificial Sequence
<220> FEATURE:
<223> OTHER INFORMATION: primer

<400> SEQUENCE: 1668
gagcgggaga tcacaaatgg                                               20

<210> SEQ ID NO 1669
<211> LENGTH: 23
<212> TYPE: DNA
<213> ORGANISM: Artificial Sequence
<220> FEATURE:
<223> OTHER INFORMATION: primer

<400> SEQUENCE: 1669
caccagtttc tctccacaca cta                                           23

<210> SEQ ID NO 1670
<211> LENGTH: 20
<212> TYPE: DNA
<213> ORGANISM: Artificial Sequence
<220> FEATURE:
<223> OTHER INFORMATION: primer

<400> SEQUENCE: 1670
gttccgcatg aagggtaga                                                20

<210> SEQ ID NO 1671
<211> LENGTH: 20
<212> TYPE: DNA
<213> ORGANISM: Artificial Sequence
<220> FEATURE:
<223> OTHER INFORMATION: primer

<400> SEQUENCE: 1671
acacgcccat ttgtgatctc                                               20

<210> SEQ ID NO 1672
<211> LENGTH: 21
<212> TYPE: DNA
<213> ORGANISM: Artificial Sequence
<220> FEATURE:
<223> OTHER INFORMATION: primer

<400> SEQUENCE: 1672
gtgtagaggt gggggaggag t                                             21

<210> SEQ ID NO 1673
<211> LENGTH: 23
<212> TYPE: DNA

```
<213> ORGANISM: Artificial Sequence
<220> FEATURE:
<223> OTHER INFORMATION: primer

<400> SEQUENCE: 1673
aaatcctgca gtttaacctg ctg                                         23

<210> SEQ ID NO 1674
<211> LENGTH: 19
<212> TYPE: DNA
<213> ORGANISM: Artificial Sequence
<220> FEATURE:
<223> OTHER INFORMATION: primer

<400> SEQUENCE: 1674
gcaggtcgta ccatgtgcc                                              19

<210> SEQ ID NO 1675
<211> LENGTH: 20
<212> TYPE: DNA
<213> ORGANISM: Artificial Sequence
<220> FEATURE:
<223> OTHER INFORMATION: primer

<400> SEQUENCE: 1675
gagccgtaca gcttcagcga                                             20

<210> SEQ ID NO 1676
<211> LENGTH: 19
<212> TYPE: DNA
<213> ORGANISM: Artificial Sequence
<220> FEATURE:
<223> OTHER INFORMATION: primer

<400> SEQUENCE: 1676
atgtacccag cccggaggt                                              19

<210> SEQ ID NO 1677
<211> LENGTH: 19
<212> TYPE: DNA
<213> ORGANISM: Artificial Sequence
<220> FEATURE:
<223> OTHER INFORMATION: primer

<400> SEQUENCE: 1677
cctggactgt ggaccacca                                              19

<210> SEQ ID NO 1678
<211> LENGTH: 23
<212> TYPE: DNA
<213> ORGANISM: Artificial Sequence
<220> FEATURE:
<223> OTHER INFORMATION: primer

<400> SEQUENCE: 1678
caggaagatg acctgtgtgt agg                                         23

<210> SEQ ID NO 1679
<211> LENGTH: 19
<212> TYPE: DNA
<213> ORGANISM: Artificial Sequence
<220> FEATURE:
<223> OTHER INFORMATION: primer

<400> SEQUENCE: 1679
gtgccagtag aggcccttg                                              19
```

<210> SEQ ID NO 1680
<211> LENGTH: 22
<212> TYPE: DNA
<213> ORGANISM: Artificial Sequence
<220> FEATURE:
<223> OTHER INFORMATION: primer

<400> SEQUENCE: 1680
ggctgtaggt gaagttggag ac                                              22

<210> SEQ ID NO 1681
<211> LENGTH: 19
<212> TYPE: DNA
<213> ORGANISM: Artificial Sequence
<220> FEATURE:
<223> OTHER INFORMATION: primer

<400> SEQUENCE: 1681
tcacaaccac agagtcccg                                                  19

<210> SEQ ID NO 1682
<211> LENGTH: 22
<212> TYPE: DNA
<213> ORGANISM: Artificial Sequence
<220> FEATURE:
<223> OTHER INFORMATION: primer

<400> SEQUENCE: 1682
agaaactgct ctcccatcaa ca                                              22

<210> SEQ ID NO 1683
<211> LENGTH: 19
<212> TYPE: DNA
<213> ORGANISM: Artificial Sequence
<220> FEATURE:
<223> OTHER INFORMATION: primer

<400> SEQUENCE: 1683
aaccgcgaga agatgaccc                                                  19

<210> SEQ ID NO 1684
<211> LENGTH: 21
<212> TYPE: DNA
<213> ORGANISM: Artificial Sequence
<220> FEATURE:
<223> OTHER INFORMATION: primer

<400> SEQUENCE: 1684
gccagaggcg tacagggata g                                               21

<210> SEQ ID NO 1685
<211> LENGTH: 23
<212> TYPE: DNA
<213> ORGANISM: Artificial Sequence
<220> FEATURE:
<223> OTHER INFORMATION: primer

<400> SEQUENCE: 1685
agctcctctg aaatgggcta cac                                             23

<210> SEQ ID NO 1686
<211> LENGTH: 23
<212> TYPE: DNA
<213> ORGANISM: Artificial Sequence
<220> FEATURE:

<223> OTHER INFORMATION: primer

<400> SEQUENCE: 1686
ggttctcagt ctccatcatc acg                                          23

<210> SEQ ID NO 1687
<211> LENGTH: 20
<212> TYPE: DNA
<213> ORGANISM: Artificial Sequence
<220> FEATURE:
<223> OTHER INFORMATION: primer

<400> SEQUENCE: 1687
atccagctaa caggcgctac                                              20

<210> SEQ ID NO 1688
<211> LENGTH: 19
<212> TYPE: DNA
<213> ORGANISM: Artificial Sequence
<220> FEATURE:
<223> OTHER INFORMATION: primer

<400> SEQUENCE: 1688
gctcctcgga gaactccac                                               19

<210> SEQ ID NO 1689
<211> LENGTH: 20
<212> TYPE: DNA
<213> ORGANISM: Artificial Sequence
<220> FEATURE:
<223> OTHER INFORMATION: primer

<400> SEQUENCE: 1689
ctgttctttg cggaccagtt                                              20

<210> SEQ ID NO 1690
<211> LENGTH: 20
<212> TYPE: DNA
<213> ORGANISM: Artificial Sequence
<220> FEATURE:
<223> OTHER INFORMATION: primer

<400> SEQUENCE: 1690
ctgagcatca ggggactgag                                              20

<210> SEQ ID NO 1691
<211> LENGTH: 20
<212> TYPE: DNA
<213> ORGANISM: Artificial Sequence
<220> FEATURE:
<223> OTHER INFORMATION: primer

<400> SEQUENCE: 1691
cgaacctcta cgggtctcac                                              20

<210> SEQ ID NO 1692
<211> LENGTH: 20
<212> TYPE: DNA
<213> ORGANISM: Artificial Sequence
<220> FEATURE:
<223> OTHER INFORMATION: primer

<400> SEQUENCE: 1692
tgctgtttag caggaacacc                                              20

```
<210> SEQ ID NO 1693
<211> LENGTH: 20
<212> TYPE: DNA
<213> ORGANISM: Artificial Sequence
<220> FEATURE:
<223> OTHER INFORMATION: primer

<400> SEQUENCE: 1693
cttagctgga ggtcgacagg                                               20

<210> SEQ ID NO 1694
<211> LENGTH: 20
<212> TYPE: DNA
<213> ORGANISM: Artificial Sequence
<220> FEATURE:
<223> OTHER INFORMATION: primer

<400> SEQUENCE: 1694
cacaacgtcc aggtactgct                                               20

<210> SEQ ID NO 1695
<211> LENGTH: 18
<212> TYPE: DNA
<213> ORGANISM: Artificial Sequence
<220> FEATURE:
<223> OTHER INFORMATION: primer

<400> SEQUENCE: 1695
cgttcatgcc gccatact                                                 18

<210> SEQ ID NO 1696
<211> LENGTH: 20
<212> TYPE: DNA
<213> ORGANISM: Artificial Sequence
<220> FEATURE:
<223> OTHER INFORMATION: primer

<400> SEQUENCE: 1696
ggtcatgttc tccaccacct                                               20

<210> SEQ ID NO 1697
<211> LENGTH: 20
<212> TYPE: DNA
<213> ORGANISM: Artificial Sequence
<220> FEATURE:
<223> OTHER INFORMATION: primer

<400> SEQUENCE: 1697
gacgtccagt ggaacgacct                                               20

<210> SEQ ID NO 1698
<211> LENGTH: 18
<212> TYPE: DNA
<213> ORGANISM: Artificial Sequence
<220> FEATURE:
<223> OTHER INFORMATION: primer

<400> SEQUENCE: 1698
gaagtcccgg aagccatc                                                 18

<210> SEQ ID NO 1699
<211> LENGTH: 19
<212> TYPE: DNA
<213> ORGANISM: Artificial Sequence
<220> FEATURE:
<223> OTHER INFORMATION: primer
```

```
<400> SEQUENCE: 1699
atcctgccat cagcagctc                                                    19

<210> SEQ ID NO 1700
<211> LENGTH: 20
<212> TYPE: DNA
<213> ORGANISM: Artificial Sequence
<220> FEATURE:
<223> OTHER INFORMATION: primer

<400> SEQUENCE: 1700
ggtctcgttg gtgatgaaaa                                                   20

<210> SEQ ID NO 1701
<211> LENGTH: 18
<212> TYPE: DNA
<213> ORGANISM: Artificial Sequence
<220> FEATURE:
<223> OTHER INFORMATION: primer

<400> SEQUENCE: 1701
cactgccttc cccgactt                                                     18

<210> SEQ ID NO 1702
<211> LENGTH: 20
<212> TYPE: DNA
<213> ORGANISM: Artificial Sequence
<220> FEATURE:
<223> OTHER INFORMATION: primer

<400> SEQUENCE: 1702
acctggtcat ggaactcagc                                                   20

<210> SEQ ID NO 1703
<211> LENGTH: 20
<212> TYPE: DNA
<213> ORGANISM: Artificial Sequence
<220> FEATURE:
<223> OTHER INFORMATION: primer

<400> SEQUENCE: 1703
acatgaacga gccttccaac                                                   20

<210> SEQ ID NO 1704
<211> LENGTH: 20
<212> TYPE: DNA
<213> ORGANISM: Artificial Sequence
<220> FEATURE:
<223> OTHER INFORMATION: primer

<400> SEQUENCE: 1704
acgtagggtg ggttctccag                                                   20

<210> SEQ ID NO 1705
<211> LENGTH: 21
<212> TYPE: DNA
<213> ORGANISM: Artificial Sequence
<220> FEATURE:
<223> OTHER INFORMATION: primer

<400> SEQUENCE: 1705
cctccagcca ccagtttctc t                                                 21

<210> SEQ ID NO 1706
<211> LENGTH: 18
```

```
<212> TYPE: DNA
<213> ORGANISM: Artificial Sequence
<220> FEATURE:
<223> OTHER INFORMATION: primer

<400> SEQUENCE: 1706
tgtgggaggc gatggctt                                                 18

<210> SEQ ID NO 1707
<211> LENGTH: 20
<212> TYPE: DNA
<213> ORGANISM: Artificial Sequence
<220> FEATURE:
<223> OTHER INFORMATION: primer

<400> SEQUENCE: 1707
gacacgccca tttgtgatct                                               20

<210> SEQ ID NO 1708
<211> LENGTH: 18
<212> TYPE: DNA
<213> ORGANISM: Artificial Sequence
<220> FEATURE:
<223> OTHER INFORMATION: primer

<400> SEQUENCE: 1708
ccaggagctc cacacgtc                                                 18

<210> SEQ ID NO 1709
<211> LENGTH: 20
<212> TYPE: DNA
<213> ORGANISM: Artificial Sequence
<220> FEATURE:
<223> OTHER INFORMATION: primer

<400> SEQUENCE: 1709
ctcagaggag ctgtgtgtgc                                               20

<210> SEQ ID NO 1710
<211> LENGTH: 20
<212> TYPE: DNA
<213> ORGANISM: Artificial Sequence
<220> FEATURE:
<223> OTHER INFORMATION: primer

<400> SEQUENCE: 1710
cagactgagc aggctgttgt                                               20

<210> SEQ ID NO 1711
<211> LENGTH: 18
<212> TYPE: DNA
<213> ORGANISM: Artificial Sequence
<220> FEATURE:
<223> OTHER INFORMATION: primer

<400> SEQUENCE: 1711
cagcaggcca tgaggaag                                                 18

<210> SEQ ID NO 1712
<211> LENGTH: 19
<212> TYPE: DNA
<213> ORGANISM: Artificial Sequence
<220> FEATURE:
<223> OTHER INFORMATION: primer

<400> SEQUENCE: 1712
```
ggcctggtgg aacagtgtg                                                    19

<210> SEQ ID NO 1713
<211> LENGTH: 20
<212> TYPE: DNA
<213> ORGANISM: Artificial Sequence
<220> FEATURE:
<223> OTHER INFORMATION: primer

<400> SEQUENCE: 1713
cccaaggact ctagcacctg                                                   20

<210> SEQ ID NO 1714
<211> LENGTH: 20
<212> TYPE: DNA
<213> ORGANISM: Artificial Sequence
<220> FEATURE:
<223> OTHER INFORMATION: primer

<400> SEQUENCE: 1714
caaggggaag tagccagtca                                                   20

<210> SEQ ID NO 1715
<211> LENGTH: 19
<212> TYPE: DNA
<213> ORGANISM: Artificial Sequence
<220> FEATURE:
<223> OTHER INFORMATION: primer

<400> SEQUENCE: 1715
gtgccagtag aggcccttg                                                    19

<210> SEQ ID NO 1716
<211> LENGTH: 20
<212> TYPE: DNA
<213> ORGANISM: Artificial Sequence
<220> FEATURE:
<223> OTHER INFORMATION: primer

<400> SEQUENCE: 1716
gaggtggacg ttgatggtgt                                                   20

<210> SEQ ID NO 1717
<211> LENGTH: 20
<212> TYPE: DNA
<213> ORGANISM: Artificial Sequence
<220> FEATURE:
<223> OTHER INFORMATION: primer

<400> SEQUENCE: 1717
gcctcacaac cacagagtcc                                                   20

<210> SEQ ID NO 1718
<211> LENGTH: 20
<212> TYPE: DNA
<213> ORGANISM: Artificial Sequence
<220> FEATURE:
<223> OTHER INFORMATION: primer

<400> SEQUENCE: 1718
tctctccatc gtcccagaac                                                   20

<210> SEQ ID NO 1719
<211> LENGTH: 20
<212> TYPE: DNA
<213> ORGANISM: Artificial Sequence

```
<220> FEATURE:
<223> OTHER INFORMATION: primer

<400> SEQUENCE: 1719
tgcagaaggt gactgtcctg                                              20

<210> SEQ ID NO 1720
<211> LENGTH: 20
<212> TYPE: DNA
<213> ORGANISM: Artificial Sequence
<220> FEATURE:
<223> OTHER INFORMATION: primer

<400> SEQUENCE: 1720
gggctgtagg tgaagttgga                                              20

<210> SEQ ID NO 1721
<211> LENGTH: 20
<212> TYPE: DNA
<213> ORGANISM: Artificial Sequence
<220> FEATURE:
<223> OTHER INFORMATION: primer

<400> SEQUENCE: 1721
gggcggagtg tgttagtctc                                              20

<210> SEQ ID NO 1722
<211> LENGTH: 20
<212> TYPE: DNA
<213> ORGANISM: Artificial Sequence
<220> FEATURE:
<223> OTHER INFORMATION: primer

<400> SEQUENCE: 1722
ctccaggtga cacatgcaac                                              20

<210> SEQ ID NO 1723
<211> LENGTH: 40
<212> TYPE: DNA
<213> ORGANISM: Homo sapiens

<400> SEQUENCE: 1723
gcttttctcg cccttccttc tggccctctc cccagtctag                        40

<210> SEQ ID NO 1724
<211> LENGTH: 55
<212> TYPE: DNA
<213> ORGANISM: Homo sapiens

<400> SEQUENCE: 1724
gctctgcact ccctgctgg agcttttctc gcccttcctt ctggccctct cccca         55

<210> SEQ ID NO 1725
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 1725
gccagaagga agggcgagaa aagct                                        25

<210> SEQ ID NO 1726
<211> LENGTH: 21
<212> TYPE: DNA
```

```
<213> ORGANISM: Artificial Sequence
<220> FEATURE:
<223> OTHER INFORMATION: antisense oligonucleotide

<400> SEQUENCE: 1726
ccagaaggaa gggcgagaaa a                                               21

<210> SEQ ID NO 1727
<211> LENGTH: 368
<212> TYPE: DNA
<213> ORGANISM: Homo sapiens

<400> SEQUENCE: 1727
aaccccagag ctgcttccct tccagatgtg gtcctgcagc cgagccctgc ccttagctgg     60
aggtcgacag gtgggatcct ggatgtctac atcttcctgg gcccagagcc caagagcgtg    120
gtgcagcagt acctggacgt tgtgggtagg gcctgctccc tggccgcggc ccccgcccca    180
aggctccctc ctccctccct catgaagtcg gcgttggcct gcaggatacc cgttcatgcc    240
gccatactgg ggcctgggct tccacctgtg ccgctgggggc tactcctcca ccgctatcac    300
ccgccaggtg gtggagaaca tgaccagggc ccacttcccc ctggtgagtt ggggtggtgg    360
caggggag                                                             368
```